US009676704B2

(12) United States Patent
LePlae, Jr. et al.

(10) Patent No.: US 9,676,704 B2
(45) Date of Patent: *Jun. 13, 2017

(54) PESTICIDAL COMPOSITIONS AND PROCESSES RELATED THERETO

(71) Applicant: Dow AgroSciences LLC, Indianapolis, IN (US)

(72) Inventors: Paul Renee LePlae, Jr., Brownsburg, IN (US); James E. Hunter, Indianapolis, IN (US); Gerald B. Watson, Zionsville, IN (US); William C. Lo, Fishers, IN (US); John Herbert, Fishers, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/733,057

(22) Filed: Jun. 8, 2015

(65) Prior Publication Data

US 2015/0353477 A1 Dec. 10, 2015

Related U.S. Application Data

(60) Provisional application No. 62/009,448, filed on Jun. 9, 2014.

(51) Int. Cl.

| | |
|---|---|
| *C07C 233/83* | (2006.01) |
| *A01N 37/34* | (2006.01) |
| *A01N 37/18* | (2006.01) |
| *C07C 255/46* | (2006.01) |
| *C07C 317/44* | (2006.01) |
| *C07C 323/60* | (2006.01) |
| *C07C 233/78* | (2006.01) |
| *C07C 243/38* | (2006.01) |
| *C07C 255/19* | (2006.01) |
| *A01N 37/20* | (2006.01) |
| *A01N 37/26* | (2006.01) |
| *A01N 37/28* | (2006.01) |
| *A01N 37/36* | (2006.01) |
| *A01N 37/44* | (2006.01) |
| *A01N 41/10* | (2006.01) |
| *A01N 53/00* | (2006.01) |

(52) U.S. Cl.
CPC ............ *C07C 233/83* (2013.01); *A01N 37/18* (2013.01); *A01N 37/20* (2013.01); *A01N 37/26* (2013.01); *A01N 37/28* (2013.01); *A01N 37/34* (2013.01); *A01N 37/36* (2013.01); *A01N 37/44* (2013.01); *A01N 41/10* (2013.01); *A01N 53/00* (2013.01); *C07C 233/78* (2013.01); *C07C 243/38* (2013.01); *C07C 255/19* (2013.01); *C07C 255/46* (2013.01); *C07C 317/44* (2013.01); *C07C 323/60* (2013.01); *C07B 2200/07* (2013.01); *C07C 2101/02* (2013.01)

(58) Field of Classification Search
None
See application file for complete search history.

(56) References Cited

U.S. PATENT DOCUMENTS

| | | | |
|---|---|---|---|
| 4,833,158 A | 5/1989 | Twydell et al. | |
| 4,873,329 A | 10/1989 | Hughes et al. | |
| 6,013,836 A | 1/2000 | Hsu et al. | |
| 7,375,232 B2 | 5/2008 | Clark et al. | |
| 7,951,828 B1* | 5/2011 | Mita | A01N 43/80 514/378 |
| 9,211,280 B2* | 12/2015 | Lo | C07D 295/10 |
| 9,211,281 B2* | 12/2015 | Lo | C07D 295/10 |
| 2002/0068838 A1* | 6/2002 | Demassey | A01N 37/22 564/133 |
| 2007/0027034 A1 | 2/2007 | Tank et al. | |

(Continued)

FOREIGN PATENT DOCUMENTS

| | | |
|---|---|---|
| EP | 2723729 A1 | 4/2014 |
| EP | 2012043418 | 2/2015 |

(Continued)

OTHER PUBLICATIONS

Cornell Environmental Backgrounder: Pesticides and Food Safety (http://psep.cce.cornell.edu/issues/foodsafety-issues.aspx, cached Jun. 29, 2010).

Peter Ertl Cheminformatics Analysis of Organic Substituents: Identification of the Most Common Substituents, Calculation of Substituent Properties, and Automatic Identification of Drug-like Bioisosteric Groups. Journal of Chemical Information and Computer Sciences 2003, 43(2), 374-380.

S. Kagabu et al. Insecticidal and Neuroblocking Activities of Thiamethoxam-Type Compounds in the American Cockroach (*Periplaneta americana* L.), Journal of Pesticide Science, 2005 [received Sep. 13, 2004; Accepted Nov. 29, 2004]. Entire document.

(Continued)

*Primary Examiner* — Mina Haghighatian
*Assistant Examiner* — Erin Hirt
(74) *Attorney, Agent, or Firm* — Carl D. Corvin

(57) ABSTRACT

This disclosure relates to the field of molecules having pesticidal utility against pests in Phyla Nematoda, Arthropoda, and/or Mollusca, processes to produce such molecules and intermediates used in such processes, compositions containing such molecules, and processes of using such molecules against such pests. These molecules may be used, for example, as nematicides, acaricides, insecticides, miticides, and/or molluscicides. This document discloses molecules having the following formula ("Formula One").

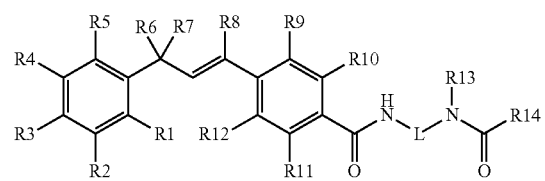

14 Claims, No Drawings

(56) References Cited

U.S. PATENT DOCUMENTS

| | | |
|---|---|---|
| 2007/0207093 A1 | 9/2007 | Bryant et al. |
| 2008/0063678 A1 | 3/2008 | von Deyn et al. |
| 2010/0093707 A1 | 4/2010 | Nakamura et al. |
| 2010/0254959 A1 | 10/2010 | Lahm et al. |
| 2010/0292253 A1 | 11/2010 | Trullinger et al. |
| 2011/0144334 A1 | 6/2011 | Mita et al. |
| 2011/0160054 A1 | 6/2011 | Breuningger et al. |
| 2012/0053146 A1 | 3/2012 | Parker et al. |
| 2012/0329649 A1 | 12/2012 | Hunter et al. |
| 2014/0171308 A1 | 6/2014 | Lo et al. |
| 2014/0171309 A1 | 6/2014 | Lo et al. |
| 2014/0171310 A1 | 6/2014 | Lo et al. |
| 2014/0171311 A1 | 6/2014 | Lo et al. |
| 2014/0171312 A1 | 6/2014 | Lo et al. |
| 2014/0171313 A1 | 6/2014 | Lo et al. |
| 2014/0171314 A1 | 6/2014 | Lo et al. |
| 2014/0171315 A1 | 6/2014 | Lo et al. |
| 2014/0206537 A1 | 7/2014 | Hunter et al. |

FOREIGN PATENT DOCUMENTS

| | | |
|---|---|---|
| WO | 867590 A1 | 12/1986 |
| WO | 2010078300 A1 | 7/2010 |
| WO | 2012004326 A1 | 1/2012 |
| WO | 2012148772 A1 | 11/2012 |
| WO | 2012043418 | 12/2012 |
| WO | 2012177813 A1 | 12/2012 |
| WO | 2013076079 | 5/2013 |
| WO | 2014100163 | 6/2014 |
| WO | 2014100163 A1 | 6/2014 |
| WO | 2014100166 | 6/2014 |
| WO | 2014100166 A1 | 6/2014 |
| WO | 2014100170 | 6/2014 |
| WO | 2014100170 A1 | 6/2014 |
| WO | 2014100190 | 6/2014 |
| WO | 2014100190 A1 | 6/2014 |
| WO | 2014100206 | 6/2014 |
| WO | 2014100206 A1 | 6/2014 |
| WO | 2014120355 A1 | 8/2014 |

OTHER PUBLICATIONS

Andreas Unsinn et al. Steroselective synthesis of tetrasubstituted alkenes via a sequential carbocupration and a new sulfur-lithium exchange. Beilstein J. Org. Chem. vol. 8, Dec. 18, 2012 (Dec. 18, 2012), pp. 2202-2206, XP55166411, DOI: 10.3762/bjoc.8.248 [retrieved on Mar. 25, 2012]. Retrieved from the Internet. <URL: http://www.beilstein-journals.org/bjoc/content/pdf/1860-5397-8-248.pdf>. Entire Document.

Y. Shiga et al. Synthesis and Acaricidal Activity of N-(1,2,4-Thiadiazol-2-yl)carboxamides. Journal of Pesticide Science, 2003 [received Sep. 20, 2002; Accepted Oct. 26, 2002]. Entire document.

Konno et al., "A first high enantiocontrol of an asymmetric tertiary carbon center attached with a fluoroalkyl group vis Rh(I)-catalyzed conjugate addition reaction", Tetrahedron Letters, Pergamon, GB, vol. 49, No. 13, Feb. 1, 2008, pp. 2106-2110, XP022502910, ISSN:0040-4039, DOI: 10.10161J. Tetlet.2008.01.12, *abstract* p. 2109; examples Scheme 3, 4*.

* cited by examiner

PESTICIDAL COMPOSITIONS AND PROCESSES RELATED THERETO

CROSS-REFERENCE TO RELATED APPLICATIONS

This application claims the benefit of, and priority from, U.S. provisional application Ser. No. 62/009,448, which was filed on Jun. 9, 2014. The entire content of this application is hereby incorporated by reference into this application.

FIELD OF THE DISCLOSURE

The invention disclosed in this document is related to the field of processes to produce molecules that are useful as pesticides (e.g., acaricides, insecticides, molluscicides, and nematicides), such molecules, and processes of using such molecules to control pests.

BACKGROUND OF THE DISCLOSURE

Pests cause millions of human deaths around the world each year. Furthermore, there are more than ten thousand species of pests that cause losses in agriculture. The world-wide agricultural losses amount to billions of U.S. dollars each year.

Termites cause damage to all kinds of private and public structures. The world-wide termite damage losses amount to billions of U.S. dollars each year.

Stored food pests eat and adulterate stored food. The world-wide stored food losses amount to billions of U.S. dollars each year, but more importantly, deprive people of needed food.

There is an acute need for new pesticides. Certain pests are developing resistance to pesticides in current use. Hundreds of pest species are resistant to one or more pesticides. The development of resistance to some of the older pesticides, such as DDT, the carbamates, and the organophosphates, is well known. But resistance has even developed to some of the newer pesticides, for example, imidacloprid.

Therefore, for many reasons, including the above reasons, a need exists for new pesticides.

DeMassey et al. discloses the following structure. For more detail, refer to US 2002/0068838.

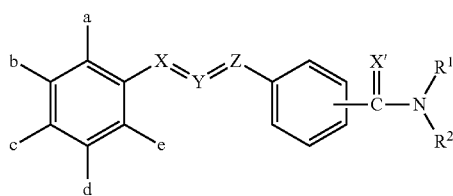

DEFINITIONS

The examples given in the definitions are generally non-exhaustive and must not be construed as limiting the invention disclosed in this document. It is understood that a substituent should comply with chemical bonding rules and steric compatibility constraints in relation to the particular molecule to which it is attached.

"Alkenyl" means an acyclic, unsaturated (at least one carbon-carbon double bond), branched or unbranched, substituent consisting of carbon and hydrogen, for example, vinyl, allyl, butenyl, pentenyl, and hexenyl.

"Alkenyloxy" means an alkenyl further consisting of a carbon-oxygen single bond, for example, allyloxy, butenyloxy, pentenyloxy, hexenyloxy.

"Alkoxy" means an alkyl further consisting of a carbon-oxygen single bond, for example, methoxy, ethoxy, propoxy, isopropoxy, butoxy, isobutoxy, and tert-butoxy.

"Alkyl" means an acyclic, saturated, branched or unbranched, substituent consisting of carbon and hydrogen, for example, methyl, ethyl, ($C_3$)alkyl which represents n-propyl and isopropyl), ($C_4$)alkyl which represents n-butyl, sec-butyl, isobutyl, and tert-butyl.

"Alkynyl" means an acyclic, unsaturated (at least one carbon-carbon triple bond), branched or unbranched, substituent consisting of carbon and hydrogen, for example, ethynyl, propargyl, butynyl, and pentynyl.

"Alkynyloxy" means an alkynyl further consisting of a carbon-oxygen single bond, for example, pentynyloxy, hexynyloxy, heptynyloxy, and octynyloxy.

"Aryl" means a cyclic, aromatic substituent consisting of hydrogen and carbon, for example, phenyl, naphthyl, and biphenyl.

"Cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, norbornenyl, bicyclo[2.2.2]octenyl, tetrahydronaphthyl, hexahydronaphthyl, and octahydronaphthyl.

"Cycloalkenyloxy" means a cycloalkenyl further consisting of a carbon-oxygen single bond, for example, cyclobutenyloxy, cyclopentenyloxy, norbornenyloxy, and bicyclo[2.2.2]octenyloxy.

"Cycloalkyl" means a monocyclic or polycyclic, saturated substituent consisting of carbon and hydrogen, for example, cyclopropyl, cyclobutyl, cyclopentyl, norbornyl, bicyclo[2.2.2]octyl, and decahydronaphthyl.

"Cycloalkoxy" means a cycloalkyl further consisting of a carbon-oxygen single bond, for example, cyclopropyloxy, cyclobutyloxy, cyclopentyloxy, norbornyloxy, and bicyclo[2.2.2]octyloxy.

"Halo" means fluoro, chloro, bromo, and iodo.

"Haloalkoxy" means an alkoxy further consisting of, from one to the maximum possible number of identical or different, halos, for example, fluoromethoxy, trifluoromethoxy, 2,2-difluoropropoxy, chloromethoxy, trichloromethoxy, 1,1,2,2-tetrafluoroethoxy, and pentafluoroethoxy.

"Haloalkyl" means an alkyl further consisting of, from one to the maximum possible number of, identical or different, halos, for example, fluoromethyl, trifluoromethyl, 2,2-difluoropropyl, chloromethyl, trichloromethyl, and 1,1,2,2-tetrafluoroethyl.

"Heterocyclyl" means a cyclic substituent that may be fully saturated, partially unsaturated, or fully unsaturated, where the cyclic structure contains at least one carbon and at least one heteroatom, where said heteroatom is nitrogen, sulfur, or oxygen. In the case of sulfur, that atom can be in other oxidation states such as a sulfoxide and sulfone. Examples of aromatic heterocyclyls include, but are not limited to, benzofuranyl, benzoisothiazolyl, benzoisoxazolyl, benzoxazolyl, benzothienyl, benzothiazolyl, cinnolinyl, furanyl, imidazolyl, indazolyl, indolyl, isoindolyl, isoquinolinyl, isothiazolyl, isoxazolyl, oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, tetrazolyl, thiazolinyl, thiazolyl, thienyl, triazinyl, and triazolyl. Examples of fully saturated heterocyclyls include, but are not limited to, piperazinyl, piperidinyl, morpholinyl, pyrrolidinyl, oxetanyl, tetrahydrofuranyl, tetrahydrothienyl and tetrahydropyranyl. Examples of partially unsaturated heterocyclyls include, but are not limited to, 1,2,3,4-tetrahydroquinolinyl, 4,5-dihydro-oxazolyl, 4,5-dihydro-1H-pyrazolyl, 4,5-dihydro-isoxazolyl, and 2,3-dihydro-[1,3,4]-oxadiazolyl.

Additional examples include the following

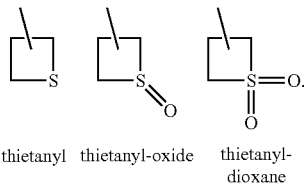

thietanyl  thietanyl-oxide  thietanyl-dioxane

DETAILED DESCRIPTION OF THE DISCLOSURE

This document discloses molecules having the following formula ("Formula One"):

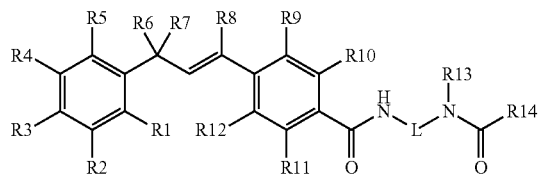

wherein:

(a) R1, R2, R3, R4, and R5, are, each independently, H, F, Cl, Br, I, CN, $(C_1-C_6)$alkyl, $(C_1-C_6)$haloalkyl, $(C_1-C_6)$alkoxy, or $(C_1-C_6)$haloalkoxy;

(b) R6 is $(C_1-C_6)$haloalkyl;

(c) R7 is H;

(d) R8 is H, $(C_1-C_6)$alkyl, or $(C_1-C_6)$haloalkyl;

(e) R9 is H, F, Cl, Br, I, $(C_1-C_6)$alkyl, or $(C_1-C_6)$haloalkyl;

(f) R10 is F, Cl, Br, I, $(C_1-C_6)$alkyl, or $(C_1-C_6)$haloalkyl;

(g) R11 and R12 are, each independently, H, F, Cl, Br, I, $(C_1-C_6)$alkyl, or $(C_1-C_6)$haloalkyl;

(h) L is (1) a linker that is a bond connecting the two nitrogen atoms, or (2) a $(C_1-C_6)$alkyl that is optionally substituted with one or more substituents, wherein each substituent is independently selected from F, Cl, Br, I, CN, OH, oxo, $(C_1-C_6)$alkoxy, $S(C_1-C_6)$alkyl, $S(O)(C_1-C_6)$alkyl, $S(O)_2$ $(C_1-C_6)$alkyl, and $N((C_1-C_6)$alkyl$)_2$ wherein each $(C_1-C_6)$alkyl is independently selected, and wherein each said alkyl or alkoxy has one or more substituents independently selected from H, F, Cl, Br, and I;

(i) R13 is (1) an H, or (2) a $(C_1-C_6)$alkyl that is optionally substituted with one or more substituents, wherein each substituent is independently selected from F, Cl, Br, I, CN, OH, oxo, $(C_1-C_6)$alkoxy, $S(C_1-C_6)$alkyl, $S(O)(C_1-C_6)$alkyl, $S(O)_2$ $(C_1-C_6)$alkyl, and $N((C_1-C_6)$alkyl$)_2$ wherein each $(C_1-C_6)$alkyl is independently selected, and wherein each said alkyl or alkoxy has one or more substituents independently selected from H, F, Cl, Br, and I; and (j) R14 is independently selected from $(C_1-C_8)$alkyl, $(C_1-C_8)$haloalkyl, $(C_3-C_8)$cycloalkyl, $(C_2-C_8)$alkenyl, or $(C_2-C_8)$alkynyl, wherein each said alkyl, haloalkyl, cycloalkyl, alkenyl, and alkynyl has one or more substituents selected from F, Cl, Br, I, CN, $NO_2$, OH, oxo, $(C_1-C_6)$alkoxy, $S(C_1-C_6)$alkyl, $S(O)(C_1-C_6)$alkyl, $S(O)_2(C_1-C_6)$alkyl, and $N((C_1-C_6)$alkyl$)_2$ wherein each $(C_1-C_6)$alkyl is independently selected, and wherein each said alkyl or alkoxy has one or more substituents independently selected from H, F, Cl, Br, and I.

In another embodiment of this invention R1 is H. This embodiment may be used in combination with the other embodiments of R2, R3, R4, R5, R6, R7, R8, R9, R10, R11, R12, R13, R14, and L.

In another embodiment of this invention R2 is Cl or Br. This embodiment may be used in combination with the other embodiments of R1, R3, R4, R5, R6, R7, R8, R9, R10, R11, R12, R13, R14, and L.

In another embodiment of this invention R3 is H, F, Cl, or Br. This embodiment may be used in combination with the other embodiments of R1, R2, R4, R5, R6, R7, R8, R9, R10, R11, R12, R13, R14, and L.

In another embodiment of this invention R4 is Cl or Br. This embodiment may be used in combination with the other embodiments of R1, R2, R3, R5, R6, R7, R8, R9, R10, R11, R12, R13, R14, and L.

In another embodiment of this invention R5 is H. This embodiment may be used in combination with the other embodiments of R1, R2, R3, R4, R6, R7, R8, R9, R10, R11, R12, R13, R14, and L.

In another embodiment of this invention R2, R3, and R4 are Cl. This embodiment may be used in combination with the other embodiments of R1, R5, R6, R7, R8, R9, R10, R11, R12, R13, R14, and L.

In another embodiment of this invention R1 and R5 are H. This embodiment may be used in combination with the other embodiments of R2, R3, R4, R6, R7, R8, R9, R10, R11, R12, R13, R14, and L.

In another embodiment of this invention R1 and R5 are H, and R2, R3, and R4 are Cl. This embodiment may be used in combination with the other embodiments of R6, R7, R8, R9, R10, R11, R12, R13, R14, and L.

In another embodiment of this invention R6 is $CF_3$. This embodiment may be used in combination with the other embodiments of R1, R2, R3, R4, R5, R7, R8, R9, R10, R11, R12, R13, R14, and L.

In another embodiment of this invention R7 H. This embodiment may be used in combination with the other embodiments of R1, R2, R3, R4, R5, R6, R8, R9, R10, R11, R12, R13, R14, and L.

In another embodiment of this invention R8 is H. This embodiment may be used in combination with the other embodiments of R1, R2, R3, R4, R5, R6, R7, R9, R10, R11, R12, R13, R14, and L.

In another embodiment of this invention R9 is H. This embodiment may be used in combination with the other embodiments of R1, R2, R3, R4, R5, R6, R7, R8, R10, R11, R12, R13, R14, and L.

In another embodiment of this invention R10 is Br, $CH_3$, or $CF_3$. This embodiment may be used in combination with the other embodiments of R1, R2, R3, R4, R5, R6, R7, R8, R9, R11, R12, R13, R14, and L.

In another embodiment of this invention R11 is H. This embodiment may be used in combination with the other embodiments of R1, R2, R3, R4, R5, R6, R7, R8, R9, R10, R12, R13, R14, and L.

In another embodiment of this invention R12 is H. This embodiment may be used in combination with the other embodiments of R1, R2, R3, R4, R5, R6, R7, R8, R9, R10, R11, R13, R14, and L.

In another embodiment L is —$CH_2$—, —$CH(CH_3)$—, —$CH(CH_2CH_3)$—, or —$CH_2CH_2$—. This embodiment may be used in combination with the other embodiments of R1, R2, R3, R4, R5, R6, R7, R8, R9, R10, R11, R12, R13, and R14.

In another embodiment of this invention R13 is H or $CH_3$. This embodiment may be used in combination with the other embodiments of R1, R2, R3, R4, R5, R6, R7, R8, R9, R10, R11, R12, R14, and L.

In another embodiment of this invention R14 is ($C_1$-$C_6$)alkyl or ($C_3$-$C_6$)cycloalkyl that is substituted with one or more substituents selected from CN, S($C_1$-$C_6$)alkyl, S(O)($C_1$-$C_6$)alkyl, and S(O)$_2$($C_1$-$C_6$)alkyl. This embodiment may be used in combination with the other embodiments of R1, R2, R3, R4, R5, R6, R7, R8, R9, R10, R11, R12, R13, and L.

In another embodiment of this invention R14 is $CF_3$, $CH_2CF_3$, $CH_2CH_2CF_3$, $CH_2CH_2CH_2CF_3$, $CH_2CH_2CH(CF_3)CH_3$, $CH(CH_3)CH_2CF_3$, $C(CH_3)_2CF_3$, $C(CH_3)_2CH_2CF_3$, $CH_3$, $CH_2CH_3$, $CH_2CH_2CH_3$, $CH_2CH_2CH_2CH_3$, $CH_2CH_2CH_2CH_2CH_3$, $CH(CH_3)_2$, $CH_2CH(CH_3)_2$, $CH_2CH_2CH(CH_3)_2$, $C(CH_3)_3$, $CH_2C(CH_3)_3$, $CH_2CH_2C(CH_3)_3$, $CH_2CH_2CH_2C(CH_3)_3$, cyclopropyl, $CH=CH_2$, $CH=CH(CH_3)$, $CH=C(CH_3)_2$, $CH_2CH=CH_2$, $CH_2CH=CH(CH_3)$, $C(CH_3)=CH_2$, $C(CH_3)=CH(CH_3)$, $C\equiv CH$, $CH_2C\equiv CH$, $CH_2CN$, $CH_2CH_2CN$, $CH_2SCH_3$, $CH_2CH_2SCH_3$, $CH_2S(O)CH_3$, $CH_2CH_2S(O)CH_3$, $CH_2S(O)_2CH_3$, $CH_2CH_2S(O)_2CH_3$. This embodiment may be used in combination with the other embodiments of R1, R2, R3, R4, R5, R6, R7, R8, R9, R10, R11, R12, R13, and L.

In another embodiment of this invention:
(a) R1 is H;
(b) R2 is H, F, Cl, or Br;
(c) R3 is H, F, Cl, or Br;
(d) R4 is H, F, Cl, or Br;
(e) R5 is H;
(f) R6 is ($C_1$-$C_8$)haloalkyl;
(g) R7 is H;
(h) R8 is H;
(i) R9 is H;
(j) R10 is selected from a group consisting of F, Cl, Br, I, ($C_1$-$C_6$)alkyl, and ($C_1$-$C_6$)haloalkyl;
(k) R11 is H;
(l) R12 is H;
(m) L is
(1) a linker that is bond connecting the two nitrogen atoms, or
(2) a ($C_1$-$C_6$)alkyl;
(n) R13 is
(1) an H, or
(2) a ($C_1$-$C_8$)alkyl;
(o) R14 is independently selected from ($C_1$-$C_8$)alkyl, ($C_1$-$C_8$)haloalkyl, ($C_3$-$C_8$)cycloalkyl, ($C_2$-$C_8$)alkenyl, or ($C_2$-$C_8$)alkynyl, wherein each said alkyl, haloalkyl, cycloalkyl, alkenyl, and alkynyl has one or more substituents selected from F, Cl, Br, I, CN, $NO_2$, OH, oxo, ($C_1$-$C_6$)alkoxy, S($C_1$-$C_6$)alkyl, S(O)($C_1$-$C_6$)alkyl, S(O)$_2$($C_1$-$C_6$)alkyl, and N(($C_1$-$C_6$)alkyl)$_2$ wherein each ($C_1$-$C_6$)alkyl is independently selected, and wherein each said alkyl or alkoxy has one or more substituents independently selected from H, F, Cl, Br, and I.

In another embodiment of this invention:
(a) R1 is H;
(b) R2 is Cl or Br;
(c) R3 is H, F, Cl, or Br;
(d) R4 is Cl or Br;
(e) R5 is H;
(f) R6 is ($C_1$-$C_8$)haloalkyl;
(g) R7 is H;
(h) R8 is H;
(i) R9 is H;
(j) R10 is Br, ($C_1$-$C_8$)alkyl, ($C_1$-$C_8$)haloalkyl;
(k) R11 is H;
(l) R12 is H;
(m) L is
(1) a linker that is bond connecting the two nitrogen atoms, or
(2) a ($C_1$-$C_6$)alkyl;
(n) R13 is
(1) an H, or
(2) a ($C_1$-$C_8$)alkyl;
(o) R14 is ($C_1$-$C_8$)alkyl, ($C_1$-$C_8$)haloalkyl, ($C_3$-$C_8$)cycloalkyl, or ($C_2$-$C_8$)alkenyl, wherein each said alkyl or cycloalkyl is substituted with CN, $SCH_3$, $S(O)CH_3$, or $S(O)_2CH_3$.

Preparation of Benzyl Bromides

Benzyl alcohol 1-3, wherein R1, R2, R3, R4, R5, R6, and R7 are as previously disclosed, may be prepared in several ways. Treatment of ketones 1-1, wherein R1, R2, R3, R4, R5, and R6 are as previously disclosed with a reducing agent, such as sodium borohydride, in the presence of a base, such as aqueous sodium hydroxide, in a polar protic solvent, such as methanol at about −10° C. to about 10° C. to provide benzyl alcohol 1-3 (Scheme 1, step a). Alternatively, aldehydes 1-2, wherein R1, R2, R3, R4, R5, and R7 are as previously disclosed, may be allowed to react with trifluorotrimethylsilane in the presence of a catalytic amount of tetrabutylammonium fluoride in a polar aprotic solvent, such as tetrahydrofuran (Scheme 1, step b) to provide benzyl alcohol 1-3. Subsequently, benzyl alcohol 1-3 may be converted into benzyl halide 1-4, wherein Y is Br, Cl, or I, and R1, R2, R3, R4, R5, R6, and R7 are as previously disclosed, by treatment with a halogenating reagent, such as N-bromosuccinimide, and triethylphosphite in a non-reactive solvent, such as dichloromethane at about 40° C. to provide benzyl halide 1-4, Y is Br; or such as thionyl chloride, and pyridine in a hydrocarbon solvent, such as toluene at about 110° C. to provide benzyl halide 1-4, where Y is Cl (Scheme 1, step c).

Scheme 1

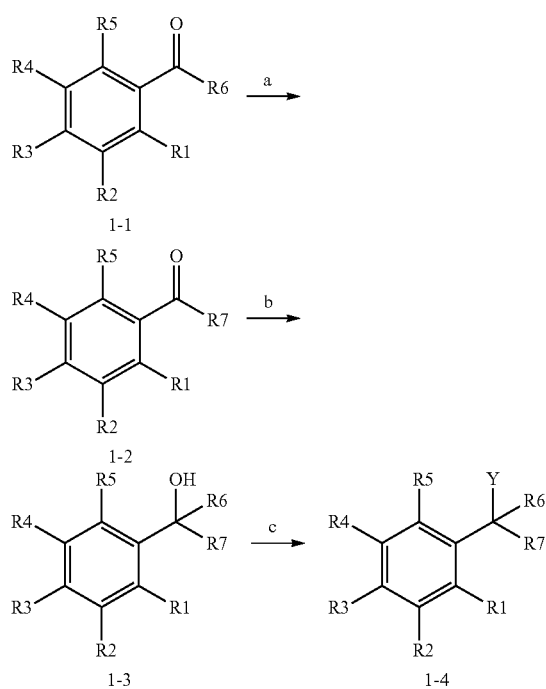

Preparation of Vinylbenzoic Acids and Esters

Halobenzoic acids 2-1, wherein R9, R10, R11, and R12 are as previously disclosed may be converted to vinylbenzoic acid ester 2-3, wherein R8, R9, R10, R11, and R12 are as previously disclosed or vinylbenzoic acids 2-4, wherein R8, R9, R10, R11, and R12 are as previously disclosed. Halobenzoic acid 2-1, may be treated with a base, such as n-butyllithium, and dimethylformamide in a polar, aprotic solvent, such as tetrahydrofuran, at a temperature of about −78° C. (Scheme 2, step a). The resulting formyl benzoic acid may be treated with an acid, such as sulfuric acid, in the presence of an alcohol, such as ethyl alcohol, to provide formyl benzoic acid ethyl ester 2-2 (Scheme 2, step b). Vinyl benzoic acid ester 2-3 may be accessed via reaction of 2-2, with a base, such as potassium carbonate, and methyl triphenylphosphonium bromide in a polar aprotic solvent, such as 1,4-dioxane, at about ambient temperature (Scheme 2, step c). Alternatively, halobenzoic acid 2-1 may be treated with di-tert-butyl dicarbonate in the presence of a base, such as triethylamine and a catalytic amount of 4-(dimethylamino)pyridine in a polar aprotic solvent, such as tetrahydrofuran, at about ambient temperature (Scheme 2, step d). The resulting benzoic acid tert-butyl ester may be treated with vinyl boronic anhydride pyridine complex in the presence of a palladium catalyst, such a tetrakis(triphenylphosphine)palladium(0), and a base,

Scheme 2

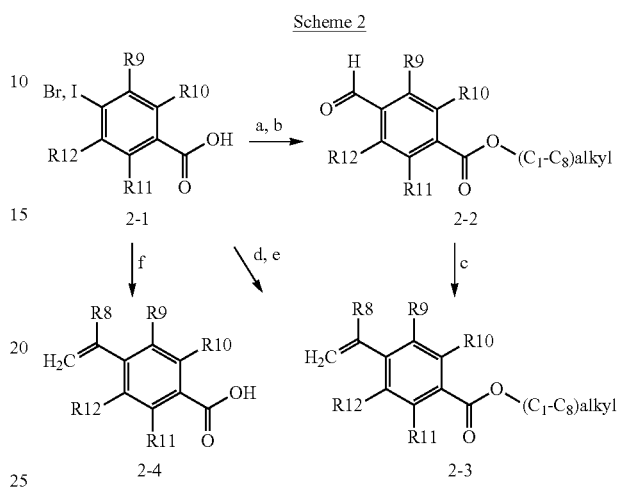

such as potassium carbonate, in a non-reactive solvent such as toluene at about 110° C., to provide vinyl benzoic acid ester 2-3 (Scheme 2, step e).

Halobenzoic acid 2-1 may be treated directly with a vinyltrifluoroborate in the presence of a palladium catalyst, such as [1,1'-bis(diphenylphosphino) ferrocene]dichloropalladium(II) and a base, such as potassium carbonate, in a non-reactive solvent such as dimethylsulfoxide at temperatures ranging from about 80° C. to about 140° C., to provide vinyl benzoic acids 2-4 (Scheme 2, step f).

Preparation of Diphenyl Allylbenzoic Acids

Benzyl halides 1-4 and vinylbenzoic acid esters 2-3 may be treated with copper(I) chloride and 2,2-bipyridyl in a solvent, such as 1,2-dichlorobenzene, at a temperature of about 180° C. to provide diphenyl allylbenzoic esters 3-1, wherein R1, R2, R3, R4, R5, R6, R7, R8, R9, R10, R11, and R12 are as previously disclosed (Scheme 3, step a). Diphenyl allylbenzoic esters 3-1 may be then converted to diphenyl allylbenzoic acids 3-2, wherein R1, R2, R3, R4, R5, R6, R7, R8, R9, R10, R11, and R12 are as previously disclosed. Treatment of diphenyl allylbenzoic esters 3-1, with an acid, such as about 11 N aqueous hydrochloric acid, in a polar aprotic solvent, such as 1,4-dioxane, at about 100° C. may provide diphenyl allylbenzoic acids 3-2 (Scheme 3, step b).

Scheme 3

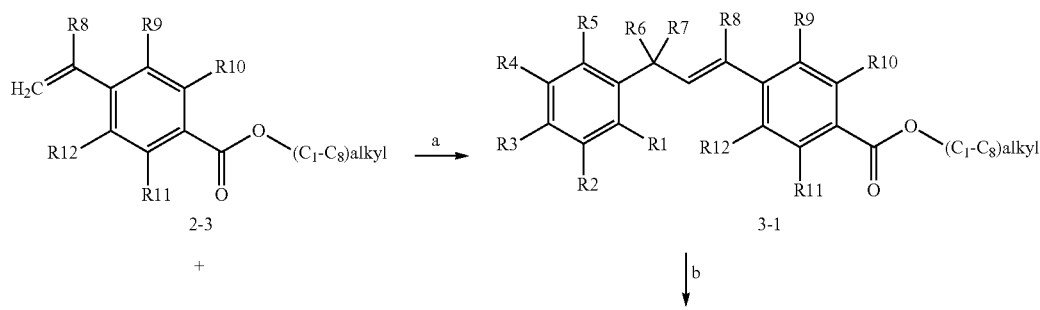

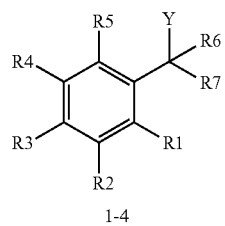

1-4

+

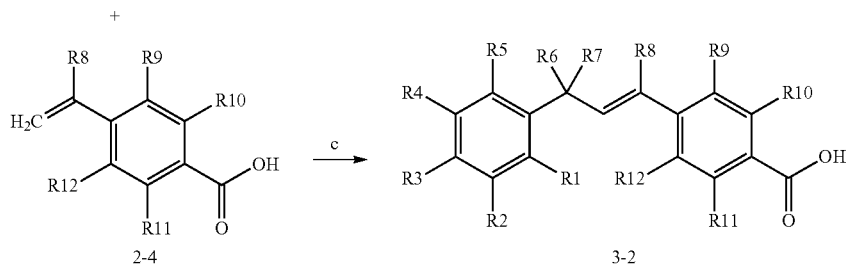

Alternatively, benzyl halides 1-4 and vinylbenzoic acids 2-4 may be treated with copper(I) chloride and 2,2-bipyridyl in a solvent, such as 1,2-dichlorobenzene or N-methylpyrolidine, at temperatures between about 60° C. and about 180° C. to provide diphenyl allylbenzoic acids 3-2 (Scheme 3, step c).

Preparation of Diacylamines

Diacylamines 4-3, wherein R1, R2, R3, R4, R5, R6, R7, R8, R9, R10, R11, R12, R13, R14, and L are as previously disclosed may be prepared by treatment with acylamine salts 4-2, wherein R13, R14, and L are as previously disclosed, and activated carboxylic acids 4-1, wherein X is an activating group, and R1, R2, R3, R4, R5, R6, R7, R8, R9, R10, R11, and R12 are as previously disclosed, with a base, such as potassium bicarbonate, triethylamine, diisopropylethylamine, or preferably 4-methylmorpholine in an anhydrous aprotic solvent such as dichloromethane, tetrahydrofuran, 1,2-dichloroethane, dimethylformamide, or any combination thereof, at temperatures between about 0° C. and about 120° C. (Scheme 4, step a).

Activated carboxylic acids 4-1 may be an acid halide, such as an acid chloride, an acid bromide, or an acid fluoride; a carboxylic ester, such as a para-nitrophenyl ester, a pentafluorophenyl ester, an ethyl (hydroxyiminio)cyanoacetate ester, a methyl ester, an ethyl ester, a benzyl ester, an N-hydroxysuccinimidyl ester, a hydroxybenzotriazol-1-yl ester, or a hydroxypyridyltriazol-1-yl ester; an O-acylisourea; an acid anhydride; or a thioester. Acid chlorides are most preferred and may be prepared from the corresponding carboxylic acids by treatment with a dehydrating chlorinating reagent, such as oxalyl chloride or thionyl chloride both with or without catalytic dimethylformamide. Activated carboxylic esters 4-1 may be prepared from carboxylic acids in situ with a uronium salt, such as 1-[bis(dimethylamino)methylene]-1H-1,2,3-triazolo[4,5-b]pyridinium 3-oxid hexafluorophosphate (HATU), O-(benzotriazol-1-yl)-N,N,N',N'-tetramethyluronium hexafluorophosphate (HBTU), or (1-cyano-2-ethoxy-2-oxoethylidenaminooxy)dimethylamino-morpholino-carbenium hexafluorophosphate (COMU). Activated carboxylic esters 4-1 may also be prepared from carboxylic acids in situ with a phosphonium salt such as benzotriazol-1-yl-oxytripyrrolidinophosphonium hexafluorophosphate (PyBop). Activated carboxylic esters 4-1 may also be prepared from carboxylic acids in situ with a coupling reagent such as 1-(3-dimethylamino propyl)-3-ethylcarbodiimide, or dicyclohexylcarbodiimide in the presence of a triazolol such as hydroxybenzotriazolemonohydrate (HOBt) or 1-hydroxy-7-azabenzotriazole (HOAt). O-Acylisoureas may be prepared with a dehydrating carbodimide such as 1-(3-dimethylamino propyl)-3-ethylcarbodiimide or dicyclohexylcarbodiimide.

Scheme 4

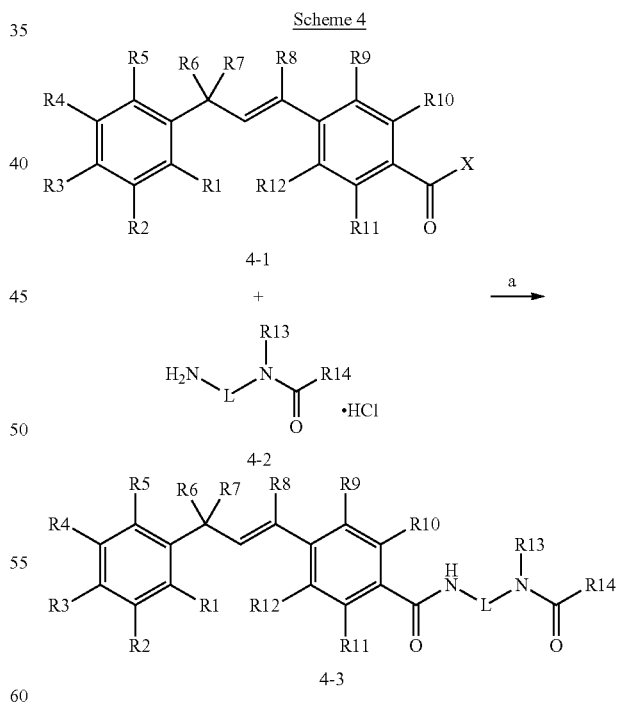

Diacylamines 4-3, wherein R14 contains a sulfide may be oxidized to the corresponding sulfoxide and sulfone by treatment with one equivalent of sodium perborate in a protic solvent such as acetic acid (sulfoxide) or two equivalents of sodium perborate (sulfone). Preferably, the oxidation will be performed at temperatures between about 40° C.

to about 100° C. using 1.5 equivalents of sodium perborate to provide chromatographically separable mixtures of sulfoxide and sulfone diacylaminals 4-3, wherein R14 contains a sulfoxide or sulfone.

Alternatively, diacylamines 5-3, wherein R1, R2, R3, R4, R5, R6, R7, R8, R9, R10, R11, R12, R14, and L are as previously disclosed may be prepared by treatment of acylamine salts 5-1, wherein R1, R2, R3, R4, R5, R6, R7, R8, R9, R10, R11, R12, and L are as previously disclosed, with activated carboxylic acids 5-2, wherein X is an activating group and R14 is as previously disclosed, with a base, such as potassium bicarbonate, triethylamine, diisopropylethylamine, or preferably 4-methylmorpholine in an anhydrous aprotic solvent such as dichloromethane, tetrahydrofuran, 1,2-dichloroethane, dimethylformamide, or any combination thereof, at temperatures between about 0° C. and about 120° C. (Scheme 5, step a).

Activated carboxylic acids 5-2 may be an acid halide, such as an acid chloride, an acid bromide, or an acid fluoride; a carboxylic ester, such as a para-nitrophenyl ester, a pentafluorophenyl ester, an ethyl (hydroxyiminio)cyanoacetate ester, a methyl ester, an ethyl ester, a benzyl ester, an N-hydroxysuccinimidyl ester, a hydroxybenzotriazol-1-yl ester, or a hydroxypyridyltriazol-1-yl ester; an O-acylisourea; an acid anhydride; or a thioester. Acid chlorides are most preferred and may be prepared from the corresponding carboxylic acids by treatment with a dehydrating chlorinating reagent, such as oxalyl chloride or thionyl chloride. Activated carboxylic esters 5-2 may be prepared from carboxylic acids in situ with a uronium salt, such as 1-[bis(dimethylamino)methylene]-1H-1,2,3-triazolo[4,5-b]pyridinium 3-oxid hexafluorophosphate (HATU), O-(benzotriazol-1-yl)-N,N,N',N'-tetramethyluronium hexafluorophosphate (HBTU), or (1-cyano-2-ethoxy-2-oxoethylidenaminooxy) dimethylamino-morpholino-carbenium hexafluorophosphate (COMU). Activated carboxylic esters 5-2 may also be prepared from carboxylic acids in situ with a phosphonium salt such as benzotriazol-1-yl-oxytripyrrolidinophosphonium hexafluorophosphate (PyBop). Activated carboxylic esters 5-2 may also be prepared from carboxylic acids in situ with a coupling reagent such as 1-(3-dimethylamino propyl)-3-ethylcarbodiimide, or dicyclohexylcarbodiimide in the presence of a triazolol such as hydroxybenzotriazole.monohydrate (HOBt) or 1-hydroxy-7-azabenzotriazole (HOAt). O-Acylisoureas may be prepared with a dehydrating carbodimide such as 1-(3-dimethylamino propyl)-3-ethylcarbodiimide or dicyclohexylcarbodiimide.

Scheme 5

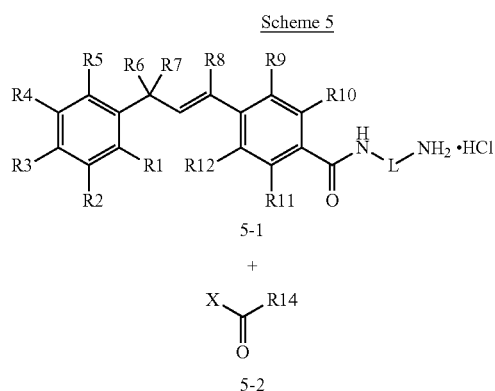

5-1

+

5-2

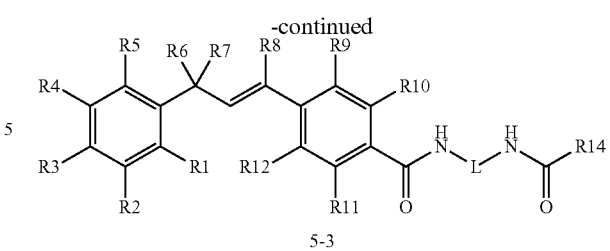

5-3

Carboxylic acid precursors to and activated carboxylic acids 5-2, wherein R14 contains a sulfide may be oxidized to the corresponding sulfoxide or sulfone by treatment with one equivalent of sodium perborate in a protic solvent such as acetic acid (sulfoxide) or two equivalents of sodium perborate (sulfone). Preferably, the oxidation will be performed at temperatures between about 40° C. to about 100° C. using 1.5 equivalents of sodium perborate to provide chromatographically separable mixtures of sulfoxide and sulfone.

Additionally, diacylamines 4-3 may be prepared by treating acylamines 5-3 with an alkylating reagent R13-Z, wherein R13 is not H and is as previously disclosed and Z is a leaving group, such as a halogen or sulfonate, wherein R13-Z is an alkyl halide, such as iodomethane, or an activated alcohol, such as ethyltriflate in the presence of a base, such as sodium hydride, cesium carbonate, silver oxide, potassium hydride, tetrabutylammonium fluoride, or potassium carbonate in a polar aprotic solvent such as dimethylformamide, tetrahydrofuran, acetone, acetonitrile, dimethylsulfoxide, or glyme. Alternatively, the alkylation of acylamines 5-3 may be conducted in a biphasic manner using an alkali metal hydroxide base, such as sodium hydroxide, in water, a phase-transfer catalysts, such as a tetraalkylammonium salt, in an organic solvent such as toluene or dichloromethane at temperatures ranging from about 0° C. and about 120° C. (Scheme 6, step a).

Scheme 6

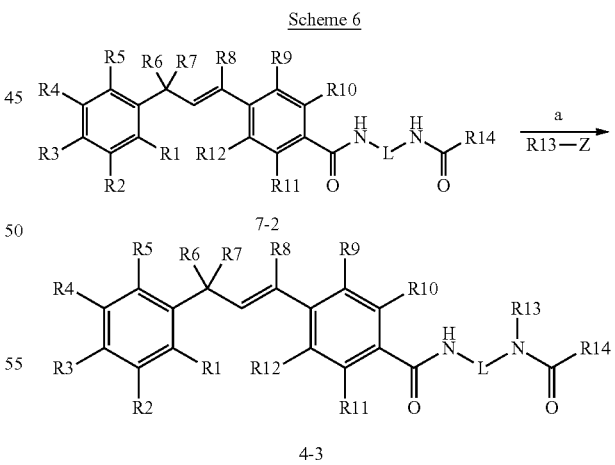

4-3

Diacylamines 5-3, wherein R14 contains a sulfide may be oxidized to the corresponding sulfoxide and sulfone by treatment with one equivalent of sodium perborate in a protic solvent such as acetic acid (sulfoxide) or two equivalents of sodium perborate (sulfone). Preferably, the oxidation will be performed at temperatures between about 40° C. to about 100° C. using 1.5 equivalents of sodium perborate to provide chromatographically separable mixtures of sulfoxide and sulfone diacylamines 5-3, wherein R14 contains a sulfoxide or sulfone.

Preparation of Acylamine Salt 5-1 Precursors

Amides 7-2, wherein R1, R2, R3, R4, R5, R6, R7, R8, R9, R10, R11, R12, and L are as previously disclosed are novel intermediates which may be used in the preparation of acylamine salts 5-1. Amides 7-2 may be prepared by reacting alpha-amino amides 7-1, wherein L is as previously disclosed, and an activated carboxylic acid 4-1 with a base, such as potassium bicarbonate, triethylamine, diisopropylethylamine, or preferably 4-methylmorpholine in an anhydrous aprotic solvent such as dichloromethane, tetrahydrofuran, 1,2-dichloroethane, dimethylformamide, or any combination thereof, at temperatures between about 0° C. and about 120° C. (Scheme 7, step a).

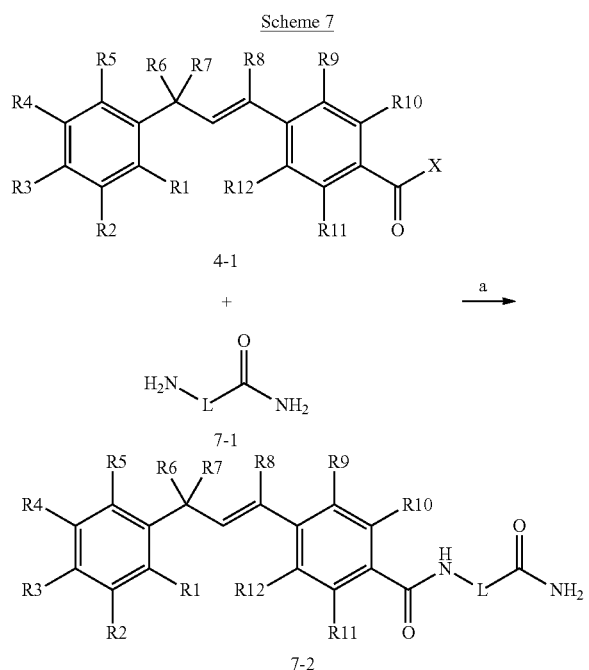

Preparation of Acylamine Salts 5-1

Acylamines 5-1 may be prepared from amides 7-2 by conversion of the primary amide nitrogen to a nitrene-like species, resulting in nitrogen migration, followed by isocyanate formation. Hydrolysis of the intermediate isocyanate with aqueous acid, such as hydrochloric acid may provide acylamine salts 5-1 (Scheme 8, step a). When an acid weaker than aqueous hydrochloric acid is employed, anion exchange may be achieved by treatment with hydrochloric acid to provide acylamine salts 5-1. Preferably amide 7-2 may be treated with iodobenzene bis(trifluoroacetate) in a solvent mixture consisting of about two parts acetonitrile and about one part deionized water at temperatures between about 0° C. and about 120° C. The resulting trifluoroacetate salt may be converted to the chloride salt by the addition of hydrochloric acid followed by evaporation of volatiles.

Preparation of Acylamine Salts 4-2

Acylamine salts 4-2 may be prepared according to those reactions outlined in Scheme 9, Scheme 10, and Scheme 11. Treatment carboxylic acids 9-1, wherein X is OH, and R13, R14, and L are as previously disclosed, or the corresponding activated acids 9-1, wherein X is an activating group as previously described may be reacted with a nitrogen nucleophile to provide amides and amide derivatives 9-2, wherein Y2 is H, N$_2$, NH tert-butoxycarbonyl, or OH) and R13, R14, and L are as previously disclosed. The resultant amides and amide derivatives 9-2 may be converted to acylamine salts 4-2 by the formation of the corresponding nitrene-like species, resulting in nitrogen migration, and subsequent hydrolysis of the resultant isocyanate.

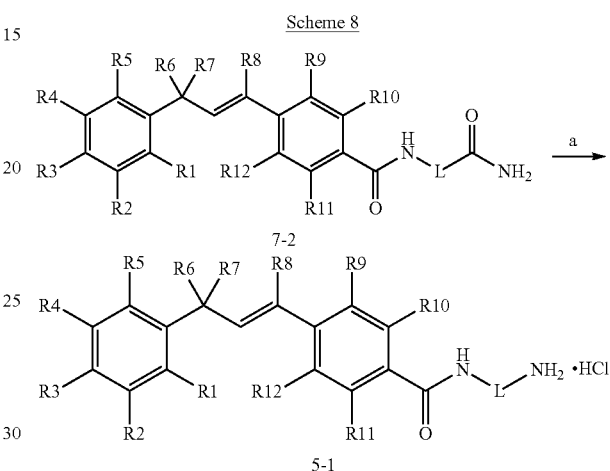

Activated amido acids 9-1, wherein X, R13, R14, and L are as previously disclosed, may be treated with ammonia (Scheme 9, step a) to provide carboxamides 9-2, wherein Y2 is H. Carboxamides 9-2, wherein Y2 is H, may be converted to acylamine 4-2 via the Hoffman rearrangement followed by acidification with hydrochloric acid or preferably by treatment with iodobenzene bis(trifluoroacetate) in a solvent mixture consisting of about one part acetonitrile and about one part deionized water at temperatures between about 0° C. and about 120° C. (Scheme 9, step e). The resulting trifluoroacetate salt may be converted to the chloride salt by the addition of hydrochloric acid followed by evaporation of volatiles.

Amido acids 9-1, wherein X is OH, and R13, R14, and L are as previously disclosed, may be treated with an azide source such as diphenylphosphoryl azide in the presence of a base, such as proton sponge or triethylamine (Scheme 9, step b) to provide acyl azides 9-2, wherein Y2 is N$_2$. Alternatively, activated amido acids 9-1, wherein X is as described above, may be treated with an azide source, such as sodium azide (Scheme 9, step b) to provide acyl azides 9-2, wherein Y2 is N$_2$. Acyl azides 9-2, may be heated to about 40° C. to about 110° C. in an aprotic solvent, such as acetonitrile, toluene, 1,2-dichloroethane, tetrahyrofuran, or 1,4-dioxane to affect a Curtius Rearrangement resulting in the formation of a non-isolated isocyanate that may be treated with aqueous hydrochloric acid to provide acylamine salts 4-2. Alternatively, the isocyanate may be treated with an alcohol, such as tert-butanol, para-methoxy benzyl alcohol, or benzyl alcohol to provide an acid labile carbamate, which after purification may be decomposed under acidic conditions to provide acylamine salts 4-2 (Scheme 9, step f).

Scheme 9

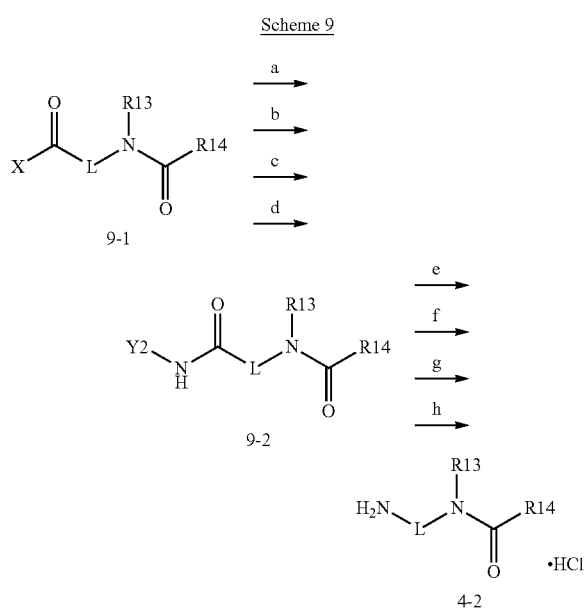

Activated amido acids 9-1, wherein X, R13, R14, and L are as previously disclosed, may be treated with protected hydrazines (Scheme 9, step c), such as tert-butyl carbazate in the presence of a base, such as 4-methylmorpholine, to provide protected hydrazides 9-2, wherein Y2 is NH tert-butoxycarbonyl. Protected hydrazides 9-2 may be deprotected by treatment with acids such as hydrochloric acid or trifluoroacetic acid in aprotic solvents such as 1,4-dioxane or dichloromethane. The resulting hydrazide salts 9-2, wherein Y2 is $NH_3Cl$, may be neutralized to provide hydrazide 9-2, wherein Y2 is $NH_2$. Hydrazides 9-2 may then be diazotized with reagents such as nitric acid or isobutyl nitrite to produce isocyanates that may be converted to acylamine salts 4-2 (Scheme 9, step g).

Activated amido acids 9-1, wherein X, R13, R14, and L are as previously disclosed, may be treated with hydroxylamine (Scheme 9, step d) to provide hydroxamic acids 9-2, wherein Y2 is OH. Hydroxamic acids 9-2 may be acylated with activated carboxylic acids, wherein activated carboxylic acids are as previously disclosed, to provide the O-acyl hydroxamic acids 9-2, wherein Y2 is O-acyl, which may be converted to isocyanates by treatment with heat or the addition of base to produce isocyanates that may be converted to acylamine salts 4-2 (Scheme 9, step h).

Carbamate acids 10-1, wherein R13 and L are as previously disclosed, may be treated with an alkylating reagent R13-Z, wherein R13 is not H and is as previously disclosed and Z is a leaving group, such as a halogen or sulfonate, wherein R13-Z is an alkyl halide, such as iodomethane, or an activated alcohol, such as ethyltriflate, in the presence of a base, such as sodium hydride, cesium carbonate, silver oxide, potassium hydride, tetrabutylammonium fluoride, or potassium carbonate in a polar aprotic solvent such as dimethylformamide, tetrahydrofuran, acetone, acetonitrile, dimethylsulfoxide, or glyme. Alternatively, the alkylation of carbamate acids 10-1 may be conducted in a biphasic manner using an alkali metal hydroxide base, such as sodium hydroxide, in water, a phase-transfer catalysts, such as a tetraalkylammonium salt, in an organic solvent such as toluene or dichloromethane at temperatures ranging from about 0° C. to about 120° C. (Scheme 10, step a).

The resultant carbamate acids 10-2, wherein R13 and L are as previously disclosed may be treated with an azide source such as diphenylphosphoryl azide in the presence of a base, such as proton sponge or triethylamine (Scheme 10, step b) to provide an acyl azide which may in turn be heated from about 40° C. to about 110° C. in an aprotic solvent, such as acetonitrile, toluene, 1,2-dichloroethane, tetrahydrofuran, or 1,4-dioxane to effect a Curtius Rearrangement resulting in the formation of an isocyanate (Scheme 10, step c). Treatment of the resultant isocyanate with benzyl alcohol may provide a differentially protected dicarbamate (Scheme 10, step d). Deprotection of the tert-butylcarbamate may be achieved by treatment with an acid, such as hydrochloric acid or trifluoroacetic acid, in a polar aprotic solvent, such as 1,4-dioxane or dichloromethane, at temperatures between about 0° C. and about 65° C., to provide benzyl carbamate amine salts 10-3, wherein R13 and L are as previously disclosed (Scheme 10, step e).

Benzyl carbamate amine salts 10-3 may treated with activated carboxylic acids 5-2 in the presence of a base, such as potassium bicarbonate, triethylamine, diisopropylethylamine, or preferably 4-methylmorpholine in an anhydrous aprotic solvent such as dichloromethane, tetrahydrofuran, 1,2-dichloroethane, dimethylformamide, or any combination thereof, at temperatures between about 0° C. and about 120° C. (Scheme 10, step f). The resultant carbamate acylamine may be treated with a source of hydrogen and a transition metal catalyst, such as palladium on carbon to provide acylamine salts 4-2 (Scheme 10, step g).

Scheme 10

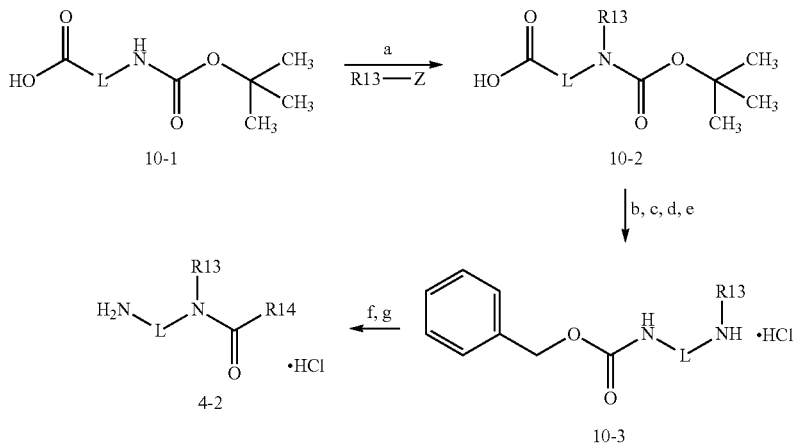

Carbamate acids 10-1 may be treated with an alkylating reagent R15-Z, wherein R15 is $(C_1$-$C_8)$alkenyl and Z is a leaving group, such as a halogen or a sulfonate, wherein R15-Z is an alkenyl halide, such as allyl bromide, or an activated alcohol, such as crotyltriflate in the presence of a base, such as sodium hydride, cesium carbonate, silver oxide, potassium hydride, tetrabutylammonium fluoride, or potassium carbonate in a polar aprotic solvent such as dimethylformamide, tetrahydrofuran, acetone, acetonitrile, dimethylsulfoxide, or glyme. Alternatively, the alkylation of amido esters 10-1 may be conducted in a biphasic manner using an alkali metal hydroxide base, such as sodium hydroxide, in water, a phase-transfer catalysts, such as a tetraalkylammonium salt, in an organic solvent such as toluene or dichloromethane at temperatures ranging from about 0° C. to about 100° C. (Scheme 11, step a).

The resultant carbamate acids 11-2, wherein R15 and L are as previously disclosed may be treated with an azide source such as diphenylphosphoryl azide in the presence of a base, such as proton sponge or triethylamine (Scheme 11, step b) to provide an acyl azide which may in turn be heated to about 40° C. to about 110° C. in an aprotic solvent, such as acetonitrile, toluene, 1,2-dichloroethane, tetrahydrofuran, or 1,4-dioxane to effect a Curtius Rearrangement resulting in the formation of an isocyanate (Scheme 11, step c). Treatment of the resultant isocyanate with benzyl alcohol may provide a differentially protected dicarbamate (Scheme 11, step d). Deprotection of the tert-butylcarbamate may be achieved by treatment with an acid, such as hydrochloric acid or trifluoroacetic acid, in a polar aprotic solvent, such as 1,4-dioxane or dichloromethane, at temperatures between about 0° C. and about 65° C., to provide benzyl carbamate aminal salts 11-3, wherein L and R15 are as previously disclosed (Scheme 11, step e).

Benzyl carbamate amine salts 11-3 may be treated with activated carboxylic acids 5-2 in the presence of a base, such as potassium bicarbonate, triethylamine, diisopropylethylamine, or preferably 4-methylmorpholine in an anhydrous aprotic solvent such as dichloromethane, tetrahydrofuran, 1,2-dichloroethane, dimethylformamide, or any combination thereof, at temperatures between about 0° C. and about 120° C. (Scheme 11, step f). The resultant carbamate acylaminal may be treated with a source of hydrogen and a transition metal catalyst, such as palladium on carbon to provide acylamine salts 4-2 (Scheme 11, step g).

Preparation of Amido Acids 9-1

Amido esters 12-2, wherein R13 and L are as previously disclosed may be prepared by treating amino esters 12-1, wherein Y3 is $O(C_1$-$C_8)$alkyl or $O(C_1$-$C_8)$alkylphenyl and L is as previously disclosed, with activated carboxylic acids 5-2 with a base, such as potassium bicarbonate, triethylamine, diisopropylethylamine, or preferably 4-methylmorpholine in an anhydrous aprotic solvent such as dichloromethane, tetrahydrofuran, 1,2-dichloroethane, dimethylformamide, or any combination thereof, at temperatures between about 0° C. and about 120° C. (Scheme 12, step a).

Scheme 12

Amido esters 12-2 may be treated with an alkylating reagent R13-Z, wherein R13 is not H and as previously disclosed and Z is a leaving group, such as a halogen or a sulfonate, wherein R13-Z is an alkyl halide, such as iodomethane or an activated alcohol, such as ethyltriflate in the presence of a base, such as sodium hydride, cesium carbonate, silver oxide, potassium hydride, tetrabutylammonium fluoride, or potassium carbonate in a polar aprotic solvent such as dimethylformamide, tetrahydrofuran, Scheme 11 acetone, acetonitrile, dimethylsulfoxide, or glyme. Alternatively, the alkylation of amido esters 12-2 may be conducted in a biphasic manner using an alkali metal hydroxide base, such as sodium hydroxide, in water, a phase-transfer catalyst, such as a tetraalkylammonium salt, in an organic solvent such as toluene or dichloromethane at temperatures ranging from about 0° C. to about 120° C. (Scheme 12, step b).

The resultant alkylated amido esters, when Y3 is O($C_1$-$C_8$)alkyl, may be treated with an acid, such as about 11 N aqueous hydrochloric acid, in a polar aprotic solvent, such as 1,4-dioxane, at about 100° C. to provide amido acids 9-1. Alternatively, alkylated amido esters, when Y3 is O-tert-butyl, may be treated with hydrochloric acid in 1,4-dioxane. Alkylated amido esters, when Y3 is O($C_1$-$C_8$)alkyl may be treated with an alkali base, such as lithium hydroxide, in a polar solvent, such as 1,4-dioxane, tetrahydrofuran, methanol, water, or mixtures thereof, at temperatures between 0° C. and about 140° C. to provide amido acids 9-1. The alkylated amido esters, when Y3 is O($C_1$-$C_8$)alkylphenyl may be treated with a source of hydrogen and a transition metal catalyst, such as palladium on carbon to provide amido acids 9-1 (Scheme 12, step c).

Amido acids 9-1 may be prepared in alternate sequences to the sequence discussed above. Step b may be initially performed to provide substituted amine esters 12-3, wherein Y3 is O($C_1$-$C_8$)alkyl or O($C_1$-$C_8$)alkylphenyl, and R13 and L are as previously disclosed, before steps a and steps c are performed to provide amido acids 9-1.

Substituted amine esters 12-3, wherein R13 is as previously disclosed, may be prepared by treating amino esters 12-1 with R16-C(O)H or R16-C(O)($C_1$-$C_8$)alkyl, wherein R16 is not H, in the presence of a reductant, such as sodium borohydride or sodium cyanoborohydride, in protic solvents such as methanol or ethanol in the presence of weak organic acids, such acetic acid. Alternatively, the imine intermediate resulting from condensation of the amine and the carbonyl may be reduced by a source of hydrogen and a transition metal catalyst, such as palladium on carbon to provide substituted amine esters 12-3, when Y3 is O($C_1$-$C_8$)alkyl (Scheme 12, step d).

Amido acids 9-1 may be prepared in a two-step sequence, by first treating substituted amine esters 12-3 with activated carboxylic acids 5-2 with a base, such as potassium bicarbonate, triethylamine, diisopropylethylamine, or preferably 4-methylmorpholine in an anhydrous aprotic solvent such as dichloromethane, tetrahydrofuran, 1,2-dichloroethane, dimethylformamide, or any combination thereof, at temperatures between about 0° C. and about 120° C. (Scheme 12, step e).

Secondly, the resultant amido esters, when Y3 is O($C_1$-$C_8$)alkyl may be treated with an acid, such as about 11 N aqueous hydrochloric acid, in a polar aprotic solvent, such as 1,4-dioxane, at about 100° C. to provide amido acids 9-1. Alternatively, amido esters, when Y3 is Otert-butyl, may be treated with hydrochloric acid in 1,4-dioxane. Amido esters, when Y3 is O($C_1$-$C_8$)alkyl may be treated with an alkali base, such as lithium hydroxide, in a polar solvent, such as 1,4-dioxane, tetrahydrofuran, methanol, water, or mixtures thereof, at temperatures between 0° C. and about 100° C. to provide amido acids 9-1. Finally, acylated amido esters, when Y3 is O($C_1$-$C_8$)alkylphenyl may be treated with a source of hydrogen and a transition metal catalyst, such as palladium on carbon to provide amido acids 9-1 (Scheme 12, step f).

Amido acids 12-2 may be prepared by treating amino esters 12-1 with an activated carboxylic acid 5-2 with a base, such as potassium bicarbonate, triethylamine, diisopropylethylamine, or preferably 4-methylmorpholine in an anhydrous aprotic solvent such as dichloromethane, tetrahydrofuran, 1,2-dichloroethane, dimethylformamide, or any combination thereof, at temperatures between about 0° C. and about 120° C. (Scheme 13, step a).

Scheme 13

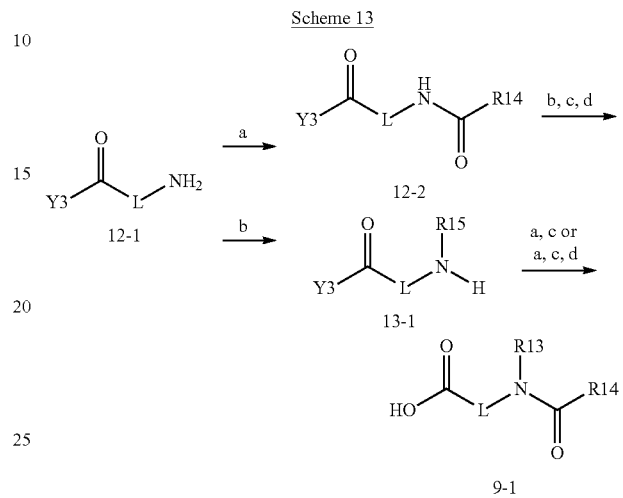

Amido esters 12-2 may be treated with an alkylating reagent R15-Z, wherein R15 is ($C_1$-$C_8$)alkenyl and Z is a leaving group, such as a halogen or a sulfonate, wherein R15-Z is an alkyl halide, such as allyl bromide, or an activated alcohol, such as crotyltriflate in the presence of a base, such as sodium hydride, cesium carbonate, silver oxide, potassium hydride, tetrabutylammonium fluoride, or potassium carbonate in a polar aprotic solvent such as dimethylformamide, tetrahydrofuran, acetone, acetonitrile, dimethylsulfoxide, or glyme. Alternatively, the alkylation of amido esters 12-2 may be conducted in a biphasic manner using an alkali metal hydroxide base, such as sodium hydroxide, in water, a phase-transfer catalysts, such as a tetraalkylammonium salt, in an organic solvent such as toluene or dichloromethane at temperatures ranging from about 0° C. to about 100° C. (Scheme 13, step b). The alkene present in R15 may be subsequently reduced by a source of hydrogen and a transition metal catalyst, such as palladium on carbon. In alkylated amido esters when Y3 is O($C_1$-$C_8$) alkylphenyl reduction of the alkene may also lead to concomitant reduction of the ester to provide amido acids 9-1 (Scheme 13, step c).

Alkylated amido esters, when Y3 is O($C_1$-$C_8$)alkyl may be treated with an acid, such as about 11 N aqueous hydrochloric acid, in a polar aprotic solvent, such as 1,4-dioxane, at about 100° C. to provide amido acids 9-1. Alternatively, amido esters, when Y3 is Otert-butyl, may be treated with hydrochloric acid in 1,4-dioxane. Alkylated amido esters, when Y3 is O($C_1$-$C_8$)alkyl may be treated with an alkali base, such as lithium hydroxide, in a polar solvent, such as 1,4-dioxane, tetrahydrofuran, methanol, water, or mixtures thereof, at temperatures between 0° C. and about 100° C. to provide amido acids 9-1 (Scheme 10, step d).

Amido acids 9-1 may be prepared in alternate sequences to the sequence discussed above. Step b may be initially performed to provide substituted amine esters 13-1, wherein Y3 is O($C_1$-$C_8$)alkyl or O($C_1$-$C_8$)alkylphenyl, and R15 and L are as previously disclosed, before steps a and steps c, or steps a, steps c, and steps d are performed to provide 9-1.

EXAMPLES

The examples are for illustration purposes and are not to be construed as limiting the invention disclosed in this document to only the embodiments disclosed in these examples.

Starting materials, reagents, and solvents that were obtained from commercial sources were used without further purification. Anhydrous solvents were purchased as Sure/Seal™ from Aldrich and were used as received. Melting points were obtained on a Thomas Hoover Unimelt capillary melting point apparatus or an OptiMelt Automated Melting Point System from Stanford Research Systems and are uncorrected. Molecules are given their known names, named according to naming programs within ISIS Draw, ChemDraw, or ACD Name Pro. If such programs are unable to name a molecule, the molecule is named using conventional naming rules. $^1$H NMR spectral data are in ppm (δ) and were recorded at 300, 400, or 600 MHz, and $^{13}$C NMR spectral data are in ppm (δ) and were recorded at 75, 100, or 150 MHz, unless otherwise stated.

Example 1: Preparation of 1-(1-bromo-2,2,2-trifluoroethyl)-3,5-dichlorobenzene (C2)

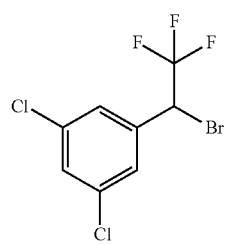 [SMILES: FC(F)(F)C(Br)c1cc(Cl)cc(Cl)c1]

Step 1 Method A.
1-(3,5-Dichlorophenyl)-2,2,2-trifluoroethanol (C1)

To a stirred solution of 1-(3,5-dichlorophenyl)-2,2,2-trifluoroethanone (procured from Rieke Metals, UK; 5.00 g, 20.5 mmol) in methanol (100 mL) at 0° C. were added sodium borohydride (3.33 g, 92.5 mL) and aqueous sodium hydroxide (1 N; 10 mL). The reaction mixture was warmed to 25° C. and stirred for 2 hours. After the reaction was deemed complete by thin layer chromatography, saturated aqueous ammonium chloride was added to the reaction mixture, and the mixture was concentrated under reduced pressure. The residue was diluted with diethyl ether and washed with water (3×50 mL). The organic layer was dried over sodium sulfate and concentrated under reduced pressure to afford the title compound as a liquid (4.00 g, 79%): $^1$H NMR (400 MHz, CDCl$_3$) δ 7.41 (m, 3H), 5.00 (m, 1H), 2.74 (s, 1H); ESIMS m/z 242.97 ([M−H]$^-$).

Step 1 Method B.
1-(3,5-Dichlorophenyl)-2,2,2-trifluoroethanol (C1)

To a stirred solution of 3,5-dichlorobenzaldehyde (10 g, 57 mmol) in tetrahydrofuran (250 mL) were added trifluoromethyltrimethylsilane (9.8 g, 69 mmol) and a catalytic amount of tetrabutylammonium fluoride. The reaction mixture was stirred at 25° C. for 8 hours. After the reaction was deemed complete by thin layer chromatography, the reaction mixture was diluted with hydrochloric acid (3 N) and then was stirred for 16 hours. The reaction mixture was diluted with water and was extracted with ethyl acetate (3 times). The combined organic extracts were washed with brine, dried over sodium sulfate, and concentrated under reduced pressure to afford the title compound as a liquid (8.4 g, 60%).

Step 2. 1-(1-Bromo-2,2,2-trifluoroethyl)-3,5-dichlorobenzene (C2)

To a stirred solution of 1-(3,5-dichlorophenyl)-2,2,2-trifluoroethanol (C1) (4.00 g, 16.3 mmol) in dichloromethane (50 mL), were added N-bromosuccinimide (2.90 g, 16.3 mmol) and triphenyl phosphite (5.06 g, 16.3 mmol), and the resultant reaction mixture was heated at reflux for 18 hours. After the reaction was deemed complete by thin layer chromatography, the reaction mixture was cooled to 25° C. and was concentrated under reduced pressure. Purification by flash column chromatography using 100% pentane as eluent afforded the title compound as a liquid (2.00 g, 40%): $^1$H NMR (400 MHz, CDCl$_3$) δ 7.41 (s, 3H), 5.00 (m, 1H); EIMS m/z 306 ([M]$^+$).

The following compounds were made in accordance with the procedures disclosed in Step 1 Method A of Example 1.

1-(3,5-difluorophenyl)-2,2,2-trifluoroethanol (C3)

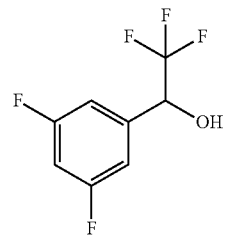

The product was isolated as a colorless oil (0.2 g, 75%): $^1$H NMR (400 MHz, CDCl$_3$) δ 7.05 (m, 2H), 6.88 (m, 1H), 5.06 (m, 1H), 2.66 (s, 1H); ESIMS m/z 212 ([M]$^+$).

1-(4-Chlorophenyl)-2,2,2-trifluoroethanol (C4)

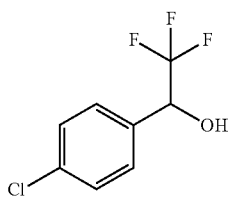 [SMILES: OC(c1ccc(Cl)cc1)C(F)(F)F]

The product was isolated as a colorless oil (5.0 g, 99%): $^1$H NMR (400 MHz, CDCl$_3$) b 7.44-7.38 (m, 4H), 5.05 (m, 1H), 2.55 (s, 1H); ESIMS m/z 210 ([M]$^+$).

2,2,2-Trifluoro-1-(4-methoxyphenyl)ethanol (C5)

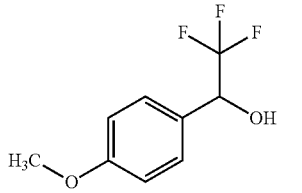

The product was isolated as a pale yellow liquid: $^1$H NMR (400 MHz, CDCl$_3$) δ 7.41 (d, J=8.8 Hz, 2H), 6.95 (m, J=8.8 Hz, 2H), 5.00 (m, 1H), 3.82 (s, 3H), 2.44 (s, 1H); ESIMS m/z 206 ([M]$^+$).

2,2,2-Trifluoro-1-(4-fluorophenyl)ethanol (C6)

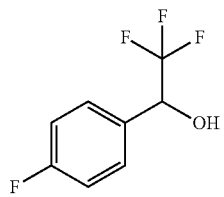 [SMILES: OC(c1ccc(F)cc1)C(F)(F)F]

The product was isolated as a colorless oil (5 g, 99%): $^1$H NMR (400 MHz, CDCl$_3$) δ 7.48-7.45 (m, 2H), 7.13-7.07 (m, 2H), 5.06 (m, 1H), 2.53 (s, 1H); ESIMS m/z 194 ([M]$^+$).

2,2,2-Trifluoro-1-(p-tolyl)ethanol (C7)

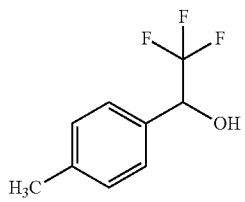

The product was isolated as colorless oil (5.0 g, 99%): $^1$H NMR (400 MHz, CDCl$_3$) δ 7.37 (d, J=8.0 Hz, 2H), 7.23 (d, J=8.0 Hz, 2H), 5.02 (m, 1H), 2.46 (m, 1H), 2.37 (s, 3H); ESIMS m/z 190 ([M]$^+$).

2,2,2-Trifluoro-1-(3-fluorophenyl)ethanol (C8)

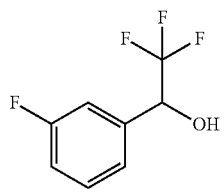 [SMILES: OC(c1cccc(F)c1)C(F)(F)F]

The product was isolated as a colorless viscous oil (2.8 g, 93%): $^1$H NMR (400 MHz, CDCl$_3$) δ 7.41 (m, 1H), 7.25 (m, 2H), 7.14 (m, 1H), 5.06 (m, 1H), 2.60 (s, 1H); ESIMS m/z 194 ([M]$^+$).

2,2,2-Trifluoro-1-(2-fluorophenyl)ethanol (C9)

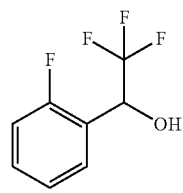 [SMILES: OC(c1ccccc1F)C(F)(F)F]

The product was isolated as a colorless oil (2.5 g, 99%): $^1$H NMR (400 MHz, CDCl$_3$) δ 7.40 (m, 1H), 7.43 (m, 1H), 7.24 (m, 1H), 7.13 (m, 1H), 5.42 (m, 1H), 2.65 (s, 1H); ESIMS m/z 194 ([M]$^+$).

The following compounds were made in accordance with the procedures disclosed in Step 1 Method B of Example 1.

2,2,2-Trifluoro-1-(3,4,5-trichlorophenyl)ethanol (C10)

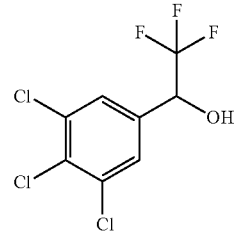

The product was isolated as a pale yellow liquid (0.500 g, 65%): $^1$H NMR (400 MHz, CDCl$_3$) δ 7.45 (s, 2H), 5.00 (m, 1H), 2.80 (s, 1H); ESIMS m/z 278 ([M+H]$^+$); IR (thin film) 3420, 1133, 718 cm$^{-1}$.

1-(3,5-Dichloro-4-fluorophenyl)-2,2,2-trifluoroethanol (C11)

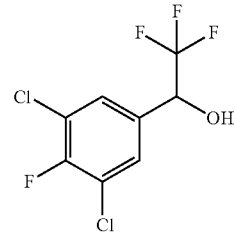 [SMILES: OC(c1cc(Cl)c(F)c(Cl)c1)C(F)(F)F]

The product was isolated as a pale yellow liquid (0.500 g, 65%): $^1$H NMR (400 MHz, CDCl$_3$) δ 7.41 (s, 2H), 5.00 (m, 1H), 2.80 (s, 1H); ESIMS m/z 262 ([M+H]$^+$); IR (thin film) 3420, 1133, 718 cm$^{-1}$.

1-(3,4-Dichlorophenyl)-2,2,2-trifluoroethanol (C12)

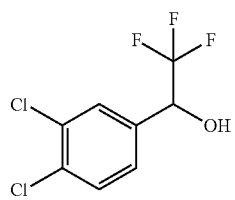 [SMILES: OC(c1ccc(Cl)c(Cl)c1)C(F)(F)F]

The product was isolated as a pale yellow liquid (0.500 g, 65%): $^1$H NMR (400 MHz, CDCl$_3$) δ 7.60 (s, 1H), 7.51 (m, 1H), 7.35 (m, 1H), 5.01 (m, 1H), 2.60 (s, 1H); EIMS m/z 244 ([M]$^+$).

1-(3-Chlorophenyl)-2,2,2-trifluoroethanol (C13)

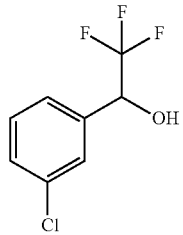 [SMILES: OC(c1cccc(Cl)c1)C(F)(F)F]

The product was isolated as a colorless viscous oil (1.5 g, 75%): $^1$H NMR (400 MHz, CDCl$_3$) δ 7.50 (s, 1H), 7.42-7.35 (m, 3H), 5.02 (m, 1H), 2.65 (br s, 1H).

2,2,2-Trifluoro-1-phenylethanol (C14)

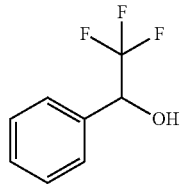 [SMILES: OC(c1ccccc1)C(F)(F)F]

The product was isolated (10 g, 80%): $^1$H NMR (300 MHz, CDCl$_3$) δ 7.48 (m, 2H), 7.40 (m, 3H), 5.02 (m, 1H), 2.65 (d, J=7.1 Hz, 1H).

1-(3,5-Dimethylphenyl)-2,2,2-trifluoroethanol (C15)

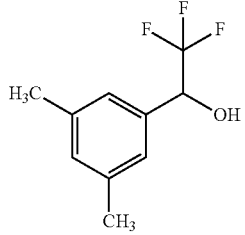

The product was isolated as an off white solid: $^1$H NMR (400 MHz, CDCl$_3$) δ 7.05 (s, 2H), 7.02 (s, 1H), 4.95 (m, 1H), 2.32 (s, 6H); ESIMS m/z 204 ([M]$^-$).

1-(2,4-Dichlorophenyl)-2,2,2-trifluoroethanol (C16)

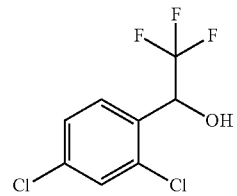 [SMILES: OC(c1ccc(Cl)cc1Cl)C(F)(F)F]

The product was isolated as an off white powder (5.3 g, 61%): mp 49-51° C.; $^1$H NMR (400 MHz, CDCl$_3$) δ 7.62-7.66 (d, 1H), 7.42-7.44 (d, 1H), 7.32-7.36 (d, 1H), 5.6 (m, 1H), 2.7 (s, 1H); ESIMS m/z 244 ([M]$^+$).

1-(2,3-Dichlorophenyl)-2,2,2-trifluoroethanol (C17)

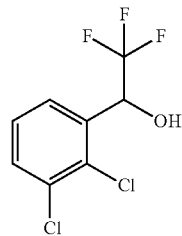 [SMILES: OC(c1cccc(Cl)c1Cl)C(F)(F)F]

The product was isolated as a pale yellow oil (5.2 g, 60%): $^1$H NMR (400 MHz, CDCl$_3$) δ 7.62-7.64 (d, 1H), 7.52-7.54 (m, 1H), 7.29-7.33 (t, 1H), 5.6-5.76 (m, 1H), 2.7 (s, 1H); ESIMS m/z 244 ([M]$^+$).

1-(2,5-Dichlorophenyl)-2,2,2-trifluoroethanol (C19)

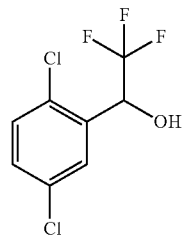 [SMILES: OC(c1cc(Cl)ccc1Cl)C(F)(F)F]

The product was isolated as a yellow oil (4.1 g, 60%): $^1$H NMR (400 MHz, CDCl$_3$) δ 7.68-7.7 (s, 1H), 7.3-7.37 (m, 2H), 5.51-5.6 (m, 1H), 2.7 (s, 1H); ESIMS m/z 244 ([M]$^+$).

1-(3,5-Bis(trifluoromethyl)phenyl)-2,2,2-trifluoroethanol (C20)

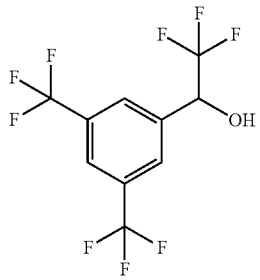 [SMILES: OC(c1cc(C(F)(F)F)cc(C(F)(F)F)c1)C(F)(F)F]

The product was isolated (3.8 g, 60%): $^1$H NMR (400 MHz, CDCl$_3$) δ 7.98 (m, 3H), 5.25 (m, 1H), 3.2 (br, 1H); ESIMS m/z 312 ([M]$^+$).

2,2,2-Trifluoro-1-(2,3,5-trichlorophenyl)ethanol (C21)

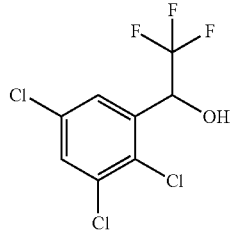 [SMILES: OC(c1cc(Cl)cc(Cl)c1Cl)C(F)(F)F]

The product was isolated as a white solid (4.0 g, 60%): mp 113-115° C.; $^1$H NMR (400 MHz, CDCl$_3$) δ 7.62 (d, 1H), 7.50 (d, 1H), 5.60-5.70 (m, 1H), 2.75 (s, 1H); ESIMS m/z 278 ([M+]).

1-(3-Chloro-5-(trifluoromethyl)phenyl)-2,2,2-trifluoroethanol (C22)

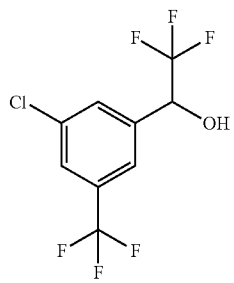 [SMILES: OC(c1cc(Cl)cc(C(F)(F)F)c1)C(F)(F)F]

The product was isolated as a pale yellow oil (2.0 g, 50%): $^1$H NMR (400 MHz, CDCl$_3$) b 7.51 (m, 3H), 5.08 (m, 1H), 2.81 (s, 1H); ESIMS m/z 278 ([M]$^+$).

1-(3,5-Dichloro-4-methoxyphenyl)-2,2,2-trifluoroethanol (C23)

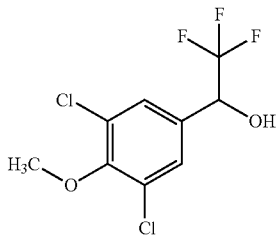 [SMILES: COc1c(Cl)cc(C(O)C(F)(F)F)cc1Cl]

The product was isolated as an off white solid (0.8 g, 60%); mp 92-95° C.: $^1$H NMR (400 MHz, CDCl$_3$) b 7.41 (s, 2H), 5.00 (m, 1H), 3.89 (s, 3H), 2.64 (m, 1H); ESIMS m/z 274 ([M]$^+$).

The following compounds were made in accordance with the procedures disclosed in Step 1 Method B of Example 1 above.

1-(3,5-Dibromophenyl)-2,2,2-trifluoroethanol (C24)

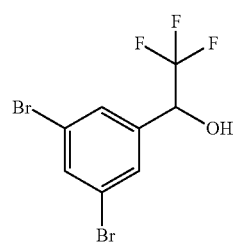 [SMILES: OC(c1cc(Br)cc(Br)c1)C(F)(F)F]

The title molecule was isolated as a colorless liquid: $^1$H NMR (300 MHz, CDCl$_3$) b 7.67 (s, 1H), 7.58 (s, 2H), 5.08-5.02 (m, 1H), 4.42 (bs, 1H); EIMS m/z 333.7 ([M]$^+$); IR (thin film) 3417, 2966, 1128, 531 cm$^{-1}$.

1-(4-Bromo-3,5-dichlorophenyl)-2,2,2-trifluoroethanol (C25)

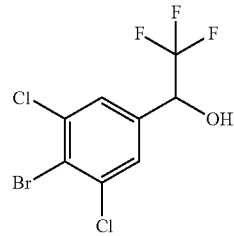

The product was isolated as a colorless liquid: $^1$H NMR (300 MHz, DMSO-d$_6$) δ 7.75 (s, 2H), 7.24 (d, J=6.0 Hz, 1H), 5.34-5.29 (m, 1H); EIMS m/z 321.88 ([M]$^+$); IR (thin film) 3420, 1706, 1267, 804, 679 cm$^{-1}$.

1-(3,5-Dibromo-4-chlorophenyl)-2,2,2-trifluoroethanol (C26)

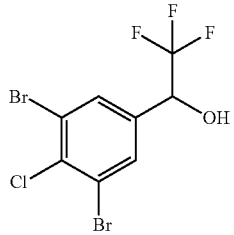

The product was isolated as a pale yellow gum: ¹H NMR (300 MHz, DMSO-$d_6$) δ 7.89 (s, 2H), 7.20 (d, J=6.0 Hz, 1H) 5.34-5.30 (m, 1H); EIMS m/z 366.0 ([M]⁺).

The following compounds were made in accordance with the procedures disclosed in Step 2 of Example 1.

5-(1-Bromo-2,2,2-trifluoroethyl)-1,2,3-trichlorobenzene (C27)

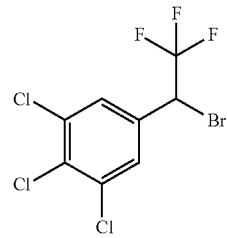 [SMILES: FC(F)(F)C(Br)c1cc(Cl)c(Cl)c(Cl)c1]

The product was isolated as a colorless oil (0.300 g, 60%): ¹H NMR (400 MHz, CDCl₃) δ 7.59 (s, 2H), 5.00 (m, 1H); EIMS m/z 340 ([M]⁺).

5-(1-Bromo-2,2,2-trifluoroethyl)-1,3-dichloro-2-fluorobenzene (C28)

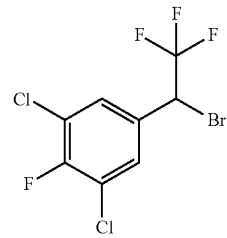 [SMILES: Fc1c(Cl)cc(C(Br)C(F)(F)F)cc1Cl]

The product was isolated as a colorless oil (0.320 g, 60%): ¹H NMR (400 MHz, CDCl₃) δ 7.45 (s, 2H), 5.00 (m, 1H); EIMS m/z 324 ([M]⁺).

4-(1-Bromo-2,2,2-trifluoroethyl)-1,2-dichlorobenzene (C29)

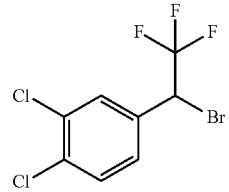 [SMILES: FC(F)(F)C(Br)c1ccc(Cl)c(Cl)c1]

The product was isolated as a colorless oil (0.300 g, 60%): ¹H NMR (400 MHz, CDCl₃) δ 7.63 (s, 1H), 7.51 (m, 1H), 7.35 (m, 1H), 5.01 (m, 1H); EIMS m/z 306 ([M]⁺).

1-(1-Bromo-2,2,2-trifluoroethyl)-3-chlorobenzene (C30)

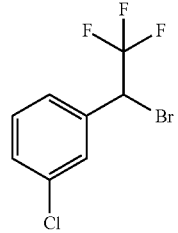 [SMILES: FC(F)(F)C(Br)c1cccc(Cl)c1]

The product was isolated (0.14 g, 22%): ¹H NMR (400 MHz, CDCl₃) δ 7.50 (br s, 1H), 7.42-7.35 (m, 3H), 5.07 (m, 1H).

(1-Bromo-2,2,2-trifluoroethyl)benzene (C31)

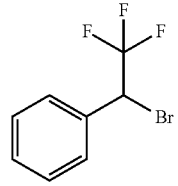 [SMILES: FC(F)(F)C(Br)c1ccccc1]

The product was isolated as a liquid (8.0 g, 60%): ¹H NMR (400 MHz, CDCl₃) δ 7.50 (m, 2H), 7.40 (m, 3H), 5.00 (q, J=7.5 Hz, 1H).

1-(1-Bromo-2,2,2-trifluoroethyl)-3,5-dimethylbenzene (C32)

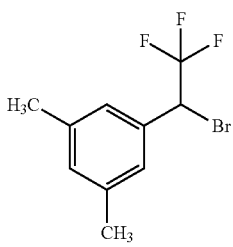

The product was isolated and carried on crude (3.0 g, 51%).

1-(1-Bromo-2,2,2-trifluoroethyl)-2,4-dichlorobenzene (C33)

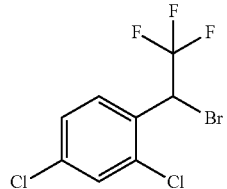 [SMILES: FC(F)(F)C(Br)c1ccc(Cl)cc1Cl]

The product was isolated (3.2 g, 50%): $^1$H NMR (400 MHz, CDCl$_3$) δ 7.62-7.72 (m, 1H), 7.4-7.42 (m, 1H), 7.3-7.38 (m, 1H), 5.7-5.8 (m, 1H).

1-(1-Bromo-2,2,2-trifluoroethyl)-2,3-dichlorobenzene (C34)

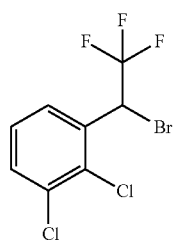 [SMILES: FC(F)(F)C(Br)c1cccc(Cl)c1Cl]

The product was isolated as an oil (8.7 g, 60%): $^1$H NMR (400 MHz, CDCl$_3$) δ 7.62-7.71 (m, 1H), 7.44-7.52 (m, 1H), 7.27-7.3 (s, 1H), 5.81-5.91 (m, 1H).

2-(1-Bromo-2,2,2-trifluoroethyl)-1,4-dichlorobenzene (C35)

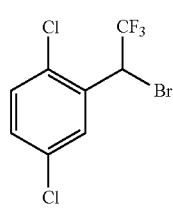 [SMILES: FC(F)(F)C(Br)c1cc(Cl)ccc1Cl]

The product was isolated (3.0 g, 60%): $^1$H NMR (400 MHz, CDCl$_3$) δ 7.7-7.78 (m, 1H), 7.3-7.4 (m, 2H), 5.7-5.8 (m, 1H).

1-(1-Bromo-2,2,2-trifluoroethyl)-3,5-bis(trifluoromethyl)benzene (C36)

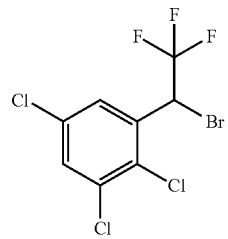 [SMILES: FC(F)(F)C(Br)c1cc(Cl)cc(Cl)c1Cl]

The product was prepared and carried on crude.

1-(1-Bromo-2,2,2-trifluoroethyl)-2,3,5-trichlorobenzene (C37)

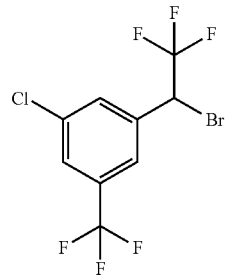 [SMILES: FC(F)(F)c1cc(Cl)cc(C(Br)C(F)(F)F)c1]

The product was isolated (2.9 g, 60%): $^1$H NMR (400 MHz, CDCl$_3$) δ 7.70 (d, 1H), 7.50 (d, 1H), 5.72-5.82 (m, 1H).

1-(1-Bromo-2,2,2-trifluoroethyl)-3-chloro-5-(trifluoromethyl)benzene (C38)

The product was isolated as an oil (2.0 g, 40%): ESIMS m/z 342 ([M]$^+$).

5-(1-Bromo-2,2,2-trifluoroethyl)-1,3-dichloro-2-methoxybenzene (C39)

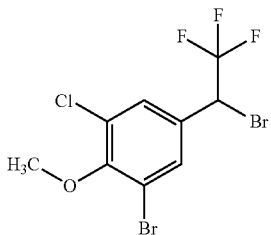 [SMILES: COc1c(Cl)cc(C(Br)C(F)(F)F)cc1Br]

The product was isolated as a colorless liquid (0.6 g, 57%).

1-(1-Bromo-2,2,2-trifluoroethyl)-3,5-difluorobenzene (C40)

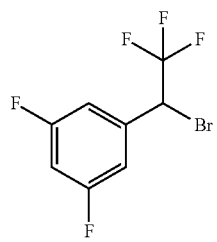 [SMILES: Fc1cc(F)cc(C(Br)C(F)(F)F)c1]

The product was isolated (3.2 g, 50%); $^1$H NMR (400 MHz, CDCl$_3$) δ 7.05 (m, 2H), 6.86 (m, 1H), 5.03 (q, J=7.4 Hz, 1H).

1-(1-Bromo-2,2,2-trifluoroethyl)-4-chlorobenzene (C41)

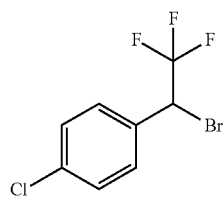 [SMILES: FC(F)(F)C(Br)c1ccc(Cl)cc1]

The product was isolated (3.0 g, 46%): $^1$H NMR (400 MHz, CDCl$_3$) δ 7.45 (d, J=8.2 Hz, 2H), 7.37 (d, J=8.2 Hz, 2H), 5.10 (q, J=7.2 Hz, 1H).

1-(1-Bromo-2,2,2-trifluoroethyl)-4-methoxybenzene (C42)

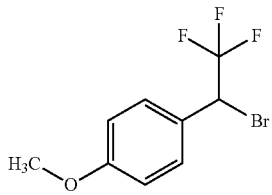

The product was isolated (3.8 g, 62%).

1-(1-Bromo-2,2,2-trifluoroethyl)-4-fluorobenzene (C43)

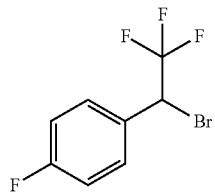

The product was prepared and carried on as crude intermediate.

1-(1-Bromo-2,2,2-trifluoroethyl)-4-methylbenzene (C44)

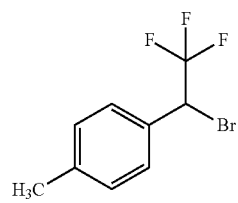

The product was isolated (3.0 g, 45%).

1-(1-Bromo-2,2,2-trifluoroethyl)-3-fluorobenzene (C45)

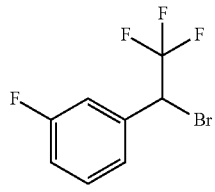

The product was isolated (2.0 g, 61%).

1-(1-Bromo-2,2,2-trifluoroethyl)-2-fluorobenzene (C46)

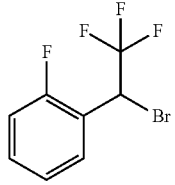 [SMILES: Fc1ccccc1C(Br)C(F)(F)F]

The product was isolated (2.0 g, 61%): $^1$H NMR (400 MHz, CDCl$_3$) δ 7.61 (m, 1H), 7.40 (m, 1H), 7.23 (m, 1H), 7.10 (m, 1H), 5.40 (m, 1H); GCMS m/z 255 ([M]$^+$).

1,3-Dibromo-5-(1-bromo-2,2,2-trifluoroethyl)benzene (C47)

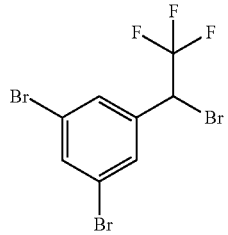

The title molecule was isolated as a colorless liquid: $^1$H NMR (300 MHz, CDCl$_3$) δ 7.71 (s, 1H), 7.59 (s, 2H), 5.04-4.97 (m, 1H); EIMS m/z 394.6 ([M]$^+$); IR (thin film) 1114, 535 cm$^{-1}$.

2-Bromo-5-(1-bromo-2,2,2-trifluoroethyl)-1,3-dichlorobenzene (C48)

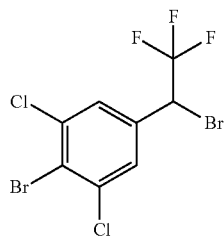 [SMILES: FC(F)(F)C(Br)c1cc(Cl)c(Br)c(Cl)c1]

The title molecule was isolated as a colorless liquid: $^1$H NMR (400 MHz, DMSO-d$_6$) δ 7.79 (s, 2H), 6.27-6.21 (m, 1H); EIMS m/z 383.9 ([M]$^+$); IR (thin film) 2924, 1114, 749, 534 cm$^{-1}$.

1,3-Dibromo-5-(1-bromo-2,2,2-trifluoroethyl)-2-chlorobenzene (C49)

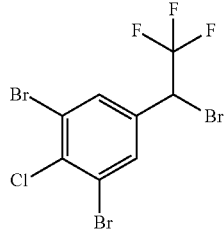

The title molecule was isolated as a pale yellow liquid: $^1$H NMR (300 MHz, DMSO-d$_6$) δ 7.97 (s, 2H), 6.27-6.19 (m, 1H); EIMS m/z 428.0 ([M]$^+$).

Example 3: Preparation of ethyl 2-methyl-4-vinylbenzoate (C52)

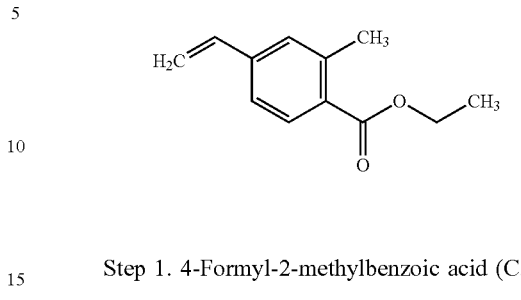

Step 1. 4-Formyl-2-methylbenzoic acid (C50)

To a stirred solution of 4-bromo-2-methylbenzoic acid (10.0 g, 46.4 mmol) in dry tetrahydrofuran (360 mL) at −78° C. was added n-butyllithium (1.6 M solution in hexane, 58.2 mL, 93.0 mmol) and dimethylformamide (8 mL). The reaction mixture was stirred at −78° C. for 1 hour then was warmed to 25° C. and stirred for 1 hour. The reaction mixture was quenched with hydrochloric acid (1 N) and extracted with ethyl acetate. The combined ethyl acetate extracts were washed with brine, dried over sodium sulfate, and concentrated under reduced pressure. The residue was washed with n-hexane to afford the title compound as a solid (3.00 g, 40%): mp 196-198° C.; $^1$H NMR (400 MHz, DMSO-d$_6$) δ 13.32 (br s, 1H), 10.05 (s, 1H), 7.98 (m, 1H), 7.84 (m, 2H), 2.61 (s, 3H); ESIMS m/z 163 ([M−H]$^-$).

Step 2. Ethyl 4-formyl-2-methylbenzoate (C51)

To a stirred solution of 4-formyl-2-methylbenzoic acid (C50) (3.00 g, 18.2 mmol) in ethyl alcohol (30 mL) was added sulfuric acid (2 mL), and the reaction mixture was heated at 80° C. for 18 hours. The reaction mixture was cooled to 25° C. and concentrated under reduced pressure. The residue was diluted with ethyl acetate and washed with water. The combined ethyl acetate extracts were washed with brine, dried over sodium sulfate and concentrated under reduced pressure to afford the title compound as a solid (2.80 g, 80%): $^1$H NMR (400 MHz, CDCl$_3$) δ 10.05 (s, 1H), 8.04 (m, 1H), 7.75 (m, 2H), 4.43 (m, 2H), 2.65 (s, 3H), 1.42 (m, 3H).

Step 3. Ethyl 2-methyl-4-vinylbenzoate (C52)

To a stirred solution of ethyl 4-formyl-2-methylbenzoate (C51) (2.8 g, 4.0 mmol) in 1,4-dioxane (20 mL) were added potassium carbonate (3.0 g, 22 mmol) and methyltriphenyl phosphonium bromide (7.8 g, 22 mmol) at 25° C. Then the reaction mixture was heated at 100° C. for 18 hours. After the reaction was deemed complete by thin layer chromatography, the reaction mixture was cooled to 25° C. and filtered, and the filtrate was concentrated under reduced pressure. The crude compound was purified by flash column chromatography using 25-30% ethyl acetate/hexanes as eluent to afford the title compound as a solid (2.0 g, 72%): $^1$H NMR (400 MHz, CDCl$_3$) δ 7.86 (m, 1H), 7.27 (m, 2H), 6.68 (dd, J=17.6, 10.8 Hz, 1H), 5.84 (d, J=17.6 Hz, 1H), 5.39 (d, J=10.8 Hz, 1H), 4.39 (m, 2H), 2.60 (s, 3H), 1.40 (m, 3H); ESIMS m/z 191 ([M−H]$^-$); IR (thin film) 2980, 1716, 1257 cm$^{-1}$.

Example 4: Preparation of tert-butyl 2-chloro-4-vinylbenzoate (C54)

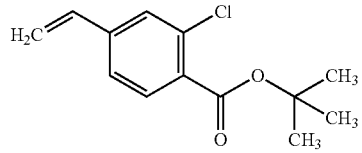 [SMILES: C=Cc1ccc(C(=O)OC(C)(C)C)c(Cl)c1]

Step 1. tert-Butyl 4-bromo-2-chlorobenzoate (C53)

To a stirred solution of 4-bromo-2-chlorobenzoic acid (5.00 g, 21.4 mmol) in tetrahydrofuran (30 mL) was added di-tert-butyl dicarbonate (25.5 g, 25.6 mmol), triethylamine (3.20 g, 32.0 mmol) and 4-dimethylaminopyridine (0.780 g, 6.40 mmol), and the reaction mixture was stirred at 25° C. for 18 hours. The reaction mixture was diluted with ethyl acetate and washed with water. The combined organic layer was washed with brine, dried over sodium sulfate, and concentrated under reduced pressure. The residue was purified by flash column chromatography using 2-3% ethyl acetate/hexanes as eluent to afford the title compound as a liquid (3.20 g, 51%): $^1$H NMR (400 MHz, CDCl$_3$) δ 7.62 (m, 2H), 7.44 (d, J=8.4 Hz, 1H), 1.59 (s, 9H); ESIMS m/z 290 ([M+H]$^+$); IR (thin film) 1728 cm$^{-1}$.

Step 2. tert-Butyl 2-chloro-4-vinylbenzoate (C54)

To a stirred solution of tert-butyl 4-bromo-2-chlorobenzoate (C53) (1.6 g, 5.5 mmol) in toluene (20 mL) was added tetrakis(triphenylphospine)palladium(0) (0.31 mg, 0.27 mmol), potassium carbonate (2.3 g, 17 mmol) and vinylboronic anhydride pyridine complex (2.0 g, 8.3 mmol) and the reaction mixture was heated to reflux for 16 hours. The reaction mixture was filtered, the filtrate was washed with water and brine, dried over sodium sulfate, and concentrated under reduced pressure. Purification by flash column chromatography using 5-6% ethyl acetate/hexanes as eluent afforded the title compound as a liquid (0.60 g, 46%): $^1$H NMR (400 MHz, CDCl$_3$) δ 7.72 (d, J=8.1 Hz, 1H), 7.44 (m, 1H), 7.31 (d, J=8.0 Hz, 1H), 6.69 (dd, J=17.6, 10.8 Hz, 1H), 5.85 (d, J=17.6 Hz, 1H), 5.40 (d, J=10.8 Hz, 1H), 1.60 (s, 9H); ESIMS m/z 239 ([M+H]$^+$); IR (thin film) 2931, 1725, 1134 cm$^{-1}$.

The following compounds were made in accordance with the procedures disclosed in Step 1 of Example 4.

tert-Butyl 2-bromo-4-iodobenzoate (C55)

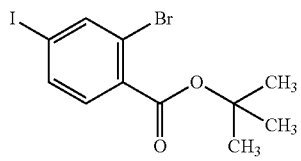

The product was isolated as a colorless oil (1.2 g, 50%): $^1$H NMR (400 MHz, CDCl$_3$) δ 8.01 (s, 1H), 7.68 (d, J=8.4 Hz, 1H), 7.41 (d, J=8.0 Hz, 1H), 1.59 (s, 9H); ESIMS m/z 382 ([M+H]$^+$); IR (thin film) 1727 cm$^{-1}$.

tert-Butyl 4-bromo-2-(trifluoromethyl)benzoate (C56)

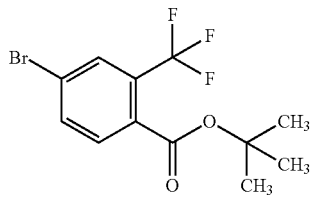 [SMILES: CC(C)(C)OC(=O)c1ccc(Br)cc1C(F)(F)F]

The product was isolated as a colorless oil (1 g, 52%): $^1$H NMR (400 MHz, CDCl$_3$) δ 7.85 (s, 1H), 7.73 (d, J=8.4 Hz, 1H), 7.62 (d, J=8.4 Hz, 1H), 1.57 (s, 9H); ESIMS m/z 324 ([M+H]$^+$); IR (thin film) 1725 cm$^{-1}$.

The following compounds were made in accordance with the procedures disclosed in Step 2 of Example 4.

tert-Butyl 2-bromo-4-vinylbenzoate (C57)

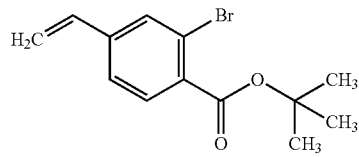 [SMILES: C=Cc1ccc(C(=O)OC(C)(C)C)c(Br)c1]

The product was isolated as a colorless oil (1 g, 52%): $^1$H NMR (400 MHz, CDCl$_3$) δ 7.68 (m, 2H), 7.36 (d, J=8.0 Hz, 1H), 6.68 (dd, 1=17.6, 10.8 Hz, 1H), 5.84 (d, J=17.6 Hz, 1H), 5.39 (d, J=10.8 Hz, 1H), 1.60 (s, 9H); ESIMS m/z 282 ([M+H]$^+$); IR (thin film) 2978, 1724, 1130 cm$^{-1}$.

tert-Butyl 2-(trifluoromethyl)-4-vinylbenzoate (C58)

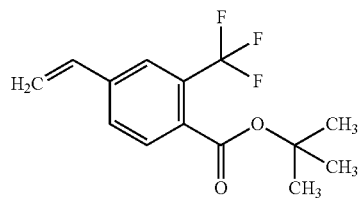 [SMILES: C=Cc1ccc(C(=O)OC(C)(C)C)c(C(F)(F)F)c1]

The product was isolated as a colorless oil (1.2 g, 50%): $^1$H NMR (400 MHz, CDCl$_3$) δ 7.71 (d, J=6.4 Hz, 2H), 7.59 (d, J=7.6 Hz, 1H), 6.77 (dd, J=17.6, 10.8 Hz, 1H), 5.89 (d, J=17.6 Hz, 1H), 5.44 (d, J=10.8 Hz, 1H), 1.58 (s, 9H); ESIMS m/z 272 ([M+H]$^+$); IR (thin film) 2982, 1727, 1159 cm$^{-1}$.

Example 5: Preparation of tert-butyl 2-cyano-4-vinylbenzoate (C59)

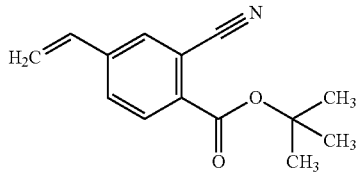 [SMILES: C=Cc1ccc(C(=O)OC(C)(C)C)c(C#N)c1]

To a stirred solution of tert-butyl 2-bromo-4-vinylbenzoate (C57) (0.5 g, 1.8 mmol) in dimethylformamide (20 mL) was added copper(I) cyanide (0.23 g, 2.7 mmol), and the reaction mixture was heated at 140° C. for 3 hours. The reaction mixture was cooled to 25° C., diluted with water, and extracted with ethyl acetate. The combined organic layer was washed with brine, dried over sodium sulfate, and concentrated under reduced pressure. The residue was purified by flash column chromatography using 15% ethyl acetate/hexanes as eluent to afford the title compound as a white solid (0.30 g, 72%): mp 51-53° C.; $^1$H NMR (400 MHz, CDCl$_3$) δ 8.03 (s, 1H), 7.77 (s, 1H), 7.64 (d, J=8.4 Hz, 1H), 6.75 (dd, J=17.6, 10.8 Hz, 1H), 5.93 (d, J=17.6 Hz, 1H), 5.51 (d, J=10.8 Hz, 1H), 1.65 (s, 9H); ESIMS m/z 230 ([M+H]$^+$); IR (thin film) 2370, 1709, 1142 cm$^{-1}$.

Example 6: Preparation of ethyl 2-bromo-4-iodobenzoate (C60)

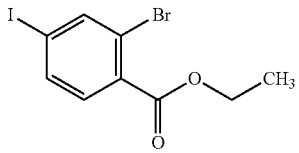

To a stirred solution of 4-iodo-2-bromobenzoic acid (5.00 g, 15.3 mmol) in ethyl alcohol (100 mL) was added sulfuric acid (5 mL), and the reaction mixture was heated at 80° C. for 18 hours. The reaction mixture was cooled to 25° C. and concentrated under reduced pressure. The residue was diluted with ethyl acetate (2×100 mL) and washed with water (100 mL). The combined ethyl acetate extracts were washed with brine, dried over sodium sulfate, and concentrated under reduced pressure to afford the compound as a pale yellow solid (5.00 g, 92%): $^1$H NMR (400 MHz, DMSO-d$_6$) δ 8.04 (d, J=1.2 Hz, 1H), 7.71 (d, J=7.6 Hz, 1H), 7.51 (d, J=8.4 Hz, 1H), 4.41 (q, J=7.2 Hz, 2H), 1.41 (t, J=7.2 Hz, 3H).

The following compounds were made in accordance with the procedures disclosed in Example 6.

Ethyl 4-bromo-2-chlorobenzoate (C61)

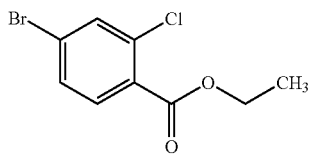

The title compound was isolated as an off-white solid (2.0 g, 80%): $^1$H NMR (400 MHz, DMSO-d$_6$) δ 8.25 (d, J=1.2 Hz, 1H), 7.79 (d, J=7.6 Hz, 1H), 7.65 (d, J=8.4 Hz, 1H), 4.65 (q, J=7.2 Hz, 2H), 1.56 (t, J=7.2 Hz, 3H).

Ethyl 4-bromo-2-methylbenzoate (C62)

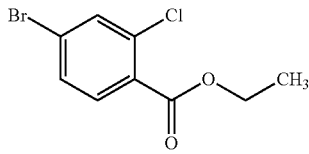

The title compound was isolated as a pale yellow liquid (3.0 g, 83%): $^1$H NMR (400 MHz, CDCl$_3$) δ 7.79 (d, J=8.4 Hz, 1H), 7.41 (s, 1H), 7.39 (d, J=8.4 Hz, 1H), 4.42 (q, J=7.2 Hz, 2H), 2.60 (s, 3H), 1.40 (t, J=7.2 Hz, 3H); ESIMS m/z 229 ([M+H]$^+$); IR (thin film) 1725 cm$^{-1}$.

Ethyl 4-bromo-2-fluorolbenzoate (C63)

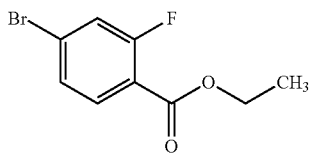

The title compound was isolated as a colorless liquid (9.0 g, 79%): $^1$H NMR (400 MHz, DMSO-d$_6$) δ 7.84 (t, J=8.4 Hz, 1H), 7.76 (d, J=2.0 Hz, 1H), 7.58 (d, J=1.6 Hz, 1H), 4.34 (q, J=7.2 Hz, 2H), 1.32 (t, J=7.2 Hz, 3H); ESIMS m/z 247 ([M+H]$^+$), IR (thin film) 1734 cm$^{-1}$.

Example 7: Preparation of ethyl 4-bromo-2-ethylbenzoate (C64)

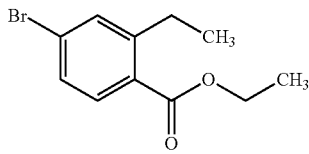

To a stirred solution of 4-bromo-2-fluorobenzoic acid (2.0 g, 9.2 mmol) in tetrahydrofuran (16 mL), was added ethyl magnesium bromide (1.0 M in tetrahydrofuran, 32 mL, 32.0 mmol) dropwise at 0° C. and the resultant reaction mixture was stirred at ambient temperature for 18 hours. The reaction mixture was quenched with hydrochloric acid (2 N) and extracted with ethyl acetate. The combined ethyl acetate layer was dried over anhydrous sodium sulfate and concentrated under reduced pressure to afford crude 4-bromo-2-ethylbenzoic acid as a colorless liquid that was used in the next step without purification (0.40 g): $^1$H NMR (400 MHz, CDCl$_3$) δ 7.64 (d, J=8.4 Hz, 1H), 7.47 (m, 1H), 7.43 (m, 1H), 2.95 (q, J=4.0 Hz, 2H), 1.32 (t, J=4.0 Hz, 3H); ESIMS m/z 229 ([M+H]$^+$).

Alternatively, the title compound was synthesized from 4-bromo-2-ethylbenzoic acid in accordance to the procedure in Example 6 and isolated as a colorless liquid (0.15 g, 68%): $^1$H NMR (400 MHz, DMSO-d$_6$) δ 7.90 (d, J=8.4 Hz, 1H), 7.47 (m, 2H), 4.40 (q, J=7.2 Hz, 2H), 3.06 (q, J=7.6 Hz, 2H), 1.42 (t, J=7.2 Hz, 3H), 1.26 (t, J=7.6 Hz, 3H); ESIMS m/z 227 ([M−H]$^-$); IR (thin film) 3443, 1686, 568 cm$^{-1}$.

Example 8: Preparation of ethyl 2-bromo-4-vinylbenzoate (C65)

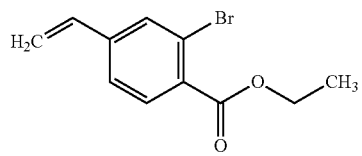

To a stirred solution of ethyl 2-bromo-4-iodobenzoate (C60) (5.00 g, 14.3 mmol) in tetrahydrofuran/water (100 mL, 9:1) was added potassium vinyltrifluoroborate (1.89 g, 14.3 mmol), cesium carbonate (18.3 g, 56.1 mmol), and triphenylphosphine (0.220 g, 0.850 mmol). The reaction mixture was degassed with argon for 20 minutes, then charged with dichloropalladium(II) (0.0500 g, 0.280 mmol). The reaction mixture was heated to reflux for 16 hours. The reaction mixture was cooled to ambient temperature and filtered through a Celite® bed and washed with ethyl acetate. The filtrate was again extracted with ethyl acetate and the combined organic layers washed with water and brine, dried over sodium sulfate, and concentrated under reduced pressure to afford crude compound. The crude compound was purified by flash column chromatography using 2% ethyl acetate/petroleum ether as eluent to afford the title compound as a light brown gummy material (2.00 g, 56%): $^1$H NMR (400 MHz, CDCl$_3$) δ 7.78 (d, J=8.4 Hz, 1H), 7.71 (d, J=1.2 Hz, 1H), 7.51 (d, J=8.4 Hz, 1H), 6.69 (dd, J=17.6, 10.8 Hz, 1H), 5.86 (d, J=17.6 Hz, 1H), 5.42 (d, J=11.2 Hz, 1H), 4.42 (q, J=7.2 Hz, 2H), 1.43 (t, J=3.6 Hz, 3H); ESIMS m/z 255 ([M+H]$^+$); IR (thin film) 1729 cm$^{-1}$.

The following compounds were made in accordance with the procedures disclosed in Example 8.

Ethyl 2-methyl-4-vinylbenzoate (C66)

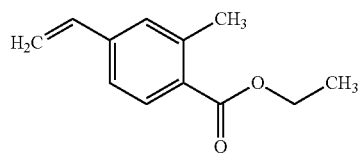

The title compound was isolated as a colorless liquid (0.8 g, 80%): $^1$H NMR (400 MHz, CDCl$_3$) δ 7.89 (d, J=8.4 Hz, 1H), 7.27 (m, 2H), 6.79 (dd, J=17.6, 10.8 Hz, 1H), 5.86 (d, J=17.6 Hz, 1H), 5.42 (d, J=11.2 Hz, 1H), 4.42 (q, J=7.2 Hz, 2H), 2.60 (s, 3H), 1.43 (t, J=7.2 Hz, 3H); ESIMS m/z 191 ([M+H]$^+$); IR (thin film) 1717, 1257 cm$^{-1}$.

Ethyl 2-fluoro-4-vinylbenzoate (C67)

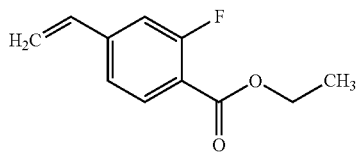

The title compound was isolated as a pale yellow liquid (2.0 g, 50%): $^1$H NMR (400 MHz, DMSO-d$_6$) δ 7.87 (t, J=8.0 Hz, 1H), 7.51 (d, J=16.0 Hz, 1H), 7.48 (d, J=16.0 Hz, 1H), 6.82 (dd, J=17.6, 10.8 Hz, 1H), 6.09 (d, J=17.6 Hz, 1H), 5.50 (d, J=10.8 Hz, 1H), 4.35 (q, J=7.2 Hz, 2H), 1.35 (t, J=7.2 Hz, 3H); ESIMS m/z 195 ([M+H]$^+$); IR (thin film) 1728 cm$^{-1}$.

Example 9: Preparation of ethyl 2-chloro-4-vinylbenzoate (C68)

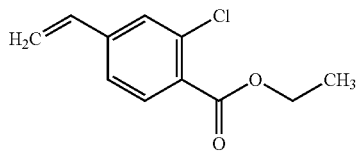

To a stirred solution of ethyl 2-chloro-4-bromobenzoate (C61) (2.00 g, 7.63 mmol) in dimethylsulfoxide (20 mL) was added potassium vinyltrifluoroborate (3.06 g, 22.9 mmol), and potassium carbonate (3.16 g, 22.9 mmol). The reaction mixture was degassed with argon for 30 minutes. Bistriphenylphosphine(diphenylphosphino ferrocene)palladium(II) dichloride (0.270 g, 0.380 mmol) was added and the reaction mixture was heated to 80° C. for 1 hour. The reaction mixture was diluted with water (100 mL), extracted with ethyl acetate (2×50 mL), washed with brine, dried over sodium sulfate, and concentrated under reduced pressure to obtain the compound as brown gummy material (1.10 g, 69%): $^1$H NMR (400 MHz, CDCl$_3$) δ 7.81 (d, J=8.4 Hz, 1H), 7.46 (s, 1H), 7.33 (d, J=8.4 Hz, 1H), 6.70 (dd, J=17.6, 11.2 Hz, 1H), 5.87 (d, J=17.6 Hz, 1H), 5.42 (d, J=10.8 Hz, 1H), 4.41 (q, J=7.2 Hz, 2H), 1.43 (t, J=7.2 Hz, 3H); ESIMS m/z 211 ([M+H]$^+$); IR (thin film) 1729, 886 cm$^{-1}$.

The following compounds were made in accordance with the procedures disclosed in Example 9.

Ethyl 2-ethyl-4-vinylbenzoate (C69)

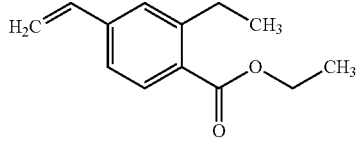

The title compound was isolated as a colorless liquid (1.0 g, 66%): $^1$H NMR (300 MHz, CDCl$_3$) δ 7.85 (m, 1H), 7.29 (m, 2H), 6.76 (d, J=10.8 Hz, 1H), 5.86 (d, J=17.6 Hz, 1H), 5.36 (d, J=10.5 Hz, 1H), 4.41 (q, J=7.2 Hz, 2H), 3.10 (q, J=7.2 Hz, 2H), 1.40 (t, J=7.2 Hz, 3H), 1.30 (t, J=7.2 Hz, 3H); ESIMS m/z 205 ([M+H]⁺); IR (thin film) 1720, 1607, 1263 cm⁻¹.

Methyl 2-methoxy-4-vinylbenzoate (C70)

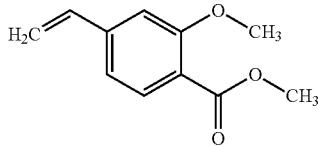

The title compound was isolated as a pale yellow liquid (1.2 g, 75%): ¹H NMR (400 MHz, CDCl₃) δ 7.79 (d, J=8.0 Hz, 1H), 7.04 (d, J=1.2 Hz, 1H), 6.97 (s, 1H), 6.74 (dd, J=11.2, 11.2 Hz, 1H), 5.86 (d, J=17.6 Hz, 1H), 5.39 (d, J=17.6 Hz, 1H) 3.93 (s, 3H), 3.91 (s, 3H); ESIMS m/z 193 ([M+H]⁺); IR (thin film) 1732 cm⁻¹.

Example 10: Preparation of (E)-ethyl 4-(3-(3,5-dichlorophenyl)-4,4,4-trifluorobut-1-enyl)-2-methyl-benzoate (C71)

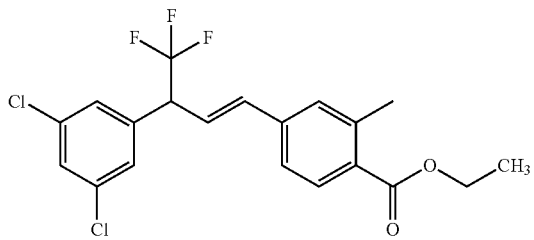 [SMILES: CCOC(=O)c1ccc(/C=C/C(c2cc(Cl)cc(Cl)c2)C(F)(F)F)cc1C]

To a stirred solution of ethyl 2-methyl-4-vinylbenzoate (C66) (2.00 g, 10.5 mmol) in 1,2-dichlorobenzene (25 mL) were added 1-(1-bromo-2,2,2-trifluoroethyl)-3,5-dichlorobenzene (C2) (6.44 g, 21.0 mmol), copper(I) chloride (0.208 g, 21.0 mmol) and 2,2'-bipyridyl (0.650 g, 4.10 mmol). The reaction mixture was degassed with argon for 30 minutes and then stirred at 180° C. for 24 hours. After the reaction was deemed complete by thin layer chromatography, the reaction mixture was cooled to 25° C. and filtered, and the filtrate was concentrated under reduced pressure. Purification by flash column chromatography using 25-30% ethyl acetate/petroleum ether as eluent afforded the title compound as a solid (1.70 g, 40%): ¹H NMR (400 MHz, CDCl₃) δ 7.91 (d, J=8.0 Hz, 1H), 7.37 (m, 1H), 7.27-7.24 (m, 4H), 6.59 (d, J=16.0 Hz, 1H), 6.59 (dd, J=16.0, 8.0 Hz, 1H), 4.38 (q, J=7.2 Hz, 2H), 4.08 (m, 1H), 2.62 (s, 3H), 1.42 (t, J=7.2 Hz, 3H); ESIMS m/z 415 ([M−H]⁻); IR (thin film) 1717, 1255, 1114 cm⁻¹.

The following compounds were made in accordance with the procedures disclosed in Example 10.

(E)-Ethyl 4-(4,4,4-trifluoro-3-(3,4,5-trichlorophenyl)but-1-enyl)-2-(trifluoromethyl)-benzoate (C72)

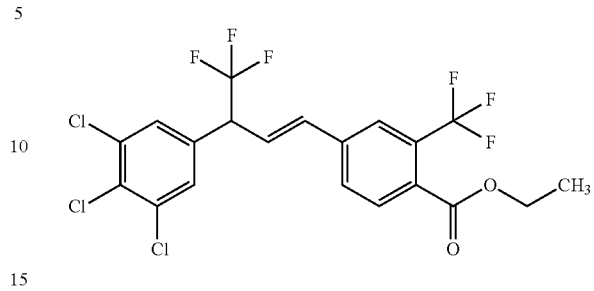

The product was isolated as a pale brown gummy liquid (0.500 g, 40%): ¹H NMR (400 MHz, CDCl₃) δ 7.79 (d, J=8.0 Hz, 1H), 7.71 (m, 1H), 7.61 (d, J=7.6 Hz, 1H), 7.42 (s, 2H), 6.70 (d, J=16.0 Hz, 1H), 6.57 (dd, J=16.0, 8.0 Hz, 1H), 4.42 (q, J=7.2 Hz, 2H), 4.19 (m, 1H), 1.40 (t, J=7.6 Hz, 3H); ESIMS m/z 503 ([M−H]⁻); IR (thin film) 1730, 1201, 1120, 749 cm⁻¹.

(E)-Ethyl 4-(3-(3,5-dichlorophenyl)-4,4,4-trifluorobut-1-enyl)-2-fluorobenzoate (C73)

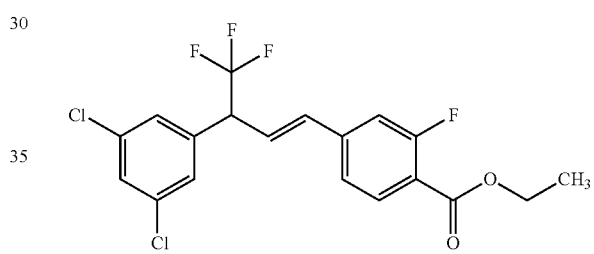

¹H NMR (400 MHz, CDCl₃) δ 7.38 (s, 1H), 7.26 (s, 3H), 7.21 (d, J=8.4 Hz, 1H), 7.16 (d, J=11.6 Hz, 1H), 6.59 (d, J=16.0 Hz, 1H), 6.47 (dd, J=, 16.0, 8.0 Hz, 1H), 4.41 (q, J=6.8 Hz, 2H), 4.18 (m, 1H), 1.41 (t, J=6.8 Hz, 3H); ESIMS m/z 419 ([M−H]⁻); IR (thin film) 1723, 1115, 802 cm⁻¹.

(E)-Ethyl 4-(3-(3,5-dichlorophenyl)-4,4,4-trifluorobut-1-enyl)-2-bromobenzoate (C74)

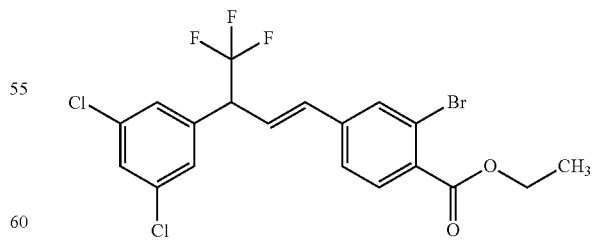

¹H NMR (400 MHz, CDCl₃) δ 7.79 (d, J=8.0 Hz, 1H), 7.67 (s, 1H), 7.38 (m, 2H), 7.26 (m, 2H), 6.56 (d, J=16.0 Hz, 1H), 6.45 (dd, J=16.0, 7.6 Hz, 1H), 4.42 (q, J=7.2 Hz, 2H), 4.39 (m, 1H), 1.42 (t, J=7.2 Hz, 3H); ESIMS m/z 481 ([M−H]⁻); IR (thin film) 1727, 1114, 801, 685 cm⁻¹.

(E)-Ethyl 2-bromo-4-(4,4,4-trifluoro-3-(3,4,5-trichlorophenyl) but-1-enyl)benzoate (C75)

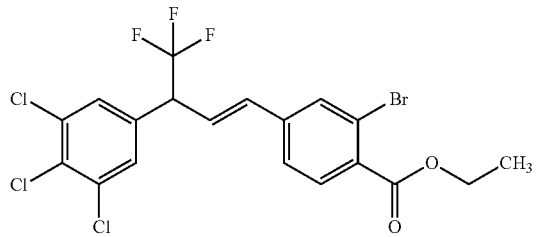 [SMILES: CCOC(=O)c1ccc(/C=C/C(c2cc(Cl)c(Cl)c(Cl)c2)C(F)(F)F)cc1Br]

$^1$H NMR (400 MHz, CDCl$_3$) δ 7.79 (d, J=8.0 Hz, 1H), 7.67 (d, J=1.6 Hz, 1H), 7.40 (s, 2H), 7.36 (d, J=1.6 Hz, 1H), 6.56 (d, J=16.0 Hz, 1H), 6.44 (dd, J=16.0, 7.6 Hz, 1H), 4.42 (q, J=6.8 Hz, 2H), 4.15 (m, 1H), 1.42 (t, J=6.8 Hz, 3H); ESIMS m/z 515 ([M−H]$^−$); IR (thin film) 1726, 1115, 808, 620 cm$^{-1}$.

(E)-Ethyl 2-methyl-4-(4,4,4-trifluoro-3-(3,4,5-trichlorophenyl) but-1-enyl)benzoate (C76)

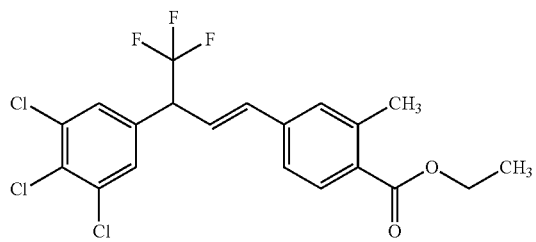 [SMILES: CCOC(=O)c1ccc(/C=C/C(c2cc(Cl)c(Cl)c(Cl)c2)C(F)(F)F)cc1C]

The title compound was isolated as a light brown gummy material: $^1$H NMR (400 MHz, CDCl$_3$) δ 7.90 (d, J=8.8 Hz, 1H), 7.34 (d, J=6.0 Hz, 2H), 7.25 (d, J=7.2 Hz, 2H), 6.59 (d, J=16.0 Hz, 1H), 6.42 (dd, J=16.0, 8.0 Hz, 1H), 4.38 (q, J=7.2 Hz, 2H), 4.19 (m, 1H), 2.63 (s, 3H), 1.41 (t, J=7.2 Hz, 3H).

(E)-Ethyl 2-chloro-4-(4,4,4-trifluoro-3-(3,4,5-trichlorophenyl) but-1-enyl)benzoate (C77)

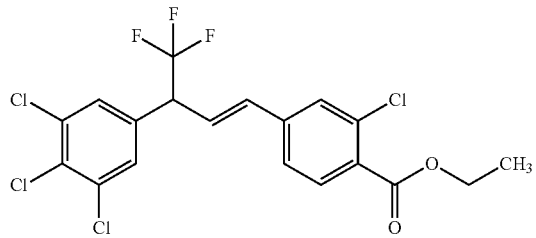 [SMILES: CCOC(=O)c1ccc(/C=C/C(c2cc(Cl)c(Cl)c(Cl)c2)C(F)(F)F)cc1Cl]

$^1$H NMR (400 MHz, CDCl$_3$) δ 7.87 (d, J=8.0 Hz, 1H), 7.46 (d, J=1.6 Hz, 1H), 7.40 (s, 2H), 7.31 (d, J=1.6 Hz, 1H), 6.57 (d, J=16.0 Hz, 1H), 6.44 (dd, J=16.0, 8.0 Hz, 1H), 4.42 (q, J=6.8 Hz, 2H), 4.15 (m, 1H), 1.42 (t, J=6.8 Hz, 3H); ESIMS m/z 471 ([M−H]$^−$); IR (thin film) 1726, 1115, 809, 3072 cm$^{-1}$.

(E)-Ethyl 4-(4,4,4-trifluoro-3-(3,4,5-trichlorophenyl) but-1-enyl)-2-(trifluoromethyl)benzoate (C78)

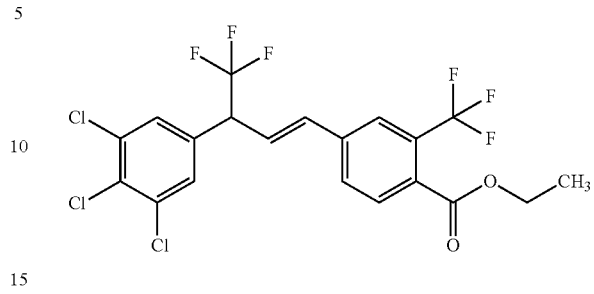

The title compound was isolated as a pale brown liquid (1.0 g, 46.3%): $^1$H NMR (400 MHz, CDCl$_3$) δ 7.79 (d, J=8.0 Hz, 1H), 7.71 (s, 1H), 7.61 (d, J=7.6 Hz, 1H), 7.41 (s, 2H) 6.65 (d, J=16.0 Hz, 1H), 6.49 (dd, J=16.0, 8.0 Hz, 1H), 4.42 (q, J=7.6 Hz, 2H), 4.15 (m, 1H), 1.42 (t, J=7.6 Hz, 3H); ESIMS m/z 503 ([M−H]$^−$); IR (thin film) 1730, 1202, 1120, 750 cm$^{-1}$.

(E)-Ethyl 2-chloro-4-(3-(3,5-dichloro-4-fluorophenyl)-4,4,4-trifluorobut-1-enyl)benzoate (C79)

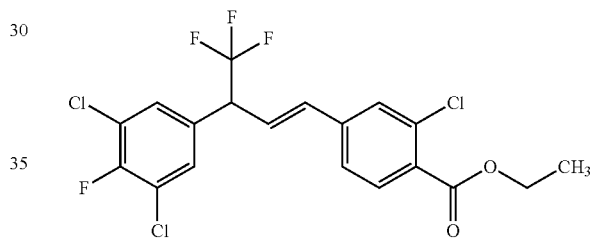

$^1$H NMR (400 MHz, CDCl$_3$) δ 7.85 (d, J=6.0 Hz, 1H), 7.46 (d, J=1.8 Hz, 2H), 7.34 (m, 1H), 7.24 (m, 1H), 6.57 (d, J=16.2 Hz, 1H), 6.45 (dd, J=16.2, 7.2 Hz, 1H), 4.43 (q, J=7.2 Hz, 2H), 4.13 (m, 1H), 1.41 (t, J=7.2 Hz, 3H); ESIMS m/z 455 ([M+H]$^+$); IR (thin film) 1728, 1115, 817 cm$^{-1}$.

(E)-Ethyl 2-fluoro-4-(3-(3,5-dichloro-4-fluorophenyl)-4,4,4-trifluorobut-1-enyl)benzoate (C80)

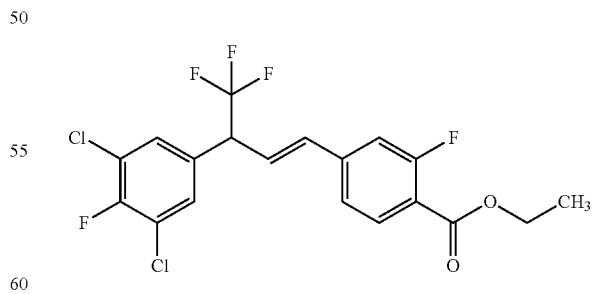

$^1$H NMR (400 MHz, CDCl$_3$) δ 7.93 (t, J=7.6 Hz, 1H), 7.34 (d, J=5.6 Hz, 2H), 7.21 (d, J=8.0 Hz, 1H), 7.16 (d, J=11.6 Hz, 1H), 6.59 (d, J=16.0 Hz, 1H), 6.49 (dd, J=16.0, 7.6 Hz, 1H), 4.42 (q, J=7.6 Hz, 2H), 4.13 (m, 1H), 1.41 (t, J=7.6 Hz, 3H); ESIMS m/z 436.81 ([M−H]$^−$); IR (thin film) 1725 cm$^{-1}$.

(E)-Ethyl 2-bromo-4-(3-(3,5-dichloro-4-fluorophenyl)-4,4,4-trifluorobut-1-enyl)benzoate (C81)

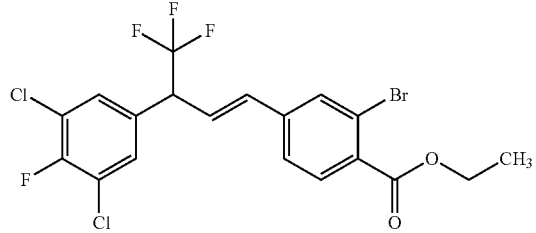 [SMILES: CCOC(=O)c1ccc(/C=C/C(c2cc(Cl)c(F)c(Cl)c2)C(F)(F)F)cc1Br]

$^1$H NMR (400 MHz, CDCl$_3$) δ 7.94 (d, J=8.0 Hz, 1H), 7.67 (s, 1H), 7.36 (m, 3H), 6.56 (d, J=15.6 Hz, 1H), 6.44 (dd, J=15.6, 8.0 Hz, 1H), 4.42 (q, J=6.8 Hz, 2H), 4.10 (m, 1H), 1.42 (t, J=6.8 Hz, 3H); ESIMS m/z 499 ([M−H]$^−$); IR (thin film) 1726, 1114, 820, 623 cm$^{−1}$.

(E)-Ethyl 2-methyl-4-(3-(3,5-dichloro-4-fluorophenyl)-4,4,4-trifluorobut-1-enyl)benzoate (C82)

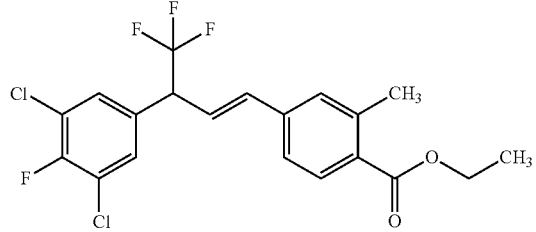 [SMILES: CCOC(=O)c1ccc(/C=C/C(c2cc(Cl)c(F)c(Cl)c2)C(F)(F)F)cc1C]

The title compound was isolated as a brown semi-solid: $^1$H NMR (400 MHz, CDCl$_3$) δ 7.90 (d, J=8.8 Hz, 1H), 7.34 (d, J=6.0 Hz, 2H), 7.25 (d, J=7.2 Hz, 2H), 6.59 (d, J=16.0 Hz, 1H), 6.42 (dd, J=16.0 Hz, 8.0 Hz, 1H), 4.38 (q, J=7.2 Hz, 2H), 4.19 (m, 1H), 2.63 (s, 3H), 1.41 (t, J=7.2 Hz, 3H); ESIMS m/z 433 ([M−H]$^−$); IR (thin film) 1715 cm$^1$.

(E)-Methyl 2-methoxy-4-(3-(3,5-dichloro-4-fluorophenyl)-4,4,4-trifluorobut-1-enyl)benzoate (C83)

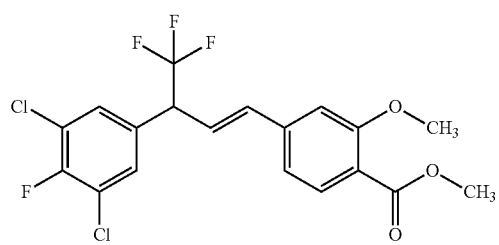 [SMILES: COC(=O)c1ccc(/C=C/C(c2cc(Cl)c(F)c(Cl)c2)C(F)(F)F)cc1OC]

$^1$H NMR (400 MHz, CDCl$_3$) δ 7.80 (d, J=8.4 Hz, 1H), 7.35 (d, J=6.0 Hz, 2H), 7.03 (d, J=1.2 Hz, 1H), 6.92 (s, 1H), 6.59 (d, J=15.6 Hz, 1H), 6.42 (dd, J=15.6, 8.0 Hz, 1H), 4.13 (m, 1H), 3.93 (s, 3H), 3.88 (s, 3H); ESIMS m/z 437 ([M+H]$^+$); IR (thin film) 1724 cm$^{−1}$.

(E)-Ethyl 2-ethyl-4-(3-(3,5-dichloro-4-fluorophenyl)-4,4,4-trifluorobut-1-enyl)benzoate (C84)

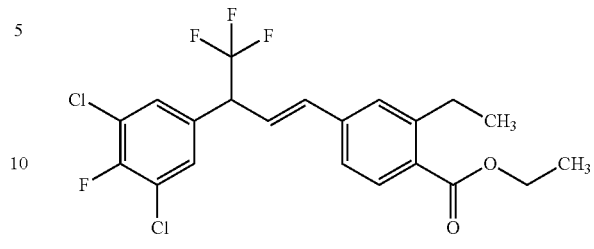

$^1$H NMR (400 MHz, CDCl$_3$) δ 7.85 (d, J=8.0 Hz, 1H), 7.35 (d, J=9.6 Hz, 2H), 7.26 (m, 1H), 7.24 (m, 1H), 6.60 (d, J=15.6 Hz, 1H), 6.42 (dd, J=15.6, 8.0 Hz, 1H), 4.38 (q, J=7.2 Hz, 2H), 4.14 (m, 1H), 3.01 (q, J=7.6 Hz 2H), 1.41 (t, J=7.2 Hz, 3H), 1.26 (t, J=7.6 Hz, 3H); ESIMS m/z 447 ([M−H]$^−$); IR (thin film) 1715, 1115, 817 cm$^{−1}$.

Example 11: Preparation of (E)-4-(3-(3,5-dichlorophenyl)-4,4,4-trifluorobut-1-enyl)-2-methylbenzoic acid (C85)

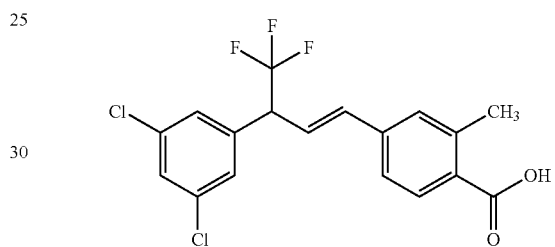

To a stirred solution of (E)-ethyl 4-(3-(3,5-dichlorophenyl)-4,4,4-trifluorobut-1-enyl)-2-methylbenzoate (C71) (1.7 g, 4.0 mmol) in 1,4-dioxane (10 mL) was added hydrochloric acid (11 N, 30 mL), and the reaction mixture was heated at 100° C. for 48 hours. The reaction mixture was cooled to 25° C. and concentrated under reduced pressure. The residue was diluted with water and extracted with chloroform. The combined organic layer was dried over sodium sulfate and concentrated under reduced pressure. The crude compound was washed with n-hexane to afford the title compound as a white solid (0.70 g, 50%): mp 142-143° C.; $^1$H NMR (400 MHz, DMSO-d$_6$) δ 12.62 (br s, 1H), 7.81 (d, J=8.0 Hz, 1H), 7.66 (s, 3H), 7.52-7.44 (m, 2H), 6.89 (dd, J=16.0, 8.0 Hz, 1H), 6.78-6.74 (d, J=16.0 Hz, 1H), 4.84 (m, 1H), 2.50 (s, 3H); ESIMS m/z 387 ([M−H]$^−$); IR (thin film) 3448, 1701, 1109, 777 cm$^{−1}$.

The following compounds were made in accordance with the procedures disclosed in Example 11.

(E)-2-Methyl-4-(4,4,4-trifluoro-3-(3,4,5-trichlorophenyl)but-1-enyl)benzoic acid (C86)

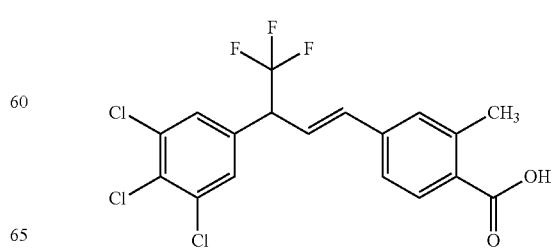

The product was isolated as a pale brown gummy liquid (1 g, 46%): ¹H NMR (400 MHz, CDCl₃) δ 7.97 (d, J=8.0 Hz, 1H), 7.77 (s, 1H), 7.65 (m, 1H), 7.41 (s, 2H), 6.68 (d, J=16.0 Hz, 1H), 6.53 (dd, J=16.0, 8.0 Hz, 1H), 4.16 (m, 1H), 2.50 (s, 3H); ESIMS m/z 423 ([M−H]⁻).

(E)-2-Chloro-4-(4,4,4-trifluoro-3-(3,4,5-trichlorophenyl)but-1-enyl)benzoic acid (C87)

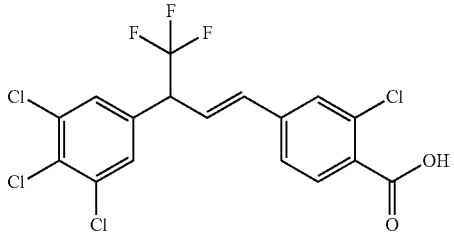 [SMILES: O=C(O)c1ccc(/C=C/C(c2cc(Cl)c(Cl)c(Cl)c2)C(F)(F)F)cc1Cl]

The product was isolated as an off-white semi-solid (1 g, 45%): ¹H NMR (400 MHz, CDCl₃) δ 7.99 (d, J=8.4 Hz, 1H), 7.50 (m, 1H), 7.40 (s, 1H), 7.36 (m, 2H), 6.59 (d, J=15.6 Hz, 1H), 6.48 (dd, J=15.6, 7.6 Hz, 1H), 4.14 (m, 1H); ESIMS m/z 443 ([M−H]⁻); IR (thin film) 3472, 1704, 1113, 808 cm⁻¹.

(E)-2-Bromo-4-(4,4,4-trifluoro-3-(3,4,5-trichlorophenyl)but-1-enyl)benzoic acid (C88)

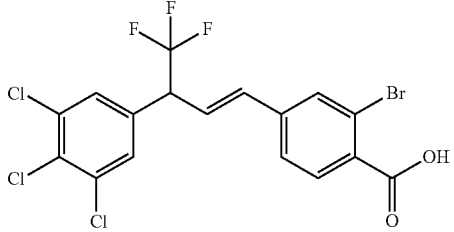 [SMILES: O=C(O)c1ccc(/C=C/C(c2cc(Cl)c(Cl)c(Cl)c2)C(F)(F)F)cc1Br]

The product was isolated as a brown solid (1 g, 45%): mp 70-71° C.; ¹H NMR (400 MHz, CDCl₃) δ 7.99 (d, J=8.0 Hz, 1H), 7.72 (s, 1H), 7.40 (m, 3H), 6.58 (d, J=16.0 Hz, 1H), 6.48 (dd, J=16.0, 8.0 Hz, 1H), 4.14 (m, 1H); ESIMS m/z 485 ([M−H]⁻); IR (thin film) 3468, 1700 cm⁻¹.

(E)-2-Cyano-4-(4,4,4-trifluoro-3-(3,4,5-trichlorophenyl)but-1-enyl)benzoic acid (C89)

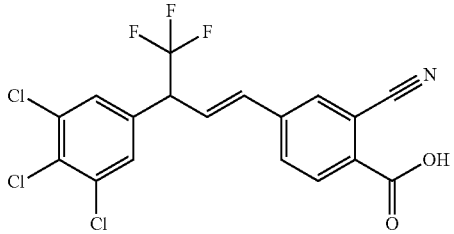 [SMILES: N#Cc1cc(/C=C/C(c2cc(Cl)c(Cl)c(Cl)c2)C(F)(F)F)ccc1C(=O)O]

The product was isolated as an off-white solid (0.500 g, 45%): mp 100-101° C.; ¹H NMR (400 MHz, CDCl₃) δ 7.90 (s, 1H), 7.85 (d, J=7.6 Hz, 1H), 7.72 (d, J=8.0 Hz, 1H), 7.65 (br s, 1H), 7.42 (s, 2H), 6.73 (d, J=16.0 Hz, 1H), 6.58 (dd, J=16.0, 8.0 Hz, 1H), 4.19 (m, 1H); ESIMS m/z 432 ([M−H]⁻).

E)-4-(3-(3,4-Dichlorophenyl)-4,4,4-trifluorobut-1-enyl)-2-methylbenzoic acid (C90)

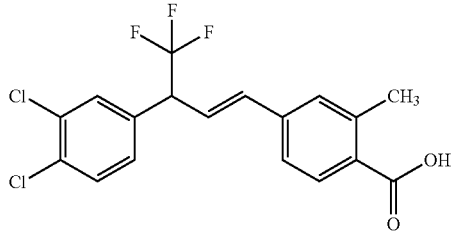 [SMILES: Cc1cc(/C=C/C(c2ccc(Cl)c(Cl)c2)C(F)(F)F)ccc1C(=O)O]

The product was isolated as a pale brown liquid (0.500 g, 46%): ¹H NMR (400 MHz, CDCl₃) b 8.03 (m, 1H), 7.49 (m, 2H), 7.29 (m, 1H), 7.22 (m, 2H), 6.73 (d, J=16.0 Hz, 1H), 6.58 (dd, J=16.0, 7.8 Hz, 1H), 4.16 (m, 1H), 2.64 (s, 3H); ESIMS m/z 387 ([M−H]⁻); IR (thin film) 3428, 1690, 1113, 780 cm⁻¹.

(E)-4-(3-(3,5-Dichloro-4-fluorophenyl)-4,4,4-trifluorobut-1-enyl)-2-methylbenzoic acid (C91)

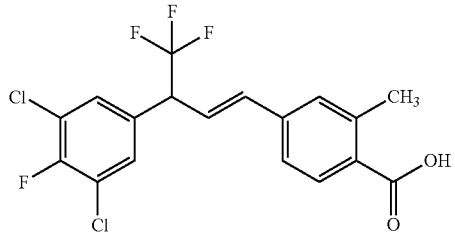 [SMILES: Cc1cc(/C=C/C(c2cc(Cl)c(F)c(Cl)c2)C(F)(F)F)ccc1C(=O)O]

The product was isolated as a white solid (500 mg, 50%): mp 91-93° C.; ¹H NMR (400 MHz, CDCl₃) b 8.02 (d, J=8.0 Hz, 1H), 7.35 (d, J=5.6 Hz, 1H), 7.30 (m, 3H), 6.61 (d, J=16.0 Hz, 1H), 6.48 (dd, J=16.0, 8.0 Hz, 1H), 4.13 (m, 1H), 2.65 (s, 3H); ESIMS m/z 407 ([M−H]⁻).

(E)-4-(4,4,4-Trifluoro-3-(3,4,5-trichlorophenyl)but-1-enyl)-2-(trifluoromethyl)benzoic acid (C92)

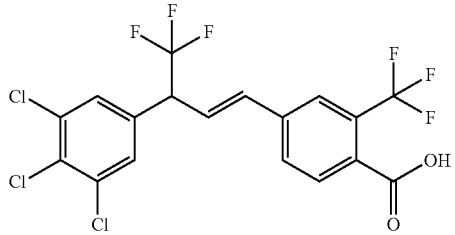

The product was isolated as a white solid (500 mg, 45%): mp 142-143° C.; ¹H NMR (400 MHz, CDCl₃) b 7.97 (d, J=8.0 Hz, 1H), 7.77 (s, 1H), 7.65 (m, 1H), 7.41 (s, 2H), 6.68

(d, J=16.0 Hz, 1H), 6.53 (dd, J=16.0, 8.0 Hz, 1H), 4.16 (m, 1H); ESIMS m/z 475 ([M−H]⁻).

(E)-2-Bromo-4-(4,4,4-trifluoro-3-(3,4,5-trichlorophenyl)but-1-enyl)benzoic acid (C93)

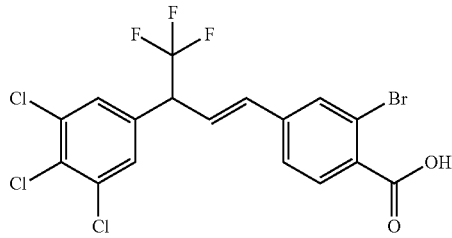 [SMILES: O=C(O)c1ccc(/C=C/C(c2cc(Cl)c(Cl)c(Cl)c2)C(F)(F)F)cc1Br]

The title compound was isolated as a brown solid (0.8 g, 28%): ¹H NMR (400 MHz, CDCl₃) δ 13.42 (br, 1H), 7.98 (d, J=1.5 Hz, 1H), 7.94 (m, 2H), 7.75 (d, J=8.1 Hz, 1H), 7.65 (m, 1H), 7.06 (dd, J=15.9, 9.0 Hz, 1H), 6.80 (d, J=15.9 Hz, 1H), 4.91 (m, 1H); ESIMS m/z 485 ([M−H]⁻); IR (thin film) 3469, 1700 cm⁻¹.

(E)-2-Bromo-4-(3-(3,5-dichloro-4-fluorophenyl)-4,4,4-trifluorobut-1-enyl)benzoic acid (C94)

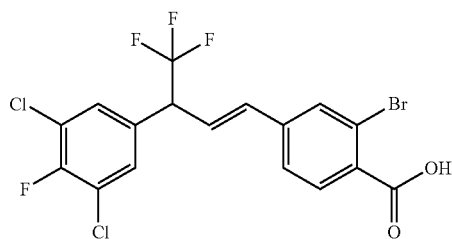 [SMILES: O=C(O)c1ccc(/C=C/C(c2cc(Cl)c(F)c(Cl)c2)C(F)(F)F)cc1Br]

The title compound was isolated as a yellow liquid (0.3 g, crude): ¹H NMR (300 MHz, CDCl₃) δ 7.79 (d, J=8.1 Hz, 1H), 7.67 (s, 1H), 7.34 (m, 3H), 6.56 (d, J=15.9 Hz, 1H), 6.45 (dd, J=15.9, 7.6 Hz, 1H), 4.43 (m, 1H); ESIMS m/z 471 ([M−H]⁻).

(E)-4-(3-(3,5-Dichloro-4-fluorophenyl)-4,4,4-trifluorobut-1-enyl)-2-ethylbenzoic acid (C95)

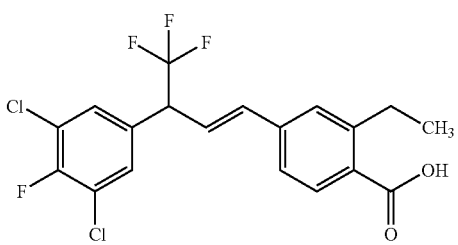 [SMILES: CCc1cc(/C=C/C(c2cc(Cl)c(F)c(Cl)c2)C(F)(F)F)ccc1C(=O)O]

The title compound was isolated as a brown gummy material (0.2 g, crude): ¹H NMR (300 MHz, DMSO-d₆) δ 12.5 (br, 1H), 7.85 (d, J=6.3 Hz, 2H), 7.75 (d, J=8.1 Hz, 1H), 7.52 (m, 2H), 6.96 (dd, J=8.7, 8.7 Hz, 1H), 6.78 (d, J=15.6 Hz, 1H), 4.80 (m, 1H), 4.06 (q, J=7.2 Hz, 2H), 1.33 (t, J=7.2 Hz, 3H); ESIMS m/z 419 ([M−H]⁻).

(E)-2-Chloro-4-(3-(3,5-dichloro-4-fluorophenyl)-4,4,4-trifluorobut-1-enyl)benzoic acid (C96)

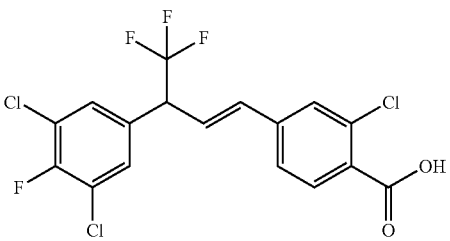 [SMILES: O=C(O)c1ccc(/C=C/C(c2cc(Cl)c(F)c(Cl)c2)C(F)(F)F)cc1Cl]

The title compound was isolated as a yellow liquid (0.7 g, 95%): ¹H NMR (300 MHz, CDCl₃) δ 7.85 (d, J=6.0 Hz, 1H), 7.46 (d, J=1.8 Hz, 1H), 7.41 (s, 3H), 6.57 (d, J=16.0 Hz, 1H), 6.45 (dd, J=16.0, 8.0 Hz, 1H), 4.16 (m, 1H); ESIMS m/z 455 ([M+H]⁺); IR (thin film) 1728, 1115, 817 cm⁻¹.

(E)-4-(3-(3,5-Dichloro-4-fluorophenyl)-4,4,4-trifluorobut-1-enyl)-2-methylbenzoic acid (C97)

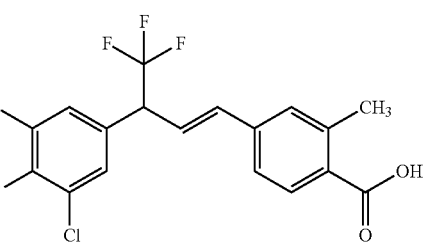

The title compound was isolated as a light brown gummy material (0.7 g, 38%): mp 91-93° C.; ¹H NMR (400 MHz, CDCl₃) δ 8.02 (d, J=8.0 Hz, 1H), 7.35 (d, J=5.6 Hz, 1H), 7.30 (m, 3H), 6.10 (d, J=16.0 Hz, 1H), 6.46 (dd, J=16.0, 8.0 Hz, 1H), 4.03 (m, 1H), 2.65 (s, 3H); ESIMS m/z 407 ([M−H]⁻).

(E)-4-(3-(3,5-Dichlorophenyl)-4,4,4-trifluorobut-1-enyl)-2-fluorobenzoic acid (C98)

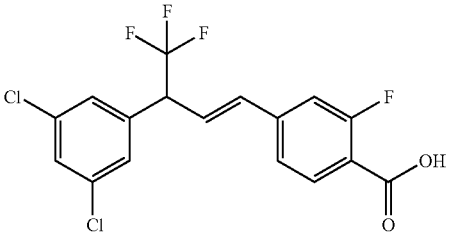 [SMILES: O=C(O)c1ccc(/C=C/C(c2cc(Cl)cc(Cl)c2)C(F)(F)F)cc1F]

The title compound was isolated as a light brown liquid (0.3 g, crude): ESIMS m/z 393 ([M−H]⁻).

(E)-2-Bromo-4-(3-(3,5-dichlorophenyl)-4,4,4-trifluorobut-1-enyl)benzoic acid (C99)

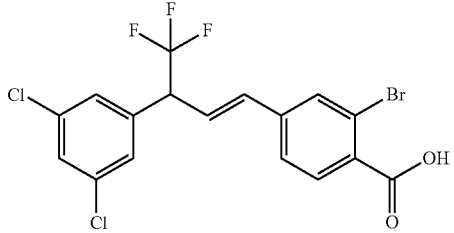 [SMILES: O=C(O)c1ccc(/C=C/C(c2cc(Cl)cc(Cl)c2)C(F)(F)F)cc1Br]

The title compound was isolated as a light brown liquid (0.35 g, crude): ESIMS m/z 452 ([M−H]⁻).

(E)-4-(3-(4-Bromo-3,5-dichlorophenyl)-4,4,4-trifluorobut-1-en-1-yl)-2-methylbenzoic acid (CA1)

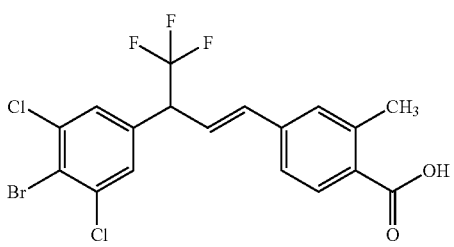

The title compound was isolated as a dark brown glass (0.900 g, 80%): ¹H NMR (500 MHz, CDCl₃) δ 8.05 (d, J=8.1 Hz, 1H), 7.40 (s, 2H), 7.30 (dd, J=8.2, 1.7 Hz, 1H), 7.28 (d, J=1.6 Hz, 1H), 6.60 (d, J=15.8 Hz, 1H), 6.44 (dd, J=15.9, 8.0 Hz, 1H), 4.11 (p, J=8.6 Hz, 1H), 2.66 (s, 3H); ¹⁹F NMR (471 MHz, CDCl₃) δ −68.63 (d, J=8.8 Hz); ESIMS m/z 466 ([M−H]⁻).

(E)-4-(3-(3,5-Dibromo-4-chlorophenyl)-4,4,4-trifluorobut-1-en-1-yl)-2-methylbenzoic acid (CA2)

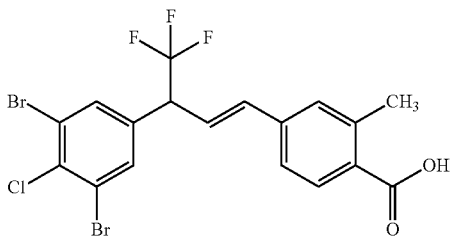

The title compound was isolated as a yellow glass (0.900 g, 68%): ¹H NMR (500 MHz, CDCl₃) δ 8.05 (d, J=8.1 Hz, 1H), 7.62 (s, 2H), 7.30 (dd, J=8.3, 1.7 Hz, 1H), 7.28 (d, J=1.5 Hz, 1H), 6.60 (d, J=15.8 Hz, 1H), 6.43 (dd, J=15.9, 8.0 Hz, 1H), 4.10 (p, J=8.6 Hz, 1H), 2.67 (s, 3H); ¹⁹F NMR (471 MHz, CDCl₃) δ −68.63 (d, J=8.8 Hz); ESIMS m/z 510 ([M−H]⁻).

(E)-4-(3-(3,5-Dibromophenyl)-4,4,4-trifluorobut-1-en-1-yl)-2-methylbenzoic acid (CA3)

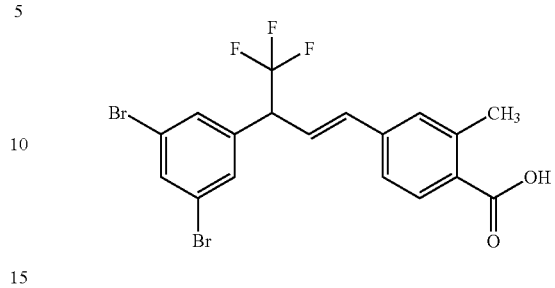

The title compound was isolated as a red solid (16.2 g, 82%): ¹H NMR (400 MHz, CDCl₃) δ 8.05 (d, J=8.1 Hz, 1H), 7.68 (t, J=1.7 Hz, 1H), 7.47 (d, J=1.7 Hz, 2H), 7.33-7.26 (m, 2H), 6.60 (d, J=15.8 Hz, 1H), 6.45 (dd, J=15.9, 8.0 Hz, 1H), 4.10 (p, 1=8.7 Hz, 1H), 2.67 (s, 3H); ¹⁹F NMR (376 MHz, CDCl₃) δ −68.54; ESIMS m/z 477 ([M−H]⁻).

Example 12: Preparation of (E)-4-(3-(3,5-dichloro-4-fluorophenyl)-4,4,4-trifluorobut-1-enyl)-2-(trifluoromethoxy)benzoic acid (C101)

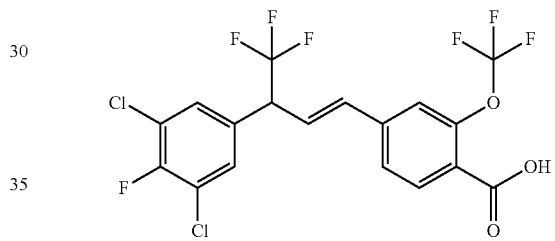

Step 1. 2-(Trifluoromethoxy)-4-vinylbenzoic acid (C100)

To a stirred solution of 4-bromo-2-(trifluoromethoxy) benzoic acid (1.00 g, 3.67 mmol) in dimethylsulfoxide (20 mL) was added potassium vinyltrifluoroborate (1.47 g, 11.0 mmol), and potassium carbonate (1.52 g, 11.0 mmol). The reaction mixture was degassed with argon for 30 minutes. Bistriphenylphosphine(diphenylphosphino ferrocene)palladium(II) dichloride (0.130 g, 0.180 mmol) was added and the reaction mixture was heated to 80° C. for 1 hour. The reaction mixture was diluted with water (100 mL), extracted with ethyl acetate (2×50 mL), washed with brine, and dried over sodium sulfate. Concentration under reduced pressure furnished the crude compound which was purified by flash column chromatography to afford the product as pale yellow gummy material (0.400 g, 47%): ¹H NMR (400 MHz, CDCl₃) δ 8.05 (d, J=8.1 Hz, 1H), 7.44 (d, J=1.8 Hz, 1H), 7.35 (s, 1H), 6.78 (dd, J=17.4.1, 11.1 Hz, 1H), 5.92 (d, J=17.4 Hz, 1H), 5.51 (d, J=10.8 Hz, 1H); ESIMS m/z 233 ([M+H]⁺).

Step 2. (E)-4-(3-(3,5-Dichloro-4-fluorophenyl)-4,4,4-trifluorobut-1-enyl)-2-(trifluoromethoxy)benzoic acid (C101)

To a stirred solution of 2-(trifluoromethoxy)-4-vinylbenzoic acid (0.356 g, 1.53 mmol) in 1N methyl pyrrolidine (5.0 mL) was added 1-(1-bromo-2,2,2-trifluoroethyl)-3,5-dichloro 4-fluorobenzene (1.0 g, 3.07 mmol), copper(I) chloride (CuCl; 0.03 g, 0.307 mmol) and 2,2 bipyridyl (0.095 g, 0.614 mmol). The reaction mixture was stirred at 150° C. for 1 h. After the reaction was complete by TLC, the reaction mixture was diluted with water (100 mL) and extracted with ethyl acetate (2×50 mL). The combined organic layers were washed with brine, dried over sodium sulfate and concentrated under reduced pressure to obtain the crude compound which was purified by flash column chromatography to afford the product as pale yellow gummy material (0.3 g, 21%): $^1$H NMR (400 MHz, CDCl$_3$) δ 8.08 (d, J=8.0 Hz, 1H), 7.45 (d, J=1.6 Hz, 1H), 7.35 (s, 3H), 6.63 (d, J=16.0 Hz, 1H), 6.50 (dd, J=16.0, 8.0 Hz, 1H), 4.15 (m, 1H); ESIMS m/z 474.81 ([M−H]$^−$).

The following molecules were made in accordance with the procedures disclosed in Step 2 in Example 12.

(E)-4-(3-(3,5-Dibromophenyl)-4,4,4-trifluorobut-1-en-1-yl)-2-(trifluoromethyl)benzoic acid (C102)

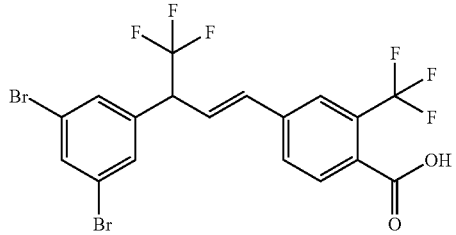 [SMILES: O=C(O)c1ccc(/C=C/C(c2cc(Br)cc(Br)c2)C(F)(F)F)cc1C(F)(F)F]

The title molecule was isolated as a brown solid: $^1$H NMR (300 MHz, DMSO-d$_6$) δ 13.5 (bs, 1H), 8.03 (s, 1H), 7.95-7.85 (m, 4H), 7.81 (d, J=7.8 Hz, 1H), 7.14 (dd, J=15.6, 9.6 Hz, 1H), 6.90 (d, J=15.9 Hz, 1H), 4.86-4.79 (m, 1H); ESIMS m/z 529 ([M−H]+); IR (thin film) 3437, 1707, 1153, 555 cm$^{-1}$.

(E)-4-(3-(3,5-Dibromo-4-chlorophenyl)-4,4,4-trifluorobut-1-en-1-yl)-2-(trifluoromethyl)benzoic acid (C103)

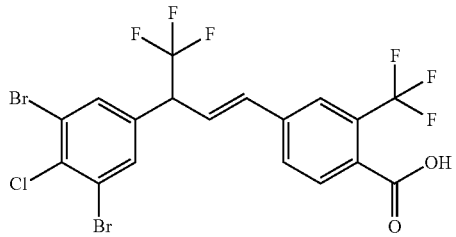 [SMILES: O=C(O)c1ccc(/C=C/C(c2cc(Br)c(Cl)c(Br)c2)C(F)(F)F)cc1C(F)(F)F]

Isolated as a brown gum: $^1$H NMR (300 MHz, DMSO-d$_6$) δ, 13.36 (bs, 1H) 8.05 (s, 2H), 7.95 (d, J=8.1 Hz, 1H), 7.87-7.67 (m, 2H), 7.14 (dd, J=9.0, 15.6 Hz, 1H), 6.96 (d, J=15.6 Hz, 1H), 4.88-4.82 (m, 1H); ESIMS m/z 565 ([M+H]$^+$).

(E)-4-(3-(4-Bromo-3,5-dichlorophenyl)-4,4,4-trifluorobut-1-en-1-yl)-2-(trifluoromethyl)benzoic acid (C104)

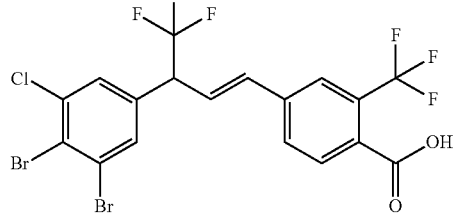

Isolated as a brown gum: $^1$H NMR (300 MHz, DMSO-d$_6$) δ 13.6 (bs, 1H) 8.03 (s, 1H), 7.95 (d, J=8.4 Hz, 1H), 7.88 (s, 2H), 7.81 (d, J=8.1 Hz, 1H), 7.13 (dd, J=16.2, 7.5 Hz, 1H), 6.91 (d, J=15.9 Hz, 1H), 4.89-4.83 (m, 1H); ESIMS m/z 532 ([M+H]$^+$).

(E)-4-(3-(3,5-Dichloro-4-fluorophenyl)-4,4,4-trifluorobut-1-en-1-yl)-2-(trifluoromethyl)benzoic acid (C105)

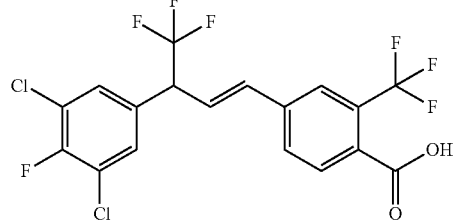

The title molecule was isolated as an off white solid: mp 140-143° C.; $^1$H NMR (400 MHz, DMSO-d6) δ13.60 (bs, 1H), 8.02 (s, 1H), 7.94-7.90 (m, 1H), 7.88-7.86 (m, 2H), 7.81-7.79 (m, 1H), 7.12 (dd, J=15.6, 8.8 Hz, 1H), 6.89 (d, J=15.6 Hz, 1H), 4.86-4.81 (m, 2H); ESIMS m/z 459 ([M−H]$^−$).

Example 13: Preparation of (E)-4-(4,4,4-trifluoro-3-(3,4,5-trichlorophenyl)but-1-en-1-yl)-2-(trifluoromethyl)benzoyl chloride (C106)

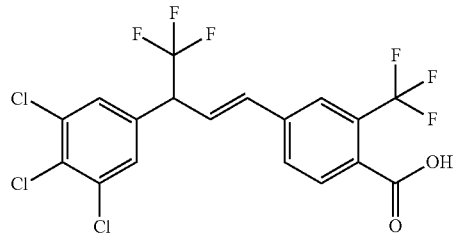 [SMILES: O=C(O)c1ccc(/C=C/C(c2cc(Cl)c(Cl)c(Cl)c2)C(F)(F)F)cc1C(F)(F)F]

To a round-bottomed flask (500 mL) equipped with a drying tube, a magnetic stir bar, and (E)-4-(4,4,4-trifluoro-3-(3,4,5-trichlorophenyl)but-1-enyl)-2-(trifluoromethyl) benzoic acid (C92) (8.70 g, 18.2 mmol) was added dichloromethane (30 mL). To this stirred solution oxalyl dichloride (3.12 mL, 36.4 mmol) was added and the reaction was left to stir for 65 hours. The solution was concentrated under reduced pressure and the resulting red oil was diluted with cyclohexane and concentrated under reduced pressure. The resulting red oil was placed in a 40° C. vacuum oven for 18 hours provided the title compound as a red gum (8.28 g, 92%): $^1$H NMR (400 MHz, CDCl$_3$) δ 8.05 (d, J=8.2 Hz, 1H), 7.83-7.75 (m, 1H), 7.70 (dd, J=8.2, 1.7 Hz, 1H), 7.42 (s, 2H), 6.67 (d, J=16.0 Hz, 1H), 6.55 (dd, J=15.9, 7.6 Hz, 1H), 4.16 (p, J=8.5 Hz, 1H); $^{19}$F NMR (376 MHz, CDCl$_3$) δ −59.59, −68.47; $^{13}$C NMR (101 MHz, CDCl$_3$) δ 165.62, 140.39, 135.01, 134.03, 133.68 (q, J=1.8 Hz), 133.18 (q, J=1.8 Hz), 132.29, 132.20, 129.63, 129.13 (q, J=33.4 Hz), 129.09, 126.32 (q, J=2.4 Hz), 125.67 (q, J=281.4 Hz), 125.28 (q, J=5.6 Hz), 122.45 (q, J=274.1 Hz), 52.38 (q, J=28.9 Hz).

Example 14: Preparation of N—((R)-1-amino-1-oxopropan-2-yl)-4-((E)-4,4,4-trifluoro-3-(3,4,5-trichlorophenyl)but-1-en-1-yl)-2-(trifluoromethyl)benzamide (C107)

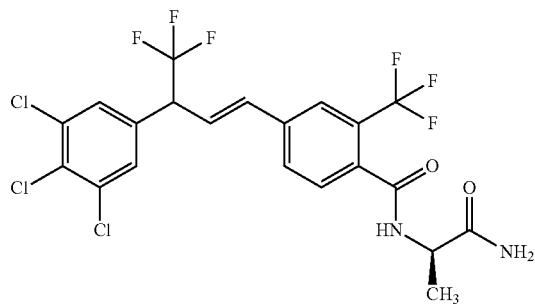 [SMILES: C[C@@H](NC(=O)c1ccc(/C=C/C(c2cc(Cl)c(Cl)c(Cl)c2)C(F)(F)F)cc1C(F)(F)F)C(N)=O]

To a vial (30 mL) containing a magnetic stir bar and (E)-4-(4,4,4-trifluoro-3-(3,4,5-trichlorophenyl)but-1-en-1-yl)-2-(trifluoromethyl)benzoyl chloride (C106) (0.980 g, 1.98 mmol) was added 1,2-dichloroethane (7.9 mL) to give a brown solution. (R)-2-Aminopropanamide-hydrochloride (0.295 g, 2.37 mmol) and 4-methylmorpholine (0.652 mL, 5.93 mmol) were added and the vial was capped and left to stir overnight. The reaction was diluted with ethyl acetate (100 mL) and citric acid (5%, 100 mL). The layers were separated and the organic layer was washed with an additional citric acid (5%, 100 mL), water (100 mL), saturated aqueous sodium bicarbonate (100 mL), and brine (20 mL). The organic phase was dried with sodium sulfate, filtered, and concentrated to give a red/brown oil. The oil was purified by flash column chromatography using 0-100% ethyl acetate/hexanes as eluent. The title compound was isolated as a beige solid (0.479 g, 44%): $^1$H NMR (400 MHz, CDCl$_3$) δ 7.68 (s, 1H), 7.58 (dd, J=8.0, 1.7 Hz, 1H), 7.51 (d, J=8.0 Hz, 1H), 7.42 (s, 2H), 6.73 (d, J=7.4 Hz, 1H), 6.62 (d, J=15.9 Hz, 1H), 6.52 (s, 1H), 6.44 (dd, J=15.9, 7.8 Hz, 1H), 5.64 (s, 1H), 4.78 (p, J=7.1 Hz, 1H), 4.21 (m, 1H), 1.50 (d, J=6.9 Hz, 3H); $^{19}$F NMR (376 MHz, CDCl$_3$) δ −59.02, −68.56; ESIMS m/z 549 ([M+H]$^+$).

Example 15: Preparation of (E)-N-(2-amino-2-oxoethyl)-4-(4,4,4-trifluoro-3-(3,4,5-trichlorophenyl)but-1-en-1-yl)-2-(trifluoromethyl)benzamide (C108)

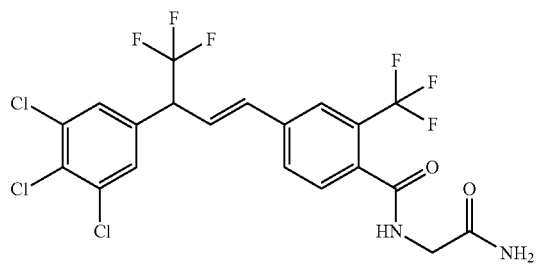 [SMILES: NC(=O)CNC(=O)c1ccc(/C=C/C(c2cc(Cl)c(Cl)c(Cl)c2)C(F)(F)F)cc1C(F)(F)F]

Into a vial (30 mL) equipped with a magnetic stir bar was added 2-aminoacetamide.hydrochloride (0.555 g, 5.02 mmol), (E)-4-(4,4,4-trifluoro-3-(3,4,5-trichlorophenyl)but-1-en-1-yl)-2-(trifluoromethyl)benzoic acid (C106) (2.00 g, 4.19 mmol), (1-cyano-2-ethoxy-2-oxoethylidenaminooxy)dimethylamino-morpholino-carbenium hexafluorophosphate (2.15 g, 5.02 mmol) and 1,2-dichloroethane (15 mL). 4-Methylmorpholine (1.38 mL, 12.6 mmol) was added to this brown solution and the reaction was capped and left to stir overnight. The reaction was diluted with ethyl acetate (150 mL) and (100 mL). The layers were separated and the organic layer was washed with an additional hydrochloric acid (1 M, 100 mL), water (100 mL), saturated aqueous sodium bicarbonate (100 mL), and brine (20 mL). The organic phase was dried with magnesium sulfate, filtered, and concentrated to give a red/brown oil. The oil was purified by flash column chromatography using 0-100% ethyl acetate/hexanes. The title compound was isolated as a beige solid (1.62, 72%): $^1$H NMR (400 MHz, CDCl$_3$) δ 7.72-7.67 (m, 1H), 7.61 (dd, J=8.0, 1.7 Hz, 1H), 7.55 (d, J=8.0 Hz, 1H), 7.42 (s, 2H), 6.71 (t, J=5.1 Hz, 1H), 6.63 (d, J=15.9 Hz, 1H), 6.45 (dd, J=15.9, 7.8 Hz, 1H), 6.24 (s, 1H), 5.56 (s, 1H), 4.19 (d, J=5.0 Hz, 2H), 4.16-4.08 (m, 1H); $^{19}$F NMR (376 MHz, CDCl$_3$) δ −59.15, −68.56; ESIMS m/z 535 ([M+H]$^+$).

The following compound was prepared in accordance to the procedure in Example 15.

N—((R)-1-Amino-1-oxobutan-2-yl)-4-((E)-4,4,4-trifluoro-3-(3,4,5-trichlorophenyl)but-1-en-1-yl)-2-(trifluoromethyl)benzamide (C109)

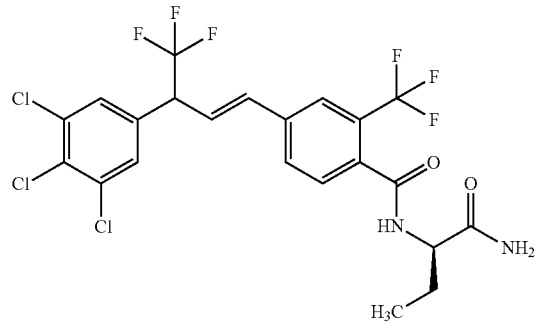 [SMILES: CC[C@@H](NC(=O)c1ccc(/C=C/C(c2cc(Cl)c(Cl)c(Cl)c2)C(F)(F)F)cc1C(F)(F)F)C(N)=O]

The title compound was prepared with (R)-2-aminobutanamide.hydrochloride in place of 2-aminoacetamide.hydrochloride (2.87, 71%): $^1$H NMR (400 MHz, CDCl$_3$) δ 7.70-7.65 (m, 1H), 7.57 (dd, J=8.0, 1.7 Hz, 1H), 7.50 (d, J=8.0 Hz, 1H), 7.42 (s, 2H), 6.74 (dd, J=7.8, 1.4 Hz, 1H), 6.62 (d, J=15.9 Hz, 1H), 6.57-6.49 (m, 1H), 6.44 (dd, J=15.9, 7.8 Hz, 1H), 5.72 (s, 1H), 4.71 (dt, J=7.7, 6.3 Hz, 1H), 4.19-4.05 (m, 1H), 1.99 (ddd, J=13.7, 7.4, 6.1 Hz, 1H), 1.85-1.70 (m, 1H), 1.01 (t, J=7.4 Hz, 3H); $^{19}$F NMR (376 MHz, CDCl$_3$) δ −59.11, −68.57; ESIMS m/z 561 ([M−H]$^−$).

Example 16: Preparation of N—((R)-1-aminoethyl)-4-((E)-4,4,4-trifluoro-3-(3,4,5-trichlorophenyl)but-1-en-1-yl)-2-(trifluoromethyl)benzamide.hydrochloride (C110)

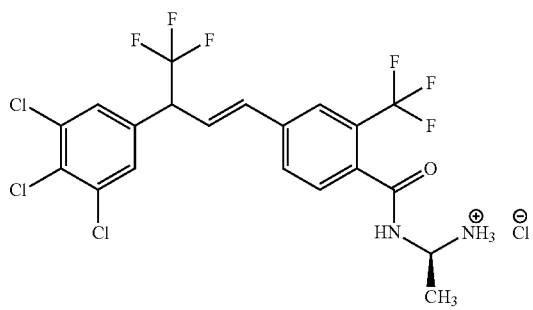 [SMILES: C[C@H]([NH3+])NC(=O)c1ccc(/C=C/C(c2cc(Cl)c(Cl)c(Cl)c2)C(F)(F)F)cc1C(F)(F)F ; [Cl-]]

To a vial (5 mL) wrapped in aluminium foil containing a magnetic stir vane and N—((R)-1-amino-1-oxopropan-2-yl)-4-((E)-4,4,4-trifluoro-3-(3,4,5-trichlorophenyl)but-1-en-1-yl)-2-(trifluoromethyl)benzamide (C107) (0.050 g, 0.091 mmol) was added acetonitrile (0.400 mL) and water (0.200 mL) to give a pale beige solution. [I,I-Bis(trifluoroacetoxy)iodo]benzene (0.039 g, 0.091 mmol, freshly prepared as described in *J. Org. Chem.*, 1984, 49, 4272-4276) was added and the reaction was left to stir for 2.5 hours. The crude reaction mixture was adsorbed onto Celite® (5 g) and was purified by reverse phase chromatography (C-18) using 10-100% acetonitrile/water as eluent. The title compound was isolated as an off-white solid (0.031 g, 66%): $^1$H NMR (400 MHz, DMSO-d$_6$) δ 9.49 (d, J=7.3 Hz, 1H), 8.44 (s, 3H), 8.05 (s, 1H), 7.97 (dt, J=8.4, 1.8 Hz, 1H), 7.94 (s, 2H), 7.61 (d, J=8.0 Hz, 1H), 7.10 (dd, J=15.8, 9.1 Hz, 1H), 6.90 (d, J=15.8 Hz, 1H), 5.13 (p, J=6.6 Hz, 1H), 4.90 (p, J=9.4 Hz, 1H), 1.45 (d, J=6.5 Hz, 3H); $^{19}$F NMR (376 MHz, DMSO-d$_6$) δ −57.73, −67.93; ESIMS m/z 519 ([M−H]$^-$).

The following compounds were prepared in accordance to the procedure in Example 16.

N—((R)-1-Aminopropyl)-4-((E)-4,4,4-trifluoro-3-(3,4,5-trichlorophenyl)but-1-en-1-yl)-2-(trifluoromethyl)benzamide.hydrochloride (C111)

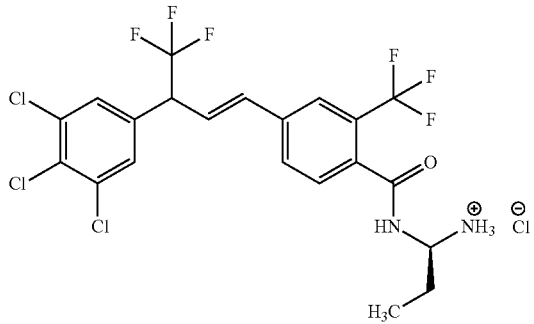 [SMILES: CC[C@H]([NH3+])NC(=O)c1ccc(/C=C/C(c2cc(Cl)c(Cl)c(Cl)c2)C(F)(F)F)cc1C(F)(F)F ; [Cl-]]

The title compound was prepared with N—((R)-1-amino-1-oxobutan-2-yl)-4-((E)-4,4,4-trifluoro-3-(3,4,5-trichlorophenyl)but-1-en-1-yl)-2-(trifluoromethyl)benzamide (C109) in place of N—((R)-1-amino-1-oxopropan-2-yl)-4-((E)-4,4,4-trifluoro-3-(3,4,5-trichlorophenyl)but-1-en-1-yl)-2-(trifluoromethyl)benzamide (C107) (0.910 g, 30%): $^1$H NMR (400 MHz, DMSO-d$_6$) δ 9.39 (dd, J=8.2, 1.4 Hz, 1H), 8.57-8.43 (m, 3H), 8.05 (t, J=1.7 Hz, 1H), 7.98 (dd, J=8.1, 1.9 Hz, 1H), 7.93 (s, 2H), 7.61 (d, J=8.0 Hz, 1H), 7.09 (dd, J=15.8, 9.1 Hz, 1H), 6.89 (d, J=15.7 Hz, 1H), 4.91 (m, 2H), 1.81 (m, 2H), 0.93 (t, J=7.3 Hz, 3H); $^{19}$F NMR (376 MHz, DMSO-d$_6$) δ −57.80, −67.93; ESIMS m/z 533 ([M−H]$^-$)

(E)-N-(Aminomethyl)-4-(4,4,4-trifluoro-3-(3,4,5-trichlorophenyl)but-1-en-1-yl)-2-(trifluoromethyl)benzamide.hydrochloride (C112)

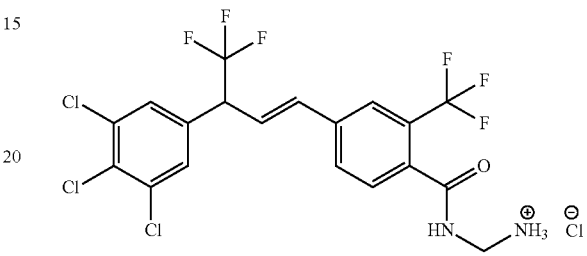

The title compound was prepared with (E)-N-(2-amino-2-oxoethyl)-4-(4,4,4-trifluoro-3-(3,4,5-trichlorophenyl)but-1-en-1-yl)-2-(trifluoromethyl)benzamide (C108) used in place of N—((R)-1-amino-1-oxopropan-2-yl)-4-((E)-4,4,4-trifluoro-3-(3,4,5-trichlorophenyl)but-1-en-1-yl)-2-(trifluoromethyl)benzamide (C107) (0.710 g, 50%): $^1$H NMR (400 MHz, DMSO-d$_6$) δ 9.27 (t, J=6.0 Hz, 1H), 8.03 (d, J=1.6 Hz, 1H), 7.95 (dd, J=8.2, 1.9 Hz, 1H), 7.93 (s, 2H), 7.57 (d, J=8.0 Hz, 1H), 7.09 (dd, J=15.8, 9.1 Hz, 1H), 6.89 (d, J=15.7 Hz, 1H), 6.52 (s, 3H), 4.88 (p, J=9.3 Hz, 1H), 4.26 (d, J=6.0 Hz, 2H); $^{19}$F NMR (376 MHz, DMSO-d$_6$) δ −57.74, −67.95; ESIMS m/z 505 ([M−H]$^-$).

Example 17: Preparation of N—((R)-1-hexanamidoethyl)-4-((E)-4,4,4-trifluoro-3-(3,4,5-trichlorophenyl)but-1-en-1-yl)-2-(trifluoromethyl)benzamide (F3)

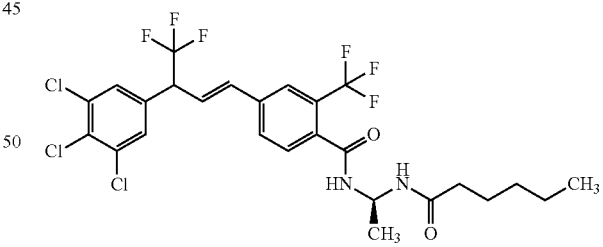

Into a vial (4 mL) equipped with a magnetic stir vane were placed dry dichloromethane (1.5 mL), N—((R)-1-aminoethyl)-4-((E)-4,4,4-trifluoro-3-(3,4,5-trichlorophenyl)but-1-en-1-yl)-2-(trifluoromethyl)benzamidehydrochloride (C110) (0.100 g, 0.180 mmol) and hexanoyl chloride (0.0380 mL, 0.270 mmol). To this solution was added 4-methylmorpholine (0.0500 mL, 0.450 mmol). The resulting suspension was stirred overnight. The reaction mixture was diluted with ethyl acetate (20 mL) and citric acid (5%, 20 mL). The layers were separated and the aqueous phase was extracted with additional ethyl acetate. The pooled organic layers were dried with sodium sulfate, filtered, and concentrated. The resulting material was purified by flash column chromatography using 0-100% ethyl acetate/hexanes as eluent. The title compound was isolated as an off-white foam (0.0860 g, 78%).

The following compounds were prepared in accordance to the procedure in Example 17.

N—((R)-1-(4-Methylpentanamido)ethyl)-4-((E)-4,4,4-trifluoro-3-(3,4,5-trichlorophenyl) but-1-en-1-yl)-2-(trifluoromethyl)benzamide (F4)

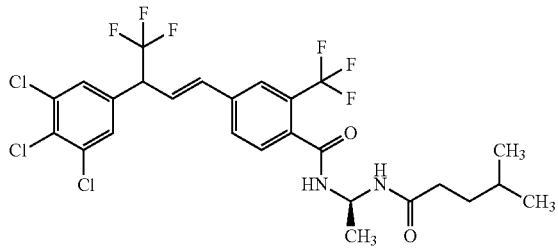 [SMILES: CC(C)CCC(=O)N[C@@H](C)NC(=O)c1ccc(/C=C/C(c2cc(Cl)c(Cl)c(Cl)c2)C(F)(F)F)cc1C(F)(F)F]

The title compound was prepared using 4-methylpentanoyl chloride and isolated as an off-white foam/glass (0.037 g, 34%).

N—((R)-1-Pentanamidoethyl)-4-((E)-4,4,4-trifluoro-3-(3,4,5-trichlorophenyl) but-1-en-1-yl)-2-(trifluoromethyl)benzamide (F5)

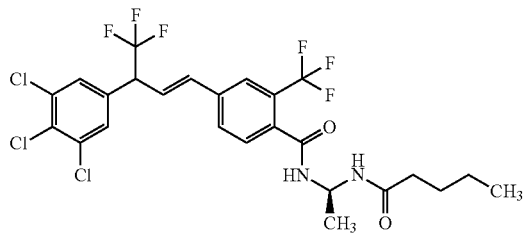 [SMILES: CCCCC(=O)N[C@@H](C)NC(=O)c1ccc(/C=C/C(c2cc(Cl)c(Cl)c(Cl)c2)C(F)(F)F)cc1C(F)(F)F]

The title compound was prepared using pentanoyl chloride and isolated as an off-white foam/solid (0.028 g, 26%).

N—((R)-1-(3-Methylbutanamido)ethyl)-4-((E)-4,4,4-trifluoro-3-(3,4,5-trichlorophenyl) but-1-en-1-yl)-2-(trifluoromethyl)benzamide (F6)

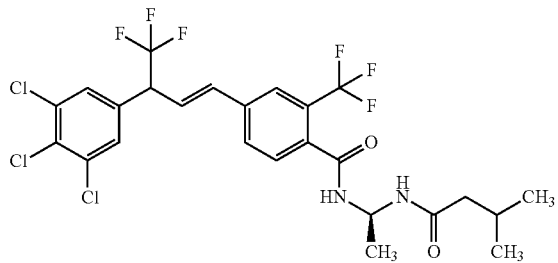

The title compound was prepared using 3-methylbutanoyl chloride and isolated as an off-white foam (0.038 g, 35%).

N—((R)-1-(Cyclopropanecarboxamido)ethyl)-4-((E)-4,4,4-trifluoro-3-(3,4,5-trichlorophenyl) but-1-en-1-yl)-2-(trifluoromethyl)benzamide (F7)

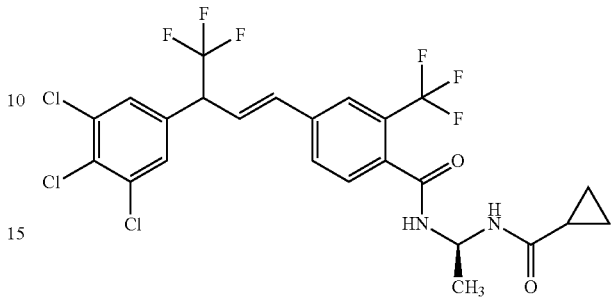

The title compound was prepared using cyclopropanecarbonyl chloride and isolated as a colorless glass/foam (0.145 g, 55%).

N—((R)-1-(3-Methylbut-2-enamido)ethyl)-4-((E)-4,4,4-trifluoro-3-(3,4,5-trichlorophenyl) but-1-en-1-yl)-2-(trifluoromethyl)benzamide (F8)

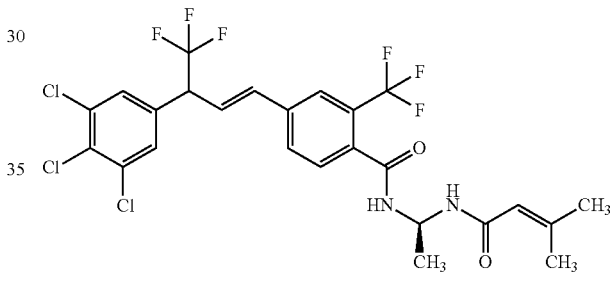

The title compound was prepared using 3-methylbut-2-enoyl chloride and isolated as a colorless glass/foam (0.096 g, 55%).

Example 18: Preparation of 4-((E)-4,4,4-trifluoro-3-(3,4,5-trichlorophenyl)but-1-en-1-yl)-2-(trifluoromethyl)-N—((R)-1-(3,3,3-trifluoropropanamido)ethyl)benzamide (F2)

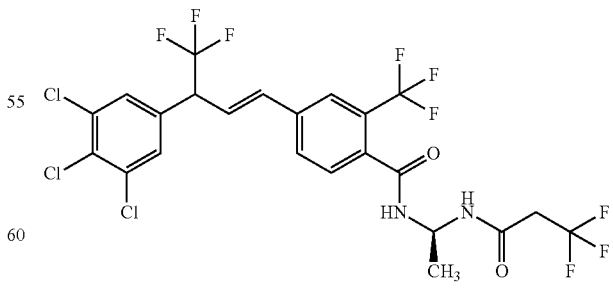

Into a vial (5 mL) equipped with a magnetic stir vane was placed N—((R)-1-aminoethyl)-4-((E)-4,4,4-trifluoro-3-(3,4,5-trichlorophenyl)but-1-en-1-yl)-2-(trifluoromethyl)benzamide.hydrochloride (C110) (0.117 g, 0.210 mmol) and 1,2-dichloroethane (3 mL). 3,3,3-Trifluoropropanoyl chloride (0.0390 g, 0.266 mmol) was added and two minutes later 4-methylmorpholine (0.0690 mL, 0.631 mmol) was added. The reaction was vortexed 5 times over a 2 minute period. After the second vortex, the solution became cloudy. The reaction was left to stir for an additional 1.5 hours. Purification by flash column chromatography using 0-100% ethyl acetate/hexanes as eluent. The title compound was isolated as an off-white solid (0.060 g, 46%).

The following compounds were prepared in accordance to the procedure in Example 18.

4-((E)-4,4,4-Trifluoro-3-(3,4,5-trichlorophenyl)but-1-en-1-yl)-N—((R)-1-(4,4,4-trifluorobutanamido)ethyl)-2-(trifluoromethyl)benzamide (F1)

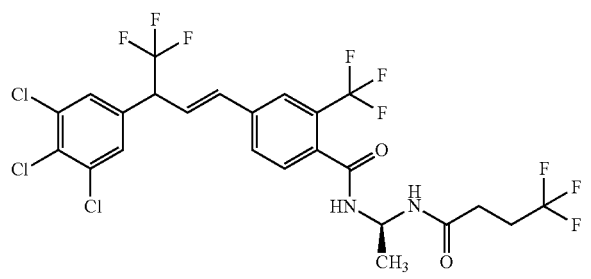

The title compound was prepared using 4,4,4-trifluorobutanoyl chloride and isolated as an off-white solid (0.066 g, 65%).

4-((E)-4,4,4-Trifluoro-3-(3,4,5-trichlorophenyl)but-1-en-1-yl)-N—((R)-1-(4,4,4-trifluorobutanamido)propyl)-2-(trifluoromethyl)benzamide (F12)

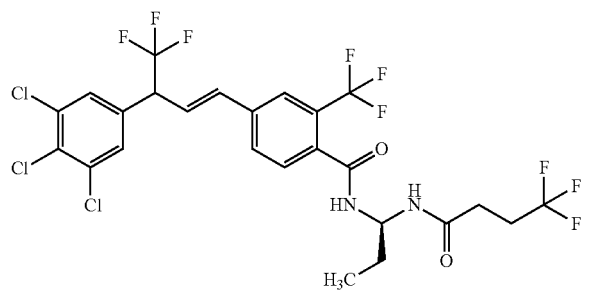 [SMILES: CC[C@H](NC(=O)CCC(F)(F)F)NC(=O)c1ccc(/C=C/C(c2cc(Cl)c(Cl)c(Cl)c2)C(F)(F)F)cc1C(F)(F)F]

The title compound was prepared using N—((R)-1-aminopropyl)-4-((E)-4,4,4-trifluoro-3-(3,4,5-trichlorophenyl)but-1-en-1-yl)-2-(trifluoromethyl)benzamide.hydrochloride (C111) and 4,4,4-trifluorobutanoyl chloride and isolated as a white solid (0.084 g, 49%).

(E)-4-(4,4,4-Trifluoro-3-(3,4,5-trichlorophenyl)but-1-en-1-yl)-N-((4,4,4-trifluorobutanamido)methyl)-2-(trifluoromethyl)benzamide (F13)

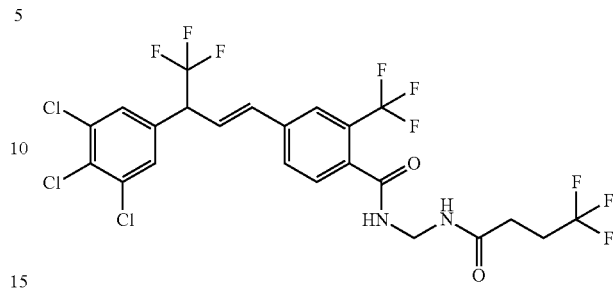

The title compound was prepared using (E)-N-(aminomethyl)-4-(4,4,4-trifluoro-3-(3,4,5-trichlorophenyl)but-1-en-1-yl)-2-(trifluoromethyl)benzamidehydrochloride (C112) and 4,4,4-trifluorobutanoyl chloride and isolated as a pale yellow solid (0.040 g, 20%).

N—((S)-1-Pivalamidoethyl)-4-((E)-4,4,4-trifluoro-3-(3,4,5-trichlorophenyl)but-1-en-1-yl)-2-(trifluoromethyl)benzamide (F19)

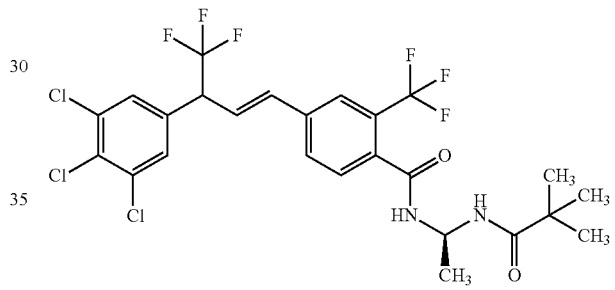

The title compound was prepared using pivaloyl chloride and isolated as a white solid (0.104 g, 64%).

Example 19: Preparation of N—((S)-1-(1-cyanocyclopropanecarboxamido)ethyl)-4-((E)-4,4,4-trifluoro-3-(3,4,5-trichlorophenyl) but-1-en-1-yl)-2-(trifluoromethyl)benzamide (F14)

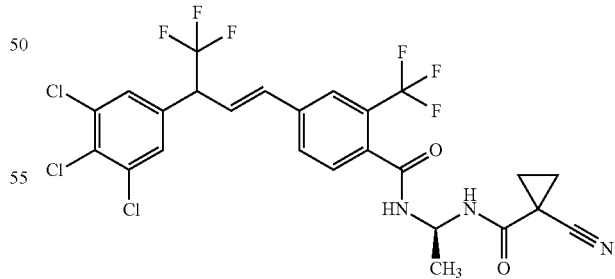

Into a vial (5 mL) equipped with a magnetic stir vane was placed 1-cyanocyclopropanecarboxylic acid (0.052 g, 0.47 mmol) and 1,2-dichloroethane (1.3 mL). Oxalyl chloride (0.040 mL, 0.47 mmol) and dimethylformamide (~1 drop) were added and the reaction was left to stir at room temperature for 3 hours. N—((R)-1-aminoethyl)-4-((E)-4,4,4-trifluoro-3-(3,4,5-trichlorophenyl)but-1-en-1-yl)-2-(trifluororomethyl)benzamide.hydrochloride (C110) (0.15 g, 0.27 mmol) and 4-methylmorpholine (0.089 mL, 0.81 mmol) were added and the reaction was capped, vortexed and left to stir. Purification by flash column chromatography using 0-100% ethyl acetate/hexanes as eluent. The title compound was isolated as a colorless foam (0.135 g, 82%).

The following compounds were prepared in accordance to the procedure in Example 19.

N—((R)-1-(3,3-Dimethylbutanamido)ethyl)-4-((E)-4,4,4-trifluoro-3-(3,4,5-trichlorophenyl)but-1-en-1-yl)-2-(trifluoromethyl)benzamide (F15)

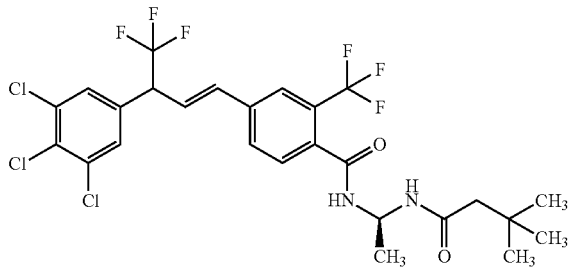 [SMILES: C[C@H](NC(=O)CC(C)(C)C)NC(=O)c1ccc(/C=C/C(c2cc(Cl)c(Cl)c(Cl)c2)C(F)(F)F)cc1C(F)(F)F]

The title compound was prepared using 3,3-dimethylbutanoic acid and isolated as a colorless glass (0.109 g, 65%).

N—((R)-1-(4,4-Dimethylpentanamido)ethyl)-4-((E)-4,4,4-trifluoro-3-(3,4,5-trichlorophenyl) but-1-en-1-yl)-2-(trifluoromethyl)benzamide (F17)

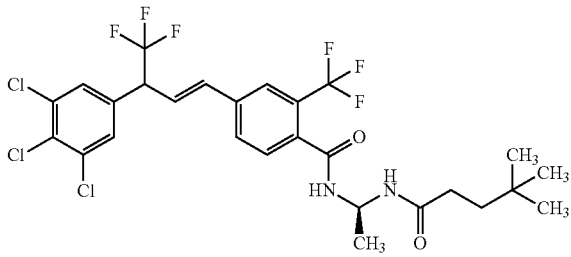 [SMILES: C[C@H](NC(=O)CCC(C)(C)C)NC(=O)c1ccc(/C=C/C(c2cc(Cl)c(Cl)c(Cl)c2)C(F)(F)F)cc1C(F)(F)F]

The title compound was prepared using 4,4-dimethylpentanoic acid and isolated as a colorless foam (0.104 g, 61%).

4-((E)-4,4,4-Trifluoro-3-(3,4,5-trichlorophenyl)but-1-en-1-yl)-N-((1R)-1-(4,4,4-trifluoro-3-methylbutanamido)ethyl)-2-(trifluoromethyl)benzamide (F16)

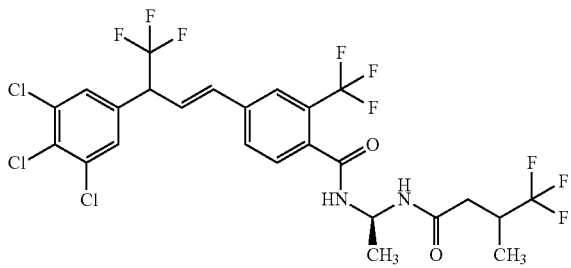

The title compound was prepared using 4,4,4-trifluoro-3-methylbutanoic acid and isolated as a white solid (0.105 g, 59%).

N—((R)-1-(5,5-Dimethylhexanamido)ethyl)-4-((E)-4,4,4-trifluoro-3-(3,4,5-trichlorophenyl) but-1-en-1-yl)-2-(trifluoromethyl)benzamide (F18)

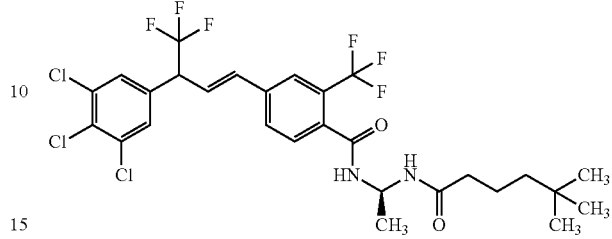

The title compound was prepared using 5,5-dimethylhexanoic acid and isolated as a white solid (0.100 g, 57%).

N—((R)-1-(4,4,4-Trifluoro-2-methylbutanamido)ethyl)-4-((E)-4,4,4-trifluoro-3-(3,4,5-trichlorophenyl)but-1-en-1-yl)-2-(trifluoromethyl)benzamide (P30)

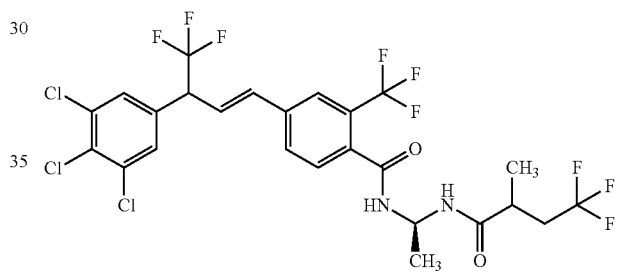

Isolated as a colorless glass (0.096 g, 24%).

N—((S)-1-(3,3,3-Trifluoro-2,2-dimethylpropanamido)ethyl)-4-((E)-4,4,4-trifluoro-3-(3,4,5-trichlorophenyl)but-1-en-1-yl)-2-(trifluoromethyl)benzamide (P33)

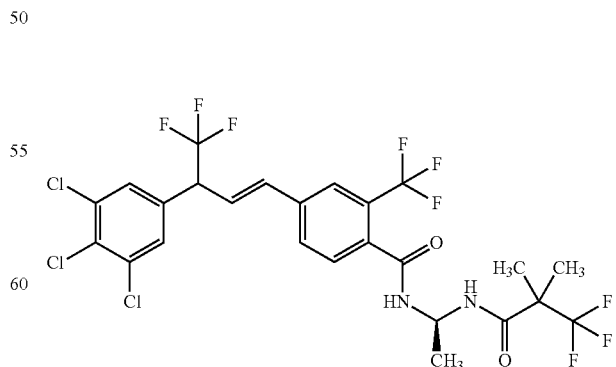

Isolated as a white solid (0.101 g, 51%).

Example 20: Preparation of N—((R)-1-(3-cyano-propanamido)ethyl)-4-((E)-4,4,4-trifluoro-3-(3,4,5-trichlorophenyl)but-1-en-1-yl)-2-(trifluoromethyl)benzamide (F9)

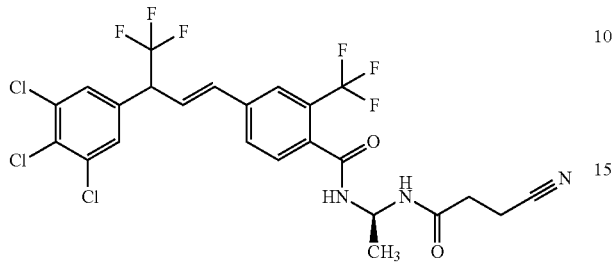

Into a vial (4 mL) equipped with a stir vane was placed 3-cyanopropanoic acid (0.080 g, 0.81 mmol)), (1-cyano-2-ethoxy-2-oxoethylidenaminooxy)dimethylamino-morpholino-carbenium hexafluorophosphate (0.37 g, 0.86 mmol), and 4-methylmorpholine (0.14 g, 1.3 mmol). Dimethylformamide (1 mL) was added and the reaction was stirred at room temperature for 5 minutes. N—((R)-1-Aminoethyl)-4-((E)-4,4,4-trifluoro-3-(3,4,5-trichlorophenyl)but-1-en-1-yl)-2-(trifluoromethyl)benzamide.hydrochloride (C110) (0.30 g, 0.54 mmol) was dissolved in dimethylformamide (0.5 mL) and was added drop-wise. The mixture was then stirred at room temperature overnight. The resulting solution was diluted with ethyl acetate (~20 mL) and was washed with water. The organic layer was dried with sodium sulfate, filtered, and concentrated. The resulting material was purified via flash column chromatography using 35% ethyl acetate/hexanes as eluent to provide the title compound as a brown glass/foam (0.073 g, 23%).

The following compounds were prepared in accordance to the procedure in Example 20.

4-((E)-4,4,4-Trifluoro-3-(3,4,5-trichlorophenyl)but-1-en-1-yl)-2-(trifluoromethyl)-N—((R)-1-(5,5,5-trifluoropentanamido)ethyl)benzamide (F10)

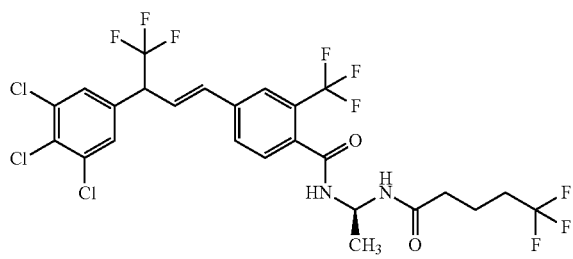

The title compound was prepared using 5,5,5-trifluoropentanoic acid and isolated as a colorless glass/foam (0.173 g, 49%).

N—((R)-1-(2-Cyanoacetamido)ethyl)-4-((E)-4,4,4-trifluoro-3-(3,4,5-trichlorophenyl)but-1-en-1-yl)-2-(trifluoromethyl)benzamide (F11)

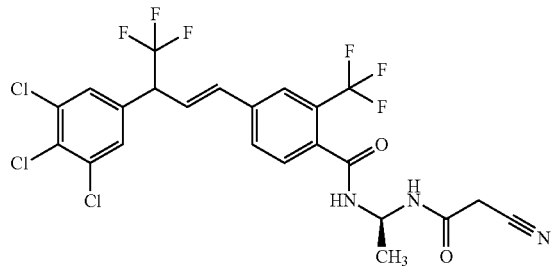 [SMILES: C[C@H](NC(=O)CC#N)NC(=O)c1ccc(/C=C/C(c2cc(Cl)c(Cl)c(Cl)c2)C(F)(F)F)cc1C(F)(F)F]

The title compound was prepared using 2-cyanoacetic acid and isolated as an off-white foam/glass (0.132 g, 42%).

Example 21: Preparation of (E)-tert-butyl methyl(2-(4-(4,4,4-trifluoro-3-(3,4,5-trichlorophenyl) but-1-en-1-yl)-2-(trifluoromethyl)benzamido)ethyl)carbamate (C113)

Into a round-bottomed flask (250 mL) was added (E)-4-(4,4,4-trifluoro-3-(3,4,5-trichlorophenyl)but-1-en-1-yl)-2-(trifluoromethyl)benzoic acid (C92) (0.75 g, 1.6 mmol), tert-butyl(2-aminoethyl)(methyl)carbamate (0.56 mL, 3.1 mmol), 1H-benzo[d][1,2,3]triazol-1-ol hydrate (0.24 g, 1.6 mmol), and 2-(1H-benzo[d][1,2,3]triazol-1-yl)-1,1,3,3-tetramethyluronium hexafluorophosphate(V) (0.60 g, 1.6 mmol) and acetonitrile (27 mL) under nitrogen. N-Ethyl-N-isopropylpropan-2-amine (0.55 mL, 3.1 mmol) was then added dropwise and the reaction was allowed to stir at room temperature overnight. The reaction mixture was then filtered through a silica gel frit, concentrated, purified by flash column chromatography using ethyl acetate/hexanes as eluent to provide the title compound as a light brown foam (0.40 g, 38%): $^1$H NMR (400 MHz, CDCl$_3$) δ 7.66 (s, 1H), 7.57-7.46 (m, 2H), 7.42 (s, 2H), 6.74 (s, 1H), 6.61 (d, J=15.9 Hz, 1H), 6.42 (dd, J=15.9, 7.8 Hz, 1H), 4.12 (p, J=8.4 Hz, 1H), 3.60 (dt, J=6.1, 4.7 Hz, 2H), 3.48 (d, J=6.2 Hz, 2H), 2.92 (s, 3H), 1.40 (s, 9H); $^{19}$F NMR (376 MHz, CDCl$_3$) δ −59.31, −68.58; ESIMS m/z 633 ([M−H]$^-$).

Example 22: Preparation of (E)-N-(2-(methyl-amino)ethyl)-4-(4,4,4-trifluoro-3-(3,4,5-trichloro-phenyl)but-1-en-1-yl)-2-(trifluoromethyl)benzamide.hydrochloride (C114)

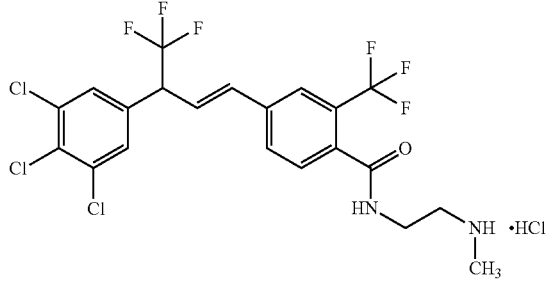 [SMILES: CNCCNC(=O)c1ccc(/C=C/C(c2cc(Cl)c(Cl)c(Cl)c2)C(F)(F)F)cc1C(F)(F)F ; Cl]

Into a round-bottomed flask (100 mL) under nitrogen was added (E)-tert-butyl methyl(2-(4-(4,4,4-trifluoro-3-(3,4,5-trichlorophenyl)but-1-en-1-yl)-2-(trifluoromethyl)ben-zamido)ethyl)carbamate (C113) (0.770 g, 1.22 mmol) and dichloromethane (1.39 mL). Hydrochloric acid (4 M in dioxane) (1.39 mL) was then added dropwise to the solution and the solution was allowed to stir at room temperature overnight. The reaction was concentrated to provide the title compound as a brown foam (0.500 g, 51%): $^1$H NMR (400 MHz, MeOH-$d_4$) δ 7.90-7.81 (m, 2H), 7.70 (s, 2H), 7.63 (d, J=8.0 Hz, 1H), 6.91-6.75 (m, 2H), 4.64-4.50 (m, 1H), 3.66 (s, 4H), 2.78 (s, 3H) (NH not observed); $^{19}$F NMR (376 MHz, MeOH-$d_4$) 5-60.51, −70.47; ESIMS m/z 533 ([M−H]$^-$).

Example 23: Preparation of (E)-4-(4,4,4-trifluoro-3-(3,4,5-trichlorophenyl)but-1-en-1-yl)-N-(2-(3,3,3-trifluoro-N-methylpropanamido)ethyl)-2-(trifluo-romethyl)benzamide (F20)

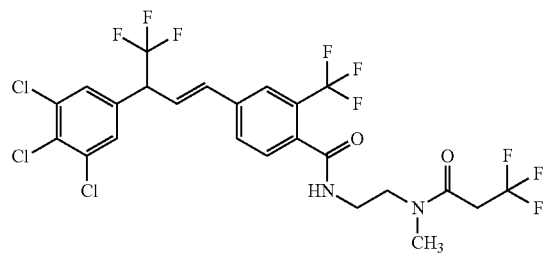 [SMILES: CN(CCNC(=O)c1ccc(/C=C/C(c2cc(Cl)c(Cl)c(Cl)c2)C(F)(F)F)cc1C(F)(F)F)C(=O)CC(F)(F)F]

Into a round-bottomed flask (100 mL) was added the 1H-benzo[d][1,2,3]triazol-1-ol hydrate (0.040 g, 0.26 mmol), 2-(1H-benzo[d][1,2,3]triazol-1-yl)-1,1,3,3-tetram-ethyluronium hexafluorophosphate(V) (0.10 g, 0.26 mmol), (E)-N-(2-(methylamino)ethyl)-4-(4,4,4-trifluoro-3-(3,4,5-trichlorophenyl)but-1-en-1-yl)-2-(trifluoromethyl)benzami-de.hydrochloride (C114) (0.15 g, 0.26 mmol), 3,3,3-trifluo-ropropanoic acid (0.046 mL, 0.53 mmol), and acetonitrile (4.5 mL) under nitrogen. This was then followed by drop-wise addition of N-ethyl-N-isopropylpropan-2-amine (0.14 mL, 0.79 mmol). The resulting solution was allowed to stir overnight at room temperature. The reaction mixture was filtered through silica gel frit, concentrated, and then purified via flash column chromatography to provide the title com-pound as a brown glass (0.094 g, 50%).

Example 24: Preparation of (E)-N-(2-(methyl-amino)ethyl)-4-(4,4,4-trifluoro-3-(3,4,5-trichloro-phenyl)but-1-en-1-yl)-2-(trifluoromethyl)benzamide (C115)

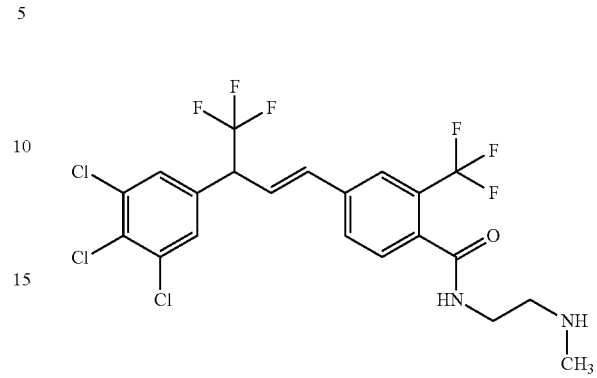

Into a round-bottomed flask (100 mL) containing (E)-N-(2-(methylamino)ethyl)-4-(4,4,4-trifluoro-3-(3,4,5-trichlo-rophenyl)but-1-en-1-yl)-2-(trifluoromethyl)benzamide.hy-drochloride (C114) (0.60 g, 1.1 mmol) was added dichloromethane (20 mL) followed by saturated sodium bicarbonate (10 mL). This mixture was allowed to stir for 10 minutes. The solution was extracted with dichloromethane. The combined organic layers were dried, concentrated, and purified by flash column chromatography using methanol/dichloromethane as eluent to provide the title compound as a yellow foam (0.30 g, 51%): $^1$H NMR (400 MHz, CDCl$_3$) δ 7.65 (s, 1H), 7.55 (d, J=7.9 Hz, 1H), 7.42 (d, J=3.3 Hz, 3H), 6.61 (d, J=15.9 Hz, 1H), 6.42 (dd, J=15.9, 7.9 Hz, 1H), 4.12 (p, J=8.7 Hz, 1H), 3.59 (q, J=5.4 Hz, 2H), 2.88 (t, J=5.5 Hz, 2H), 2.47 (s, 3H) (N$\underline{H}$ not observed); $^{19}$F NMR (376 MHz, CDCl$_3$) δ −59.11, −68.60; ESIMS m/z 535 ([M+H]$^+$).

Example 25: Preparation of (E)-4-(4,4,4-trifluoro-3-(3,4,5-trichlorophenyl)but-1-en-1-yl)-N-(2-(2,2,2-trifluoro-N-methylacetamido)ethyl)-2-(trifluorom-ethyl)benzamide (F21)

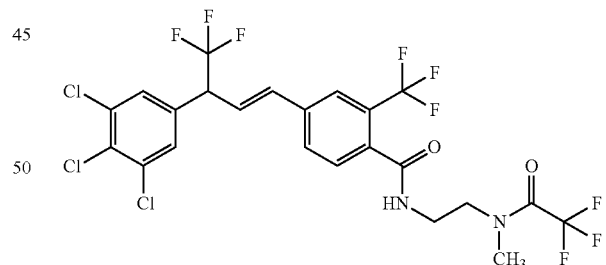

Into a round-bottomed flask (100 mL) was added the (E)-N-(2-(methylamino)ethyl)-4-(4,4,4-trifluoro-3-(3,4,5-trichlorophenyl)but-1-en-1-yl)-2-(trifluoromethyl)benz-amide (C115) (0.125 g, 0.234 mmol), tetrahydrofuran (0.781 mL), and dichloromethane (0.781 mL) under nitrogen. This was followed by the dropwise addition of the trifluoroacetic anhydride (0.0350 mL, 0.246 mmol). The reaction was then allowed to stir at room temperature for 18 hours. The mixture was diluted with dichloromethane, concentrated, and purified via flash column chromatography using ethyl acetate/hexanes as eluent to provide the title compound as a very light yellow glass/foam (0.0720 g, 46%).

Example 26: Preparation of (E)-tert-butyl 1-methyl-2-(4-(4,4,4-trifluoro-3-(3,4,5-trichlorophenyl)but-1-en-1-yl)-2-(trifluoromethyl)benzoyl)hydrazinecarboxylate (C116)

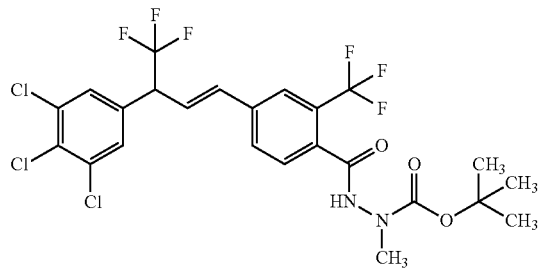 [SMILES: CN(NC(=O)c1ccc(/C=C/C(c2cc(Cl)c(Cl)c(Cl)c2)C(F)(F)F)cc1C(F)(F)F)C(=O)OC(C)(C)C]

To N-ethyl-N-isopropylpropan-2-amine (1.21 mL, 7.08 mmol), benzotriazol-1-yl-oxytripyrrolidinophosphonium hexafluorophosphate (1.35 g, 2.60 mmol), tert-butyl N-amino-N-methyl-carbamate (0.380 g, 2.60 mmol) was added (E)-4-(4,4,4-trifluoro-3-(3,4,5-trichlorophenyl)but-1-en-1-yl)-2-(trifluoromethyl)benzoic acid (C92) (1.00 g, 2.36 mmol) in dichloromethane (5 mL). The reaction was stirred at room temperature for 12 hours. The reaction mixture was poured into water and extracted with dichloromethane (20 mL). The separated organic layer was washed with water, brine, dried over sodium sulfate, filtered, and concentrated. The residue was purified via flash column chromatography using 30% ethyl acetate/petroleum ether as eluent to provide the title compound as a colorless liquid (0.750 g, 49%): IR (thin film) 3418, 2928, 1714, 1160, 865 cm$^{-1}$; $^1$H NMR (400 MHz, DMSO-d$_6$) δ 10.4 (s, 1H), 7.89 (s, 2H), 7.48-7.43 (m, 2H), 7.33 (d, J=8.0 Hz, 1H), 6.90 (dd, J=15.6, 8.8 Hz, 1H), 6.76 (d, J=15.6 Hz, 1H), 4.86-4.82 (m, 1H), 2.38 (s, 3H), 1.45 (s, 9H); ESIMS m/z 603 ([M−H]$^−$).

Example 27: Preparation of (E)-N'-methyl-4-(4,4,4-trifluoro-3-(3,4,5-trichlorophenyl)but-1-en-1-yl)-2-(trifluoromethyl)benzohydrazide.hydrochloride (C117)

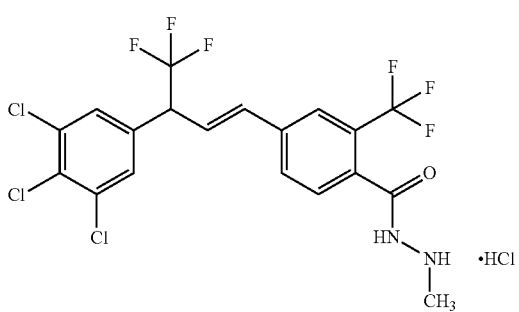 [SMILES: CNNC(=O)c1ccc(/C=C/C(c2cc(Cl)c(Cl)c(Cl)c2)C(F)(F)F)cc1C(F)(F)F ; Cl]

To (E)-tert-butyl 1-methyl-2-(4-(4,4,4-trifluoro-3-(3,4,5-trichlorophenyl)but-1-en-1-yl)-2-(trifluoromethyl)benzoyl)hydrazinecarboxylate (C116) (1.0 g, 1.7 mmol) in dioxane (10 mL) was added hydrochloric acid (4 M in dioxane) (10 mL). The solution was allowed to stir at room temperature for 2 hours. The reaction was concentrated, washed with pentane, filtered, and dried to provide the title compound as a yellow solid (0.80 g, 89%): $^1$H NMR (300 MHz, DMSO-d$_6$) δ 11.30 (bs, 2H), 8.09 (bs, 1H), 7.97 (d, J=6.6 Hz, 2H), 7.92 (s, 1H), 7.65 (d, J=8.4 Hz, 2H), 7.14 (dd, J=15.9, 8.7 Hz, 1H), 6.91 (d, J=15.9 Hz, 1H), 4.90 (t, J=6.9 Hz, 1H), 2.73 (bs, 3H); ESIMS m/z 505 ([M+H]$^+$).

Example 28: Preparation of (E)-N'-methyl-4-(4,4,4-trifluoro-3-(3,4,5-trichlorophenyl) but-1-en-1-yl)-2-(trifluoromethyl)-N'-(3,3,3-trifluoropropanoyl)benzohydrazide (F22)

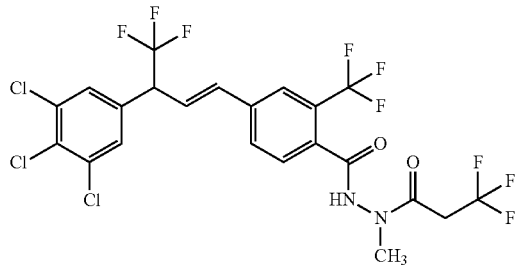 [SMILES: CN(NC(=O)c1ccc(/C=C/C(c2cc(Cl)c(Cl)c(Cl)c2)C(F)(F)F)cc1C(F)(F)F)C(=O)CC(F)(F)F]

To N-ethyl-N-isopropylpropan-2-amine (0.14 mL, 0.83 mmol), benzotriazol-1-yl-oxytripyrrolidinophosphonium hexafluorophosphate (0.16 g, 0.30 mmol) was added (E)-N'-methyl-4-(4,4,4-trifluoro-3-(3,4,5-trichlorophenyl)but-1-en-1-yl)-2-(trifluoromethyl)benzohydrazide.hydrochloride (C117) (0.15 g, 0.28 mmol) and 3,3,3-trifluoropropanoic acid (0.046 mL, 0.53 mmol) in dichloromethane (5 mL). The reaction was stirred at room temperature for 6 hours. The reaction mixture was then diluted with dichloromethane and washed with water. The organic layer was dried over sodium sulfate, filtered, and concentrated. The residue was purified via flash column chromatography using 20% ethyl acetate/petroleum ether as eluent to provide the title compound as a pale yellow gum (0.15 g, 86%).

The following compounds were prepared in accordance to the procedure in Example 28.

(E)-N'-Methyl-4-(4,4,4-trifluoro-3-(3,4,5-trichlorophenyl)but-1-en-1-yl)-N'-(4,4,4-trifluorobutanoyl)-2-(trifluoromethyl)benzohydrazide (F23)

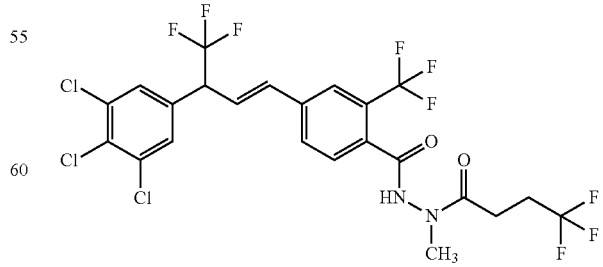

The title compound was prepared using 4,4,4-trifluorobutanoic acid and isolated as a pale yellow gum (0.21 g, 91%).

Example 29: Preparation of 3,5-Dibromo-4-chlorobenzaldehyde (C121)

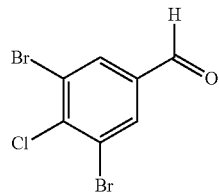

Step 1. Methyl 4-amino-3,5-dibromobenzoate (C118)

Concentrated sulfuric acid (1.35 mL, 25.5 mmol) was added dropwise to a stirred solution of 4-amino-3,5-dibromobenzoic acid (5.00 g, 17.0 mmol) in methanol (50 mL) at ambient temperature and the reaction mixture was then stirred at 80° C. for 8 hours. The reaction mixture was allowed to cool to ambient temperature, volatiles were evaporated, ice-water was added to the residue, and extracted with ethyl acetate. The organic layer was washed with aqueous sodium bicarbonate solution followed by brine and water, dried (sodium sulfate), filtered, and concentrated to afford the title compound as an off white solid (5.00 g, 95%): $^1$H NMR (300 MHz, DMSO-$d_6$) δ 7.91 (s, 2H), 6.20 (bs, 2H), 3.78 (s, 3H); ESIMS m/z 307 ([M]$^+$); IR (thin film) 3312, 2953, 1726, 595 cm$^{-1}$.

Step 2. Methyl 3,5-dibromo-4-chlorobenzoate (C119)

Copper(II) chloride (2.82 g, 21.0 mmol) in acetonitrile (30 mL) was stirred at 80° C. for 30 minutes. tert-Butylnitrite (2.70 mL, 23.0 mmol) was then added dropwise at the same temperature and the mixture was stirred for another 10 minutes. Methyl 4-amino-3,5-dibromobenzoate (C118) (5.00 g, 16.0 mmol) in acetonitrile (30 mL) was added dropwise to the reaction mixture and stirred at 80° C. for 30 minutes. The reaction mixture was allowed to cool to ambient temperature and an aqueous ammonia solution (20 mL) was added to the reaction mixture followed by extraction with petroleum ether. The organic layer was washed with brine followed by water, dried (sodium sulfate), filtered, and concentrated to afford the title compound as an off white solid (4.50 g, 84%): $^1$H NMR (300 MHz, DMSO-$d_6$) δ 8.21 (s, 2H), 3.94 (s, 3H); ESIMS m/z 326 ([M]$^+$); IR (thin film) 1732, 746 cm$^{-1}$.

Step 3. (3,5-Dibromo-4-chlorophenyl)methanol (C120)

Sodium borohydride (1.53 g, 40.7 mmol) was added portionwise to a stirred solution of methyl 3,5-dibromo-4-chlorobenzoate (C119) (4.45 g, 13.6 mmol) in methanol (50 mL) at 0° C. The reaction mixture was then stirred at ambient temperature for 8 hours. The volatiles were evaporated and the residue was diluted with dichloromethane and washed with brine followed by water. The organic layer was dried (sodium sulfate), filtered, and concentrated to afford the title compound as an off white solid (3.30 g, 80%): $^1$H NMR (300 MHz, DMSO-$d_6$) δ 7.71 (s, 2H), 5.49 (bs, 1H), 4.48 (d, J=4.5 Hz, 2H); ESIMS m/z 298 ([M]$^+$); IR (thin film) 3460, 747, 534 cm$^{-1}$.

Step 4. 3,5-Dibromo-4-chlorobenzaldehyde (C121)

Pyridinium chlorochormate (3.44 g, 15.9 mmol) was added in one portion to a stirred solution of (3,5-dibromo-4-chlorophenyl)methanol (C120) (3.2 g, 11.0 mmol) in chloroform (40 mL) at ambient temperature and the reaction mixture was stirred overnight. The reaction mixture was filtered through Celite®, the Celite® pad was washed with chloroform, and the filtrate was concentrated to afford the title compound as an off white solid (2.00 g, 62%): mp 110-113° C.; $^1$H NMR (300 MHz, DMSO-$d_6$) δ 9.93 (s, 1H), 8.27 (s, 2H); ESIMS m/z 297 ([M]$^+$).

The following compounds were prepared in accordance to the procedures in Example 29.

4-Bromo-3,5-dichlorobenzaldehyde (C125)

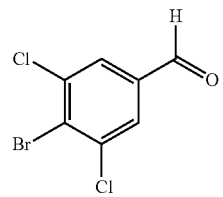 [SMILES: O=Cc1cc(Cl)c(Br)c(Cl)c1]

Step 1. Methyl 4-amino-3,5-dichlorobenzoate (C122)

The title compound was isolated as a white solid (7.5 g, 70%): $^1$H NMR (300 MHz, DMSO-$d_6$) δ 8.05 (s, 2H), 3.96 (s, 3H); ESIMS m/z 282 ([M]$^+$); IR (KBr): 1733, 762, 514 cm$^{-1}$.

Step 2. Methyl 4-bromo-3,5-dichlorobenzoate (C123)

The title compound was isolated as an off white solid (7.5 g, 77%): $^1$H NMR (300 MHz, DMSO-$d_6$) δ 8.02 (s, 2H), 3.94 (s, 3H); ESIMS m/z 282 ([M]$^+$); IR (thin film) 1733, 762, 514 cm$^{-1}$.

Step 3. (4-Bromo-3,5-dichlorophenyl)methanol (C124)

The title compound was isolated as an off white solid which was taken to next step without purification.

Step 4. 4-Bromo-3,5-dichlorobenzaldehyde (C125)

The title compound was isolated as an off white solid (3.5 g, 67%): mp 125-128° C.; $^1$H NMR (300 MHz, DMSO-$d_6$) δ 9.96 (s, 1H), 8.10 (s, 2H); ESIMS m/z 252 ([M]$^+$).

Example 30: Preparation of 4-((E)-3-(3,5-dichloro-4-fluorophenyl)-4,4,4-trifluorobut-1-en-1-yl)-2-(trifluoromethyl)-N—((R)-1-(3,3,3-trifluoropropanamido)ethyl)benzamide (P24)

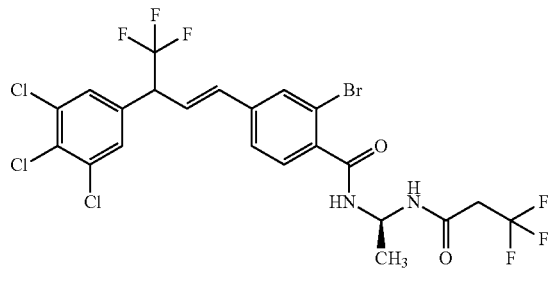

To a vial (50 mL) under a nitrogen atmosphere was added (E)-2-bromo-4-(4,4,4-trifluoro-3-(3,4,5-trichlorophenyl)but-1-en-1-yl)benzoic acid (C88) (0.306 g, 0.626 mmol) and 1,2-dichloroethane (2 mL). Oxalyl dichloride (0.100 mL, 1.17 mmol) and N,N-dimethylformamide (0.00400 mL, 0.0510 mmol) were added, and the resulting suspension was stirred for 1 hour. The reaction mixture was concentrated to remove any excess oxalyl chloride. The resulting orange oil was diluted with 1,2-dichloroethane (5 mL) and added to a vial (25 mL) containing (S)—N-(1-aminoethyl)-3,3,3-trifluoropropanamide hydrochloride (CA5) (0.168 g, 0.814 mmol). The reaction mixture was vortexed, and 4-methylmorpholine (0.172 mL, 1.57 mmol) was added. The reaction vial was capped and vortexed several times over a 1 minute period. The reaction mixture was allowed to stir with occasional vortexing for 1 hour. The reaction mixture was concentrated under a stream of nitrogen gas, dissolved in N,N-dimethylformamide:water (5:1, 3.2 mL), and partially purified via preparative C-18 reverse phase HPLC purification using 5-95% acetonitrile (0.1% acetic acid) and water (0.1% acetic acid) as eluent. The obtained material was dissolved in methanol containing an excess of Amberlite IRA-65 weak anion exchange resin in the free base form (IRA-67 free base), and the mixture was vortexed and left to stand for 1 hour. The mixture was gravity filtered, and the resin was washed with excess methanol. The filtrate was concentrated to provide the desired compound as a white solid (0.172 g, 39%).

The following compounds were prepared in accordance to the procedures in Example 30.

4-((E)-3-(3,5-Dichloro-4-fluorophenyl)-4,4,4-trifluorobut-1-en-1-yl)-2-(trifluoromethyl)-N—((R)-1-(3,3,3-trifluoropropanamido)ethyl)benzamide (P1)

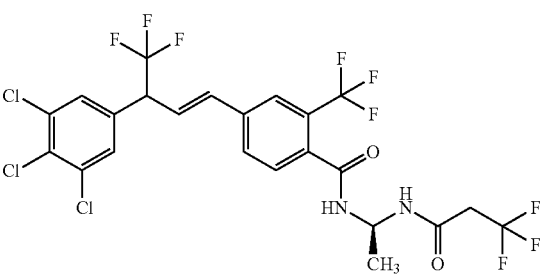

Isolated as an amber glass (0.041 g, 10%).

4-((E)-3-(3,5-Dibromo-4-chlorophenyl)-4,4,4-trifluorobut-1-en-1-yl)-2-(trifluoromethyl)-N—((R)-1-(3,3,3-trifluoropropanamido)ethyl)benzamide (P2)

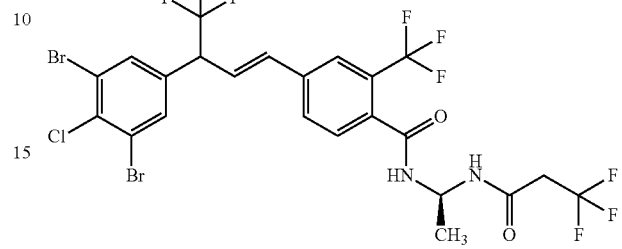

Isolated as an amber glass (0.223 g, 55%).

4-((E)-3-(3,5-Dibromophenyl)-4,4,4-trifluorobut-1-en-1-yl)-2-(trifluoromethyl)-N—((R)-1-(3,3,3-trifluoropropanamido)ethyl)benzamide (P3)

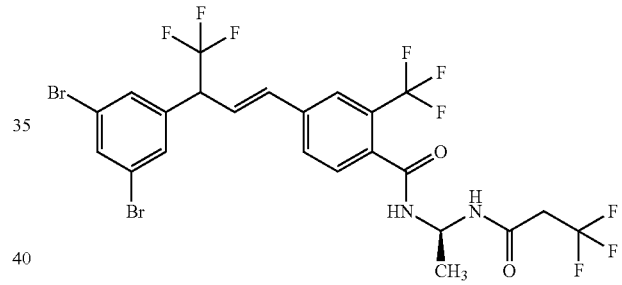

Isolated as a brown amorphous solid (0.226 g, 52%).

4-((E)-3-(4-Bromo-3,5-dichlorophenyl)-4,4,4-trifluorobut-1-en-1-yl)-2-(trifluoromethyl)-N—((R)-1-(3,3,3-trifluoropropanamido)ethyl)benzamide (P4)

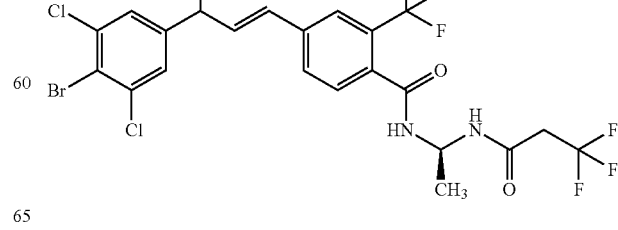

Isolated as a brown amorphous solid (0.226 g, 52%).

4-((E)-3-(3,5-Dichloro-4-fluorophenyl)-4,4,4-trifluorobut-1-en-1-yl)-2-methyl-N—((R)-1-(3,3,3-trifluoropropanamido)ethyl)benzamide (P5)

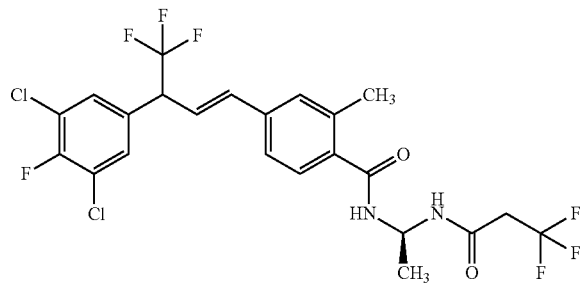 [SMILES: Cc1cc(/C=C/C(c2cc(Cl)c(F)c(Cl)c2)C(F)(F)F)ccc1C(=O)N[C@H](C)NC(=O)CC(F)(F)F]

Isolated as a pale yellow glass (0.215 g, 49%).

4-((E)-3-(3,5-Dibromo-4-chlorophenyl)-4,4,4-trifluorobut-1-en-1-yl)-2-methyl-N—((R)-1-(3,3,3-trifluoropropanamido)ethyl)benzamide (P6)

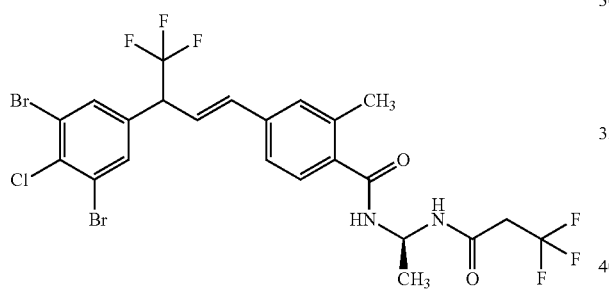

Isolated as a pale orange glass (0.211 g, 49%).

4-((E)-3-(3,5-Dibromophenyl)-4,4,4-trifluorobut-1-en-1-yl)-2-methyl-N—((R)-1-(3,3,3-trifluoropropanamido)ethyl)benzamide (P7)

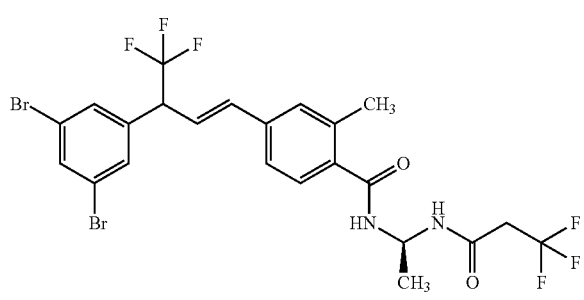

Isolated as a brown amorphous solid (0.226 g, 54%).

4-((E)-3-(4-Bromo-3,5-dichlorophenyl)-4,4,4-trifluorobut-1-en-1-yl)-2-methyl-N—((R)-1-(3,3,3-trifluoropropanamido)ethyl)benzamide (P8)

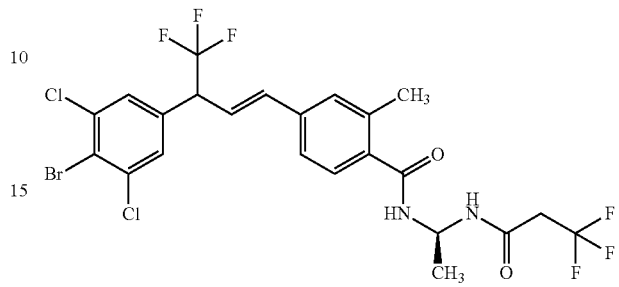

Isolated as a pale yellow solid (0.148 g, 35%).

4-((E)-3-(3,5-Dichloro-4-fluorophenyl)-4,4,4-trifluorobut-1-en-1-yl)-N—((R)-1-(4,4,4-trifluorobutanamido)ethyl)-2-(trifluoromethyl)benzamide (P9)

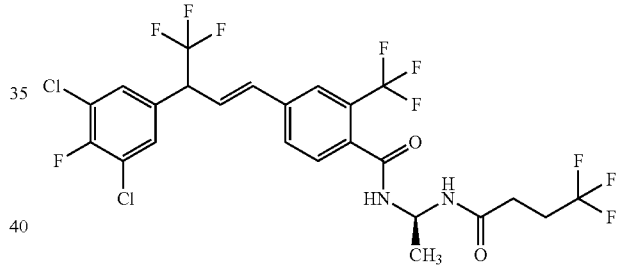

Isolated as a colorless glass (0.036 g, 8%).

4-((E)-3-(3,5-Dibromo-4-chlorophenyl)-4,4,4-trifluorobut-1-en-1-yl)-N—((R)-1-(4,4,4-trifluorobutanamido)ethyl)-2-(trifluoromethyl)benzamide (P10)

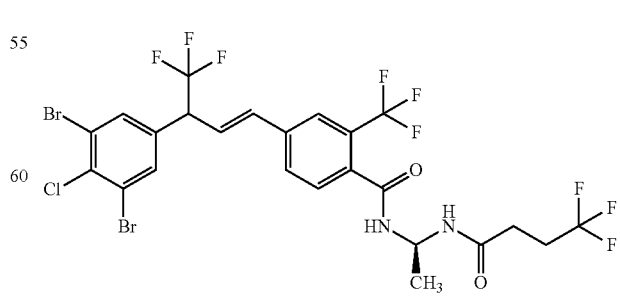

Isolated as a pale yellow glass (0.171 g, 39%).

4-((E)-3-(3,5-Dibromophenyl)-4,4,4-trifluorobut-1-en-1-yl)-N—((R)-1-(4,4,4-trifluorobutanamido)ethyl)-2-(trifluoromethyl)benzamide (P11)

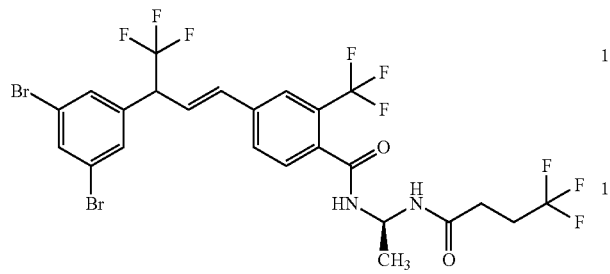

Isolated as an amber glass (0.181 g, 39%).

4-((E)-3-(4-Bromo-3,5-dichlorophenyl)-4,4,4-trifluorobut-1-en-1-yl)-N—((R)-1-(4,4,4-trifluorobutanamido)ethyl)-2-(trifluoromethyl)benzamide (P12)

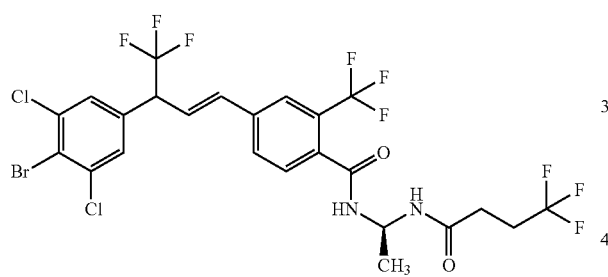

Isolated as an orange glass (0.135 g, 29%).

4-((E)-3-(3,5-Dichloro-4-fluorophenyl)-4,4,4-trifluorobut-1-en-1-yl)-2-methyl-N—((R)-1-(4,4,4-trifluorobutanamido)ethyl)benzamide (P13)

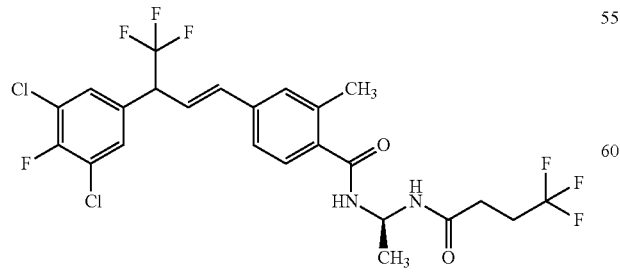

Isolated as a light yellow solid (0.197 g, 42%).

4-((E)-3-(3,5-Dibromo-4-chlorophenyl)-4,4,4-trifluorobut-1-en-1-yl)-2-methyl-N—((R)-1-(4,4,4-trifluorobutanamido)ethyl)benzamide (P14)

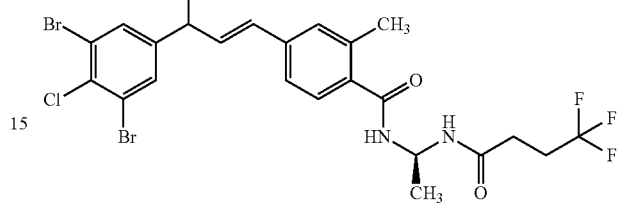

Isolated as a white solid (0.104 g, 16%).

4-((E)-3-(3,5-Dibromophenyl)-4,4,4-trifluorobut-1-en-1-yl)-2-methyl-N—((R)-1-(4,4,4-trifluorobutanamido)ethyl)benzamide (P15)

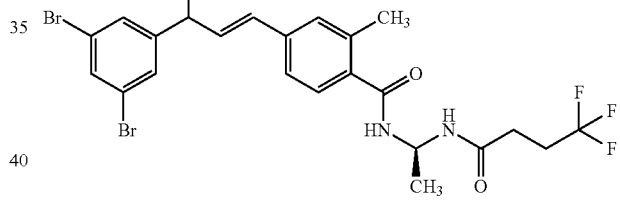

Isolated as a beige solid (0.150 g, 33%).

4-((E)-3-(4-Bromo-3,5-dichlorophenyl)-4,4,4-trifluorobut-1-en-1-yl)-2-methyl-N—((R)-1-(4,4,4-trifluorobutanamido)ethyl)benzamide (P16)

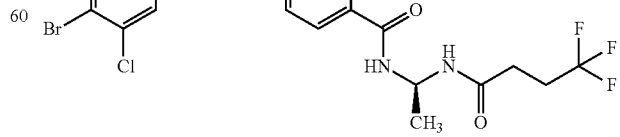

Isolated as a white solid (0.122 g, 20%).

81

2-Methyl-4-((E)-4,4,4-trifluoro-3-(3,4,5-trichlorophenyl)but-1-en-1-yl)-N—((R)-1-(3,3,3-trifluoropropanamido)ethyl)benzamide (P22)

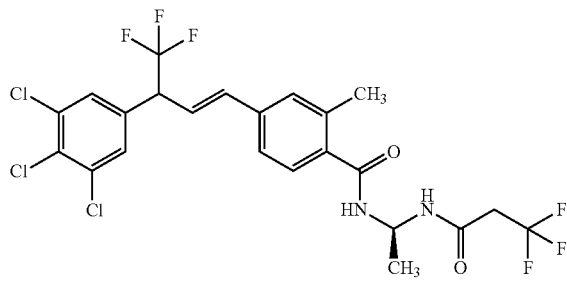

Isolated as a beige solid (0.241 g, 52%).

2-Methyl-4-((E)-4,4,4-trifluoro-3-(3,4,5-trichlorophenyl)but-1-en-1-yl)-N—((R)-1-(4,4,4-trifluorobutanamido)ethyl)benzamide (P25)

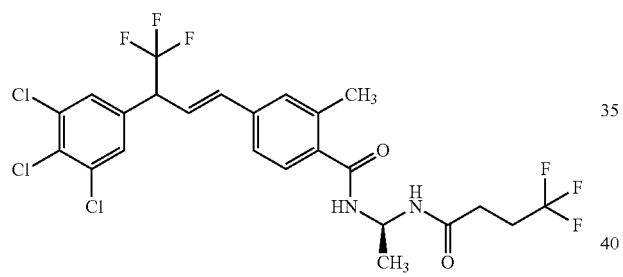

Isolated as a beige solid (0.157 g, 32%).

2-Bromo-4-((E)-4,4,4-trifluoro-3-(3,4,5-trichlorophenyl)but-1-en-1-yl)-N—((R)-1-(4,4,4-trifluorobutanamido)ethyl)benzamide (P27)

Isolated as a pale yellow solid (0.110 g, 24%).

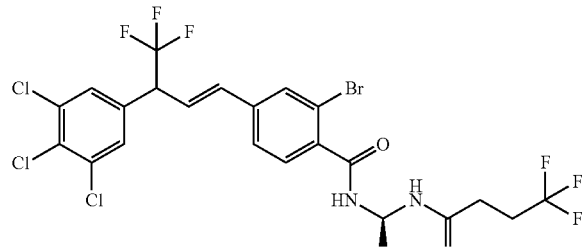

82

N—((R)-1-(3-(Methylthio)propanamido)ethyl)-4-((E)-4,4,4-trifluoro-3-(3,4,5-trichlorophenyl) but-1-en-1-yl)-2-(trifluoromethyl)benzamide (P53)

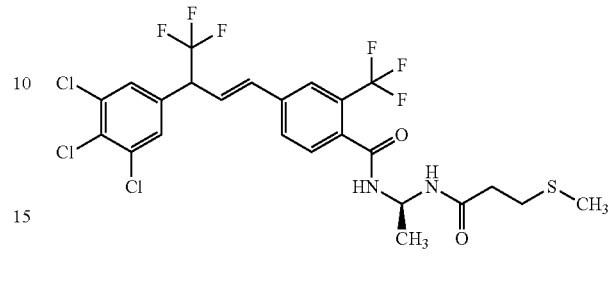

Isolated as a white foam (0.225 g, 36%).

N—((S)-1-(2-(Methylthio)acetamido)ethyl)-4-((E)-4,4,4-trifluoro-3-(3,4,5-trichlorophenyl) but-1-en-1-yl)-2-(trifluoromethyl)benzamide (P54)

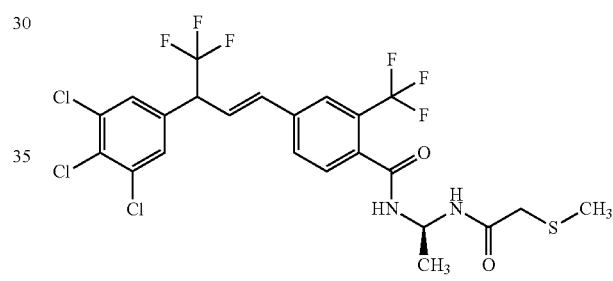

Isolated as a white foam (0.353 g, 55%).

4-((E)-4,4,4-Trifluoro-3-(3,4,5-trichlorophenyl)but-1-en-1-yl)-N—((R)-1-(4,4,4-trifluorobutanamido)ethyl)benzamide (FC1)

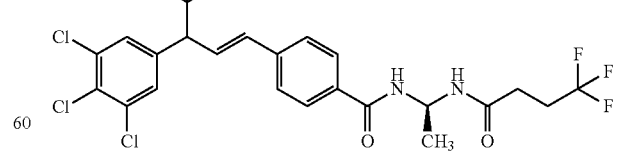

Isolated as a yellow foam (0.0423 g, 40%, approximately 30% pure).

83

4-((E)-4,4,4-Trifluoro-3-(3,4,5-trichlorophenyl)but-1-en-1-yl)-N—((R)-1-(3,3,3-trifluoropropanamido)ethyl)benzamide (FC2)

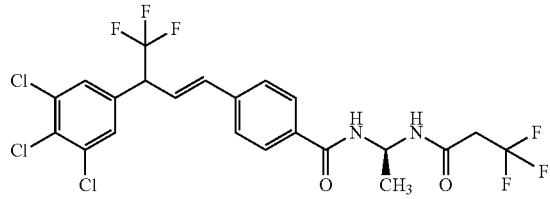

Isolated as a white solid (0.052 g, 47%).

Example 31: Preparation of N—((R)-1-(3-(methylsulfonyl)propanamido)ethyl)-4-((E)-4,4,4-trifluoro-3-(3,4,5-trichlorophenyl)but-1-en-1-yl)-2-(trifluoromethyl)benzamide (P47) and N-((1R)-1-(3-(methylsulfinyl)propanamido)ethyl)-4-((E)-4,4,4-trifluoro-3-(3,4,5-trichlorophenyl) but-1-en-1-yl)-2-(trifluoromethyl)benzamide (P49)

P47
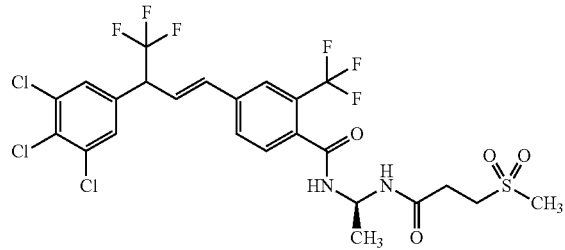 [SMILES: CSCCC(=O)N[C@@H](C)NC(=O)c1ccc(/C=C/C(c2cc(Cl)c(Cl)c(Cl)c2)C(F)(F)F)cc1C(F)(F)F]

P49
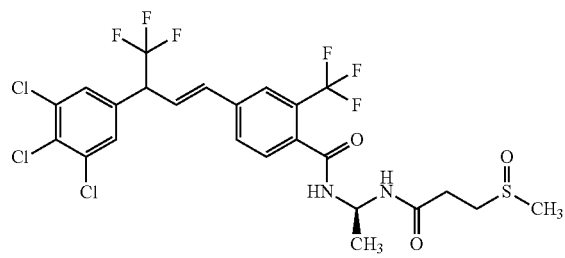

To a vial (25 mL) was added N—((R)-1-(3-(methylthio)propanamido)ethyl)-4-((E)-4,4,4-trifluoro-3-(3,4,5-trichlorophenyl)but-1-en-1-yl)-2-(trifluoromethyl)benzamide (P53) (0.150 g, 0.241 mmol), sodium perborate tetrahydrate (0.0557 g, 0.362 mmol), and acetic acid (5 mL). The vial was capped, and the reaction was stirred and heated at 55° C. overnight. The reaction mixture was concentrated under a stream of nitrogen gas. Purification by flash column chromatography using 20-100% ethyl acetate/hexanes followed by 0-40% methanol/dichloromethane as eluent provided the title compound (P47) as a coloroless glass (0.0630 g, 72%) and (P49) as a colorless glass (0.0360 g, 42%).

The following compounds were prepared in accordance to the procedures in Example 31.

84

N-((1S)-1-(2-(Methylsulfinyl)acetamido)ethyl)-4-((E)-4,4,4-trifluoro-3-(3,4,5-trichlorophenyl) but-1-en-1-yl)-2-(trifluoromethyl)benzamide (P36)

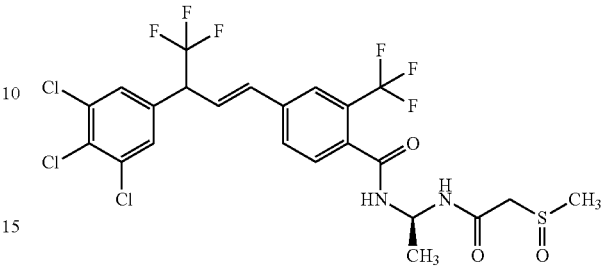

Isolated as a colorless glass (0.054 g, 34%).

N—((S)-1-(2-(Methylsulfonyl)acetamido)ethyl)-4-((E)-4,4,4-trifluoro-3-(3,4,5-trichlorophenyl) but-1-en-1-yl)-2-(trifluoromethyl)benzamide (P43)

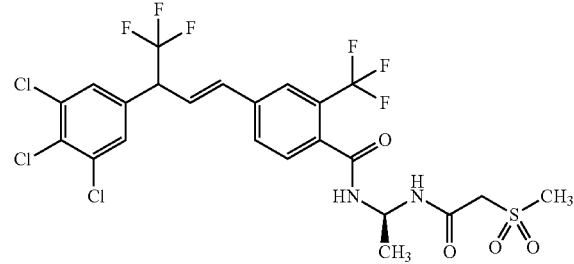 [SMILES: C[C@H](NC(=O)CS(C)(=O)=O)NC(=O)c1ccc(/C=C/C(c2cc(Cl)c(Cl)c(Cl)c2)C(F)(F)F)cc1C(F)(F)F]

Isolated as a colorless glass (0.138 g, 85%).

Example 32: Preparation of (S)—N-(1-aminoethyl)-4,4,4-trifluorobutanamide hydrochloride (CA4)

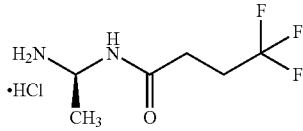

(S)—N-(1-Amino-1-oxopropan-2-yl)-4,4,4-trifluorobutanamide (CA6) (3.00 g, 14.1 mmol) was dissolved in water (21 mL) and acetonitrile (21 mL), after which [I,I-bis(trifluoroacetoxy)iodo]benzene (6.08 g, 14.1 mmol) was added. The reaction mixture was stirred in a flask wrapped in aluminum foil overnight. The reaction mixture was then poured into hydrochloric acid (1 N, 35 mL) and diethyl ether (35 mL). The organic layer was separated, and the aqueous layer was azeotroped (2×125 mL) with isopropanol. Purification by reverse phase flash column chromatography using 20% acetonitrile/water as eluent provided the title compound as a white, highly hygroscopic solid (1.50 g, 48%): $^1$H NMR (400 MHz, DMSO-$d_6$) δ 9.11 (d, J=7.4 Hz, 1H), 8.36 (s, 3H), 4.94 (p, J=6.6 Hz, 1H), 2.66-2.32 (m, 4H), 1.40 (d, J=6.5 Hz, 3H); $^{19}$F NMR (376 MHz, DMSO-$d_6$) δ −65.19; ESIMS m/z 185 ([M+H]$^+$).

The following compound was prepared in accordance to the procedures in Example 32.

(S)—N-(1-Aminoethyl)-3,3,3-trifluoropropanamide hydrochloride (CA5)

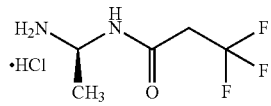

Isolated as an off-white solid (2.8 g, 90%): mp 125° C. (dec.); $^1$H NMR (400 MHz, DMSO-d$_6$) δ 9.47 (d, J=7.3 Hz, 1H), 8.48 (s, 3H), 4.96 (p, J=6.6 Hz, 1H), 3.44 (m, 2H), 1.42 (d, J=6.5 Hz, 3H); $^{19}$F NMR (376 MHz, DMSO-d$_6$) δ −61.28.

Example 33: Preparation of (S)—N-(1-amino-1-oxopropan-2-yl)-4,4,4-trifluorobutanamide (CA6)

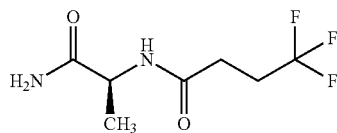

To a round bottomed flask (500 mL) was added sodium bicarbonate (saturated solution, 54.6 mL, 60.1 mmol) and (S)-2-aminopropanamide hydrochloride (3.74 g, 30.0 mmol). The solution was allowed to stir until gas evolution ceased, after which time trifluoroethanol (54.6 mL) was added. 3,3,3-Trifluoropropanoyl chloride (2.81 ml, 27.3 mmol) was added in small portions (gas evolution). Addition rate was determined by the rate of gas evolution. After addition was complete, the reaction mixture was left to stir open to air at room temperature overnight. Hydrochloric acid (2 M, ~15 mL) was added until gas evolution ceased, and the solution was concentrated. The resulting slurry was diluted with ethyl acetate and water, the layers were separated and the aqueous layer was extracted with ethyl acetate (3×100 mL). The resulting organic layer was dried over sodium sulfate, filtered, and concentrated to provide the title compound as a white solid (3.30 g, 55%): $^1$H NMR (300 MHz, DMSO-d$_6$) δ 8.15 (d, J=7.6 Hz, 1H), 7.33 (s, 1H), 6.98 (s, 1H), 4.21 (p, J=7.2 Hz, 1H), 2.49-2.34 (m, 4H), 1.19 (d, J=7.1 Hz, 3H); $^{19}$F NMR (376 MHz, DMSO-d$_6$) δ −61.46; ESIMS m/z 197 ([M−H]$^-$).

The following compound was prepared in accordance to the procedures in Example 33.

(S)—N-(1-Amino-1-oxopropan-2-yl)-3,3,3-trifluoropropanamide (CA7)

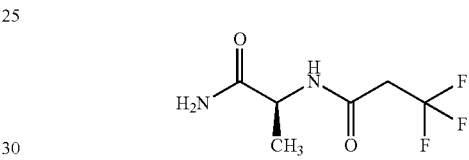

Isolated as a white solid (1.5 g, 39%): $^1$H NMR (400 MHz, DMSO-d$_6$) δ 8.38 (d, J=7.6 Hz, 1H), 7.43 (s, 1H), 7.04 (s, 1H), 4.25 (p, J=7.1 Hz, 1H), 3.32 (q, J=11.3 Hz, 2H), 1.20 (d, J=7.1 Hz, 3H); $^{19}$F NMR (376 MHz, DMSO-d$_6$) δ −65.18.

The following prophetic molecules could be made in accordance with the procedures disclosed above:

TABLE 1

Structure and Preparation Method for P Series Compounds

| No. | Structure | Prep. according to example or scheme: |
|---|---|---|
| P1 | 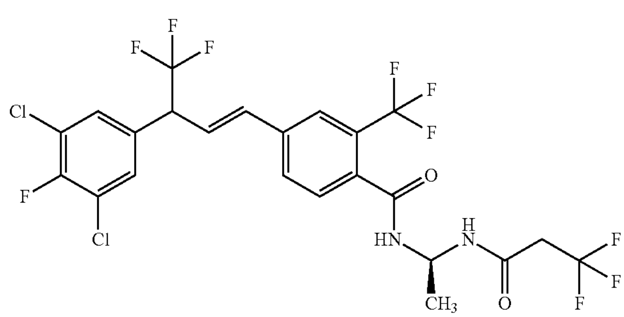 | Example 18 |

TABLE 1-continued

Structure and Preparation Method for P Series Compounds

| No. | Structure | Prep. according to example or scheme: |
|---|---|---|
| P2 | 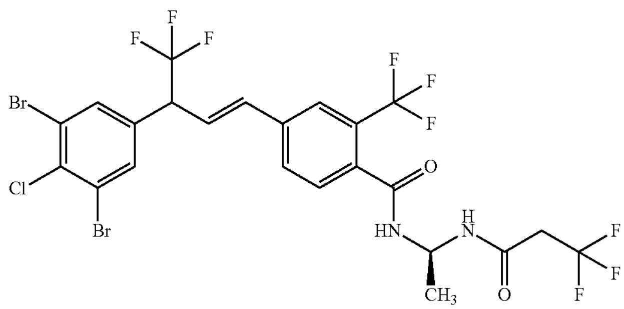 | Example 18 |
| P3 | 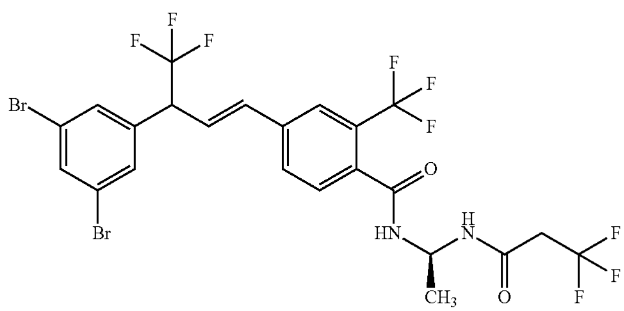 | Example 18 |
| P4 | 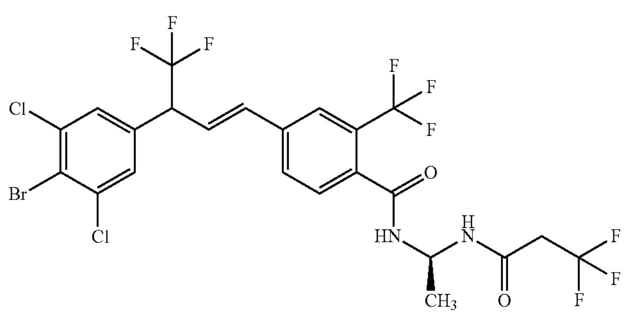 | Example 18 |
| P5 | 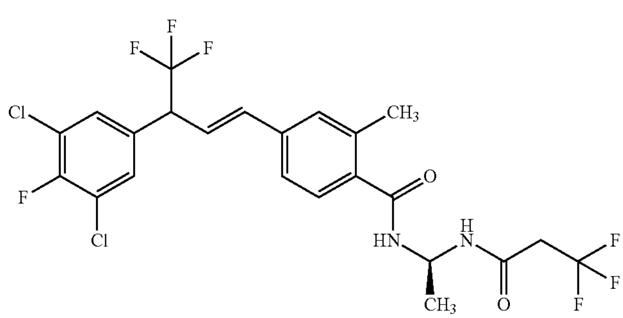 | Example 18 |

TABLE 1-continued
Structure and Preparation Method for P Series Compounds
| No. | Structure | Prep. according to example or scheme: |
|---|---|---|
| P6 | 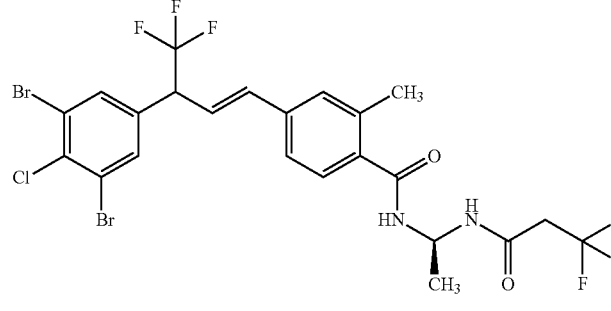 | Example 18 |
| P7 | 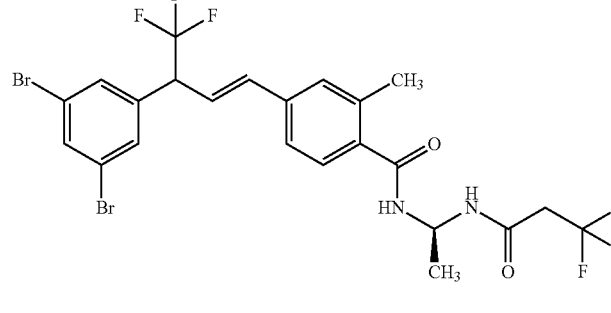 | Example 18 |
| P8 | 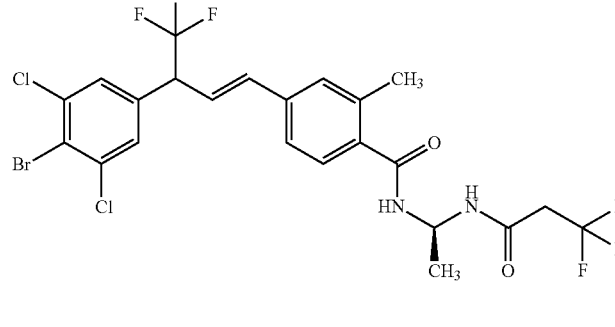 | Example 18 |
| P9 | 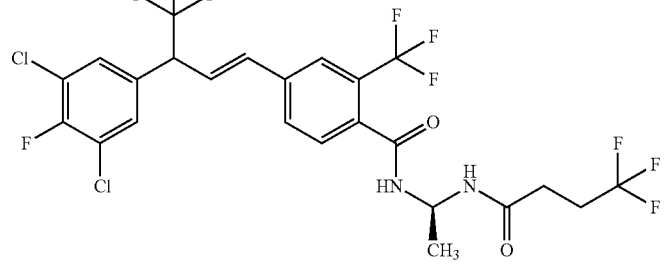 | Example 18 |

TABLE 1-continued

Structure and Preparation Method for P Series Compounds

| No. | Structure | Prep. according to example or scheme: |
|-----|-----------|----------------------------------------|
| P10 | 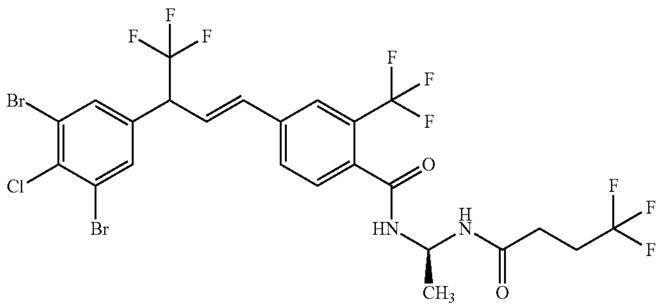 [SMILES: C[C@H](NC(=O)CCC(F)(F)F)NC(=O)c1ccc(/C=C/C(c2cc(Cl)c(F)c(Cl)c2)C(F)(F)F)cc1C(F)(F)F] | Example 18 |
| P11 | 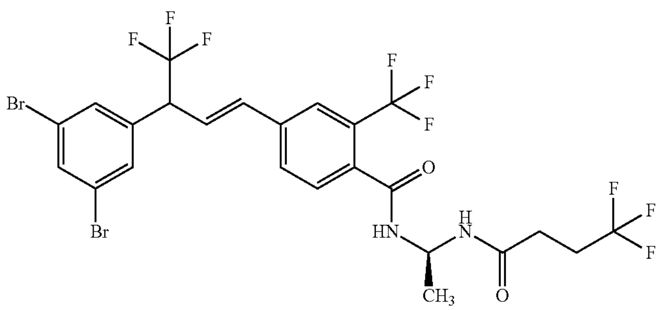 [SMILES: C[C@H](NC(=O)CCC(F)(F)F)NC(=O)c1ccc(/C=C/C(c2cc(Br)cc(Br)c2)C(F)(F)F)cc1C(F)(F)F] | Example 18 |
| P12 | 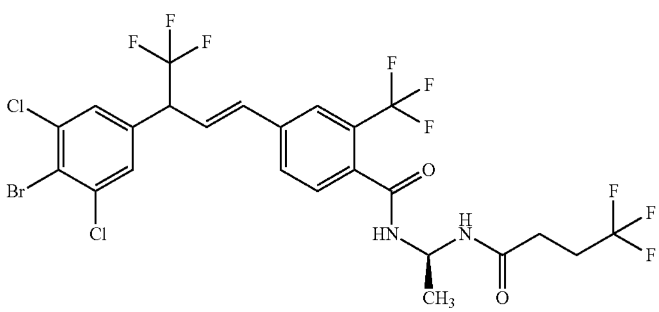 | Example 18 |
| P13 | 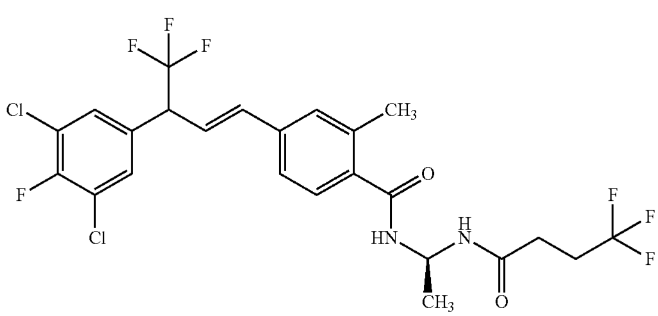 [SMILES: Cc1cc(/C=C/C(c2cc(Cl)c(F)c(Cl)c2)C(F)(F)F)ccc1C(=O)N[C@H](C)NC(=O)CCC(F)(F)F] | Example 18 |

TABLE 1-continued

Structure and Preparation Method for P Series Compounds

| No. | Structure | Prep. according to example or scheme: |
|---|---|---|
| P14 | 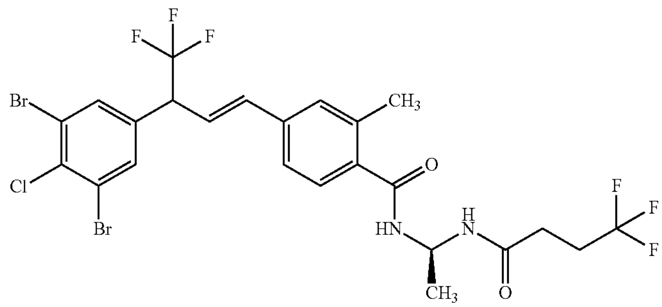 | Example 18 |
| P15 | 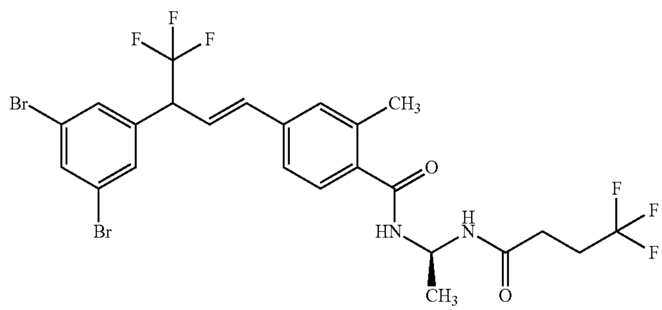 [SMILES: Cc1cc(/C=C/C(c2cc(Br)cc(Br)c2)C(F)(F)F)ccc1C(=O)N[C@H](C)NC(=O)CCC(F)(F)F] | Example 18 |
| P16 | 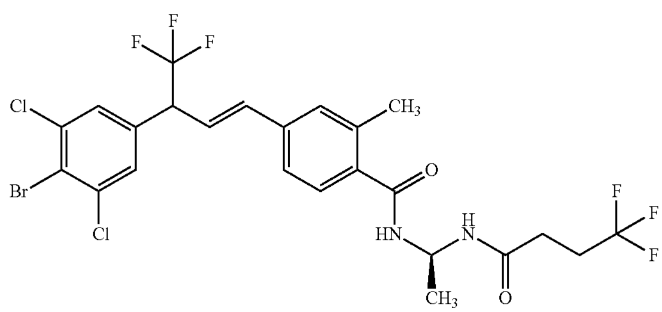 | Example 18 |
| P17 | 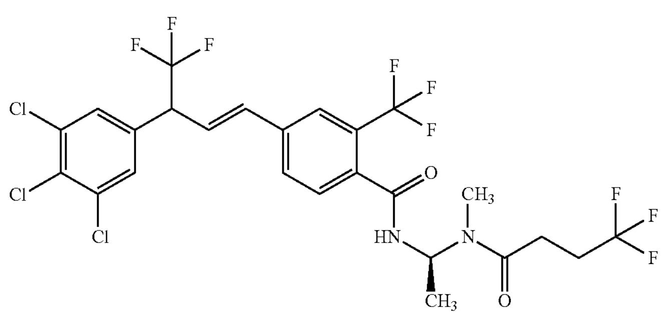 [SMILES: C[C@@H](NC(=O)c1ccc(/C=C/C(c2cc(Cl)c(Cl)c(Cl)c2)C(F)(F)F)cc1C(F)(F)F)N(C)C(=O)CCC(F)(F)F] | Scheme 4 |

TABLE 1-continued

Structure and Preparation Method for P Series Compounds

| No. | Structure | Prep. according to example or scheme: |
|---|---|---|
| P18 | 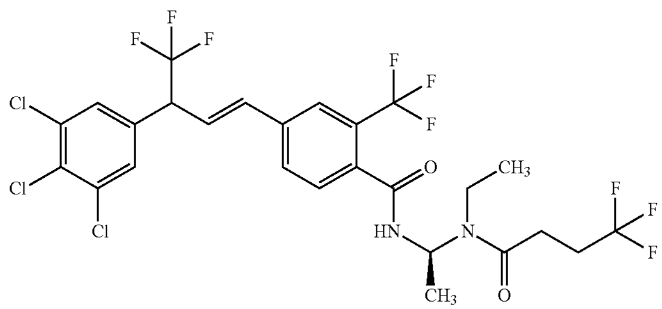 [SMILES: CCN(C(=O)CCC(F)(F)F)[C@@H](C)NC(=O)c1ccc(/C=C/C(c2cc(Cl)c(Cl)c(Cl)c2)C(F)(F)F)cc1C(F)(F)F] | Scheme 4 |
| P19 | 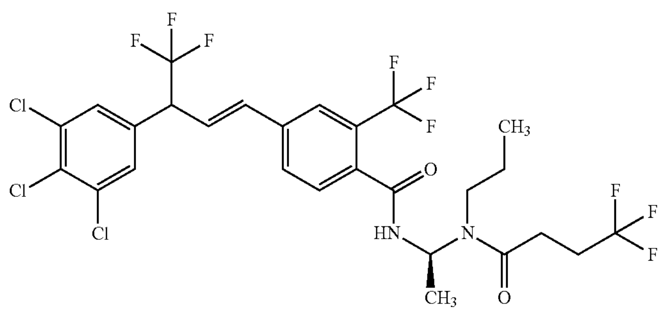 [SMILES: CCCN(C(=O)CCC(F)(F)F)[C@@H](C)NC(=O)c1ccc(/C=C/C(c2cc(Cl)c(Cl)c(Cl)c2)C(F)(F)F)cc1C(F)(F)F] | Scheme 4 |
| P20 | 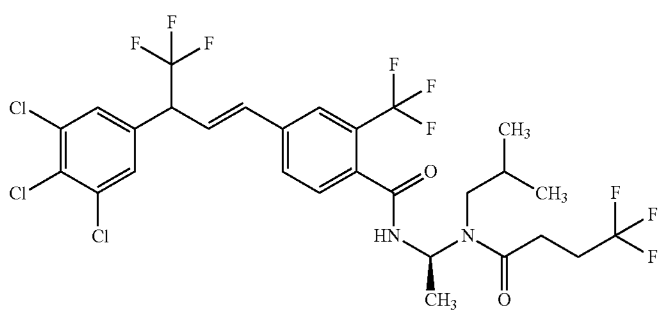 [SMILES: CC(C)CN(C(=O)CCC(F)(F)F)[C@@H](C)NC(=O)c1ccc(/C=C/C(c2cc(Cl)c(Cl)c(Cl)c2)C(F)(F)F)cc1C(F)(F)F] | Scheme 4 |
| P21 | 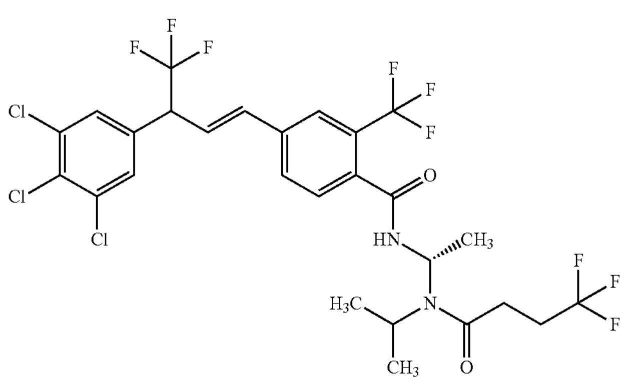 [SMILES: CC(C)N(C(=O)CCC(F)(F)F)[C@@H](C)NC(=O)c1ccc(/C=C/C(c2cc(Cl)c(Cl)c(Cl)c2)C(F)(F)F)cc1C(F)(F)F] | Scheme 4 |

TABLE 1-continued

Structure and Preparation Method for P Series Compounds

| No. | Structure | Prep. according to example or scheme: |
|---|---|---|
| P22 | 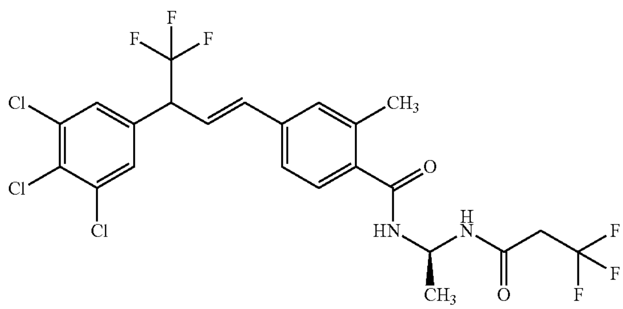 | Example 18 |
| P23 | 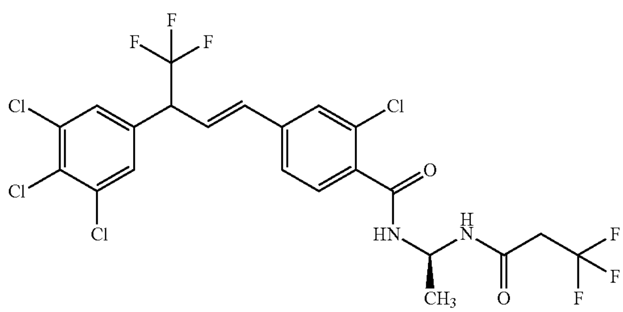 | Example 18 |
| P24 | 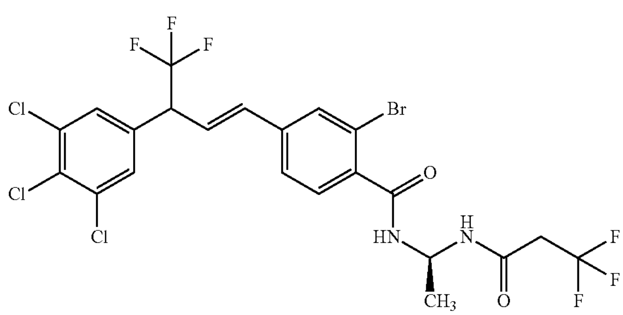 | Example 18 |
| P25 | 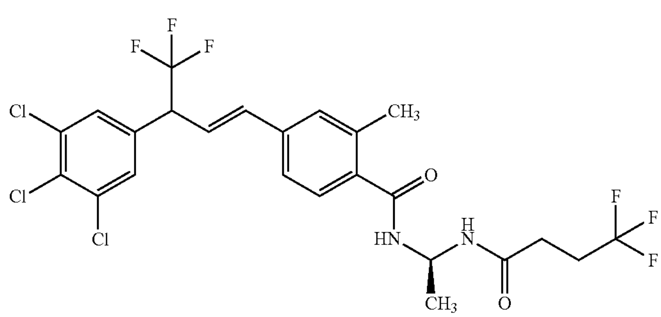 | Example 18 |

TABLE 1-continued

Structure and Preparation Method for P Series Compounds

| No. | Structure | Prep. according to example or scheme: |
|---|---|---|
| P26 | 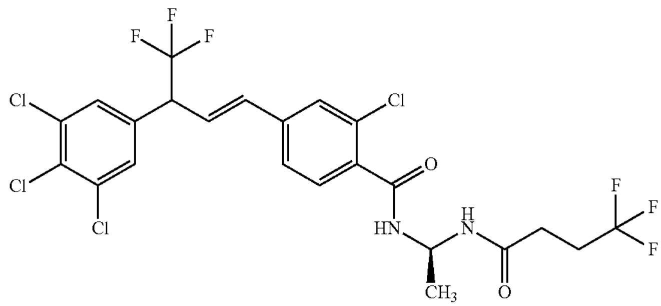 | Example 18 |
| P27 | 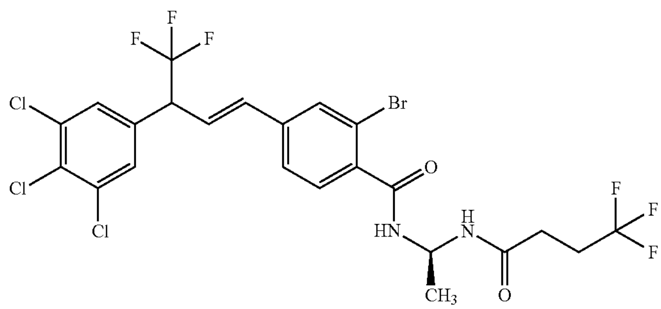 | Example 18 |
| P28 | 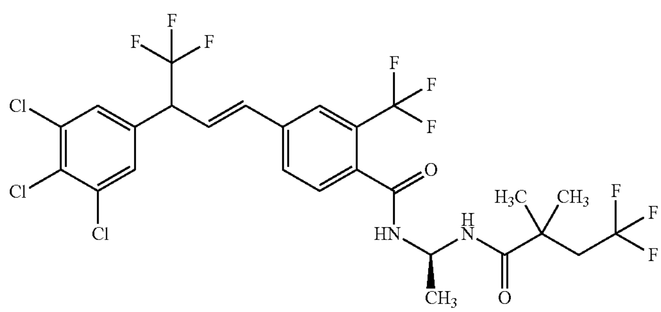 [SMILES: C[C@@H](NC(=O)c1ccc(/C=C/C(c2cc(Cl)c(Cl)c(Cl)c2)C(F)(F)F)cc1C(F)(F)F)NC(=O)C(C)(C)CC(F)(F)F] | Examples 18, 19, 20, or 21 |
| P29 | 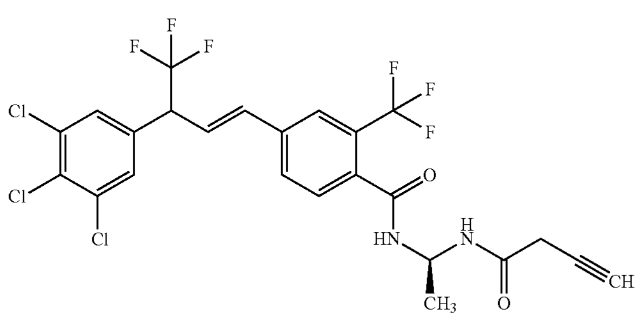 [SMILES: C#CCC(=O)N[C@@H](C)NC(=O)c1ccc(/C=C/C(c2cc(Cl)c(Cl)c(Cl)c2)C(F)(F)F)cc1C(F)(F)F] | Examples 18, 19, 20, or 21 |

TABLE 1-continued
Structure and Preparation Method for P Series Compounds
| No. | Structure | Prep. according to example or scheme: |
|---|---|---|
| P30 | 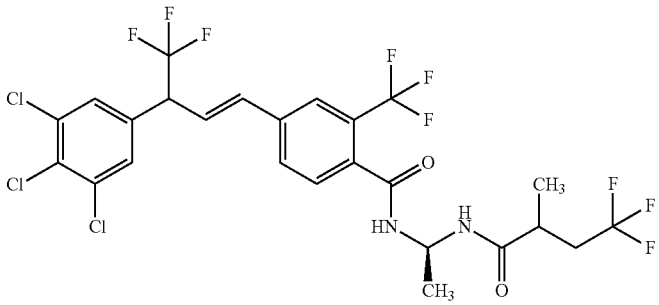 [SMILES: CC(CC(F)(F)F)C(=O)N[C@@H](C)NC(=O)c1ccc(/C=C/C(c2cc(Cl)c(Cl)c(Cl)c2)C(F)(F)F)cc1C(F)(F)F] | Examples 18, 19, 20, or 21 |
| P31 | 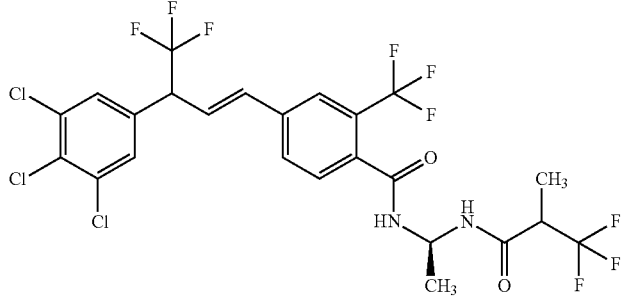 | Examples 18, 19, 20, or 21 |
| P32 | 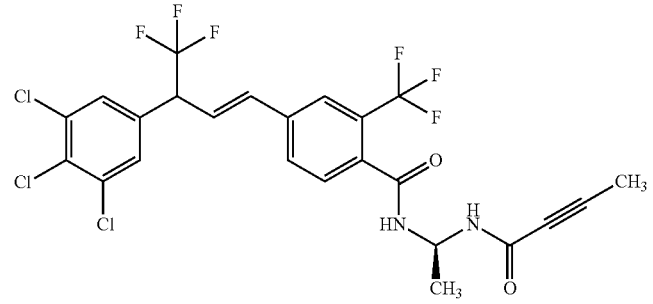 [SMILES: CC#CC(=O)N[C@@H](C)NC(=O)c1ccc(/C=C/C(c2cc(Cl)c(Cl)c(Cl)c2)C(F)(F)F)cc1C(F)(F)F] | Examples 18, 19, 20, or 21 |
| P33 | 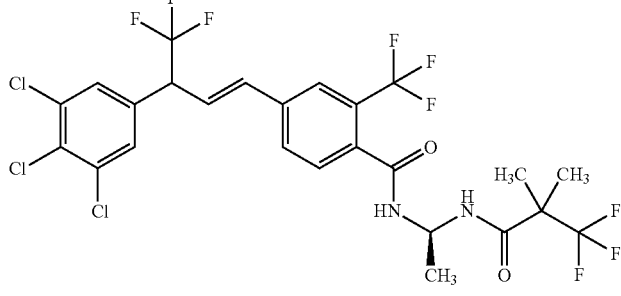 | Examples 18, 19, 20, or 21 |

TABLE 1-continued

Structure and Preparation Method for P Series Compounds

| No. | Structure | Prep. according to example or scheme: |
|---|---|---|
| P34 | 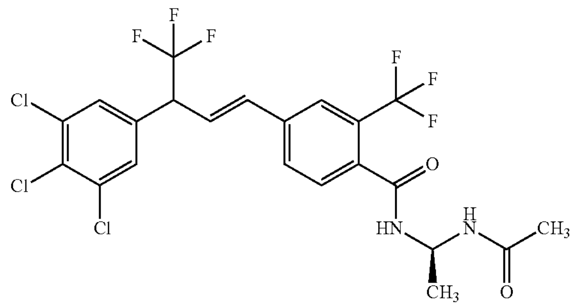 [SMILES: CC(=O)N[C@@H](C)NC(=O)c1ccc(/C=C/C(c2cc(Cl)c(Cl)c(Cl)c2)C(F)(F)F)cc1C(F)(F)F] | Examples 18, 19, 20, or 21 |
| P35 | 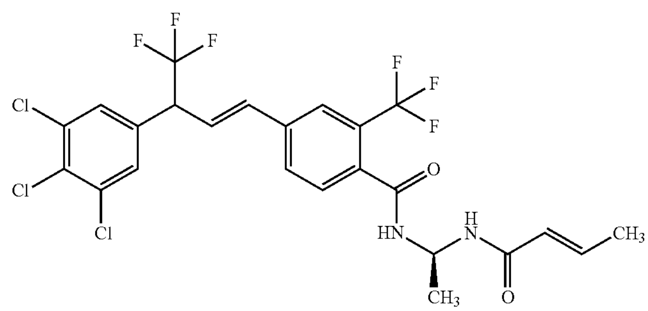 | Examples 18, 19, 20, or 21 |
| P36 | 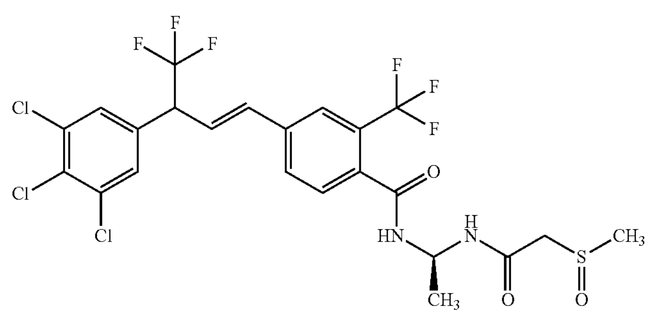 [SMILES: C[C@H](NC(=O)CS(C)=O)NC(=O)c1ccc(/C=C/C(c2cc(Cl)c(Cl)c(Cl)c2)C(F)(F)F)cc1C(F)(F)F] | Examples 18, 19, 20, or 21 |
| P37 | 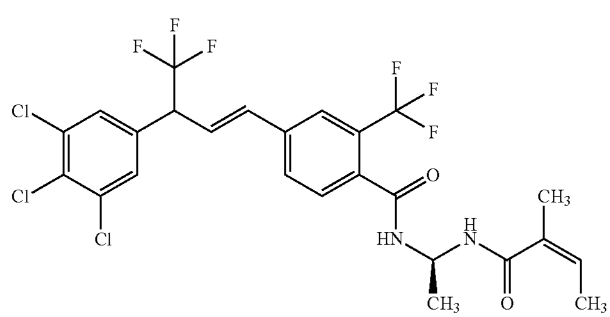 [SMILES: C/C=C(/C)C(=O)N[C@@H](C)NC(=O)c1ccc(/C=C/C(c2cc(Cl)c(Cl)c(Cl)c2)C(F)(F)F)cc1C(F)(F)F] | Examples 18, 19, 20, or 21 |

TABLE 1-continued

Structure and Preparation Method for P Series Compounds

| No. | Structure | Prep. according to example or scheme: |
|---|---|---|
| P38 | 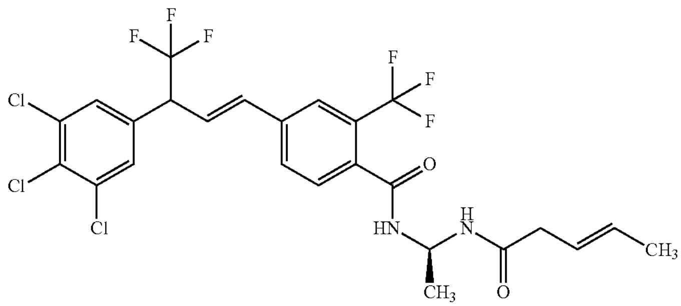 [SMILES: C/C=C/CC(=O)N[C@@H](C)NC(=O)c1ccc(/C=C/C(c2cc(Cl)c(Cl)c(Cl)c2)C(F)(F)F)cc1C(F)(F)F] | Examples 18, 19, 20, or 21 |
| P39 | 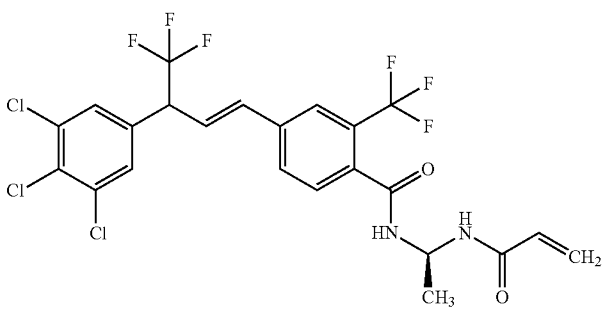 [SMILES: C=CC(=O)N[C@@H](C)NC(=O)c1ccc(/C=C/C(c2cc(Cl)c(Cl)c(Cl)c2)C(F)(F)F)cc1C(F)(F)F] | Examples 18, 19, 20, or 21 |
| P40 | 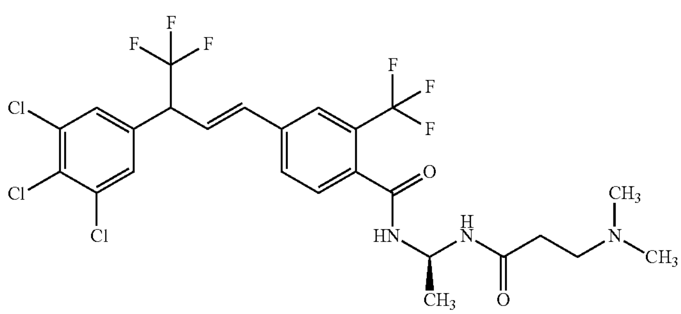 | Examples 18, 19, 20, or 21 |
| P41 | 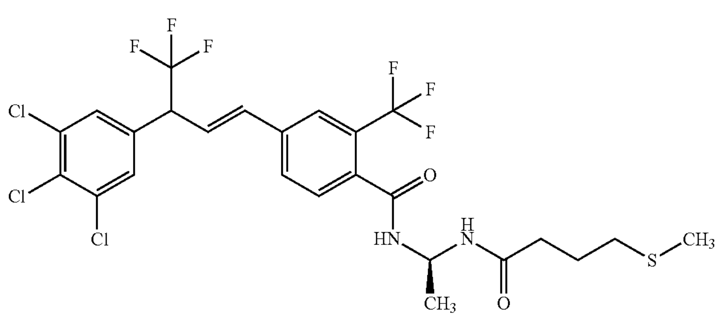 | Examples 18, 19, 20, or 21 |

TABLE 1-continued

Structure and Preparation Method for P Series Compounds

| No. | Structure | Prep. according to example or scheme: |
|---|---|---|
| P42 | 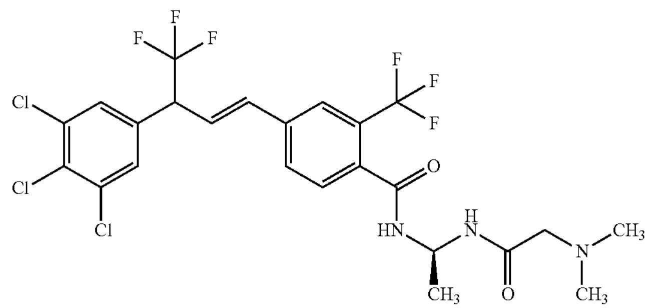 | Examples 18, 19, 20, or 21 |
| P43 | 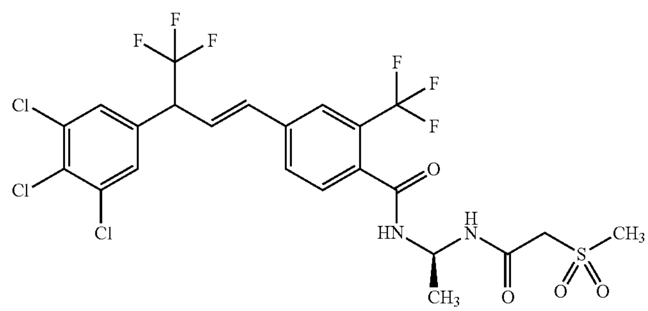 [SMILES: C[C@H](NC(=O)CS(C)(=O)=O)NC(=O)c1ccc(/C=C/C(c2cc(Cl)c(Cl)c(Cl)c2)C(F)(F)F)cc1C(F)(F)F] | Examples 18, 19, 20, or 21 |
| P44 | 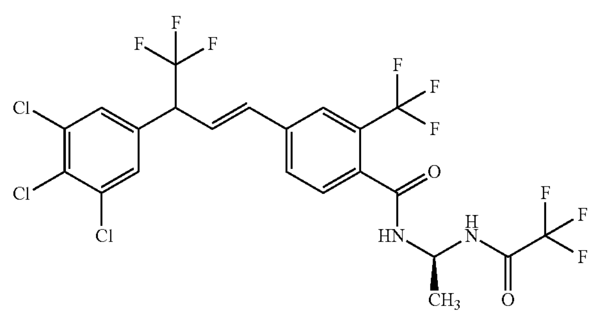 [SMILES: C[C@@H](NC(=O)c1ccc(/C=C/C(c2cc(Cl)c(Cl)c(Cl)c2)C(F)(F)F)cc1C(F)(F)F)NC(=O)C(F)(F)F] | Examples 18, 19, 20, or 21 |
| P45 | 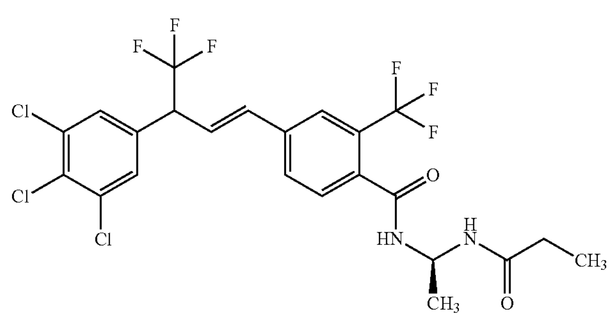 [SMILES: CCC(=O)N[C@@H](C)NC(=O)c1ccc(/C=C/C(c2cc(Cl)c(Cl)c(Cl)c2)C(F)(F)F)cc1C(F)(F)F] | Examples 18, 19, 20, or 21 |

TABLE 1-continued
Structure and Preparation Method for P Series Compounds
| No. | Structure | Prep. according to example or scheme: |
|---|---|---|
| P46 | 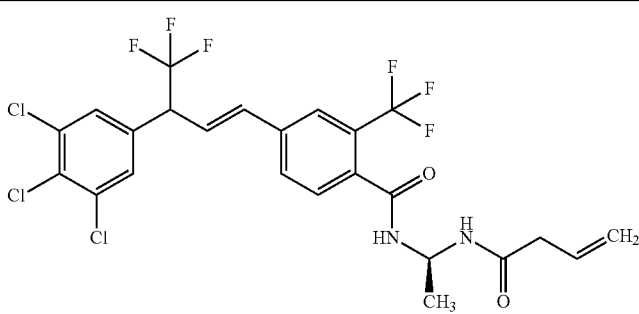 | Examples 18, 19, 20, or 21 |
| P47 | 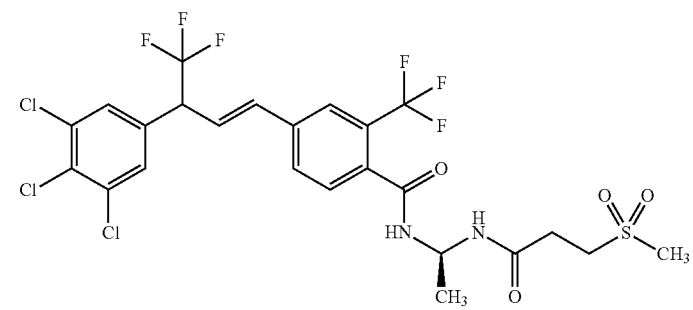 [SMILES: C[C@H](NC(=O)CCS(C)(=O)=O)NC(=O)c1ccc(/C=C/C(c2cc(Cl)c(Cl)c(Cl)c2)C(F)(F)F)cc1C(F)(F)F] | Examples 18, 19, 20, or 21 |
| P48 | 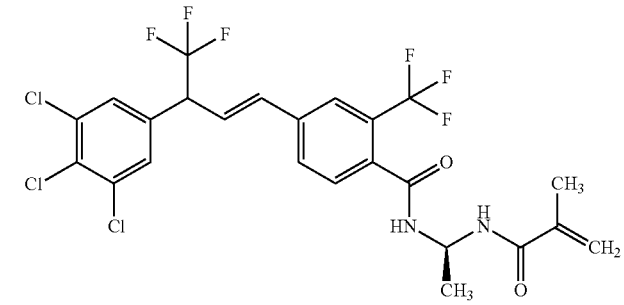 | Examples 18, 19, 20, or 21 |
| P49 | 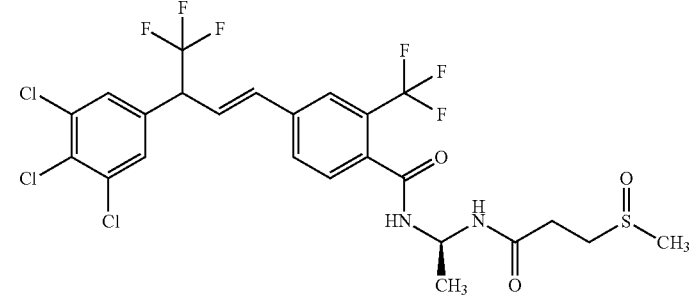 [SMILES: C[C@H](NC(=O)CCS(C)=O)NC(=O)c1ccc(/C=C/C(c2cc(Cl)c(Cl)c(Cl)c2)C(F)(F)F)cc1C(F)(F)F] | Examples 18, 19, 20, or 21 |

TABLE 1-continued

Structure and Preparation Method for P Series Compounds

| No. | Structure | Prep. according to example or scheme: |
|---|---|---|
| P50 | 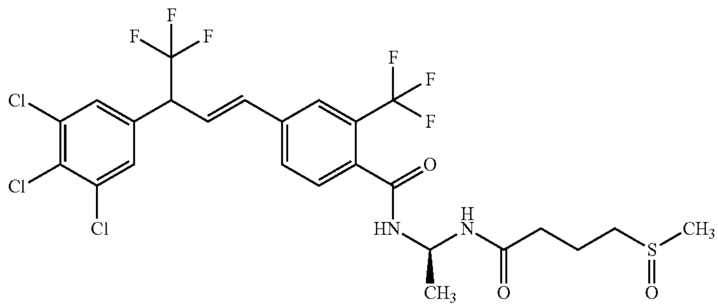 [SMILES: C[C@H](NC(=O)CCCS(C)=O)NC(=O)c1ccc(/C=C/C(c2cc(Cl)c(Cl)c(Cl)c2)C(F)(F)F)cc1C(F)(F)F] | Examples 18, 19, 20, or 21 |
| P51 | 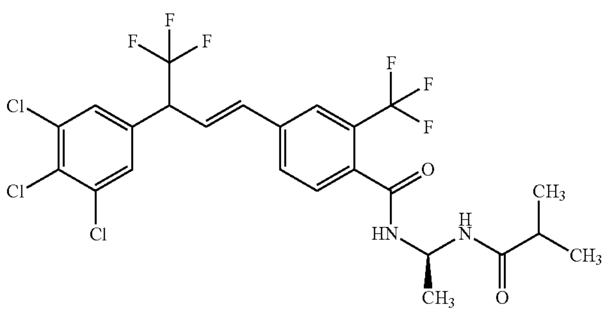 [SMILES: CC(C)C(=O)N[C@@H](C)NC(=O)c1ccc(/C=C/C(c2cc(Cl)c(Cl)c(Cl)c2)C(F)(F)F)cc1C(F)(F)F] | Examples 18, 19, 20, or 21 |
| P52 | 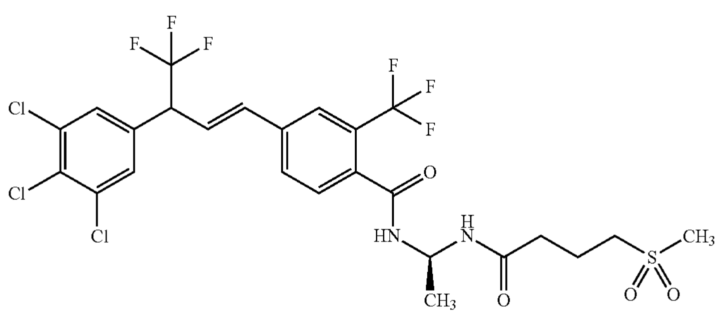 [SMILES: C[C@H](NC(=O)CCCS(C)(=O)=O)NC(=O)c1ccc(/C=C/C(c2cc(Cl)c(Cl)c(Cl)c2)C(F)(F)F)cc1C(F)(F)F] | Examples 18, 19, 20, or 21 |
| P53 | 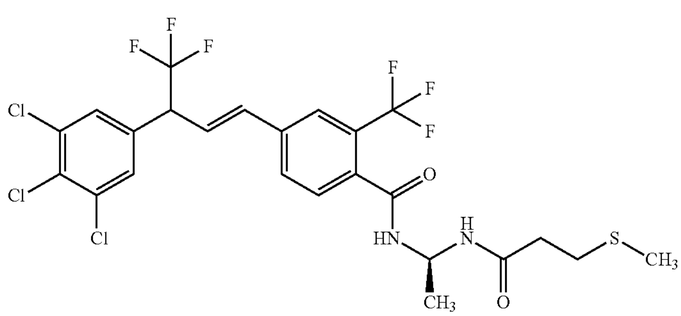 | Examples 18, 19, 20, or 21 |

TABLE 1-continued

Structure and Preparation Method for P Series Compounds

| No. | Structure | Prep. according to example or scheme: |
|---|---|---|
| P54 | 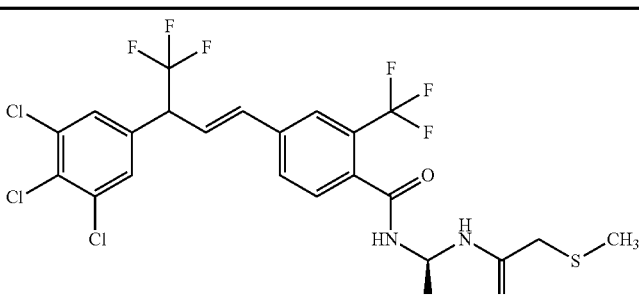 | Examples 18, 19, 20, or 21 |

Example A: Bioassays on Beet Armyworm ("BAW") and Cabbage Looper ("CL")

BAW has few effective parasites, diseases, or predators to lower its population. BAW infests many weeds, trees, grasses, legumes, and field crops. In various places, it is of economic concern upon asparagus, cotton, corn, soybeans, tobacco, alfalfa, sugar beets, peppers, tomatoes, potatoes, onions, peas, sunflowers, and citrus, among other plants. CEW is known to attack corn and tomatoes, but it also attacks artichoke, asparagus, cabbage, cantaloupe, collards, cowpeas, cucumbers, eggplant, lettuce, lima beans, melon, okra, peas, peppers, potatoes, pumpkin, snap beans, spinach, squash, sweet potatoes, and watermelon, among other plants. CEW is also known to be resistant to certain insecticides. CL feeds on a wide variety of cultivated plants and weeds. It feeds readily on crucifers, and has been reported damaging broccoli, cabbage, cauliflower, Chinese cabbage, collards, kale, mustard, radish, rutabaga, turnip, and watercress. Other vegetable crops injured include beet, cantaloupe, celery, cucumber, lima bean, lettuce, parsnip, pea, pepper, potato, snap bean, spinach, squash, sweet potato, tomato, and watermelon. CL is also known to be resistant to certain insecticides. Consequently, because of the above factors control of these pests is important. Furthermore, molecules that control these pests are useful in controlling other pests.

Certain molecules disclosed in this document were tested against BAW and CEW and CL using procedures described in the following examples. In the reporting of the results, the "BAW & CL Rating Table" was used (See Table Section).

Bioassays on BAW (*Spodoptera exigua*)

Bioassays on BAW were conducted using a 128-well diet tray assay. one to five second instar BAW larvae were placed in each well (3 mL) of the diet tray that had been previously filled with 1 mL of artificial diet to which 50 µg/cm² of the test compound (dissolved in 50 µL of 90:10 acetone-water mixture) had been applied (to each of eight wells) and then allowed to dry. Trays were covered with a clear self-adhesive cover, and held at 25° C., 14:10 light-dark for five to seven days. Percent mortality was recorded for the larvae in each well; activity in the eight wells was then averaged. The results are indicated in the tables entitled "Table ABC: Assay Results (F)", "Table ABCD: Assay Results (C)", and "Table ABCDE: Assay Results (P)" (See Table Section).

Bioassays on CL (*Trichoplusia ni*)

Bioassays on CL were conducted using a 128-well diet tray assay. One to five second instar CL larvae were placed in each well (3 mL) of the diet tray that had been previously filled with 1 mL of artificial diet to which 50 µg/cm² of the test compound (dissolved in 50 µL of 90:10 acetone-water mixture) had been applied (to each of eight wells) and then allowed to dry. Trays were covered with a clear self-adhesive cover, and held at 25° C., 14:10 light-dark for five to seven days. Percent mortality was recorded for the larvae in each well; activity in the eight wells was then averaged. The results are indicated in the table entitled "Table ABC: Assay Results (F)", "Table ABCD: Assay Results (C)", and "Table ABCDE: Assay Results (P)" (See Table Section).

Example B: Bioassays on Green Peach APHID ("GPA") (*Myzus persicae*)

GPA is the most significant aphid pest of peach trees, causing decreased growth, shriveling of the leaves, and the death of various tissues. It is also hazardous because it acts as a vector for the transport of plant viruses, such as potato virus Y and potato leafroll virus to members of the nightshade/potato family Solanaceae, and various mosaic viruses to many other food crops. GPA attacks such plants as broccoli, burdock, cabbage, carrot, cauliflower, daikon, eggplant, green beans, lettuce, macadamia, papaya, peppers, sweet potatoes, tomatoes, watercress, and zucchini, among other plants. GPA also attacks many ornamental crops such as carnation, chrysanthemum, flowering white cabbage, poinsettia, and roses. GPA has developed resistance to many pesticides.

Certain molecules disclosed in this document were tested against GPA using procedures described in the following example. In the reporting of the results, the "GPA & YFM Rating Table" was used (See Table Section).

Cabbage seedlings grown in 3-inch pots, with 2-3 small (3-5 cm) true leaves, were used as test substrate. The seedlings were infested with 20-50 GPA (wingless adult and nymph stages) one day prior to chemical application. Four pots with individual seedlings were used for each treatment. Test compounds (2 mg) were dissolved in 2 mL of acetone/MeOH (1:1) solvent, forming stock solutions of 1000 ppm test compound. The stock solutions were diluted 5× with 0.025% Tween 20 in water to obtain the solution at 200 ppm test compound. A hand-held aspirator-type sprayer was used for spraying a solution to both sides of cabbage leaves until runoff. Reference plants (solvent check) were sprayed with the diluent only containing 20% by volume of acetone/MeOH (1:1) solvent. Treated plants were held in a holding room for three days at approximately 25° C. and ambient relative humidity (RH) prior to grading. Evaluation was conducted by counting the number of live aphids per plant under a microscope. Percent Control was measured by using Abbott's correction formula (W. S. Abbott, "A Method of Computing the Effectiveness of an Insecticide" J. Econ. Entomol. 18 (1925), pp. 265-267) as follows. Corrected % Control=100*(X−Y)/X where X=No. of live aphids on solvent check plants and Y=No. of live aphids on treated plants. The results are indicated in the table entitled "Table ABC: Assay Results (F)" and "Table ABCD: Assay Results (C)" (See Table Section).

Example C: Bioassays on Yellow Fever Mosquito "YFM" (*Aedes aegypti*)

YFM prefers to feed on humans during the daytime and is most frequently found in or near human habitations. YFM is a vector for transmitting several diseases. It is a mosquito that can spread the dengue fever and yellow fever viruses. Yellow fever is the second most dangerous mosquito-borne disease after malaria. Yellow fever is an acute viral hemorrhagic disease and up to 50% of severely affected persons without treatment will die from yellow fever. There are an estimated 200,000 cases of yellow fever, causing 30,000 deaths, worldwide each year. Dengue fever is a nasty, viral disease; it is sometimes called "breakbone fever" or "breakheart fever" because of the intense pain it can produce. Dengue fever kills about 20,000 people annually. Consequently, because of the above factors control of this pest is important. Furthermore, molecules that control this pest (YFM), which is known as a sucking pest, are useful in controlling other pests that cause human and animal suffering.

Certain molecules disclosed in this document were tested against YFM using procedures described in the following paragraph. In the reporting of the results, the "GPA & YFM Rating Table" was used (See Table Section).
Master plates containing 400 μg of a molecule dissolved in 100 μL of dimethyl sulfoxide (DMSO) (equivalent to a 4000 ppm solution) are used. A master plate of assembled molecules contains 15 μL per well. To this plate, 135 μL of a 90:10 water:acetone mixture is added to each well. A robot (Biomek® NXP Laboratory Automation Workstation) is programmed to dispense 15 μL aspirations from the master plate into an empty 96-well shallow plate ("daughter" plate). There are 6 reps ("daughter" plates) created per master. The created daughter plates are then immediately infested with YFM larvae. The day before plates are to be treated, mosquito eggs are placed in Millipore water containing liver powder to begin hatching (4 g. into 400 mL). After the daughter plates are created using the robot, they are infested with 220 μL of the liver powder/larval mosquito mixture (about 1 day-old larvae). After plates are infested with mosquito larvae, a non-evaporative lid is used to cover the plate to reduce drying. Plates are held at room temperature for 3 days prior to grading. After 3 days, each well is observed and scored based on mortality. The results are indicated in the table entitled "Table ABC: Assay Results (F)" and "Table ABCD: Assay Results (C)" (See Table Section).

Pesticidally Acceptable Acid Addition Salts, Salt Derivatives, Solvates, Ester Derivatives, Polymorphs, Isotopes and Radionuclides Molecules of Formula One may be formulated into pesticidally acceptable acid addition salts. By way of a non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic acids. Additionally, by way of a non-limiting example, an acid function can form salts including those derived from alkali or alkaline earth metals and those derived from ammonia and amines. Examples of preferred cations include sodium, potassium, and magnesium.

Molecules of Formula One may be formulated into salt derivatives. By way of a non-limiting example, a salt derivative can be prepared by contacting a free base with a sufficient amount of the desired acid to produce a salt. A free base may be regenerated by treating the salt with a suitable dilute aqueous base solution such as dilute aqueous sodium hydroxide (NaOH), potassium carbonate, ammonia, and sodium bicarbonate. As an example, in many cases, a pesticide, such as 2,4-D, is made more water-soluble by converting it to its dimethylamine salt.

Molecules of Formula One may be formulated into stable complexes with a solvent, such that the complex remains intact after the non-complexed solvent is removed. These complexes are often referred to as "solvates." However, it is particularly desirable to form stable hydrates with water as the solvent.

Molecules of Formula One may be made into ester derivatives. These ester derivatives can then be applied in the same manner as the invention disclosed in this document is applied.

Molecules of Formula One may be made as various crystal polymorphs. Polymorphism is important in the development of agrochemicals since different crystal polymorphs or structures of the same molecule can have vastly different physical properties and biological performances.

Molecules of Formula One may be made with different isotopes. Of particular importance are molecules having $^2$H (also known as deuterium) in place of $^1$H.

Molecules of Formula One may be made with different radionuclides. Of particular importance are molecules having $^{14}$C.

Stereoisomers

Molecules of Formula One may exist as one or more stereoisomers. Thus, certain molecules can be produced as racemic mixtures. It will be appreciated by those skilled in the art that one stereoisomer may be more active than the other stereoisomers. Individual stereoisomers may be obtained by known selective synthetic procedures, by conventional synthetic procedures using resolved starting materials, or by conventional resolution procedures. Certain molecules disclosed in this document can exist as two or more isomers. The various isomers include geometric isomers, diastereomers, and enantiomers. Thus, the molecules disclosed in this document include geometric isomers, racemic mixtures, individual stereoisomers, and optically active mixtures. It will be appreciated by those skilled in the art that one isomer may be more active than the others. The structures disclosed in the present disclosure are drawn in only one geometric form for clarity, but are intended to represent all geometric forms of the molecule.

Combinations

Molecules of Formula One may also be used in combination (such as, in a compositional mixture, or a simultaneous or sequential application) with one or more compounds having acaricidal, algicidal, avicidal, bactericidal, fungicidal, herbicidal, insecticidal, molluscicidal, nematicidal, rodenticidal, or virucidal properties. Additionally, the molecules of Formula One may also be used in combination (such as, in a compositional mixture, or a simultaneous or sequential application) with compounds that are antifeedants, bird repellents, chemosterilants, herbicide safeners, insect attractants, insect repellents, mammal repellents, mating disrupters, plant activators, plant growth regulators, or synergists. Examples of such compounds in the above groups that may be used with the Molecules of Formula One are—(3-ethoxypropyl)mercury bromide, 1,2-dichloropropane, 1,3-dichloropropene, 1-methylcyclopropene, 1-naphthol, 2-(octylthio)ethanol, 2,3,5-tri-iodobenzoic acid, 2,3,6-TBA, 2,3,6-TBA-dimethylammonium, 2,3,6-TBA-lithium, 2,3,6-TBA-potassium, 2,3,6-TBA-sodium, 2,4,5-T, 2,4,5-T-2-butoxypropyl, 2,4,5-T-2-ethylhexyl, 2,4,5-T-3-butoxypropyl, 2,4,5-TB, 2,4,5-T-butometyl, 2,4,5-T-butotyl, 2,4,5-T-butyl, 2,4,5-T-isobutyl, 2,4,5-T-isoctyl, 2,4,5-T-isopropyl, 2,4,5-T-methyl, 2,4,5-T-pentyl, 2,4,5-T-sodium, 2,4,5-T-triethylammonium, 2,4,5-T-trolamine, 2,4-D, 2,4-D-2-butoxypropyl, 2,4-D-2-ethylhexyl, 2,4-D-3-butoxypropyl, 2,4-D-ammonium, 2,4-DB, 2,4-DB-butyl, 2,4-DB-dimethylammonium, 2,4-DB-isoctyl, 2,4-DB-potassium, 2,4-DB-sodium, 2,4-D-butotyl, 2,4-D-butyl, 2,4-D-diethylammonium, 2,4-D-dimethylammonium, 2,4-D-diolamine, 2,4-D-dodecylammonium, 2,4-DEB, 2,4-DEP, 2,4-D-ethyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-potassium, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, 2iP, 2-methoxyethylmercury chloride, 2-phenylphenol, 3,4-DA, 3,4-DB, 3,4-DP, 4-aminopyridine, 4-CPA, 4-CPA-potassium, 4-CPA-sodium, 4-CPB, 4-CPP, 4-hydroxyphenethyl alcohol, 8-hydroxyquinoline sulfate, 8-phenylmercurioxyquinoline, abamectin, abscisic acid, ACC, acephate, acequinocyl, acetamiprid, acethion, acetochlor, acetophos, acetoprole, acibenzolar, acibenzolar-S-methyl, acifluorfen, acifluorfen-methyl, acifluorfen-sodium, aclonifen, acrep, acrinathrin, acrolein, acrylonitrile, acypetacs, acypetacs-copper, acypetacs-zinc, alachlor, alanycarb, albendazole, aldicarb, aldimorph, aldoxycarb, aldrin, allethrin, allicin, allidochlor, allosamidin, alloxydim, alloxydim-sodium, allyl alcohol, allyxycarb, alorac, alpha-cypermethrin, alpha-endosulfan, ametoctradin, ametridione, ametryn, amibuzin, amicarbazone, amicarthiazol, amidithion, amidoflumet, amidosulfuron, aminocarb, aminocyclopyrachlor, aminocyclopyrachlor-methyl, aminocyclopyrachlor-potassium, aminopyralid, aminopyralid-potassium, aminopyralid-tris(2-hydroxypropyl)ammonium, amiprofos-methyl, amiprophos, amisulbrom, amiton, amiton oxalate, amitraz, amitrole, ammonium sulfamate, ammonium α-naphthaleneacetate, amobam, ampropylfos, anabasine, ancymidol, anilazine, anilofos, anisuron, anthraquinone, antu, apholate, aramite, arsenous oxide, asomate, aspirin, asulam, asulam-potassium, asulam-sodium, athidathion, atraton, atrazine, aureofungin, aviglycine, aviglycine hydrochloride, azaconazole, azadirachtin, azafenidin, azamethiphos, azimsulfuron, azinphos-ethyl, azinphos-methyl, aziprotryne, azithiram, azobenzene, azocyclotin, azothoate, azoxystrobin, bachmedesh, barban, barium hexafluorosilicate, barium polysulfide, barthrin, BCPC, beflubutamid, benalaxyl, benalaxyl-M, benazolin, benazolin-dimethylammonium, benazolin-ethyl, benazolin-potassium, bencarbazone, benclothiaz, bendiocarb, benfluralin, benfuracarb, benfuresate, benodanil, benomyl, benoxacor, benoxafos, benquinox, bensulfuron, bensulfuron-methyl, bensulide, bensultap, bentaluron, bentazone, bentazone-sodium, benthiavalicarb, benthiavalicarb-isopropyl, benthiazole, bentranil, benzadox, benzadox-ammonium, benzalkonium chloride, benzamacril, benzamacril-isobutyl, benzamorf, benzfendizone, benzipram, benzobicyclon, benzofenap, benzofluor, benzohydroxamic acid, benzoximate, benzoylprop, benzoylprop-ethyl, benzthiazuron, benzyl benzoate, benzyladenine, berberine, berberine chloride, beta-cyfluthrin, beta-cypermethrin, bethoxazin, bicyclopyrone, bifenazate, bifenox, bifenthrin, bifujunzhi, bilanafos, bilanafos-sodium, binapacryl, bingqingxiao, bioallethrin, bioethanomethrin, biopermethrin, bioresmethrin, biphenyl, bisazir, bismerthiazol, bispyribac, bispyribac-sodium, bistrifluron, bitertanol, bithionol, bixafen, blasticidin-S, borax, Bordeaux mixture, boric acid, boscalid, brassinolide, brassinolide-ethyl, brevicomin, brodifacoum, brofenvalerate, brofluthrinate, bromacil, bromacil-lithium, bromacil-sodium, bromadiolone, bromethalin, bromethrin, bromfenvinfos, bromoacetamide, bromobonil, bromobutide, bromocyclen, bromo-DDT, bromofenoxim, bromophos, bromophos-ethyl, bromopropylate, bromothalonil, bromoxynil, bromoxynil butyrate, bromoxynil heptanoate, bromoxynil octanoate, bromoxynil-potassium, brompyrazon, bromuconazole, bronopol, bucarpolate, bufencarb, buminafos, bupirimate, buprofezin, Burgundy mixture, busulfan, butacarb, butachlor, butafenacil, butamifos, butathiofos, butenachlor, butethrin, buthidazole, buthiobate, buthiuron, butocarboxim, butonate, butopyronoxyl, butoxycarboxim, butralin, butroxydim, buturon, butylamine, butylate, cacodylic acid, cadusafos, cafenstrole, calcium arsenate, calcium chlorate, calcium cyanamide, calcium polysulfide, calvinphos, cambendichlor, camphechlor, camphor, captafol, captan, carbamorph, carbanolate, carbaryl, carbasulam, carbendazim, carbendazim benzenesulfonate, carbendazim sulfite, carbetamide, carbofuran, carbon disulfide, carbon tetrachloride, carbophenothion, carbosulfan, carboxazole, carboxide, carboxin, carfentrazone, carfentrazone-ethyl, carpropamid, cartap, cartap hydrochloride, carvacrol, carvone, CDEA, cellocidin, CEPC, ceralure, Cheshunt mixture, chinomethionat, chitosan, chlobenthiazone, chlomethoxyfen, chloralose, chloramben, chloramben-ammonium, chloramben-diolamine, chloramben-methyl, chloramben-methylammonium, chloramben-sodium, chloramine phosphorus, chloramphenicol, chloraniformethan, chloranil, chloranocryl, chlorantraniliprole, chlorazifop, chlorazifop-propargyl, chlorazine, chlorbenside, chlorbenzuron, chlorbicyclen, chlorbromuron, chlorbufam, chlordane, chlordecone, chlordimeform, chlordimeform hydrochloride, chlorempenthrin, chlorethoxyfos, chloreturon, chlorfenac, chlorfenac-ammonium, chlorfenac-sodium, chlorfenapyr, chlorfenazole, chlorfenethol, chlorfenprop, chlorfenson, chlorfensulphide, chlorfenvinphos, chlorfluazuron, chlorflurazole, chlorfluren, chlorfluren-methyl, chlorflurenol, chlorflurenol-methyl, chloridazon, chlorimuron, chlorimuron-ethyl, chlormephos, chlormequat, chlormequat chloride, chlornidine, chlornitrofen, chlorobenzilate, chlorodinitronaphthalenes, chloroform, chloromebuform, chloromethiuron, chloroneb, chlorophacinone, chlorophacinone-sodium, chloropicrin, chloropon, chloropropylate, chlorothalonil, chlorotoluron, chloroxuron, chloroxynil, chlorphonium, chlorphonium chloride, chlorphoxim, chlorprazophos, chlorprocarb, chlorpropham, chlorpyrifos, chlorpyrifos-methyl, chlorquinox, chlorsulfuron, chlorthal, chlorthal-dimethyl, chlorthal-monomethyl, chlorthiamid, chlorthiophos, chlozolinate, choline chloride, chromafenozide, cinerin I, cinerin II, cinerins, cinidon-ethyl, cinmethylin, cinosulfuron, ciobutide, cisanilide, cismethrin, clethodim, climbazole, cliodinate, clodinafop, clodinafop-propargyl, cloethocarb, clofencet, clofencet-potassium, clofentezine, clofibric acid, clofop, clofop-isobutyl, clomazone, clomeprop, cloprop, cloproxydim, clopyralid, clopyralid-methyl, clopyralid-olamine, clopyralid-potassium, clopyralid-tris(2-hydroxypropyl)ammonium, cloquintocet, cloquintocet-mexyl, cloransulam, cloransulam-methyl, closantel, clothianidin, clotrimazole, cloxyfonac, cloxyfonac-sodium, CMA, codlelure, colophonate, copper acetate, copper acetoarsenite, copper arsenate, copper carbonate, basic, copper hydroxide, copper naphthenate, copper oleate, copper oxychloride, copper silicate, copper sulfate, copper zinc chromate, coumachlor, coumafuryl, coumaphos, coumatetralyl, coumithoate, coumoxystrobin, CPMC, CPMF, CPPC, credazine, cresol, crimidine, crotamiton, crotoxyphos, crufomate, cryolite, cue-lure, cufraneb, cumyluron, cuprobam, cuprous oxide, curcumenol, cyanamide, cyanatryn, cyanazine, cyanofenphos, cyanophos, cyanthoate, cyantraniliprole, cyazofamid, cybutryne, cyclafuramid, cyclanilide, cyclethrin, cycloate, cycloheximide, cyclopate, cycloprothrin, cyclosulfamuron, cycloxaprid, cycloxydim, cycluron, cyenopyrafen, cyflufenamid, cyflumetofen, cyfluthrin, cyhalofop, cyhalofop-butyl, cyhalothrin, cyhexatin, cymiazole, cymiazole hydrochloride, cymoxanil, cyometrinil, cypendazole, cypermethrin, cyperquat, cyperquat chloride, cyphenothrin, cyprazine, cyprazole, cyproconazole, cyprodinil, cyprofuram, cypromid, cyprosulfamide, cyromazine, cythioate, daimuron, dalapon, dalapon-calcium, dalapon-magnesium, dalapon-sodium, daminozide, dayoutong, dazomet, dazomet-sodium, DBCP, d-camphor, DCIP, DCPTA, DDT, debacarb, decafentin, decarbofuran, dehydroacetic acid, delachlor, deltamethrin, demephion, demephion-O, demephion-S, demeton, demeton-methyl, demeton-O, demeton-O-methyl, demeton-S, demeton-S-methyl, demeton-S-methylsulphon, desmedipham, desmetryn, d-fanshiluquebingjuzhi, diafenthiuron, dialifos, di-allate, diamidafos, diatomaceous earth, diazinon, dibutyl phthalate, dibutyl succinate, dicamba, dicamba-diglycolamine, dicamba-dimethylammonium, dicamba-diolamine, dicamba-isopropylammonium, dicamba-methyl, dicamba-olamine, dicamba-potassium, dicamba-sodium, dicamba-trolamine, dicapthon, dichlobenil, dichlofenthion, dichlofluanid, dichlone, dichloralurea, dichlorbenzuron, dichlorflurenol, dichlorflurenol-methyl, dichlormate, dichlormid, dichlorophen, dichlorprop, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-2-ethylhexyl, dichlorprop-P-dimethylammonium, dichlorprop-potassium, dichlorprop-sodium, dichlorvos, dichlozoline, diclobutrazol, diclocymet, diclofop, diclofop-methyl, diclomezine, diclomezine-sodium, dicloran, diclosulam, dicofol, dicoumarol, dicresyl, dicrotophos, dicyclanil, dicyclonon, dieldrin, dienochlor, diethamquat, diethamquat dichloride, diethatyl, diethatyl-ethyl, diethofencarb, dietholate, diethyl pyrocarbonate, diethyltoluamide, difenacoum, difenoconazole, difenopenten, difenopenten-ethyl, difenoxuron, difenzoquat, difenzoquat metilsulfate, difethialone, diflovidazin, diflubenzuron, diflufenican, diflufenzopyr, diflufenzopyr-sodium, diflumetorim, dikegulac, dikegulac-sodium, dilor, dimatif, dimefluthrin, dimefox, dimefuron, dimepiperate, dimetachlone, dimetan, dimethacarb, dimethachlor, dimethametryn, dimethenamid, dimethenamid-P, dimethipin, dimethirimol, dimethoate, dimethomorph, dimethrin, dimethyl carbate, dimethyl phthalate, dimethylvinphos, dimetilan, dimexano, dimidazon, dimoxystrobin, dinex, dinex-diclexine, dingjunezuo, diniconazole, diniconazole-M, dinitramine, dinobuton, dinocap, dinocap-4, dinocap-6, dinocton, dinofenate, dinopenton, dinoprop, dinosam, dinoseb, dinoseb acetate, dinoseb-ammonium, dinoseb-diolamine, dinoseb-sodium, dinoseb-trolamine, dinosulfon, dinotefuran, dinoterb, dinoterb acetate, dinoterbon, diofenolan, dioxabenzofos, dioxacarb, dioxathion, diphacinone, diphacinone-sodium, diphenamid, diphenyl sulfone, diphenylamine, dipropalin, dipropetryn, dipyrithione, diquat, diquat dibromide, disparlure, disul, disulfiram, disulfoton, disul-sodium, ditalimfos, dithianon, dithicrofos, dithioether, dithiopyr, diuron, d-limonene, DMPA, DNOC, DNOC-ammonium, DNOC-potassium, DNOC-sodium, dodemorph, dodemorph acetate, dodemorph benzoate, dodicin, dodicin hydrochloride, dodicin-sodium, dodine, dofenapyn, dominicalure, doramectin, drazoxolon, DSMA, dufulin, EBEP, EBP, ecdysterone, edifenphos, eglinazine, eglinazine-ethyl, emamectin, emamectin benzoate, EMPC, empenthrin, endosulfan, endothal, endothal-diammonium, endothal-dipotassium, endothal-disodium, endothion, endrin, enestroburin, EPN, epocholeone, epofenonane, epoxiconazole, eprinomectin, epronaz, EPTC, erbon, ergocalciferol, erlujixiancaoan, esdépalléthrine, esfenvalerate, esprocarb, etacelasil, etaconazole, etaphos, etem, ethaboxam, ethachlor, ethalfluralin, ethametsulfuron, ethametsulfuron-methyl, ethaprochlor, ethephon, ethidimuron, ethiofencarb, ethiolate, ethion, ethiozin, ethiprole, ethirimol, ethoate-methyl, ethofumesate, ethohexadiol, ethoprophos, ethoxyfen, ethoxyfen-ethyl, ethoxyquin, ethoxysulfuron, ethychlozate, ethyl formate, ethyl α-naphthaleneacetate, ethyl-DDD, ethylene, ethylene dibromide, ethylene dichloride, ethylene oxide, ethylicin, ethylmercury 2,3-dihydroxypropyl mercaptide, ethylmercury acetate, ethylmercury bromide, ethylmercury chloride, ethylmercury phosphate, etinofen, etnipromid, etobenzanid, etofenprox, etoxazole, etridiazole, etrimfos, eugenol, EXD, famoxadone, famphur, fenamidone, fenaminosulf, fenamiphos, fenapanil, fenarimol, fenasulam, fenazaflor, fenazaquin, fenbuconazole, fenbutatin oxide, fenchlorazole, fenchlorazole-ethyl, fenchlorphos, fenclorim, fenethacarb, fenfluthrin, fenfuram, fenhexamid, fenitropan, fenitrothion, fenjuntong, fenobucarb, fenoprop, fenoprop-3-butoxypropyl, fenoprop-butometyl, fenoprop-butotyl, fenoprop-butyl, fenoprop-isoctyl, fenoprop-methyl, fenoprop-potassium, fenothiocarb, fenoxacrim, fenoxanil, fenoxaprop, fenoxaprop-ethyl, fenoxaprop-P, fenoxaprop-P-ethyl, fenoxasulfone, fenoxycarb, fenpiclonil, fenpirithrin, fenpropathrin, fenpropidin, fenpropimorph, fenpyrazamine, fenpyroximate, fenridazon, fenridazon-potassium, fenridazon-propyl, fenson, fensulfothion, fenteracol, fenthiaprop, fenthiaprop-ethyl, fenthion, fenthion-ethyl, fentin, fentin acetate, fentin chloride, fentin hydroxide, fentrazamide, fentrifanil, fenuron, fenuron TCA, fenvalerate, ferbam, ferimzone, ferrous sulfate, fipronil, flamprop, flamprop-isopropyl, flamprop-M, flamprop-methyl, flamprop-M-isopropyl, flamprop-M-methyl, flazasulfuron, flocoumafen, flometoquin, flonicamid, florasulam, fluacrypyrim, fluazifop, fluazifop-butyl, fluazifop-methyl, fluazifop-P, fluazifop-P-butyl, fluazinam, fluazolate, fluazuron, flubendiamide, flubenzimine, flucarbazone, flucarbazone-sodium, flucetosulfuron, fluchloralin, flucofuron, flucycloxuron, flucythrinate, fludioxonil, fluenetil, fluensulfone, flufenacet, flufenerim, flufenican, flufenoxuron, flufenprox, flufenpyr, flufenpyr-ethyl, flufiprole, flumethrin, flumetover, flumetralin, flumetsulam, flumezin, flumiclorac, flumiclorac-pentyl, flumioxazin, flumipropyn, flumorph, fluometuron, fluopicolide, fluopyram, fluorbenside, fluoridamid, fluoroacetamide, fluorodifen, fluoroglycofen, fluoroglycofen-ethyl, fluoroimide, fluoromidine, fluoronitrofen, fluothiuron, fluotrimazole, fluoxastrobin, flupoxam, flupropacil, flupropadine, flupropanate, flupropanate-sodium, flupyradifurone, flupyrsulfuron, flupyrsulfuron-methyl, flupyrsulfuron-methyl-sodium, fluquinconazole, flurazole, flurenol, flurenol-butyl, flurenol-methyl, fluridone, flurochloridone, fluroxypyr, fluroxypyr-butometyl, fluroxypyr-meptyl, flurprimidol, flursulamid, flurtamone, flusilazole, flusulfamide, fluthiacet, fluthiacet-methyl, flutianil, flutolanil, flutriafol, fluvalinate, fluxapyroxad, fluxofenim, folpet, fomesafen, fomesafen-sodium, fonofos, foramsulfuron, forchlorfenuron, formaldehyde, formetanate, formetanate hydrochloride, formothion, formparanate, formparanate hydrochloride, fosamine, fosamine-ammonium, fosetyl, fosetyl-aluminium, fosmethilan, fospirate, fosthiazate, fosthietan, frontalin, fuberidazole, fucaojing, fucaomi, funaihecaoling, fuphenthiourea, furalane, furalaxyl, furamethrin, furametpyr, furathiocarb, furcarbanil, furconazole, furconazole-cis, furethrin, furfural, furilazole, furmecyclox, furophanate, furyloxyfen, gamma-cyhalothrin, gamma-HCH, genit, gibberellic acid, gibberellins, gliftor, glufosinate, glufosinate-ammonium, glufosinate-P, glufosinate-P-ammonium, glufosinate-P-sodium, glyodin, glyoxime, glyphosate, glyphosate-diammonium, glyphosate-dimethylammonium, glyphosate-isopropylammonium, glyphosate-monoammonium, glyphosate-potassium, glyphosate-sesquisodium, glyphosate-trimesium, glyphosine, gossyplure, grandlure, griseofulvin, guazatine, guazatine acetates, halacrinate, halfenprox, halofenozide, halosafen, halosulfuron, halosulfuron-methyl, haloxydine, haloxyfop, haloxyfop-etotyl, haloxyfop-methyl, haloxyfop-P, haloxyfop-P-etotyl, haloxyfop-P-methyl, haloxyfop-sodium, HCH, hemel, hempa, HEOD, heptachlor, heptenophos, heptopargil, heterophos, hexachloroacetone, hexachlorobenzene, hexachlorobutadiene, hexachlorophene, hexaconazole, hexaflumuron, hexaflurate, hexalure, hexamide, hexazinone, hexylthiofos, hexythiazox, HHDN, holosulf, huancaiwo, huangcaoling, huanjunzuo, hydramethylnon, hydrargaphen, hydrated lime, hydrogen cyanide, hydroprene, hymexazol, hyquincarb, IAA, IBA, icaridin, imazalil, imazalil nitrate, imazalil sulfate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin-methyl, imazaquin-sodium, imazethapyr, imazethapyr-ammonium, imazosulfuron, imibenconazole, imicyafos, imidacloprid, imidaclothiz, iminoctadine, iminoctadine triacetate, iminoctadine trialbesilate, imiprothrin, inabenfide, indanofan, indaziflam, indoxacarb, inezin, iodobonil, iodocarb, iodomethane, iodosulfuron, iodosulfuron-methyl, iodosulfuron-methyl-sodium, iofensulfuron, iofensulfuron-sodium, ioxynil, ioxynil octanoate, ioxynil-lithium, ioxynil-sodium, ipazine, ipconazole, ipfencarbazone, iprobenfos, iprodione, iprovalicarb, iprymidam, ipsdienol, ipsenol, IPSP, isamidofos, isazofos, isobenzan, isocarbamid, isocarbophos, isocil, isodrin, isofenphos, isofenphos-methyl, isolan, isomethiozin, isonoruron, isopolinate, isoprocarb, isopropalin, isoprothiolane, isoproturon, isopyrazam, isopyrimol, isothioate, isotianil, isouron, isovaledione, isoxaben, isoxachlortole, isoxadifen, isoxadifen-ethyl, isoxaflutole, isoxapyrifop, isoxathion, ivermectin, izopamfos, japonilure, japothrins, jasmolin I, jasmolin II, jasmonic acid, jiahuangchongzong, jiajizengxiaolin, jiaxiangjunzhi, jiecaowan, jiecaoxi, jodfenphos, juvenile hormone I, juvenile hormone II, juvenile hormone III, kadethrin, karbutilate, karetazan, karetazan-potassium, kasugamycin, kasugamycin hydrochloride, kejunlin, kelevan, ketospiradox, ketospiradox-potassium, kinetin, kinoprene, kresoxim-methyl, kuicaoxi, lactofen, lambda-cyhalothrin, latilure, lead arsenate, lenacil, lepimectin, leptophos, lindane, lineatin, linuron, lirimfos, litlure, looplure, lufenuron, lvdingjunzhi, lvxiancaolin, lythidathion, MAA, malathion, maleic hydrazide, malonoben, maltodextrin, MAMA, mancopper, mancozeb, mandipropamid, maneb, matrine, mazidox, MCPA, MCPA-2-ethylhexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-potassium, MCPA-sodium, MCPA-thioethyl, MCPA-trolamine, MCPB, MCPB-ethyl, MCPB-methyl, MCPB-sodium, mebenil, mecarbam, mecarbinzid, mecarphon, mecoprop, mecoprop-2-ethylhexyl, mecoprop-dimethylammonium, mecoprop-diolamine, mecoprop-ethadyl, mecoprop-isoctyl, mecoprop-methyl, mecoprop-P, mecoprop-P-2-ethylhexyl, mecoprop-P-dimethylammonium, mecoprop-P-isobutyl, mecoprop-potassium, mecoprop-P-potassium, mecoprop-sodium, mecoprop-trolamine, medimeform, medinoterb, medinoterb acetate, medlure, mefenacet, mefenpyr, mefenpyr-diethyl, mefluidide, mefluidide-diolamine, mefluidide-potassium, megatomoic acid, menazon, mepanipyrim, meperfluthrin, mephenate, mephosfolan, mepiquat, mepiquat chloride, mepiquat pentaborate, mepronil, meptyldinocap, mercuric chloride, mercuric oxide, mercurous chloride, merphos, mesoprazine, mesosulfuron, mesosulfuron-methyl, mesotrione, mesulfen, mesulfenfos, metaflumizone, metalaxyl, metalaxyl-M, metaldehyde, metam, metam-ammonium, metamifop, metamitron, metam-potassium, metam-sodium, metazachlor, metazosulfuron, metazoxolon, metconazole, metepa, metflurazon, methabenzthiazuron, methacrifos, methalpropalin, methamidophos, methasulfocarb, methazole, methfuroxam, methidathion, methiobencarb, methiocarb, methiopyrisulfuron, methiotepa, methiozolin, methiuron, methocrotophos, methometon, methomyl, methoprene, methoprotryne, methoquin-butyl, methothrin, methoxychlor, methoxyfenozide, methoxyphenone, methyl apholate, methyl bromide, methyl eugenol, methyl iodide, methyl isothiocyanate, methylacetophos, methylchloroform, methyldymron, methylene chloride, methylmercury benzoate, methylmercury dicyandiamide, methylmercury pentachlorophenoxide, methylneodecanamide, metiram, metobenzuron, metobromuron, metofluthrin, metolachlor, metolcarb, metominostrobin, metosulam, metoxadiazone, metoxuron, metrafenone, metribuzin, metsulfovax, metsulfuron, metsulfuron-methyl, mevinphos, mexacarbate, mieshuan, milbemectin, milbemycin oxime, milneb, mipafox, mirex, MNAF, moguchun, molinate, molosultap, monalide, monisouron, monochloroacetic acid, monocrotophos, monolinuron, monosulfuron, monosulfuron-ester, monuron, monuron TCA, morfamquat, morfamquat dichloride, moroxydine, moroxydine hydrochloride, morphothion, morzid, moxidectin, MSMA, muscalure, myclobutanil, myclozolin, N-(ethylmercury)-p-toluenesulphonanilide, nabam, naftalofos, naled, naphthalene, naphthaleneacetamide, naphthalic anhydride, naphthoxyacetic acids, naproanilide, napropamide, naptalam, naptalam-sodium, natamycin, neburon, niclosamide, niclosamide-olamine, nicosulfuron, nicotine, nifluridide, nipyraclofen, nitenpyram, nithiazine, nitralin, nitrapyrin, nitrilacarb, nitrofen, nitrofluorfen, nitrostyrene, nitrothal-isopropyl, norbormide, norflurazon, nornicotine, noruron, novaluron, noviflumuron, nuarimol, OCH, octachlorodipropyl ether, octhilinone, ofurace, omethoate, orbencarb, orfralure, ortho-dichlorobenzene, orthosulfamuron, oryctalure, orysastrobin, oryzalin, osthol, ostramone, oxabetrinil, oxadiargyl, oxadiazon, oxadixyl, oxamate, oxamyl, oxapyrazon, oxapyrazon-dimolamine, oxapyrazon-sodium, oxasulfuron, oxaziclomefone, oxine-copper, oxolinic acid, oxpoconazole, oxpoconazole fumarate, oxycarboxin, oxydemeton-methyl, oxydeprofos, oxydisulfoton, oxyfluorfen, oxymatrine, oxytetracycline, oxytetracycline hydrochloride, paclobutrazol, paichongding, para-dichlorobenzene, parafluron, paraquat, paraquat dichloride, paraquat dimetilsulfate, parathion, parathion-methyl, parinol, pebulate, pefurazoate, pelargonic acid, penconazole, pencycuron, pendimethalin, penflufen, penfluron, penoxsulam, pentachlorophenol, pentanochlor, penthiopyrad, pentmethrin, pentoxazone, perfluidone, permethrin, pethoxamid, phenamacril, phenazine oxide, phenisopham, phenkapton, phenmedipham, phenmedipham-ethyl, phenobenzuron, phenothrin, phenproxide, phenthoate, phenylmercuriurea, phenylmercury acetate, phenylmercury chloride, phenylmercury derivative of pyrocatechol, phenylmercury nitrate, phenylmercury salicylate, phorate, phosacetim, phosalone, phosdiphen, phosfolan, phosfolan-methyl, phosglycin, phosmet, phosnichlor, phosphamidon, phosphine, phosphocarb, phosphorus, phostin, phoxim, phoxim-methyl, phthalide, picloram, picloram-2-ethylhexyl, picloram-isoctyl, picloram-methyl, picloram-olamine, picloram-potassium, picloram-triethylammonium, picloram-tris(2-hydroxypropyl)ammonium, picolinafen, picoxystrobin, pindone, pindone-sodium, pinoxaden, piperalin, piperonyl butoxide, piperonyl cyclonene, piperophos, piproctanyl, piproctanyl bromide, piprotal, pirimetaphos, pirimicarb, pirimioxyphos, pirimiphos-ethyl, pirimiphos-methyl, plifenate, polycarbamate, polyoxins, polyoxorim, polyoxorim-zinc, polythialan, potassium arsenite, potassium azide, potassium cyanate, potassium gibberellate, potassium naphthenate, potassium polysulfide, potassium thiocyanate, potassium α-naphthaleneacetate, pp'-DDT, prallethrin, precocene I, precocene II, precocene III, pretilachlor, primidophos, primisulfuron, primisulfuron-methyl, probenazole, prochloraz, prochloraz-manganese, proclonol, procyazine, procymidone, prodiamine, profenofos, profluazol, profluralin, profluthrin, profoxydim, proglinazine, proglinazine-ethyl, prohexadione, prohexadione-calcium, prohydrojasmon, promacyl, promecarb, prometon, prometryn, promurit, propachlor, propamidine, propamidine dihydrochloride, propamocarb, propamocarb hydrochloride, propanil, propaphos, propaquizafop, propargite, proparthrin, propazine, propetamphos, propham, propiconazole, propineb, propisochlor, propoxur, propoxycarbazone, propoxycarbazone-sodium, propyl isome, propyrisulfuron, propyzamide, proquinazid, prosuler, prosulfalin, prosulfocarb, prosulfuron, prothidathion, prothiocarb, prothiocarb hydrochloride, prothioconazole, prothiofos, prothoate, protrifenbute, proxan, proxan-sodium, prynachlor, pydanon, pymetrozine, pyracarbolid, pyraclofos, pyraclonil, pyraclostrobin, pyraflufen, pyraflufen-ethyl, pyrafluprole, pyramat, pyrametostrobin, pyraoxystrobin, pyrasulfotole, pyrazolynate, pyrazophos, pyrazosulfuron, pyrazosulfuron-ethyl, pyrazothion, pyrazoxyfen, pyresmethrin, pyrethrin I, pyrethrin II, pyrethrins, pyribambenz-isopropyl, pyribambenz-propyl, pyribencarb, pyribenzoxim, pyributicarb, pyriclor, pyridaben, pyridafol, pyridalyl, pyridaphenthion, pyridate, pyridinitril, pyrifenox, pyrifluquinazon, pyriftalid, pyrimethanil, pyrimidifen, pyriminobac, pyriminobac-methyl, pyrimisulfan, pyrimitate, pyrinuron, pyriofenone, pyriprole, pyripropanol, pyriproxyfen, pyrithiobac, pyrithiobac-sodium, pyrolan, pyroquilon, pyroxasulfone, pyroxsulam, pyroxychlor, pyroxyfur, quassia, quinacetol, quinacetol sulfate, quinalphos, quinalphos-methyl, quinazamid, quinclorac, quinconazole, quinmerac, quinoclamine, quinonamid, quinothion, quinoxyfen, quintiofos, quintozene, quizalofop, quizalofop-ethyl, quizalofop-P, quizalofop-P-ethyl, quizalofop-P-tefuryl, quwenzhi, quyingding, rabenzazole, rafoxanide, rebemide, resmethrin, rhodethanil, rhodojaponin-III, ribavirin, rimsulfuron, rotenone, ryania, saflufenacil, saijunmao, saisentong, salicylanilide, sanguinarine, santonin, schradan, scilliroside, sebuthylazine, secbumeton, sedaxane, selamectin, semiamitraz, semiamitraz chloride, sesamex, sesamolin, sethoxydim, shuangjiaancaolin, siduron, siglure, silafluofen, silatrane, silica gel, silthiofam, simazine, simeconazole, simeton, simetryn, sintofen, SMA, S-metolachlor, sodium arsenite, sodium azide, sodium chlorate, sodium fluoride, sodium fluoroacetate, sodium hexafluorosilicate, sodium naphthenate, sodium orthophenylphenoxide, sodium pentachlorophenoxide, sodium polysulfide, sodium thiocyanate, sodium α-naphthaleneacetate, sophamide, spinetoram, spinosad, spirodiclofen, spiromesifen, spirotetramat, spiroxamine, streptomycin, streptomycin sesquisulfate, strychnine, sulcatol, sulcofuron, sulcofuron-sodium, sulcotrione, sulfallate, sulfentrazone, sulfiram, sulfluramid, sulfometuron, sulfometuron-methyl, sulfosulfuron, sulfotep, sulfoxaflor, sulfoxide, sulfoxime, sulfur, sulfuric acid, sulfuryl fluoride, sulglycapin, sulprofos, sultropen, swep, tau-fluvalinate, tavron, tazimcarb, TCA, TCA-ammonium, TCA-calcium, TCA-ethadyl, TCA-magnesium, TCA-sodium, TDE, tebuconazole, tebufenozide, tebufenpyrad, tebufloquin, tebupirimfos, tebutam, tebuthiuron, tecloftalam, tecnazene, tecoram, teflubenzuron, tefluthrin, tefuryltrione, tembotrione, temephos, tepa, TEPP, tepraloxydim, terallethrin, terbacil, terbucarb, terbuchlor, terbufos, terbumeton, terbuthylazine, terbutryn, tetcyclacis, tetrachloroethane, tetrachlorvinphos, tetraconazole, tetradifon, tetrafluron, tetramethrin, tetramethylfluthrin, tetramine, tetranactin, tetrasul, thallium sulfate, thenylchlor, theta-cypermethrin, thiabendazole, thiacloprid, thiadifluor, thiamethoxam, thiapronil, thiazafluron, thiazopyr, thicrofos, thicyofen, thidiazimin, thidiazuron, thiencarbazone, thiencarbazone-methyl, thifensulfuron, thifensulfuron-methyl, thifluzamide, thiobencarb, thiocarboxime, thiochlorfenphim, thiocyclam, thiocyclam hydrochloride, thiocyclam oxalate, thiodiazole-copper, thiodicarb, thiofanox, thiofluoximate, thiohempa, thiomersal, thiometon, thionazin, thiophanate, thiophanate-methyl, thioquinox, thiosemicarbazide, thiosultap, thiosultap-diammonium, thiosultap-disodium, thiosultap-monosodium, thiotepa, thiram, thuringiensin, tiadinil, tiaojiean, tiocarbazil, tioclorim, tioxymid, tirpate, tolclofos-methyl, tolfenpyrad, tolylfluanid, tolylmercury acetate, topramezone, tralkoxydim, tralocythrin, tralomethrin, tralopyril, transfluthrin, transpermethrin, tretamine, triacontanol, triadimefon, triadimenol, triafamone, tri-allate, triamiphos, triapenthenol, triarathene, triarimol, triasulfuron, triazamate, triazbutil, triaziflam, triazophos, triazoxide, tribenuron, tribenuron-methyl, tribufos, tributyltin oxide, tricamba, trichlamide, trichlorfon, trichlormetaphos-3, trichloronat, triclopyr, triclopyr-butotyl, triclopyr-ethyl, triclopyr-triethylammonium, tricyclazole, tridemorph, tridiphane, trietazine, trifenmorph, trifenofos, trifloxystrobin, trifloxysulfuron, trifloxysulfuron-sodium, triflumizole, triflumuron, trifluralin, triflusulfuron, triflusulfuron-methyl, trifop, trifop-methyl, trifopsime, triforine, trihydroxytriazine, trimedlure, trimethacarb, trimeturon, trinexapac, trinexapac-ethyl, triprene, tripropindan, triptolide, tritac, triticonazole, tritosulfuron, trunc-call, uniconazole, uniconazole-P, urbacide, uredepa, valerate, validamycin, valifenalate, valone, vamidothion, vangard, vaniliprole, vernolate, vinclozolin, warfarin, warfarin-potassium, warfarin-sodium, xiaochongliulin, xinjunan, xiwojunan, XMC, xylachlor, xylenols, xylylcarb, yishijing, zarilamid, zeatin, zengxiaoan, zeta-cypermethrin, zinc naphthenate, zinc phosphide, zinc thiazole, zineb, ziram, zolaprofos, zoxamide, zuomihuanglong, α-chlorohydrin, α-ecdysone, α-multistriatin, and α-naphthaleneacetic acid. For more information consult the "COMPENDIUM OF PESTICIDE COMMON NAMES" located at alanwood.net. Also consult "THE PESTICIDE MANUAL" 14th Edition, edited by C D S Tomlin, copyright 2006 by British Crop Production Council, or its prior or more recent editions.

Biopesticides

Molecules of Formula One may also be used in combination (such as in a compositional mixture, or a simultaneous or sequential application) with one or more biopesticides. The term "biopesticide" is used for microbial biological pest control agents that are applied in a similar manner to chemical pesticides. Commonly these are bacterial, but there are also examples of fungal control agents, including *Trichoderma* spp. and *Ampelomyces quisqualis* (a control agent for grape powdery mildew). *Bacillus subtilis* are used to control plant pathogens. Weeds and rodents have also been controlled with microbial agents. One well-known insecticide example is *Bacillus thuringiensis*, a bacterial disease of Lepidoptera, Coleoptera, and Diptera. Because it has little effect on other organisms, it is considered more environmentally friendly than synthetic pesticides. Biological insecticides include products based on:

1. entomopathogenic fungi (e.g. *Metarhizium anisopliae*);
2. entomopathogenic nematodes (e.g. *Steinernema feltiae*); and
3. entomopathogenic viruses (e.g. *Cydia pomonella* granulovirus).

Other examples of entomopathogenic organisms include, but are not limited to, baculoviruses, bacteria and other prokaryotic organisms, fungi, protozoa and Microsproridia. Biologically derived insecticides include, but not limited to, rotenone, veratridine, as well as microbial toxins; insect tolerant or resistant plant varieties; and organisms modified by recombinant DNA technology to either produce insecticides or to convey an insect resistant property to the genetically modified organism. In one embodiment, the molecules of Formula One may be used with one or more biopesticides in the area of seed treatments and soil amendments. *The Manual of Biocontrol Agents* gives a review of the available biological insecticide (and other biology-based control) products. Copping L. G. (ed.) (2004). *The Manual of Biocontrol Agents* (formerly the *Biopesticide Manual*) 3rd Edition. British Crop Production Council (BCPC), Farnham, Surrey UK.

Other Active Compounds

Molecules of Formula One may also be used in combination (such as in a compositional mixture, or a simultaneous or sequential application) with one or more of the following:

1. 3-(4-chloro-2,6-dimethylphenyl)-4-hydroxy-8-oxa-1-azaspiro[4,5]dec-3-en-2-one;
2. 3-(4'-chloro-2,4-dimethyl[1,1'-biphenyl]-3-yl)-4-hydroxy-8-oxa-1-azaspiro[4,5]dec-3-en-2-one;
3. 4-[[(6-chloro-3-pyridinyl)methyl]methylamino]-2(5H)-furanone;
4. 4-[[(6-chloro-3-pyridinyl)methyl]cyclopropylamino]-2(5H)-furanone;
5. 3-chloro-N2-[(1S)-1-methyl-2-(methylsulfonyl)ethyl]-N1-[2-methyl-4-[1,2,2,2-tetrafluoro-1-(trifluoromethyl)ethyl]phenyl]-1,2-benzenedicarboxamide;
6. 2-cyano-N-ethyl-4-fluoro-3-methoxy-benenesulfonamide;
7. 2-cyano-N-ethyl-3-methoxy-benzenesulfonamide;
8. 2-cyano-3-difluoromethoxy-N-ethyl-4-fluoro-benzenesulfonamide;
9. 2-cyano-3-fluoromethoxy-N-ethyl-benzenesulfonamide;
10. 2-cyano-6-fluoro-3-methoxy-N,N-dimethyl-benzenesulfonamide;
11. 2-cyano-N-ethyl-6-fluoro-3-methoxy-N-methyl-benzenesulfonamide;
12. 2-cyano-3-difluoromethoxy-N,N-dimethylbenzenesulfon-amide;
13. 3-(difluoromethyl)-N-[2-(3,3-dimethylbutyl)phenyl]-1-methyl-1H-pyrazole-4-carboxamide;
14. N-ethyl-2,2-dimethylpropionamide-2-(2,6-dichloro-α,α,α-trifluoro-p-tolyl) hydrazone;
15. N-ethyl-2,2-dichloro-1-methylcyclopropane-carboxamide-2-(2,6-dichloro-α,α,α-trifluoro-p-tolyl) hydrazone nicotine;
16. O-{(E-)-[2-(4-chloro-phenyl)-2-cyano-1-(2-trifluoromethylphenyl)-vinyl]}S-methyl thiocarbonate;
17. (E)-N1-[(2-chloro-1,3-thiazol-5-ylmethyl)]-N2-cyano-N1-methylacetamidine;
18. 1-(6-chloropyridin-3-ylmethyl)-7-methyl-8-nitro-1,2,3,5,6,7-hexahydro-imidazo[1,2-a]pyridin-5-ol;
19. 4-[4-chlorophenyl-(2-butylidine-hydrazono)methyl)]phenyl mesylate; and
20. N-Ethyl-2,2-dichloro-1-methylcyclopropanecarboxamide-2-(2,6-dichloro-alpha,alpha,alpha-trifluoro-p-tolyl) hydrazone.

Synergistic Mixtures

Molecules of Formula One may be used with certain active compounds to form synergistic mixtures where the mode of action of such compounds compared to the mode of action of the molecules of Formula One are the same, similar, or different. Examples of modes of action include, but are not limited to: acetylcholinesterase inhibitor; sodium channel modulator; chitin biosynthesis inhibitor; GABA and glutamate-gated chloride channel antagonist; GABA and glutamate-gated chloride channel agonist; acetylcholine receptor agonist; acetylcholine receptor antagonist; MET I inhibitor; Mg-stimulated ATPase inhibitor; nicotinic acetylcholine receptor; Midgut membrane disrupter; oxidative phosphorylation disrupter, and ryanodine receptor (RyRs). Generally, weight ratios of the molecules of Formula One in a synergistic mixture with another compound are from about 10:1 to about 1:10, in another embodiment from about 5:1 to about 1:5, and in another embodiment from about 3:1, and in another embodiment about 1:1.

Formulations

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra-low volume solutions. For further information on formulation types see "Catalogue of Pesticide Formulation Types and International Coding System" Technical Monograph n° 2, 5th Edition by CropLife International (2002).

Pesticides are applied most often as aqueous suspensions or emulsions prepared from concentrated formulations of such pesticides. Such water-soluble, water-suspendable, or emulsifiable formulations are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually selected from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are selected from conventional anionic and non-ionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to about 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They can be used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use, this embodiment will be referred to as "OIWE".

For further information consult "Insect Pest Management" 2nd Edition by D. Dent, copyright CAB International (2000). Additionally, for more detailed information consult "Handbook of Pest Control—The Behavior, Life History, and Control of Household Pests" by Arnold Mallis, 9th Edition, copyright 2004 by GIE Media Inc.

Other Formulation Components

Generally, when the molecules disclosed in Formula One are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alkyl ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, oil-in-water emulsions, suspoemulsions, and ultra-low volume formulations, and to a lesser extent, granular formulations. Sometimes mixtures of solvents are used. The first main groups of solvents are aliphatic paraffinic oils such as kerosene or refined paraffins. The second main group (and the most common) comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, bentonite, magnesium aluminum silicate, and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms can cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g. plant and animal sources. Specific examples are: vegetable oils, seed oils, and esters thereof, also alkoxylated alkyl polyglucosides.

For further information, see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

Pests

In general, the molecules of Formula One may be used to control pests e.g. beetles, earwigs, cockroaches, flies, aphids, scales, whiteflies, leafhoppers, ants, wasps, termites, moths, butterflies, lice, grasshoppers, locusts, crickets, fleas, thrips, bristletails, mites, ticks, nematodes, and symphylans.

In another embodiment, the molecules of Formula One may be used to control pests in the Phyla Nematoda and/or Arthropoda.

In another embodiment, the molecules of Formula One may be used to control pests in the Subphyla Chelicerata, Myriapoda, and/or Hexapoda.

In another embodiment, the molecules of Formula One may be used to control pests in the Classes of Arachnida, Symphyla, and/or Insecta.

In another embodiment, the molecules of Formula One may be used to control pests of the Order Anoplura. A non-exhaustive list of particular genera includes, but is not limited to, *Haematopinus* spp., *Hoplopleura* spp., *Linognathus* spp., *Pediculus* spp., and *Polyplax* spp. A non-exhaustive list of particular species includes, but is not limited to, *Haematopinus asini*, *Haematopinus suis*, *Linognathus setosus*, *Linognathus ovillus*, *Pediculus humanus capitis*, *Pediculus humanus humanus*, and *Pthirus pubis*.

In another embodiment, the molecules of Formula One may be used to control pests in the Order Coleoptera. A non-exhaustive list of particular genera includes, but *is not limited to, Acanthoscelides* spp., *Agriotes* spp., *Anthonomus* spp., *Apion* spp., *Apogonia* spp., *Aulacophora* spp., *Bruchus* spp., *Cerosterna* spp., *Cerotoma* spp., *Ceutorhynchus* spp., *Chaetocnema* spp., *Colaspis* spp., *Ctenicera* spp., *Curculio* spp., *Cyclocephala* spp., *Diabrotica* spp., *Hypera* spp., *Ips* spp., *Lyctus* spp., *Megascelis* spp., *Meligethes* spp., *Otiorhynchus* spp., *Pantomorus* spp., *Phyllophaga* spp., *Phyllotreta* spp., *Rhizotrogus* spp., *Rhynchites* spp., *Rhynchophorus* spp., *Scolytus* spp., *Sphenophorus* spp., *Sitophilus* spp., and *Tribolium* spp. A non-exhaustive list of particular species includes, but is not limited to, *Acanthoscelides obtectus*, *Agrilus planipennis*, *Anoplophora glabripennis*, *Anthonomus grandis*, *Ataenius spretulus*, *Atomaria linearis*, *Bothynoderes punctiventris*, *Bruchus pisorum*, *Callosobruchus maculatus*, *Carpophilus hemipterus*, *Cassida vittata*, *Cerotoma trifurcata*, *Ceutorhynchus assimilis*, *Ceutorhynchus napi*, *Conoderus scalaris*, *Conoderus stigmosus*, *Conotrachelus nenuphar*, *Cotinis nitida*, *Crioceris asparagi*, *Cryptolestes ferrugineus*, *Cryptolestes pusillus*, *Cryptolestes turcicus*, *Cylindrocopturus adspersus*, *Deporaus marginatus*, *Dermestes lardarius*, *Dermestes maculatus*, *Epilachna varivestis*, *Faustinus cubae*, *Hylobius pales*, *Hypera postica*, *Hypothenemus hampei*, *Lasioderma serricorne*, *Leptinotarsa decemlineata*, *Liogenys fuscus*, *Liogenys suturalis*, *Lissorhoptrus oryzophilus*, *Maecolaspis joliveti*, *Melanotus communis*, *Meligethes aeneus*, *Melolontha melolontha*, *Oberea brevis*, *Oberea linearis*, *Oryctes rhinoceros*, *Oryzaephilus mercator*, *Oryzaephilus surinamensis*, *Oulema melanopus*, *Oulema oryzae*, *Phyllophaga cuyabana*, *Popillia japonica*, *Prostephanus truncatus*, *Rhyzopertha dominica*, *Sitona lineatus*, *Sitophilus granarius*, *Sitophilus oryzae*, *Sitophilus zeamais*, *Stegobium paniceum*, *Tribolium castaneum*, *Tribolium confusum*, *Trogoderma variabile*, and *Zabrus tenebrioides*.

In another embodiment, the molecules of Formula One may be used to control pests of the Order Dermaptera.

In another embodiment, the molecules of Formula One may be used to control pests of the Order Blattaria. A non-exhaustive list of particular species includes, but is not limited to, *Blattella germanica*, *Blatta orientalis*, *Parcoblatta pennsylvanica*, *Periplaneta americana*, *Periplaneta australasiae*, *Periplaneta brunnea*, *Periplaneta fuliginosa*, *Pycnoscelus surinamensis*, and *Supella longipalpa*.

In another embodiment, the molecules of Formula One may be used to control pests of the Order Diptera. A non-exhaustive list of particular genera includes, but is not limited to, *Aedes* spp., *Agromyza* spp., *Anastrepha* spp., *Anopheles* spp., *Bactrocera* spp., *Ceratitis* spp., *Chrysops* spp., *Cochliomyia* spp., *Contarinia* spp., *Culex* spp., *Dasineura* spp., *Delia* spp., *Drosophila* spp., *Fannia* spp., *Hylemyia* spp., *Liriomyza* spp., *Musca* spp., *Phorbia* spp., *Tabanus* spp., and *Tipula* spp. A non-exhaustive list of particular species includes, but is not limited to, *Agromyza frontella*, *Anastrepha suspensa*, *Anastrepha ludens*, *Anastrepha obliqa*, *Bactrocera cucurbitae*, *Bactrocera dorsalis*, *Bactrocera invadens*, *Bactrocera zonata*, *Ceratitis capitata*, *Dasineura brassicae*, *Delia platura*, *Fannia canicularis*, *Fannia scalaris*, *Gasterophilus intestinalis*, *Gracillia perseae*, *Haematobia irritans*, *Hypoderma lineatum*, *Liriomyza brassicae*, *Melophagus ovinus*, *Musca autumnalis*, *Musca domestica*, *Oestrus ovis*, *Oscinella frit*, *Pegomya betae*, *Psila rosae*, *Rhagoletis cerasi*, *Rhagoletis pomonella*, *Rhagoletis mendax*, *Sitodiplosis mosellana*, and *Stomoxys calcitrans*.

In another embodiment, the molecules of Formula One may be used to control pests of the Order Hemiptera. A non-exhaustive list of particular genera includes, but is not limited to, *Adelges* spp., *Aulacaspis* spp., *Aphrophora* spp., *Aphis* spp., *Bemisia* spp., *Ceroplastes* spp., *Chionaspis* spp., *Chrysomphalus* spp., *Coccus* spp., *Empoasca* spp., *Lepidosaphes* spp., *Lagynotomus* spp., *Lygus* spp., *Macrosiphum* spp., *Nephotettix* spp., *Nezara* spp., *Philaenus* spp., *Phytocoris* spp., *Piezodorus* spp., *Planococcus* spp., *Pseudococcus* spp., *Rhopalosiphum* spp., *Saissetia* spp., *Therioaphis* spp., *Toumeyella* spp., *Toxoptera* spp., *Trialeurodes* spp., *Triatoma* spp. and *Unaspis* spp. A non-exhaustive list of particular species includes, but is not limited to, *Acrosternum hilare*, *Acyrthosiphon pisum*, *Aleyrodes proletella*, *Aleurodicus dispersus*, *Aleurothrixus floccosus*, *Amrasca biguttula biguttula*, *Aonidiella aurantii*, *Aphis gossypii*,

*Aphis glycines, Aphis pomi, Aulacorthum solani, Bemisia argentifolii, Bemisia tabaci, Blissus leucopterus, Brachycorynella asparagi, Brevennia rehi, Brevicoryne brassicae, Calocoris norvegicus, Ceroplastes rubens, Cimex hemipterus, Cimex lectularius, Dagbertus fasciatus, Dichelops furcatus, Diuraphis noxia, Diaphorina citri, Dysaphis plantaginea, Dysdercus suturellus, Edessa meditabunda, Eriosoma lanigerum, Eurygaster maura, Euschistus heros, Euschistus servus, Helopeltis antonii, Helopeltis theivora, Icerya purchasi, Idioscopus nitidulus, Laodelphax striatellus, Leptocorisa oratorius, Leptocorisa varicornis, Lygus hesperus, Maconellicoccus hirsutus, Macrosiphum euphorbiae, Macrosiphum granarium, Macrosiphum rosae, Macrosteles quadrilineatus, Mahanarva frimbiolata, Metopolophium dirhodum, Mictis longicornis, Myzus persicae, Nephotettix cinctipes, Neurocolpus longirostris, Nezara viridula, Nilaparvata lugens, Parlatoria pergandii, Parlatoria ziziphi, Peregrinus maidis, Phylloxera vitifoliae, Physokermes piceae, Phytocoris californicus, Phytocoris relativus, Piezodorus guildinii, Poecilocapsus lineatus, Psallus vaccinicola, Pseudacysta perseae, Pseudococcus brevipes, Quadraspidiotus perniciosus, Rhopalosiphum maidis, Rhopalosiphum padi, Saissetia oleae, Scaptocoris castanea, Schizaphis graminum, Sitobion avenae, Sogatella furcifera, Trialeurodes vaporariorum, Trialeurodes abutiloneus, Unaspis yanonensis,* and *Zulia entrerriana.*

In another embodiment, the molecules of Formula One may be used to control pests of the Order Hymenoptera. A non-exhaustive list of particular genera includes, but is not limited to, *Acromyrmex* spp., *Atta* spp., *Camponotus* spp., *Diprion* spp., *Formica* spp., *Monomorium* spp., *Neodiprion* spp., *Pogonomyrmex* spp., *Polistes* spp., *Solenopsis* spp., *Vespula* spp., and *Xylocopa* spp. A non-exhaustive list of particular species includes, but is not limited to, *Athalia rosae, Atta texana, Iridomyrmex humilis, Monomorium minimum, Monomorium pharaonis, Solenopsis invicta, Solenopsis geminata, Solenopsis molesta, Solenopsis richtery, Solenopsis xyloni,* and *Tapinoma sessile.*

In another embodiment, the molecules of Formula One may be used to control pests of the Order Isoptera. A non-exhaustive list of particular genera includes, but is not limited to, *Coptotermes* spp., *Cornitermes* spp., *Cryptotermes* spp., *Heterotermes* spp., *Kalotermes* spp., *Incisitermes* spp., *Macrotermes* spp., *Marginitermes* spp., *Microcerotermes* spp., *Procornitermes* spp., *Reticulitermes* spp., *Schedorhinotermes* spp., and *Zootermopsis* spp. A non-exhaustive list of particular species includes, but is not limited to, *Coptotermes curvignathus, Coptotermes frenchi, Coptotermes formosanus, Heterotermes aureus, Microtermes obesi, Reticulitermes banyulensis, Reticulitermes grassei, Reticulitermes flavipes, Reticulitermes hageni, Reticulitermes hesperus, Reticulitermes santonensis, Reticulitermes speratus, Reticulitermes tibialis,* and *Reticulitermes virginicus.*

In another embodiment, the molecules of Formula One may be used to control pests of the Order Lepidoptera. A non-exhaustive list of particular genera includes, but is not limited to, *Adoxophyes* spp., *Agrotis* spp., *Argyrotaenia* spp., *Cacoecia* spp., *Caloptilia* spp., *Chilo* spp., *Chrysodeixis* spp., *Colias* spp., *Crambus* spp., *Diaphania* spp., *Diatraea* spp., *Earias* spp., *Ephestia* spp., *Epimecis* spp., *Feltia* spp., *Gortyna* spp., *Helicoverpa* spp., *Heliothis* spp., *Indarbela* spp., *Lithocolletis* spp., *Loxagrotis* spp., *Malacosoma* spp., *Peridroma* spp., *Phyllonorycter* spp., *Pseudaletia* spp., *Sesamia* spp., *Spodoptera* spp., *Synanthedon* spp., and *Yponomeuta* spp. A non-exhaustive list of particular species includes, but is not limited to, *Achaea janata, Adoxophyes orana, Agrotis ipsilon, Alabama argillacea, Amorbia cuneana, Amyelois transitella, Anacamptodes defectaria, Anarsia lineatella, Anomis sabulifera, Anticarsia gemmatalis, Archips argyrospila, Archips rosana, Argyrotaenia citrana, Autographa gamma, Bonagota cranaodes, Borbo cinnara, Bucculatrix thurberiella, Capua reticulana, Carposina niponensis, Chilo suppressalis, Chilo polychrysus, Chlumetia transversa, Choristoneura rosaceana, Cnaphalocrocis medinalis, Conopomorpha cramerella, Cossus cossus, Cydia caryana, Cydia funebrana, Cydia molesta, Cydia nigricana, Cydia pomonella, Darna diducta, Diatraea saccharalis, Diatraea grandiosella, Earias insulana, Earias vittella, Ecdytolopha aurantianum, Elasmopalpus lignosellus, Ephestia cautella, Ephestia elutella, Ephestia kuehniella, Epinotia aporema, Epiphyas postvittana, Erionota thrax, Eupoecilia ambiguella, Euxoa auxiliaris, Grapholita molesta, Hedylepta indicata, Helicoverpa armigera, Helicoverpa zea, Heliothis virescens, Hellula undalis, Keiferia lycopersicella, Leucinodes orbonalis, Leucoptera coffeella, Leucoptera malifoliella, Lobesia botrana, Loxagrotis albicosta, Lymantria dispar, Lyonetia clerkella, Mahasena corbetti, Mamestra brassicae, Maruca testulalis, Metisa plana, Mythimna unipuncta, Neoleucinodes elegantalis, Nymphula depunctalis, Operophtera brumata, Ostrinia nubilalis, Oxydia vesulia, Pandemis cerasana, Pandemis heparana, Papilio demodocus, Pectinophora gossypiella, Peridroma saucia, Perileucoptera coffeella, Phthorimaea operculella, Phyllocnistis citrella, Pieris rapae, Plathypena scabra, Plodia interpunctella, Plutella xylostella, Polychrosis viteana, Prays endocarpa, Prays oleae, Pseudaletia unipuncta, Pseudoplusia includens, Rachiplusia nu, Scirpophaga incertulas, Sesamia inferens, Sesamia nonagrioides, Setora nitens, Sitotroga cerealella, Sparganothis pilleriana, Spodoptera exigua, Spodoptera frugiperda, Spodoptera eridania, Thecla basilides, Tineola bisselliella, Trichoplusia ni, Tuta absoluta, Zeuzera coffeae,* and *Zeuzera pyrina.*

In another embodiment, the molecules of Formula One may be used to control pests of the Order Mallophaga. A non-exhaustive list of particular genera includes, but is not limited to, *Anaticola* spp., *Bovicola* spp., *Chelopistes* spp., *Goniodes* spp., *Menacanthus* spp., and *Trichodectes* spp. A non-exhaustive list of particular species includes, but is not limited to, *Bovicola bovis, Bovicola caprae, Bovicola ovis, Chelopistes meleagridis, Goniodes dissimilis, Goniodes gigas, Menacanthus stramineus, Menopon gallinae,* and *Trichodectes canis.*

In another embodiment, the molecules of Formula One may be used to control pests of the Order Orthoptera. A non-exhaustive list of particular genera includes, but is not limited to, *Melanoplus* spp., and *Pterophylla* spp. A non-exhaustive list of particular species includes, but is not limited to, *Anabrus simplex, Gryllotalpa africana, Gryllotalpa australis, Gryllotalpa brachyptera, Gryllotalpa hexadactyla, Locusta migratoria, Microcentrum retinerve, Schistocerca gregaria,* and *Scudderia furcata.*

In another embodiment, the molecules of Formula One may be used to control pests of the Order Siphonaptera. A non-exhaustive list of particular species includes, but is not limited to, *Ceratophyllus gallinae, Ceratophyllus niger, Ctenocephalides canis, Ctenocephalides felis,* and *Pulex irritans.*

In another embodiment, the molecules of Formula One may be used to control pests of the Order Thysanoptera. A non-exhaustive list of particular genera includes, but is not limited to, *Caliothrips* spp., *Frankliniella* spp., *Scirtothrips* spp., and *Thrips* spp. A non-exhaustive list of particular sp.

includes, but is not limited to, *Frankliniella fusca, Frankliniella occidentalis, Frankliniella schultzei, Frankliniella williamsi, Heliothrips haemorrhoidalis, Rhipiphorothrips cruentatus, Scirtothrips citri, Scirtothrips dorsalis*, and *Taeniothrips rhopalantennalis, Thrips hawaiiensis, Thrips nigropilosus, Thrips orientalis, Thrips tabaci*.

In another embodiment, the molecules of Formula One may be used to control pests of the Order Thysanura. A non-exhaustive list of particular genera includes, but is not limited to, *Lepisma* spp. and *Thermobia* spp.

In another embodiment, the molecules of Formula One may be used to control pests of the Order Acarina. A non-exhaustive list of particular genera includes, but is not limited to, *Acarus* spp., *Aculops* spp., *Boophilus* spp., *Demodex* spp., *Dermacentor* spp., *Epitrimerus* spp., *Eriophyes* spp., *Ixodes* spp., *Oligonychus* spp., *Panonychus* spp., *Rhizoglyphus* spp., and *Tetranychus* spp. A non-exhaustive list of particular species includes, but is not limited to, *Acarapis woodi, Acarus siro, Aceria mangiferae, Aculops lycopersici, Aculus pelekassi, Aculus schlechtendali, Amblyomma americanum, Brevipalpus obovatus, Brevipalpus phoenicis, Dermacentor variabilis, Dermatophagoides pteronyssinus, Eotetranychus carpini, Notoedres cati, Oligonychus coffeae, Oligonychus ilicis, Panonychus citri, Panonychus ulmi, Phyllocoptruta oleivora, Polyphagotarsonemus latus, Rhipicephalus sanguineus, Sarcoptes scabiei, Tegolophus perseaflorae, Tetranychus urticae*, and *Varroa destructor*.

In another embodiment, the molecules of Formula One may be used to control pest of the Order Symphyla. A non-exhaustive list of particular sp. includes, but is not limited to, *Scutigerella immaculata*.

In another embodiment, the molecules of Formula One may be used to control pests of the Phylum Nematoda. A non-exhaustive list of particular genera includes, but is not limited to, *Aphelenchoides* spp., *Belonolaimus* spp., *Criconemella* spp., *Ditylenchus* spp., *Heterodera* spp., *Hirschmanniella* spp., *Hoplolaimus* spp., *Meloidogyne* spp., *Pratylenchus* spp., and *Radopholus* spp. A non-exhaustive list of particular sp. includes, but is not limited to, *Dirofilaria immitis, Heterodera zeae, Meloidogyne incognita, Meloidogyne javanica, Onchocerca volvulus, Radopholus similis*, and *Rotylenchulus reniformis*.

For additional information consult "HANDBOOK OF PEST CONTROL—THE BEHAVIOR, LIFE HISTORY, AND CONTROL OF HOUSEHOLD PESTS" by Arnold Mallis, 9th Edition, copyright 2004 by GIE Media Inc.

Applications

Molecules of Formula One are generally used in amounts from about 0.01 grams per hectare to about 5000 grams per hectare to provide control. Amounts from about 0.1 grams per hectare to about 500 grams per hectare are generally preferred, and amounts from about 1 gram per hectare to about 50 grams per hectare are generally more preferred.

The area to which a molecule of Formula One is applied can be any area inhabited (or maybe inhabited, or traversed by) a pest, for example: where crops, trees, fruits, cereals, fodder species, vines, turf and ornamental plants, are growing; where domesticated animals are residing; the interior or exterior surfaces of buildings (such as places where grains are stored), the materials of construction used in building (such as impregnated wood), and the soil around buildings. Particular crop areas to use a molecule of Formula One include areas where apples, corn, sunflowers, cotton, soybeans, canola, wheat, rice, sorghum, barley, oats, potatoes, oranges, alfalfa, lettuce, strawberries, tomatoes, peppers, crucifers, pears, tobacco, almonds, sugar beets, beans and other valuable crops are growing or the seeds thereof are going to be planted. It is also advantageous to use ammonium sulfate with a molecule of Formula One when growing various plants.

Controlling pests generally means that pest populations, pest activity, or both, are reduced in an area. This can come about when: pest populations are repulsed from an area; when pests are incapacitated in or around an area; or pests are exterminated, in whole, or in part, in or around an area. Of course, a combination of these results can occur. Generally, pest populations, activity, or both are desirably reduced more than fifty percent, preferably more than 90 percent. Generally, the area is not in or on a human; consequently, the locus is generally a non-human area.

The molecules of Formula One may be used in mixtures, applied simultaneously or sequentially, alone or with other compounds to enhance plant vigor (e.g. to grow a better root system, to better withstand stressful growing conditions). Such other compounds are, for example, compounds that modulate plant ethylene receptors, most notably 1-methylcyclopropene (also known as 1-MCP). Furthermore, such molecules may be used during times when pest activity is low, such as before the plants that are growing begin to produce valuable agricultural commodities. Such times include the early planting season when pest pressure is usually low.

The molecules of Formula One can be applied to the foliar and fruiting portions of plants to control pests. The molecules will either come in direct contact with the pest, or the pest will consume the pesticide when eating leaf, fruit mass, or extracting sap, that contains the pesticide. The molecules of Formula One can also be applied to the soil, and when applied in this manner, root and stem feeding pests can be controlled. The roots can absorb a molecule taking it up into the foliar portions of the plant to control above ground chewing and sap feeding pests.

Generally, with baits, the baits are placed in the ground where, for example, termites can come into contact with, and/or be attracted to, the bait. Baits can also be applied to a surface of a building, (horizontal, vertical, or slant surface) where, for example, ants, termites, cockroaches, and flies, can come into contact with, and/or be attracted to, the bait. Baits can comprise a molecule of Formula One.

The molecules of Formula One can be encapsulated inside, or placed on the surface of a capsule. The size of the capsules can range from nanometer size (about 100-900 nanometers in diameter) to micrometer size (about 10-900 microns in diameter).

Because of the unique ability of the eggs of some pests to resist certain pesticides, repeated applications of the molecules of Formula One may be desirable to control newly emerged larvae.

Systemic movement of pesticides in plants may be utilized to control pests on one portion of the plant by applying (for example by spraying an area) the molecules of Formula One to a different portion of the plant. For example, control of foliar-feeding insects can be achieved by drip irrigation or furrow application, by treating the soil with for example pre- or post-planting soil drench, or by treating the seeds of a plant before planting.

Seed treatment can be applied to all types of seeds, including those from which plants genetically modified to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement, drought resistance, or any other beneficial traits. Furthermore, such seed treatments with the molecules of Formula One may further enhance the ability of a plant to better withstand stressful growing conditions. This results in a healthier, more vigorous plant, which can lead to higher yields at harvest time. Generally, about 1 gram of the molecules of Formula One to about 500 grams per 100,000 seeds is expected to provide good benefits, amounts from about 10 grams to about 100 grams per 100,000 seeds is expected to provide better benefits, and amounts from about 25 grams to about 75 grams per 100,000 seeds is expected to provide even better benefits.

It should be readily apparent that the molecules of Formula One may be used on, in, or around plants genetically modified to express specialized traits, such as *Bacillus thuringiensis* or other insecticidal toxins, or those expressing herbicide resistance, or those with TABLE 2-continued Structure and Preparation Method for F Series Compounds

| No. | Structure | Prep. according to example |
|-----|-----------|----------------------------|
| F2  | 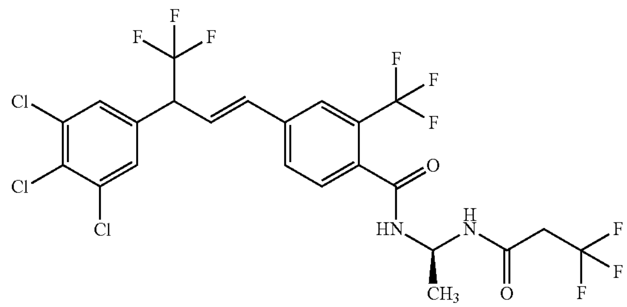          | 18 |
| F3  | 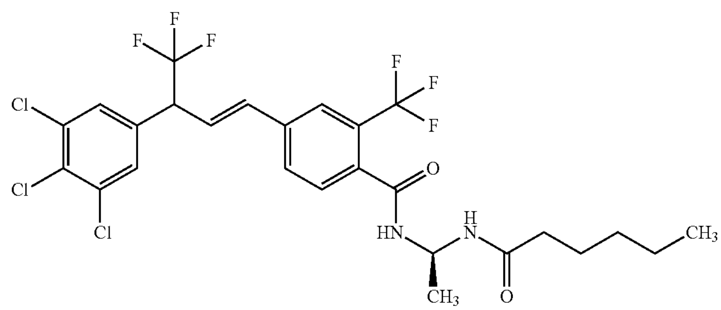          | 17 |
| F4  | 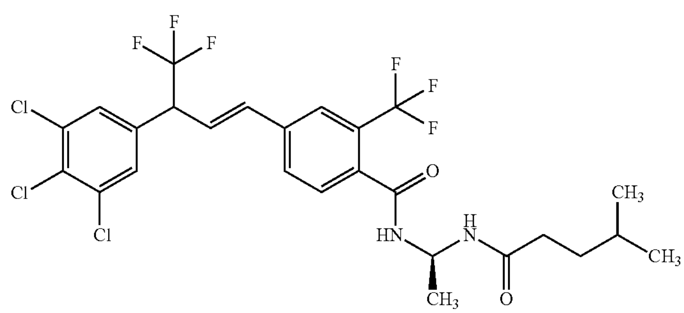          | 17 |
| F5  | 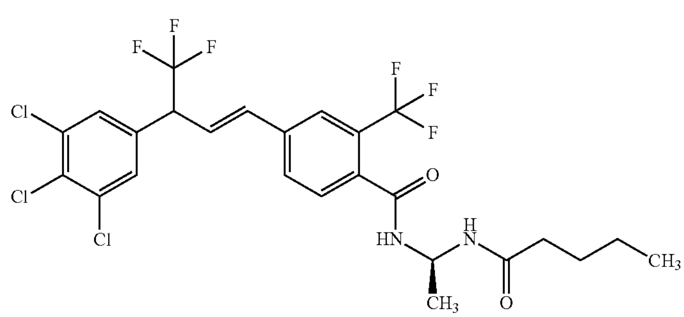 [SMILES: CSCCC(=O)N[C@@H](C)NC(=O)c1ccc(/C=C/C(c2cc(Cl)c(Cl)c(Cl)c2)C(F)(F)F)cc1C(F)(F)F]          | 17 |

TABLE 2-continued

Structure and Preparation Method for F Series Compounds

| No. | Structure | Prep. according to example |
|---|---|---|
| F6 | 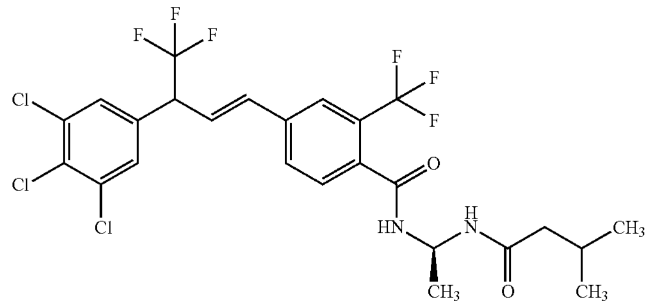 | 17 |
| F7 | 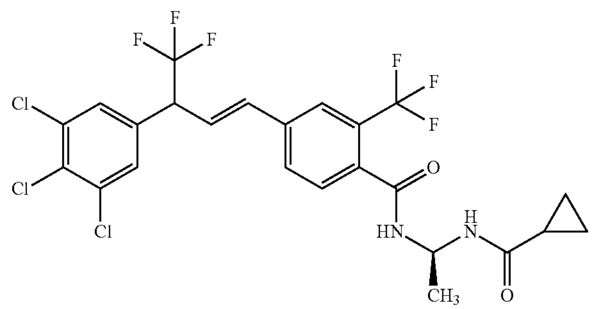 [SMILES: C[C@@H](NC(=O)c1ccc(/C=C/C(c2cc(Cl)c(Cl)c(Cl)c2)C(F)(F)F)cc1C(F)(F)F)NC(=O)C1CC1] | 17 |
| F8 | 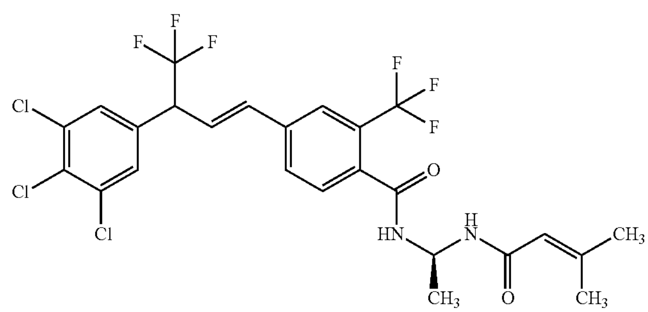 [SMILES: CC(C)=CC(=O)N[C@@H](C)NC(=O)c1ccc(/C=C/C(c2cc(Cl)c(Cl)c(Cl)c2)C(F)(F)F)cc1C(F)(F)F] | 17 |
| F9 | 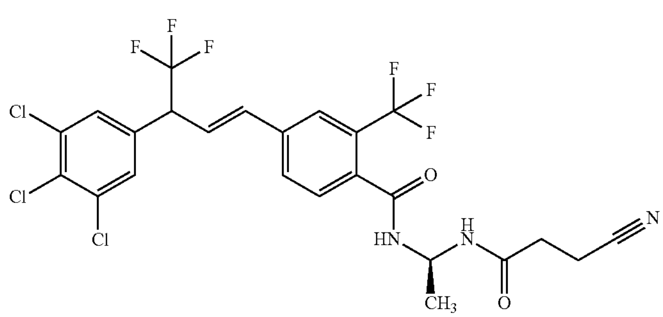 [SMILES: C[C@H](NC(=O)CCC#N)NC(=O)c1ccc(/C=C/C(c2cc(Cl)c(Cl)c(Cl)c2)C(F)(F)F)cc1C(F)(F)F] | 20 |

TABLE 2-continued

Structure and Preparation Method for F Series Compounds

| No. | Structure | Prep. according to example |
|---|---|---|
| F10 | 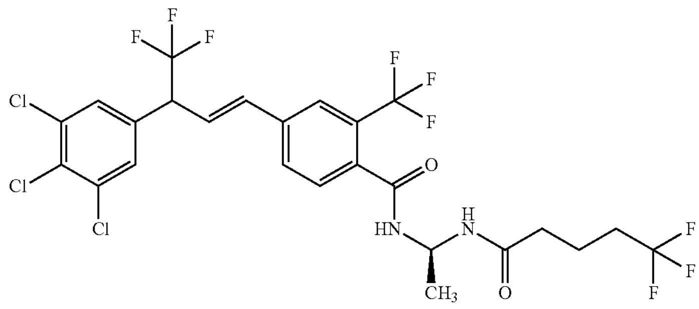 [SMILES: C[C@H](NC(=O)CCCC(F)(F)F)NC(=O)c1ccc(/C=C/C(c2cc(Cl)c(Cl)c(Cl)c2)C(F)(F)F)cc1C(F)(F)F] | 20 |
| F11 | 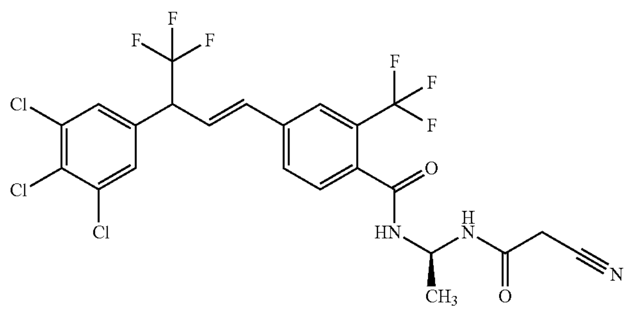 [SMILES: C[C@H](NC(=O)CC#N)NC(=O)c1ccc(/C=C/C(c2cc(Cl)c(Cl)c(Cl)c2)C(F)(F)F)cc1C(F)(F)F] | 20 |
| F12 | 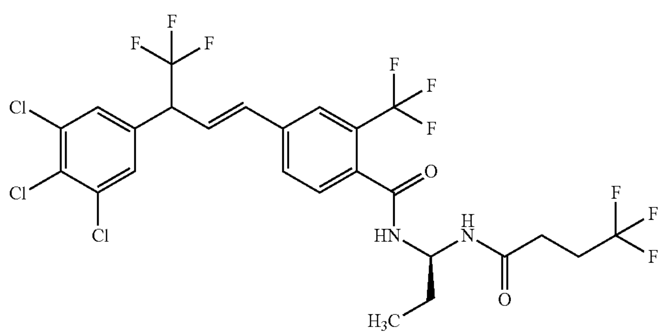 [SMILES: CC[C@H](NC(=O)CCC(F)(F)F)NC(=O)c1ccc(/C=C/C(c2cc(Cl)c(Cl)c(Cl)c2)C(F)(F)F)cc1C(F)(F)F] | 18 |
| F13 | 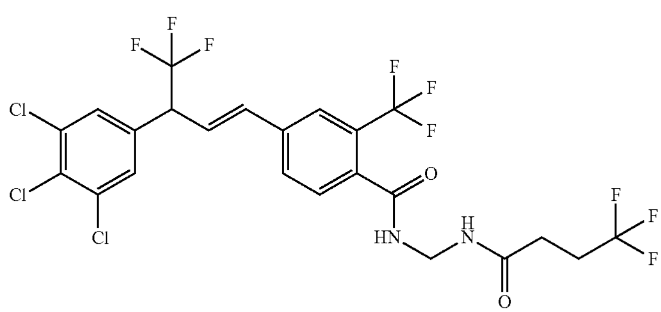 [SMILES: O=C(CCC(F)(F)F)NCNC(=O)c1ccc(/C=C/C(c2cc(Cl)c(Cl)c(Cl)c2)C(F)(F)F)cc1C(F)(F)F] | 18 |

TABLE 2-continued

Structure and Preparation Method for F Series Compounds

| No. | Structure | Prep. according to example |
|---|---|---|
| F14 | 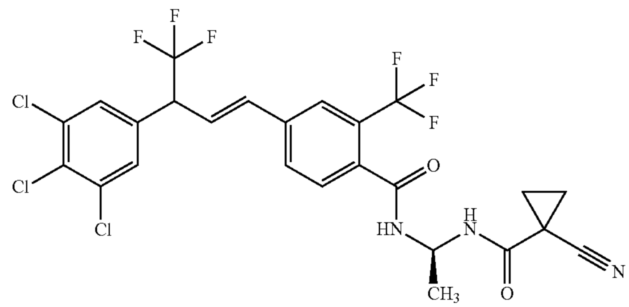 [SMILES: C[C@@H](NC(=O)c1ccc(/C=C/C(c2cc(Cl)c(Cl)c(Cl)c2)C(F)(F)F)cc1C(F)(F)F)NC(=O)C1(C#N)CC1] | 19 |
| F15 | 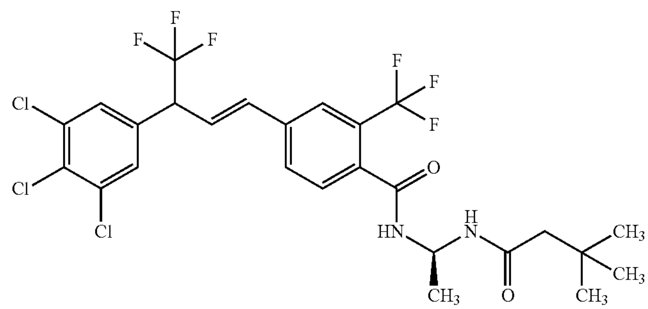 [SMILES: C[C@H](NC(=O)CC(C)(C)C)NC(=O)c1ccc(/C=C/C(c2cc(Cl)c(Cl)c(Cl)c2)C(F)(F)F)cc1C(F)(F)F] | 19 |
| F16 | 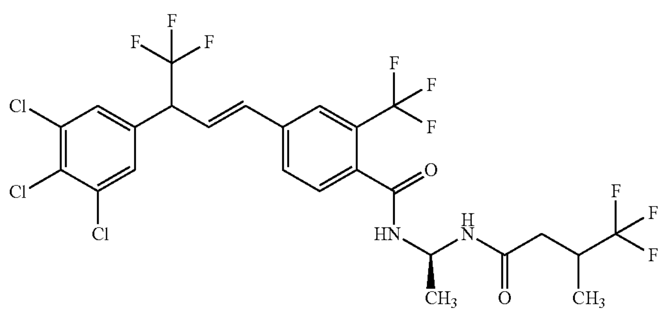 [SMILES: CC(CC(=O)N[C@@H](C)NC(=O)c1ccc(/C=C/C(c2cc(Cl)c(Cl)c(Cl)c2)C(F)(F)F)cc1C(F)(F)F)C(F)(F)F] | 19 |
| F17 | 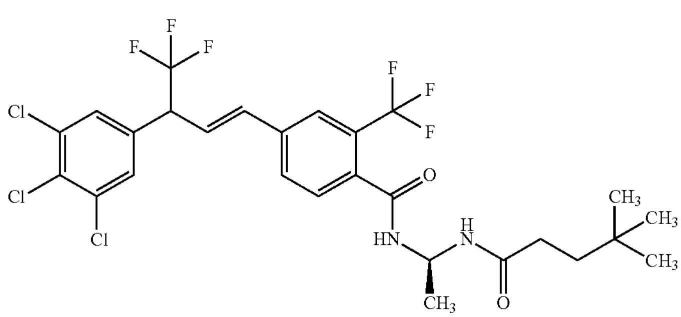 [SMILES: C[C@H](NC(=O)CCC(C)(C)C)NC(=O)c1ccc(/C=C/C(c2cc(Cl)c(Cl)c(Cl)c2)C(F)(F)F)cc1C(F)(F)F] | 19 |

TABLE 2-continued

Structure and Preparation Method for F Series Compounds

| No. | Structure | Prep. according to example |
|---|---|---|
| F18 | 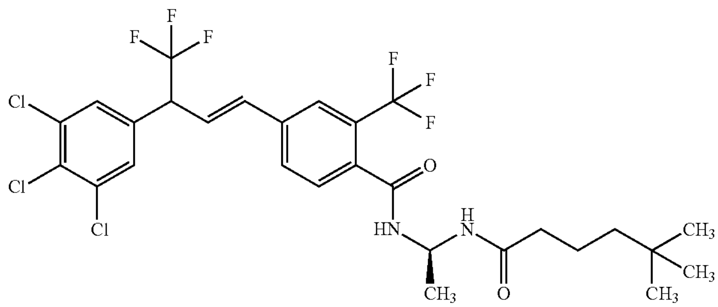 [SMILES: C[C@H](NC(=O)CCCC(C)(C)C)NC(=O)c1ccc(/C=C/C(c2cc(Cl)c(Cl)c(Cl)c2)C(F)(F)F)cc1C(F)(F)F] | 19 |
| F19 | 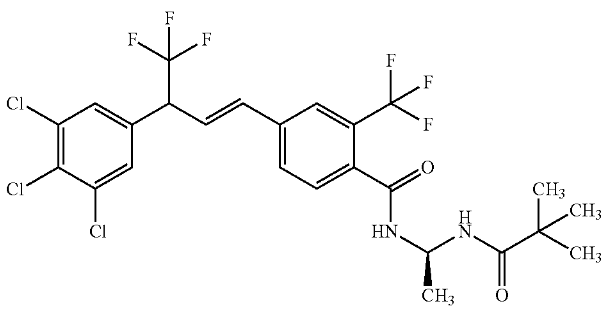 [SMILES: C[C@@H](NC(=O)c1ccc(/C=C/C(c2cc(Cl)c(Cl)c(Cl)c2)C(F)(F)F)cc1C(F)(F)F)NC(=O)C(C)(C)C] | 18 |
| F20 | 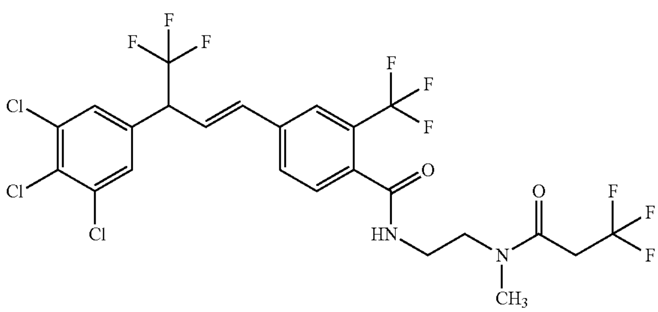 [SMILES: CN(CCNC(=O)c1ccc(/C=C/C(c2cc(Cl)c(Cl)c(Cl)c2)C(F)(F)F)cc1C(F)(F)F)C(=O)CC(F)(F)F] | 23 |
| F21 | 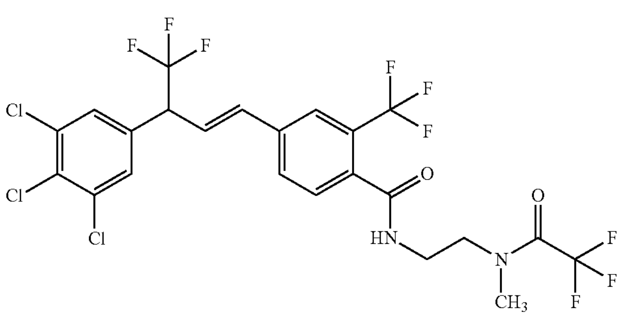 [SMILES: CN(CCNC(=O)c1ccc(/C=C/C(c2cc(Cl)c(Cl)c(Cl)c2)C(F)(F)F)cc1C(F)(F)F)C(=O)C(F)(F)F] | 25 |

TABLE 2-continued

Structure and Preparation Method for F Series Compounds

| No. | Structure | Prep. according to example |
|---|---|---|
| F22 | (structure) | 28 |
| F23 | (structure) | 28 |

TABLE 3

Analytical Data for Compounds in Table 2

| No. | Mass (m/z) | $^1$H NMR | $^{19}$F NMR |
|---|---|---|---|
| F1 | ESIMS m/z 643 ([M − H]$^-$) | $^1$H NMR (400 MHz, CDCl$_3$) δ 7.79-7.69 (m, 1H), 7.61 (d, J = 8.1 Hz, 1H), 7.55 (d, J = 5.4 Hz, 1H), 7.45 (d, J = 8.0 Hz, 1H), 7.40 (s, 2H), 7.34 (d, J = 7.9 Hz, 1H), 6.55 (dd, J = 16.0, 4.5 Hz, 1H), 6.39 (ddd, J = 15.9, 8.0, 2.6 Hz, 1H), 5.64 (h, J = 7.5 Hz, 1H), 4.10 (pd, J = 8.7, 3.0 Hz, 1H), 2.44-2.00 (m, 4H), 1.51 (d, J = 6.7 Hz, 3H) | $^{19}$F NMR (376 MHz, CDCl$_3$) δ −59.34, −66.97, −68.61. |
| F2 | ESIMS m/z 629 ([M − H]$^-$) | $^1$H NMR (400 MHz, CDCl$_3$) δ 8.27 (d, J = 17.8 Hz, 2H), 7.43-7.33 (m, 3H), 7.28 (d, J = 8.3 Hz, 1H), 7.17 (dd, J = 7.8, 3.2 Hz, 1H), 6.53-6.43 (m, 1H), 6.33 (ddd, J = 15.9, 8.0, 5.0 Hz, 1H), 5.89 (dq, J = 13.8, 6.2 Hz, 1H), 4.07 (hept, J = 8.3 Hz, 1H), 3.04 (p, J = 11.2 Hz, 1H), 2.87 (p, J = 10.5 Hz, 1H), 1.41 (d, J = 6.4 Hz, 3H) | $^{19}$F NMR (376 MHz, CDCl$_3$) δ −59.63, −63.29, −68.60 |
| F3 | ESIMS m/z 617 ([M − H]$^-$) | $^1$H NMR (400 MHz, CDCl$_3$) δ 7.69-7.63 (m, 1H), 7.57 (dd, J = 8.0, 1.7 Hz, 1H), 7.47 (d, J = 8.0 Hz, 1H), 7.41 (s, 2H), 6.91 (d, J = 7.4 Hz, 1H), 6.66-6.55 (m, 2H), 6.42 (dd, J = 15.9, 7.8 Hz, 1H), 5.42 (h, J = 7.0 Hz, 1H), 4.12 (p, J = 8.4 Hz, 1H), 2.16 (dd, J = 8.3, 6.9 Hz, 2H), 1.68 (d, J = 6.7 Hz, 3H), 1.62 (q, J = 7.5 Hz, 2H), 1.38-1.22 (m, 4H), 0.93-0.85 (m, 3H) | $^{19}$F NMR (376 MHz, CDCl$_3$) δ −59.06, −68.57 |
| F4 | ESIMS m/z 617 ([M − H]$^-$) | $^1$H NMR (400 MHz, CDCl$_3$) δ 7.68 (d, J = 12.0 Hz, 1H), 7.64-7.54 (m, 1H), 7.47 (d, J = 7.9 Hz, 1H), 7.41 (s, 2H), 6.86 (d, J = 7.4 Hz, 1H), 6.62 (dd, J = 15.9, 7.5 Hz, 1H), 6.55 (d, J = 7.6 Hz, 1H), 6.43 (dd, J = 15.9, 7.9 Hz, 1H), 5.42 (q, J = 7.2 Hz, | $^{19}$F NMR (376 MHz, DMSO-d$_6$) δ −57.81, −67.95 |

TABLE 3-continued

Analytical Data for Compounds in Table 2

| No. | Mass (m/z) | $^1$H NMR | $^{19}$F NMR |
|---|---|---|---|
| | | 1H), 4.12 (p, J = 8.5 Hz, 1H), 2.22-2.13 (m, 2H), 1.69 (d, J = 6.8 Hz, 3H), 1.63-1.41 (m, 3H), 0.90 (d, J = 6.4 Hz, 6H) | |
| F5 | ESIMS m/z 603 ([M − H]$^-$) | $^1$H NMR (400 MHz, CDCl$_3$) δ 7.66 (s, 1H), 7.57 (d, J = 8.0 Hz, 1H), 7.45 (d, J = 27.1 Hz, 3H), 6.85 (d, J = 7.3 Hz, 1H), 6.66-6.50 (m, 2H), 6.43 (dd, J = 15.9, 7.8 Hz, 1H), 5.42 (q, J = 7.2 Hz, 1H), 4.12 (p, J = 8.6 Hz, 1H), 2.22-2.13 (m, 2H), 1.69 (d, J = 6.8 Hz, 3H), 1.64-1.55 (m, 2H), 1.42-1.23 (m, 2H), 0.92 (t, J = 7.3 Hz, 3H) | $^{19}$F NMR (376 MHz, DMSO-d$_6$) δ −57.81, −67.95 |
| F6 | ESIMS m/z 603 ([M − H]$^-$) | $^1$H NMR (400 MHz, CDCl$_3$) δ 7.66 (d, J = 1.5 Hz, 1H), 7.57 (d, J = 7.9 Hz, 1H), 7.47 (d, J = 8.0 Hz, 1H), 7.41 (s, 2H), 6.88 (d, J = 7.4 Hz, 1H), 6.61 (d, J = 15.9 Hz, 1H), 6.54 (d, J = 7.6 Hz, 1H), 6.43 (dd, J = 15.9, 7.8 Hz, 1H), 5.44 (p, J = 7.0 Hz, 1H), 4.12 (p, J = 8.6 Hz, 1H), 2.17-2.00 (m, 2H), 1.69 (d, J = 6.8 Hz, 3H), 0.95 (d, J = 6.2 Hz, 7H) | $^{19}$F NMR (376 MHz, DMSO-d$_6$) δ −57.81, −67.95 |
| F7 | ESIMS m/z 589 ([M + H]$^+$) | $^1$H NMR (400 MHz, CDCl$_3$) δ 7.66 (d, J = 1.6 Hz, 1H), 7.57 (dd, J = 8.0, 1.7 Hz, 1H), 7.47 (d, J = 8.0 Hz, 1H), 7.41 (s, 2H), 6.92 (d, J = 7.4 Hz, 1H), 6.79 (d, J = 7.6 Hz, 1H), 6.61 (d, J = 15.9 Hz, 1H), 6.42 (dd, J = 15.9, 7.8 Hz, 1H), 5.43 (h, J = 6.9 Hz, 1H), 4.12 (p, J = 8.5 Hz, 1H), 1.69 (d, J = 6.8 Hz, 3H), 1.36 (tt, J = 7.8, 4.5 Hz, 1H), 0.93 (dt, J = 4.6, 3.2 Hz, 2H), 0.77 (dt, J = 7.9, 3.4 Hz, 2H) | $^{19}$F NMR (376 MHz, CDCl$_3$) δ −59.06, −68.57 |
| F8 | ESIMS m/z 603 ([M + H]$^+$) | $^1$H NMR (400 MHz, CDCl$_3$) δ 7.72-7.63 (m, 1H), 7.63-7.52 (m, 1H), 7.48 (d, J = 7.9 Hz, 1H), 7.41 (d, J = 1.2 Hz, 2H), 6.95 (d, J = 7.4 Hz, 1H), 6.62 (dd, J = 15.9, 9.0 Hz, 1H), 6.43 (ddd, J = 16.0, 10.0, 7.9 Hz, 2H), 5.57-5.52 (m, 1H), 5.46 (h, J = 7.0 Hz, 1H), 4.13 (p, J = 8.5 Hz, 1H), 2.13 (d, J = 1.3 Hz, 3H), 1.85 (d, J = 1.4 Hz, 3H), 1.70 (d, J = 6.8 Hz, 3H) | $^{19}$F NMR (376 MHz, CDCl$_3$) δ rotomers −59.04 & −59.08, −68.57 |
| F9 | ESIMS m/z 602 ([M + H]$^+$) | $^1$H NMR (400 MHz, CDCl$_3$) δ 7.67 (s, 1H), 7.59 (d, J = 7.9 Hz, 1H), 7.50 (d, J = 8.0 Hz, 1H), 7.41 (s, 2H), 6.75 (t, J = 7.4 Hz, 2H), 6.61 (d, J = 15.9 Hz, 1H), 6.43 (dd, J = 15.9, 7.8 Hz, 1H), 5.44 (q, J = 7.2 Hz, 1H), 4.17-4.07 (m, 1H), 2.67 (td, J = 7.1, 1.0 Hz, 2H), 2.55 (t, J = 6.9 Hz, 2H), 1.70 (d, J = 6.8 Hz, 3H) | $^{19}$F NMR (376 MHz, CDCl$_3$) δ −59.02, −68.56 |
| F10 | ESIMS m/z 659 ([M + H]$^+$) | $^1$H NMR (400 MHz, CDCl$_3$) δ 7.66 (s, 1H), 7.57 (d, J = 8.0 Hz, 1H), 7.46 (d, J = 7.9 Hz, 1H), 7.41 (s, 2H), 6.90 (s, 1H), 6.72 (d, J = 7.9 Hz, 1H), 6.61 (d, J = 15.9 Hz, 1H), 6.43 (dd, J = 15.9, 7.8 Hz, 1H), 5.43 (h, J = 7.0 Hz, 1H), 4.12 (p, J = 8.5 Hz, 1H), 2.30-2.22 (m, 2H), 2.20-2.02 (m, 2H), 1.89 (p, J = 7.4 Hz, 2H), 1.68 (d, J = 6.8 Hz, 3H) | $^{19}$F NMR (376 MHz, CDCl$_3$) δ −59.06, −66.23, −68.57 |
| F11 | ESIMS m/z 588 ([M + H]$^+$) | $^1$H NMR (400 MHz, CDCl$_3$) δ 7.66 (s, 1H), 7.57 (d, J = 8.0 Hz, 1H), 7.47 (d, J = 8.0 Hz, 1H), 7.41 (s, 2H), 7.34 (d, J = 7.4 Hz, 1H), 6.88 (d, J = 7.6 Hz, 1H), 6.61 (d, J = 16.0 Hz, 1H), 6.44 (dd, J = 15.9, 7.8 Hz, 1H), 5.51 (h, J = 6.9 Hz, 1H), 4.19-4.06 (m, 1H), 3.37 (s, 2H), 1.69 (d, J = 6.8 Hz, 3H) | $^{19}$F NMR (376 MHz, CDCl$_3$) δ −58.97, −68.55 |
| F12 | ESIMS m/z 659 ([M + H]$^+$) | $^1$H NMR (400 MHz, DMSO-d$_6$) δ 8.71 (d, J = 7.6 Hz, 1H), 8.31 (d, J = 7.7 Hz, 1H), 7.99 (d, J = 1.6 Hz, 1H), 7.95-7.86 (m, 3H), 7.45 (d, J = 7.9 Hz, 1H), 7.05 (dd, J = 15.8, 9.1 Hz, 1H), 6.86 (d, J = 15.7 Hz, 1H), 5.39 (p, J = 7.3 Hz, 1H), 4.86 (p, J = 9.4 Hz, 1H), 2.50 (dt, J = 3.7, 1.9 Hz, 2H), 2.43-2.28 (m, 2H), 1.68 (dq, J = 11.6, 6.7 Hz, 2H), 0.88 (t, J = 7.4 Hz, 3H) | $^{19}$F NMR (376 MHz, DMSO-d$_6$) δ −57.83, −65.19, −67.95 |

TABLE 3-continued

Analytical Data for Compounds in Table 2

| No. | Mass (m/z) | $^1$H NMR | $^{19}$F NMR |
|---|---|---|---|
| F13 | ESIMS m/z 629 ([M + H]$^+$) | $^1$H NMR (400 MHz, DMSO-d$_6$) δ 9.13 (t, J = 5.9 Hz, 1H), 8.78 (t, J = 6.0 Hz, 1H), 7.98 (d, J = 1.6 Hz, 1H), 7.93 (s, 2H), 7.89 (dd, J = 8.0, 1.8 Hz, 1H), 7.45 (d, J = 8.0 Hz, 1H), 7.06 (dd, J = 15.8, 9.1 Hz, 1H), 6.86 (d, J = 15.8 Hz, 1H), 4.85 (q, J = 9.4 Hz, 1H), 4.54 (t, J = 5.9 Hz, 2H), 2.61-2.28 (m, 4H) | $^{19}$F NMR (376 MHz, DMSO-d$_6$) δ −57.82, −65.21, −67.95 |
| F14 | ESIMS m/z 612 ([M − H]$^−$) | $^1$H NMR (400 MHz, DMSO-d$_6$) δ 8.70 (d, J = 7.3 Hz, 1H), 8.28 (d, J = 7.6 Hz, 1H), 8.00 (d, J = 1.6 Hz, 1H), 7.93 (s, 2H), 7.92-7.87 (m, 1H), 7.53 (d, J = 8.0 Hz, 1H), 7.06 (dd, J = 15.7, 9.1 Hz, 1H), 6.87 (d, J = 15.7 Hz, 1H), 5.65 (h, J = 6.8 Hz, 1H), 4.85 (q, J = 9.5 Hz, 1H), 1.62-1.43 (m, 4H), 1.36 (d, J = 6.5 Hz, 3H) | $^{19}$F NMR (376 MHz, DMSO-d$_6$) δ −57.78, −67.93 |
| F15 | ESIMS m/z 617 ([M − H]$^−$) | $^1$H NMR (400 MHz, DMSO-d$_6$) δ 8.72 (d, J = 7.4 Hz, 1H), 8.05 (d, J = 7.5 Hz, 1H), 7.98 (d, J = 1.7 Hz, 1H), 7.93 (s, 2H), 7.92-7.85 (m, 1H), 7.45 (d, J = 8.0 Hz, 1H), 7.05 (dd, J = 15.7, 9.1 Hz, 1H), 6.86 (d, J = 15.7 Hz, 1H), 5.58 (h, J = 6.8 Hz, 1H), 4.86 (p, J = 9.4 Hz, 1H), 1.97 (d, J = 2.7 Hz, 2H), 1.31 (d, J = 6.5 Hz, 3H), 0.97 (s, 9H) | $^{19}$F NMR (376 MHz, DMSO-d$_6$) δ −57.81, −67.96 |
| F16 | ESIMS m/z 657 ([M − H]$^−$) | $^1$H NMR (400 MHz, DMSO-d$_6$) mixture of diastereomers δ 8.89-8.72 (m, 1H), 8.53-8.41 (m, 1H), 8.01-7.96 (m, 1H), 7.93 (s, 2H), 7.92-7.86 (m, 1H), 7.51-7.42 (m, 1H), 7.06 (dd, J = 15.8, 9.1 Hz, 1H), 6.87 (d, J = 15.7 Hz, 1H), 5.68-5.50 (m, 1H), 4.86 (p, J = 9.4 Hz, 1H), 2.88-2.70 (m, 1H), 2.46-2.38 (m, 1H), 2.22-2.11 (m, 1H), 1.39-1.28 (m, 3H), 1.11-1.03 (m, 3H) | $^{19}$F NMR (376 MHz, DMSO-d$_6$), mixture of diastereomers δ −57.84, −67.96, −72.25, −72.26 |
| F17 | ESIMS m/z 631 ([M − H]$^−$) | $^1$H NMR (400 MHz, DMSO-d$_6$) δ 8.70 (d, J = 7.2 Hz, 1H), 8.16 (d, J = 7.5 Hz, 1H), 7.98 (d, J = 1.8 Hz, 1H), 7.96-7.86 (m, 3H), 7.45 (d, J = 8.0 Hz, 1H), 7.05 (dd, J = 15.8, 9.1 Hz, 1H), 6.86 (d, J = 15.7 Hz, 1H), 5.55 (h, J = 6.7 Hz, 1H), 4.86 (p, J = 9.4 Hz, 1H), 2.11-2.00 (m, 2H), 1.47-1.37 (m, 2H), 1.31 (d, J = 6.5 Hz, 3H), 0.86 (s, 9H) | $^{19}$F NMR (376 MHz, DMSO-d$_6$) δ −57.80, −67.95 |
| F18 | ESIMS m/z 647 ([M + H]$^+$) | $^1$H NMR (400 MHz, DMSO-d$_6$) δ 8.71 (d, J = 7.2 Hz, 1H), 8.12 (d, J = 7.5 Hz, 1H), 8.00-7.95 (m, 1H), 7.92 (s, 2H), 7.88 (dd, J = 7.9, 1.6 Hz, 1H), 7.45 (d, J = 7.9 Hz, 1H), 7.05 (dd, J = 15.8, 9.1 Hz, 1H), 6.86 (d, J = 15.7 Hz, 1H), 5.56 (h, J = 6.7 Hz, 1H), 4.86 (p, J = 9.5 Hz, 1H), 2.04 (t, J = 7.4 Hz, 2H), 1.46 (dtd, J = 9.7, 7.5, 4.5 Hz, 2H), 1.32 (d, J = 6.5 Hz, 3H), 1.18-1.09 (m, 2H), 0.85 (s, 9H) | $^{19}$F NMR (376 MHz, DMSO-d$_6$) δ −57.78, −67.95 |
| F19 | ESIMS m/z 603 ([M − H]$^−$) | $^1$H NMR (400 MHz, DMSO-d$_6$) δ 8.57 (d, J = 7.3 Hz, 1H), 7.99 (d, J = 1.6 Hz, 1H), 7.92 (s, 2H), 7.89 (dd, J = 8.1, 1.6 Hz, 1H), 7.58 (d, J = 7.7 Hz, 1H), 7.48 (d, J = 8.0 Hz, 1H), 7.05 (dd, J = 15.8, 9.1 Hz, 1H), 6.86 (d, J = 15.7 Hz, 1H), 5.59 (h, J = 6.8 Hz, 1H), 4.86 (p, J = 9.4 Hz, 1H), 1.34 (d, J = 6.5 Hz, 3H), 1.10 (s, 9H) | $^{19}$F NMR (376 MHz, DMSO-d$_6$) δ −57.76, −67.95 |
| F20 | ESIMS m/z 643 ([M − H]$^−$) | $^1$H NMR (400 MHz, CDCl$_3$) δ 7.71-7.63 (m, 1H), 7.65-7.53 (m, 1H), 7.47 (d, J = 7.9 Hz, 1H), 7.41 (s, 2H), 6.66-6.56 (m, 1H), 6.42 (dd, J = 16.0, 7.8 Hz, 1H), 6.42 (s, 1H), 4.12 (p, J = 8.8 Hz, 1H), 3.73-3.63 (m, 4H), 3.22 (q, J = 9.9 Hz, 2H), 3.13 (s, 3H) | $^{19}$F NMR (376 MHz, CDCl$_3$) δ −59.32, −62.60, −68.59 |
| F21 | ESIMS m/z 629 ([M − H]$^−$) | $^1$H NMR (400 MHz, CDCl$_3$) δ 7.67 (d, J = 1.6 Hz, 1H), 7.59 (dd, J = 7.9, 1.7 Hz, 1H), 7.45 (d, J = 7.9 Hz, 1H), 7.41 (s, 2H), 6.66-6.57 (m, 1H), 6.43 (dd, J = 15.9, | $^{19}$F NMR (376 MHz, CDCl$_3$) δ −59.22, −68.59, −69.88 |

TABLE 3-continued

Analytical Data for Compounds in Table 2

| No. | Mass (m/z) | $^1$H NMR | $^{19}$F NMR |
|---|---|---|---|
|  |  | 7.9 Hz, 1H), 6.18 (s, 1H), 4.12 (p, J = 8.8 Hz, 1H), 3.72 (d, J = 3.2 Hz, 4H), 3.25 (q, J = 1.5 Hz, 3H) |  |
| F22 | ESIMS m/z 615 ([M + H]$^+$) | $^1$H NMR (400 MHz, DMSO-d$_6$) δ 11.05 (bs, 1H), 8.11 (s, 1H), 7.98 (d, J = 8.4 Hz, 1H), 7.92 (s, 2H), 7.79 (s, J = 7.6 Hz, 1H), 7.15 (dd, J = 16.4, 9.6 Hz, 1H), 6.92 (d, J = 16.0 Hz, 1H), 4.90-4.83 (m, 1H), 3.10 (s, 3H), 2.50 (s, 2H) | IR (thin film) 3256, 1698, 1114, 749 (cm$^{-1}$) |
| F23 | ESIMS m/z 629 ([M + H]$^+$) | $^1$H NMR (400 MHz, DMSO-d$_6$) δ 11.01 (bs, 1H), 8.10 (s, 1H), 7.99 (d, J = 8.4 Hz, 1H), 7.92 (s, 2H), 7.68 (s, J = 8.0 Hz, 1H), 7.15 (dd, J = 15.6, 8.8 Hz, 1H), 6.92 (d, J = 15.6 Hz, 1H), 4.90-4.83 (m, 1H), 3.11 (s, 3H), 2.97 (s, 1H), 2.67-2.58 (m, 3H) | IR (thin film) 3436, 1689, 1275, 750 (cm$^{-1}$) |

TABLE 4

Structure and Preparation Method for C Series Compounds

| No. | Structure | Prep. according to example |
|---|---|---|
| C113 | 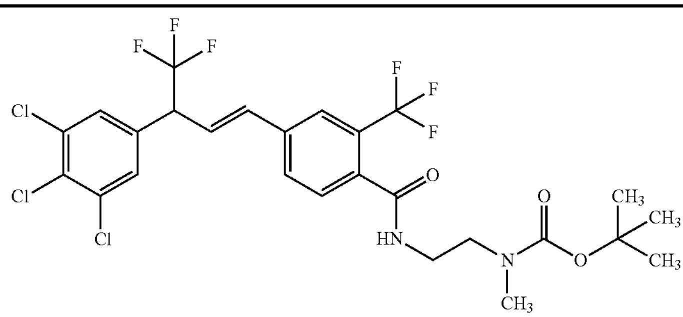 | 21 |
| C115 | 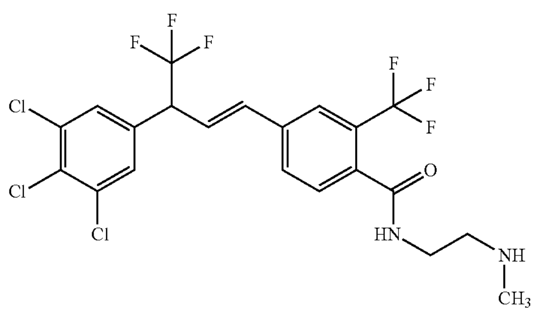 [SMILES: CNCCNC(=O)c1ccc(/C=C/C(c2cc(Cl)c(Cl)c(Cl)c2)C(F)(F)F)cc1C(F)(F)F] | 24 |
| C116 | 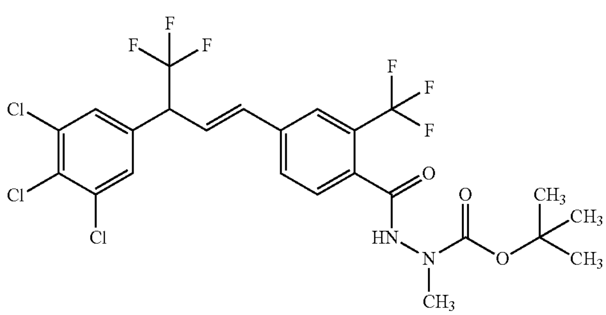 [SMILES: CN(NC(=O)c1ccc(/C=C/C(c2cc(Cl)c(Cl)c(Cl)c2)C(F)(F)F)cc1C(F)(F)F)C(=O)OC(C)(C)C] | 26 |

TABLE 5

Structure and Preparation Method for Exemplified P Series Compounds

| No. | Structure | Prep. according to example: |
|---|---|---|
| P1 | 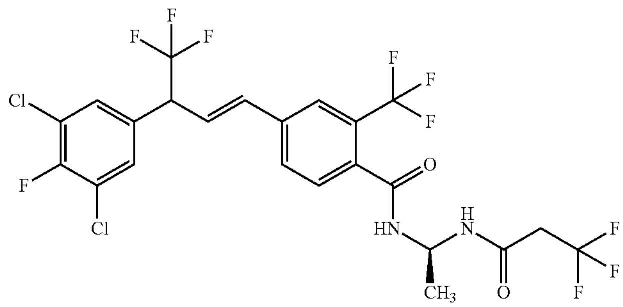 [SMILES: C[C@H](NC(=O)CC(F)(F)F)NC(=O)c1ccc(/C=C/C(c2cc(Cl)c(F)c(Cl)c2)C(F)(F)F)cc1C(F)(F)F] | 30 |
| P2 | 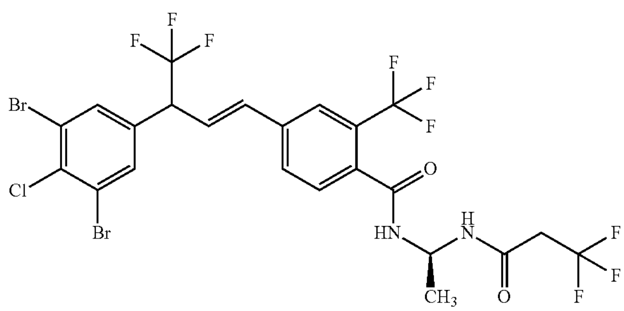 | 30 |
| P3 | 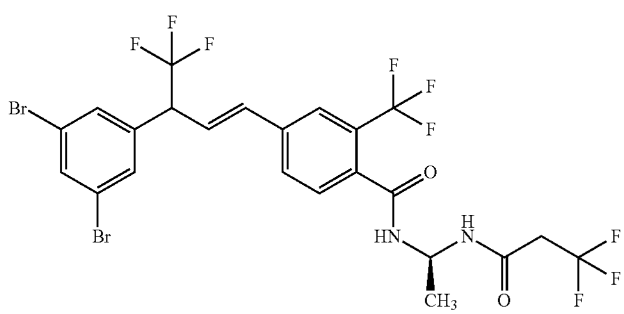 | 30 |
| P4 | 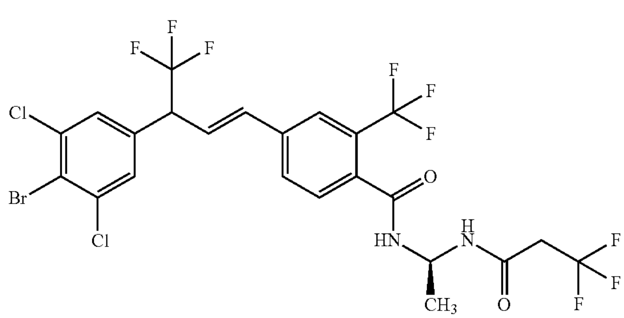 | 30 |

TABLE 5-continued

Structure and Preparation Method for Exemplified P Series Compounds

| No. | Structure | Prep. according to example: |
|---|---|---|
| P5 | 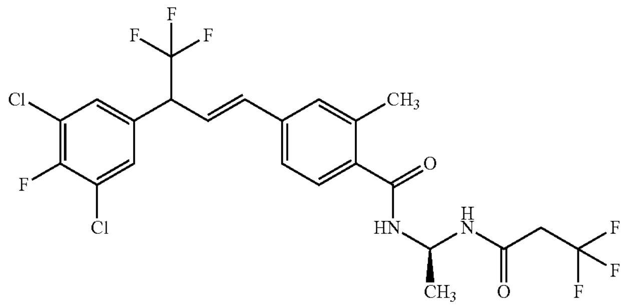 | 30 |
| P6 | 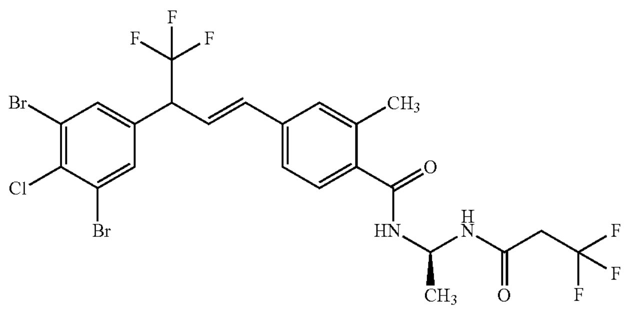 | 30 |
| P7 | 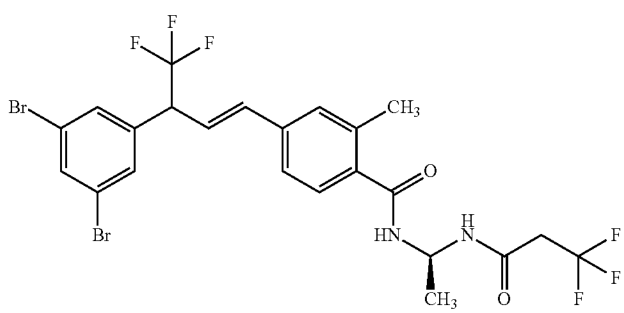 | 30 |
| P8 | 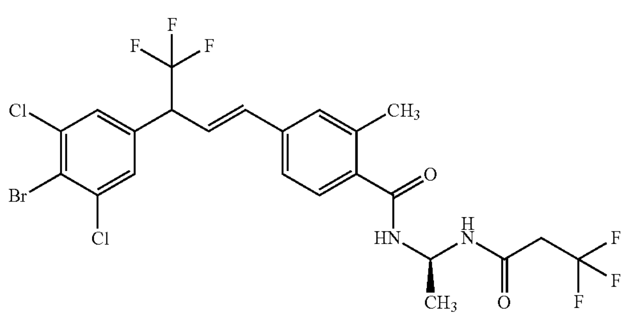 | 30 |

TABLE 5-continued

Structure and Preparation Method for Exemplified P Series Compounds

| No. | Structure | Prep. according to example: |
|---|---|---|
| P9 | 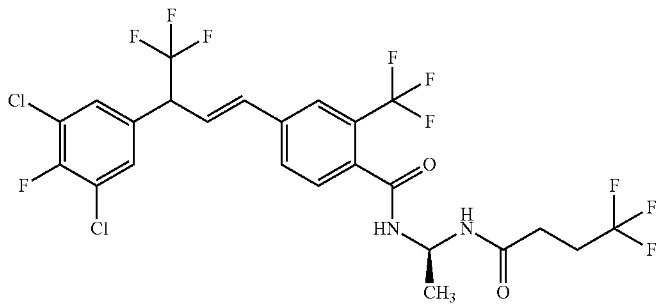 | 30 |
| P10 | 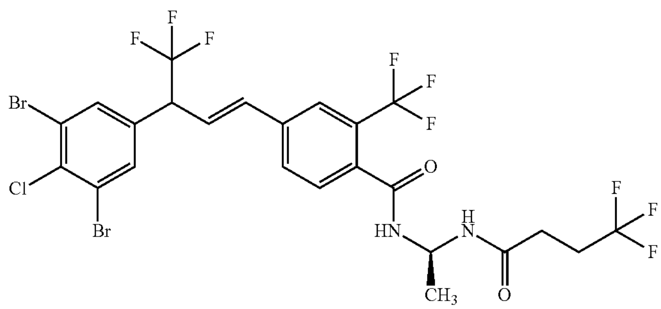 | 30 |
| P11 | 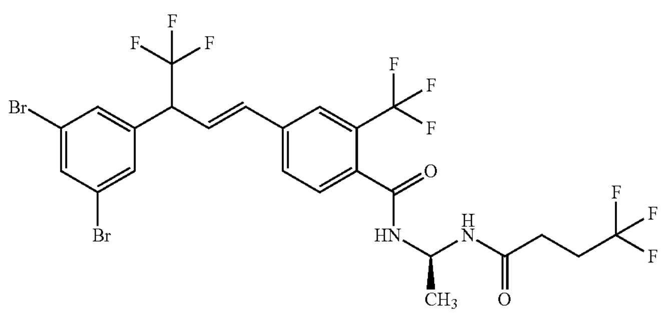 [SMILES: C[C@H](NC(=O)CCC(F)(F)F)NC(=O)c1ccc(/C=C/C(c2cc(Br)cc(Br)c2)C(F)(F)F)cc1C(F)(F)F] | 30 |
| P12 | 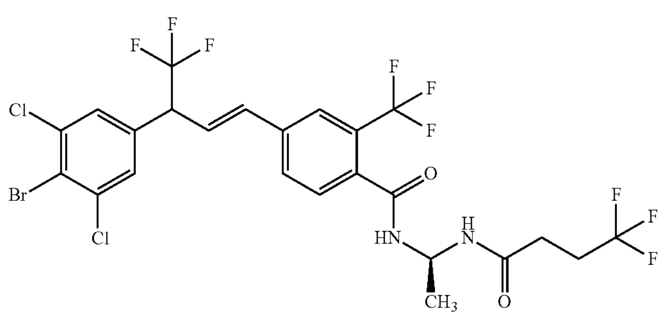 | 30 |

TABLE 5-continued

Structure and Preparation Method for Exemplified P Series Compounds

| No. | Structure | Prep. according to example: |
|---|---|---|
| P13 | (structure) | 30 |
| P14 | (structure) | 30 |
| P15 | (structure) | 30 |
| P16 | (structure) | 30 |

TABLE 5-continued

Structure and Preparation Method for Exemplified P Series Compounds

| No. | Structure | Prep. according to example: |
|---|---|---|
| P22 | 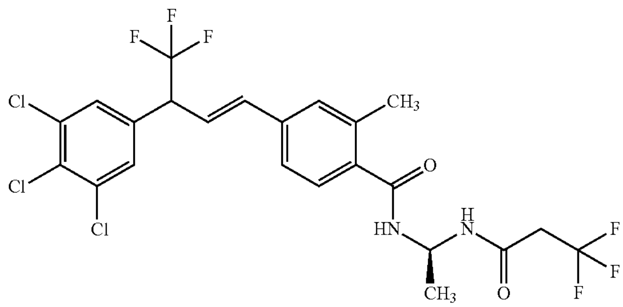 | 30 |
| P24 | 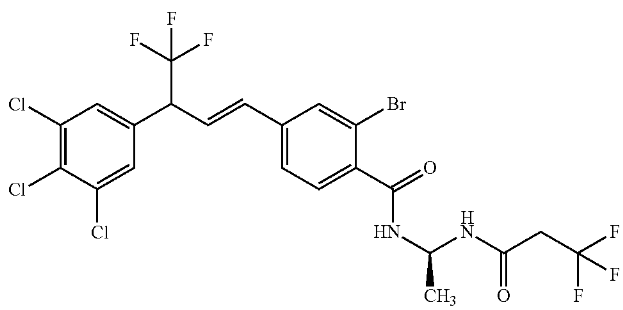 | 30 |
| P25 | 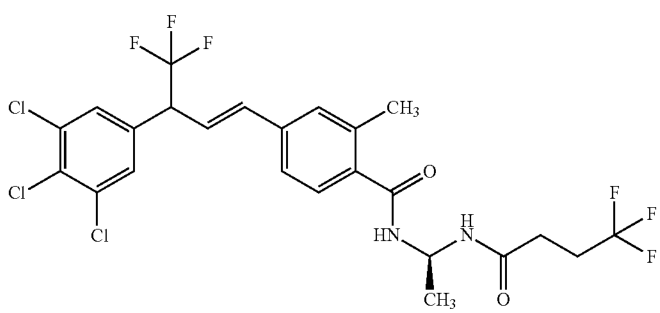 | 30 |
| P27 | 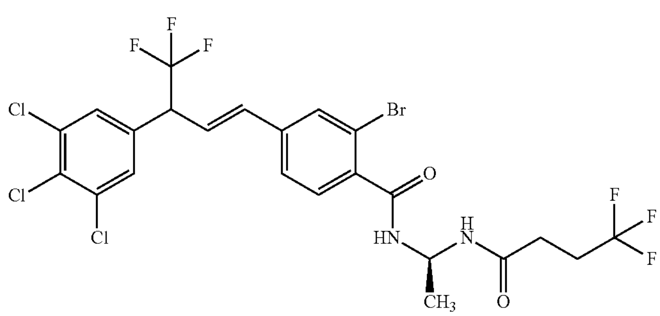 | 30 |

TABLE 5-continued

Structure and Preparation Method for Exemplified P Series Compounds

| No. | Structure | Prep. according to example: |
|---|---|---|
| P30 | 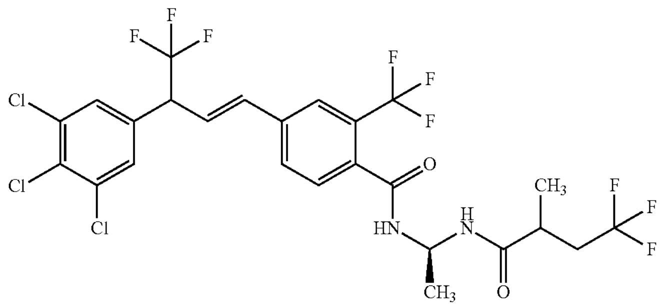 [SMILES: CC(CC(F)(F)F)C(=O)N[C@@H](C)NC(=O)c1ccc(/C=C/C(c2cc(Cl)c(Cl)c(Cl)c2)C(F)(F)F)cc1C(F)(F)F] | 19 |
| P33 | 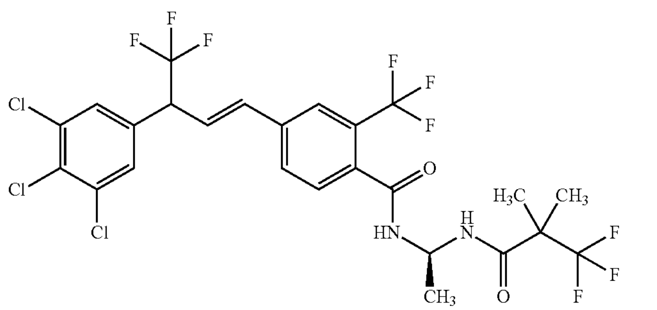 [SMILES: C[C@@H](NC(=O)c1ccc(/C=C/C(c2cc(Cl)c(Cl)c(Cl)c2)C(F)(F)F)cc1C(F)(F)F)NC(=O)C(C)(C)C(F)(F)F] | 19 |
| P36 | 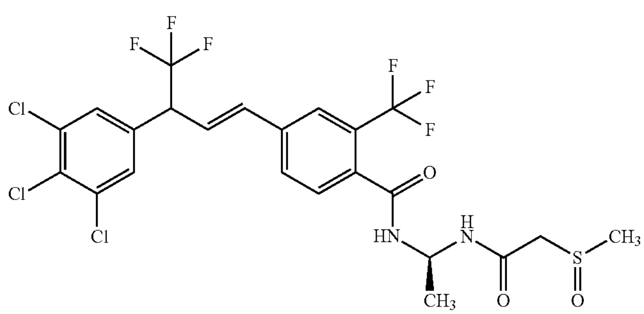 [SMILES: C[C@H](NC(=O)CS(C)=O)NC(=O)c1ccc(/C=C/C(c2cc(Cl)c(Cl)c(Cl)c2)C(F)(F)F)cc1C(F)(F)F] | 31 |
| P43 | 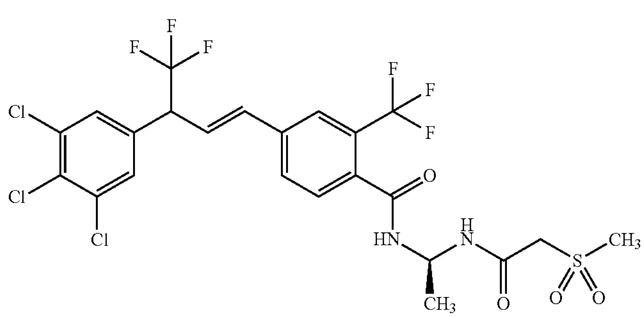 [SMILES: C[C@H](NC(=O)CS(C)(=O)=O)NC(=O)c1ccc(/C=C/C(c2cc(Cl)c(Cl)c(Cl)c2)C(F)(F)F)cc1C(F)(F)F] | 31 |

TABLE 5-continued

Structure and Preparation Method for Exemplified P Series Compounds

| No. | Structure | Prep. according to example: |
|---|---|---|
| P47 | 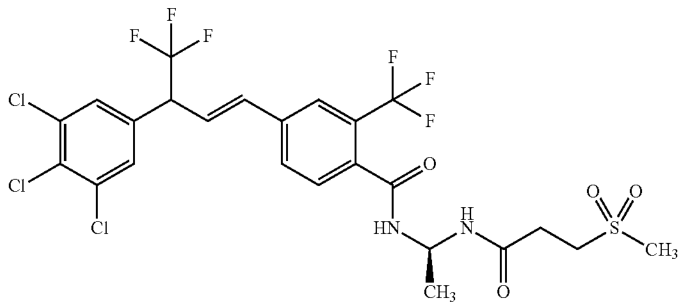 [SMILES: C[C@H](NC(=O)CCS(C)(=O)=O)NC(=O)c1ccc(/C=C/C(c2cc(Cl)c(Cl)c(Cl)c2)C(F)(F)F)cc1C(F)(F)F] | 31 |
| P49 | 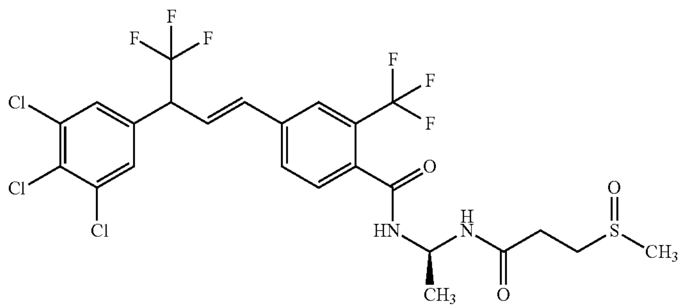 | 31 |
| P53 | 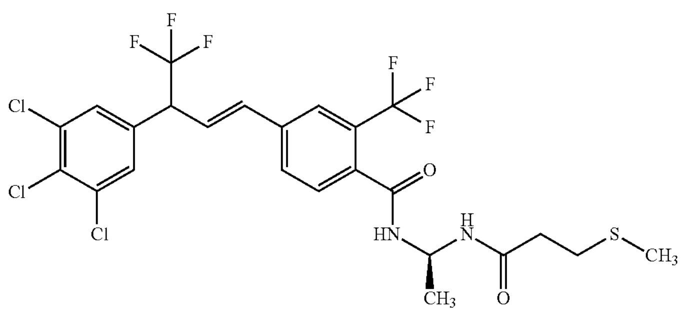 | 30 |
| P54 | 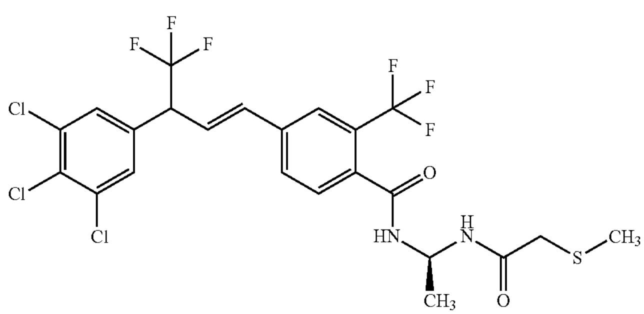 [SMILES: CSCC(=O)N[C@@H](C)NC(=O)c1ccc(/C=C/C(c2cc(Cl)c(Cl)c(Cl)c2)C(F)(F)F)cc1C(F)(F)F] | 30 |

TABLE 6

Analytical Data for Compounds in Table 5

| No. | Mass (m/z) | $^1$H NMR | $^{19}$F NMR/IR |
|---|---|---|---|
| P1 | HRMS-ESI [M + H]$^+$ calcd for $C_{23}H_{16}Cl_2F_{10}N_2O_2$, 613.0502; Found, 613.0494 | $^1$H NMR (500 MHz, DMSO-d$_6$) δ 8.90 (d, J = 7.3 Hz, 1H), 8.65 (d, J = 7.4 Hz, 1H), 8.02-7.97 (m, 1H), 7.89 (dd, J = 10.3, 7.1 Hz, 3H), 7.45 (d, J = 7.9 Hz, 1H), 7.05 (dd, J = 15.8, 9.2 Hz, | IR (thin film) 1678 cm$^{-1}$ |

TABLE 6-continued

Analytical Data for Compounds in Table 5

| No. | Mass (m/z) | $^1$H NMR | $^{19}$F NMR/IR |
|---|---|---|---|
| | | 1H), 6.86 (d, J = 15.7 Hz, 1H), 5.58 (h, J = 6.8 Hz, 1H), 4.83 (p, J = 9.4 Hz, 1H), 3.27 (q, J = 11.3 Hz, 2H), 1.35 (d, J = 6.5 Hz, 3H) | |
| P2 | HRMS-ESI [M + H]$^+$ calcd for $C_{23}H_{17}Br_2ClF_9N_2O_2$, 718.9176; Found, 718.9181 | $^1$H NMR (500 MHz, DMSO-d$_6$) δ 8.89 (d, J = 7.4 Hz, 1H), 8.63 (d, J = 7.4 Hz, 1H), 8.06 (s, 2H), 8.01-7.97 (m, 1H), 7.93-7.87 (m, 1H), 7.45 (d, J = 8.0 Hz, 1H), 7.06 (dd, J = 15.8, 9.2 Hz, 1H), 6.85 (d, J = 15.7 Hz, 1H), 5.57 (h, J = 6.8 Hz, 1H), 4.84 (p, J = 9.4 Hz, 1H), 3.27 (q, J = 11.3 Hz, 2H), 1.35 (d, J = 6.5 Hz, 3H) | IR (thin film) 1675 cm$^{-1}$ |
| P3 | HRMS-ESI [M + H]$^+$ calcd for $C_{23}H_{17}Br_2F_9N_2O_2$, 684.9567; Found, 684.9570 | $^1$H NMR (500 MHz, DMSO-d$_6$) δ 8.90 (d, J = 7.4 Hz, 1H), 8.64 (d, J = 7.4 Hz, 1H), 8.01-7.97 (m, 1H), 7.93-7.88 (m, 2H), 7.85 (d, J = 1.7 Hz, 2H), 7.45 (d, J = 7.9 Hz, 1H), 7.06 (dd, J = 15.8, 9.2 Hz, 1H), 6.86 (d, J = 15.7 Hz, 1H), 5.58 (h, J = 6.8 Hz, 1H), 4.82 (p, J = 9.5 Hz, 1H), 3.27 (q, J = 11.3 Hz, 2H), 1.35 (d, J = 6.5 Hz, 3H) | IR (thin film) 1677 cm$^{-1}$ |
| P4 | HRMS-ESI [M + H]$^+$ calcd for $C_{24}H_{18}Br_2ClF_9N_2O_2$, 674.9679; Found, 674.9681 | $^1$H NMR (500 MHz, DMSO-d$_6$) δ 8.89 (d, J = 7.4 Hz, 1H), 8.63 (d, J = 7.4 Hz, 1H), 8.01-7.97 (m, 1H), 7.92-7.84 (m, 3H), 7.45 (d, J = 7.9 Hz, 1H), 7.05 (dd, J = 15.8, 9.1 Hz, 1H), 6.86 (d, J = 15.7 Hz, 1H), 5.57 (h, J = 6.8 Hz, 1H), 4.85 (p, J = 9.2 Hz, 1H), 3.27 (q, J = 11.5 Hz, 2H), 1.35 (d, J = 6.6 Hz, 3H) | IR (thin film) 1675 cm$^{-1}$ |
| P5 | HRMS-ESI [M + H]$^+$ calcd for $C_{23}H_{19}Cl_2F_7N_2O_2$, 559.0785; Found, 559.0794 | $^1$H NMR (500 MHz, DMSO-d$_6$) δ 8.62-8.54 (m, 2H), 7.84 (d, J = 6.3 Hz, 2H), 7.45 (d, J = 1.8 Hz, 1H), 7.40 (dd, J = 8.0, 1.7 Hz, 1H), 7.29 (d, J = 7.9 Hz, 1H), 6.84 (dd, J = 15.8, 9.1 Hz, 1H), 6.72 (d, J = 15.7 Hz, 1H), 5.60 (h, J = 6.8 Hz, 1H), 4.80 (p, J = 9.4 Hz, 1H), 3.27 (q, J = 11.3 Hz, 2H), 2.33 (s, 3H), 1.35 (d, J = 6.5 Hz, 3H) | IR (thin film) 1672 cm$^{-1}$ |
| P6 | HRMS-ESI [M + H]$^+$ calcd for $C_{23}H_{19}BrCl_2F_6N_2O_2$, 732.9332; Found, 732.9342 | $^1$H NMR (500 MHz, DMSO-d$_6$) δ 8.60 (d, J = 7.5 Hz, 1H), 8.57 (d, J = 7.2 Hz, 1H), 7.85 (s, 2H), 7.45 (d, J = 1.7 Hz, 1H), 7.40 (dd, J = 8.0, 1.7 Hz, 1H), 7.29 (d, J = 7.8 Hz, 1H), 6.83 (dd, J = 15.7, 9.0 Hz, 1H), 6.72 (d, J = 15.6 Hz, 1H), 5.60 (h, J = 6.8 Hz, 1H), 4.81 (p, J = 9.4 Hz, 1H), 3.26 (q, J = 11.3 Hz, 2H), 2.33 (s, 3H), 1.35 (d, J = 6.5 Hz, 3H) | IR (thin film) 1672 cm$^{-1}$ |
| P7 | HRMS-ESI [M + H]$^+$ calcd for $C_{23}H_{21}Br_2F_6N_2O_2$, 630.9850; Found, 630.9858 | $^1$H NMR (500 MHz, DMSO-d$_6$) δ 8.59 (d, J = 7.5 Hz, 1H), 8.56 (d, J = 7.2 Hz, 1H), 7.89 (t, J = 1.7 Hz, 1H), 7.82 (d, J = 1.7 Hz, 2H), 7.47-7.43 (m, 1H), 7.40 (dd, J = 8.0, 1.7 Hz, 1H), 7.29 (d, J = 7.8 Hz, 1H), 6.83 (dd, J = 15.7, 9.1 Hz, 1H), 6.72 (d, J = 15.6 Hz, 1H), 5.60 (h, J = 6.8 Hz, 1H), 4.79 (p, J = 9.5 Hz, 1H), 3.27 (q, J = 11.3 Hz, 2H), 2.33 (s, 3H), 1.35 (d, J = 6.5 Hz, 3H) | IR (thin film) 1656 cm$^{-1}$ |
| P8 | HRMS-ESI [M + H]$^+$ calcd for $C_{23}H_{20}Br_2ClF_6N_2O_2$, 664.9458; Found, 664.9465 | $^1$H NMR (500 MHz, DMSO-d$_6$) δ 8.60 (d, J = 7.5 Hz, 1H), 8.57 (d, J = 7.3 Hz, 1H), 8.03 (s, 2H), 7.45 (d, J = 1.8 Hz, 1H), 7.41 (dd, J = 8.1, 1.7 Hz, 1H), 7.29 (d, J = 7.9 Hz, 1H), 6.84 (dd, J = 15.7, 9.1 Hz, 1H), 6.72 (d, J = 15.7 Hz, 1H), 5.60 (h, J = 6.8 Hz, 1H), 4.81 (p, J = 9.5 Hz, 1H), 3.27 (q, J = 11.3 Hz, 2H), 2.33 (s, 3H), 1.35 (d, J = 6.5 Hz, 3H) | IR (thin film) 1673 cm$^{-1}$ |

TABLE 6-continued

Analytical Data for Compounds in Table 5

| No. | Mass (m/z) | $^1$H NMR | $^{19}$F NMR/IR |
|---|---|---|---|
| P9 | HRMS-ESI [M + H]$^+$ calcd for $C_{24}H_{18}Cl_2F_{10}N_2O_2$, 627.0658; Found, 627.0662 | $^1$H NMR (400 MHz, DMSO-$d_6$) δ 8.78 (d, J = 7.2 Hz, 1H), 8.41 (d, J = 7.5 Hz, 1H), 8.00-7.96 (m, 1H), 7.91-7.85 (m, 3H), 7.46 (d, J = 7.9 Hz, 1H), 7.05 (dd, J = 15.8, 9.1 Hz, 1H), 6.86 (d, J = 15.8 Hz, 1H), 5.58 (h, J = 6.7 Hz, 1H), 4.84 (p, J = 9.4 Hz, 1H), 2.58-2.28 (m, 4H), 1.33 (d, J = 6.5 Hz, 3H) | IR (thin film) 1667 cm$^{-1}$ |
| P10 | HRMS-ESI [M + H]$^+$ calcd for $C_{24}H_{18}Br_2ClF_9N_2O_2$, 732.9332; Found, 732.9342 | $^1$H NMR (500 MHz, DMSO-$d_6$) δ 8.77 (d, J = 7.2 Hz, 1H), 8.40 (d, J = 7.5 Hz, 1H), 8.06 (s, 2H), 7.98 (d, J = 1.7 Hz, 1H), 7.92-7.85 (m, 1H), 7.45 (d, J = 8.0 Hz, 1H), 7.05 (dd, J = 15.8, 9.2 Hz, 1H), 6.86 (d, J = 15.7 Hz, 1H), 5.57 (h, J = 6.7 Hz, 1H), 4.84 (p, J = 9.4 Hz, 1H), 2.52-2.29 (m, 4H), 1.33 (d, J = 6.5 Hz, 3H) | IR (thin film) 1665 cm$^{-1}$ |
| P11 | HRMS-ESI [M + H]$^+$ calcd for $C_{24}H_{19}Br_2F_9N_2O_2$, 698.9723; Found, 698.9721 | $^1$H NMR (500 MHz, DMSO-$d_6$) δ 8.78 (d, J = 7.1 Hz, 1H), 8.41 (d, J = 7.4 Hz, 1H), 7.98 (d, J = 1.6 Hz, 1H), 7.93-7.87 (m, 2H), 7.86 (d, J = 1.7 Hz, 2H), 7.45 (d, J = 7.9 Hz, 1H), 7.05 (dd, J = 15.8, 9.2 Hz, 1H), 6.86 (d, J = 15.7 Hz, 1H), 5.58 (h, J = 6.8 Hz, 1H), 4.82 (p, J = 9.5 Hz, 1H), 2.57-2.28 (m, 4H), 1.33 (d, J = 6.5 Hz, 3H) | IR (thin film) 1665 cm$^{-1}$ |
| P12 | HRMS-ESI [M + H]$^+$ calcd for $C_{24}H_{19}BrCl_2F_9N_2O_2$, 688.9836; Found, 688.9845 | $^1$H NMR (500 MHz, DMSO-$d_6$) δ 8.78 (d, J = 7.2 Hz, 1H), 8.41 (d, J = 7.5 Hz, 1H), 8.00-7.96 (m, 1H), 7.88 (s, 3H), 7.46 (d, J = 7.9 Hz, 1H), 7.05 (dd, J = 15.7, 9.1 Hz, 1H), 6.86 (d, J = 15.7 Hz, 1H), 5.58 (h, J = 6.8 Hz, 1H), 4.85 (p, J = 9.4 Hz, 1H), 2.54-2.29 (m, 4H), 1.33 (d, J = 6.5 Hz, 3H) | IR (thin film) 1666 cm$^{-1}$ |
| P13 | HRMS-ESI [M + H]$^+$ calcd for $C_{24}H_{21}Cl_2F_7N_2O_2$, 573.0941; Found, 573.0911 | $^1$H NMR (500 MHz, DMSO-$d_6$) δ 8.47 (d, J = 7.3 Hz, 1H), 8.35 (d, J = 7.2 Hz, 1H), 7.84 (d, J = 6.2 Hz, 2H), 7.45 (d, J = 1.8 Hz, 1H), 7.42-7.37 (m, 1H), 7.29 (d, J = 7.8 Hz, 1H), 6.84 (dd, J = 15.7, 9.1 Hz, 1H), 6.72 (d, J = 15.7 Hz, 1H), 5.61 (h, J = 6.7 Hz, 1H), 4.80 (p, J = 9.4 Hz, 1H), 2.58-2.21 (m, 7H), 1.33 (d, J = 6.5 Hz, 3H) | IR (thin film) 1655 cm$^{-1}$ |
| P14 | HRMS-ESI [M + H]$^+$ calcd for $C_{24}H_{18}Br_2ClF_9N_2O_2$, 678.9615; Found, 678.9623 | $^1$H NMR (500 MHz, DMSO-$d_6$) δ 8.46 (d, J = 7.3 Hz, 1H), 8.33 (d, J = 7.2 Hz, 1H), 8.03 (s, 2H), 7.44 (d, J = 1.7 Hz, 1H), 7.39 (dd, J = 8.0, 1.7 Hz, 1H), 7.29 (d, J = 7.8 Hz, 1H), 6.83 (dd, J = 15.7, 9.1 Hz, 1H), 6.72 (d, J = 15.6 Hz, 1H), 5.60 (h, J = 6.8 Hz, 1H), 4.81 (p, J = 9.5 Hz, 1H), 2.49-2.42 (m, 2H), 2.42-2.28 (m, 5H), 1.33 (d, J = 6.5 Hz, 3H) | IR (thin film) 1660 cm$^{-1}$ |
| P15 | HRMS-ESI [M + H]$^+$ calcd for $C_{24}H_{22}Br_2F_6N_2O_2$, 645.0006; Found, 645.0004 | $^1$H NMR (500 MHz, DMSO-$d_6$) δ 8.48 (d, J = 7.3 Hz, 1H), 8.35 (d, J = 7.2 Hz, 1H), 7.89 (t, J = 1.8 Hz, 1H), 7.82 (d, J = 1.8 Hz, 2H), 7.45 (d, J = 1.7 Hz, 1H), 7.41-7.37 (m, 1H), 7.29 (d, J = 7.9 Hz, 1H), 6.82 (dd, J = 15.7, 9.1 Hz, 1H), 6.72 (d, J = 15.6 Hz, 1H), 5.61 (h, J = 6.7 Hz, 1H), 4.79 (p, J = 9.5 Hz, 1H), 2.56-2.28 (m, 7H), 1.33 (d, J = 6.5 Hz, 3H) | IR (thin film) 1660 cm$^{-1}$ |
| P16 | HRMS-ESI [M + H]$^+$ calcd for $C_{24}H_{21}BrCl_2F_6N_2O_2$, 632.0118; Found, 635.0128 | $^1$H NMR (400 MHz, DMSO-$d_6$) δ 8.47 (d, J = 7.3 Hz, 1H), 8.34 (d, J = 7.2 Hz, 1H), 7.85 (s, 2H), 7.50-7.42 (m, 1H), 7.40 (dd, J = 7.9, 1.7 Hz, 1H), 7.29 (d, J = 7.9 Hz, 1H), 6.83 (dd, J = 15.7, 8.9 Hz, 1H), 6.72 (d, J = 15.7 Hz, 1H), 5.60 (h, J = 6.8 Hz, 1H), 4.82 (p, J = 9.4 Hz, 1H), 2.61-2.22 (m, 7H), 1.33 (d, J = 6.5 Hz, 3H) | IR (thin film) 1660 cm$^{-1}$ |

TABLE 6-continued

Analytical Data for Compounds in Table 5

| No. | Mass (m/z) | $^1$H NMR | $^{19}$F NMR/IR |
|---|---|---|---|
| P22 | HRMS-ESI [M + H]$^+$ calcd for $C_{23}H_{20}Cl_3F_6N_2O_2$, 577.0463; Found, 577.0470 | $^1$H NMR (500 MHz, DMSO-d$_6$) δ 8.59 (d, J = 7.5 Hz, 1H), 8.56 (d, J = 7.3 Hz, 1H), 7.89 (s, 2H), 7.45 (d, J = 1.8 Hz, 1H), 7.40 (dd, J = 8.0, 1.7 Hz, 1H), 7.29 (d, J = 7.9 Hz, 1H), 6.84 (dd, J = 15.7, 9.1 Hz, 1H), 6.73 (d, J = 15.7 Hz, 1H), 5.60 (h, J = 6.8 Hz, 1H), 4.83 (p, J = 9.4 Hz, 1H), 3.26 (q, J = 11.3 Hz, 2H), 2.33 (s, 3H), 1.35 (d, J = 6.5 Hz, 3H) | IR (thin film) 1671 cm$^{-1}$ |
| P24 | HRMS-ESI [M + H]$^+$ calcd for $C_{22}H_{17}BrCl_3F_6N_2O_2$, 640.9414; Found, 640.9414 | $^1$H NMR (500 MHz, DMSO-d$_6$) δ 8.84 (dd, J = 7.6, 1.6 Hz, 1H), 8.63 (d, J = 7.6 Hz, 1H), 7.89 (s, 2H), 7.63 (d, J = 8.2 Hz, 1H), 7.58-7.50 (m, 2H), 6.90 (dd, J = 15.7, 9.1 Hz, 1H), 6.76 (d, J = 15.7 Hz, 1H), 5.64 (h, J = 6.8 Hz, 1H), 4.84 (p, J = 9.3 Hz, 1H), 3.29 (q, J = 11.3 Hz, 2H), 1.38 (d, J = 6.5 Hz, 3H) | IR (thin film) 1675 cm$^{-1}$ |
| P25 | HRMS-ESI [M + H]$^+$ calcd for $C_{24}H_{21}Cl_3F_6N_2O_2$, 589.0646; Found, 589.0657 | $^1$H NMR (500 MHz, DMSO-d$_6$) δ 8.47 (d, J = 7.3 Hz, 1H), 8.34 (d, J = 7.2 Hz, 1H), 7.89 (s, 2H), 7.45 (d, J = 1.7 Hz, 1H), 7.43-7.37 (m, 1H), 7.29 (d, J = 7.8 Hz, 1H), 6.84 (dd, J = 15.7, 9.1 Hz, 1H), 6.73 (d, J = 15.7 Hz, 1H), 5.60 (h, J = 6.7 Hz, 1H), 4.83 (p, J = 9.4 Hz, 1H), 2.56-2.28 (m, 7H), 1.33 (d, J = 6.5 Hz, 3H) | IR (thin film) 1656 cm$^{-1}$ |
| P27 | HRMS-ESI [M + H]$^+$ calcd for $C_{23}H_{19}BrCl_3F_6N_2O_2$, 654.9571; Found, 654.9582 | $^1$H NMR (500 MHz, DMSO-d$_6$) δ 8.70 (dd, J = 7.2, 1.9 Hz, 1H), 8.37 (d, J = 7.6 Hz, 1H), 7.89 (s, 2H), 7.62 (d, J = 8.3 Hz, 1H), 7.55 (t, J = 1.9 Hz, 1H), 7.52 (ddd, J = 8.0, 5.3, 2.2 Hz, 1H), 6.89 (ddd, J = 15.8, 9.1, 1.8 Hz, 1H), 6.75 (d, J = 15.6 Hz, 1H), 5.62 (h, J = 6.7 Hz, 1H), 4.83 (p, J = 9.5 Hz, 1H), 2.56-2.43 (m, 2H), 2.42-2.29 (m, 2H), 1.35 (d, J = 6.5 Hz, 3H) | IR (thin film) 1666 cm$^{-1}$ |
| P30 | ESIMS 657 ([M − H]$^-$) | Mixture of diastereomers: $^1$H NMR (400 MHz, CDCl$_3$) δ 7.67-7.63 (m, 1H), 7.59-7.51 (m, 1H), 7.46-7.40 (m, 3H), 7.18-7.04 (m, 2H), 6.61 (d, J = 15.9 Hz, 1H), 6.42 (dd, J = 16.0, 7.9 Hz, 1H), 5.40 (hept, J = 7.0 Hz, 1H), 4.12 (p, J = 8.6 Hz, 1H), 2.71-2.45 (m, 2H), 2.20-1.97 (m, 1H), 1.71-1.61 (m, 3H), 1.24-1.19 (m, 3H) | Mixture of diastereomers: (Major) $^{19}$F NMR (376 MHz, CDCl$_3$) δ −59.09, −64.97, −68.59; (Minor) 19F NMR (376 MHz, CDCl$_3$) δ −59.11, −64.96, −68.60 |
| P33 | ESIMS 657 ([M − H]$^-$) | $^1$H NMR (400 MHz, CDCl$_3$) δ 7.64 (d, J = 1.7 Hz, 1H), 7.55 (dd, J = 8.0, 1.7 Hz, 1H), 7.45-7.40 (m, 3H), 7.30 (d, J = 7.3 Hz, 1H), 7.23 (d, J = 7.5 Hz, 1H), 6.61 (d, J = 15.9 Hz, 1H), 6.42 (dd, J = 15.9, 7.9 Hz, 1H), 5.46 (h, J = 7.0 Hz, 1H), 4.20-4.03 (m, 1H), 1.66 (d, J = 6.7 Hz, 3H), 1.38 (s, 6H) | $^{19}$F NMR (376 MHz, CDCl$_3$) δ −59.12, −68.60, −74.48 |
| P36 | HRMS-ESI [M + H]$^+$ calcd for $C_{23}H_{19}Cl_3F_6N_2O_3S$, 625.0132; Found, 625.0136 | $^1$H NMR (500 MHz, DMSO-d$_6$) δ 8.92-8.86 (m, 1H), 8.64-8.56 (m, 1H), 7.99 (s, 1H), 7.91 (d, J = 16.8 Hz, 3H), 7.50-7.45 (m, 1H), 7.06 (dd, J = 15.7, 9.1 Hz, 1H), 6.87 (d, J = 15.7 Hz, 1H), 5.65-5.56 (m, 1H), 4.86 (p, J = 9.4 Hz, 1H), 3.74-3.59 (m, 2H), 2.65-2.61 (m, 3H), 1.39-1.31 (m, 3H) | IR (thin film) 1671 cm$^{-1}$ |
| P43 | HRMS-ESI [M + H]$^+$ calcd for $C_{23}H_{19}Cl_3F_6N_2O_4S$, 641.0082; Found, 641.0089 | $^1$H NMR (500 MHz, DMSO-d$_6$) δ 8.93 (d, J = 7.5 Hz, 1H), 8.72 (d, J = 7.4 Hz, 1H), 8.03-7.96 (m, 1H), 7.91 (d, J = 14.8 Hz, 3H), 7.47 (d, J = 7.9 Hz, 1H), 7.06 (dd, J = 15.8, 9.1 Hz, 1H), 6.87 (d, J = 15.7 Hz, 1H), 5.60 (h, J = 6.8 Hz, 1H), 4.86 (p, J = 9.4 Hz, 1H), 4.15 (d, J = 14.2 Hz, 1H), | IR (thin film) 1677 cm$^{-1}$ |

TABLE 6-continued

Analytical Data for Compounds in Table 5

| No. | Mass (m/z) | $^1$H NMR | $^{19}$F NMR/IR |
|---|---|---|---|
| | | 4.06-4.02 (m, 1H), 3.12 (s, 3H), 1.35 (d, J = 6.5 Hz, 3H) | |
| P47 | HRMS-ESI [M + H]$^+$ calcd for C$_{24}$H$_{21}$Cl$_3$F$_6$N$_2$O$_4$S, 655.0238; Found, 655.026 | $^1$H NMR (500 MHz, DMSO-d$_6$) δ 8.77 (d, J = 7.1 Hz, 1H), 8.46 (d, J = 7.4 Hz, 1H), 7.98 (d, J = 1.7 Hz, 1H), 7.94-7.86 (m, 3H), 7.47 (d, J = 7.9 Hz, 1H), 7.05 (dd, J = 15.8, 9.1 Hz, 1H), 6.86 (d, J = 15.7 Hz, 1H), 5.58 (h, J = 6.7 Hz, 1H), 4.86 (p, J = 9.4 Hz, 1H), 3.35-3.29 (m, 2H), 2.98 (s, 3H), 2.63-2.52 (m, 2H), 1.33 (d, J = 6.5 Hz, 3H) | IR (thin film) 1670 cm$^{-1}$ |
| P49 | HRMS-ESI [M + H]$^+$ calcd for C$_{24}$H$_{21}$Cl$_3$F$_6$N$_2$O$_3$S, 639.0289; Found, 639.0299 | $^1$H NMR (500 MHz, DMSO-d$_6$) δ 8.80-8.74 (m, 1H), 8.45-8.39 (m, 1H), 7.99-7.97 (m, 1H), 7.90 (d, J = 22.0 Hz, 3H), 7.47 (d, J = 7.9 Hz, 1H), 7.05 (dd, J = 15.7, 9.1 Hz, 1H), 6.87 (d, J = 15.7 Hz, 1H), 5.58 (h, J = 6.7 Hz, 1H), 4.86 (p, J = 9.4 Hz, 1H), 3.06-2.97 (m, 1H), 2.81 (ddt, J = 11.3, 7.1, 5.5 Hz, 1H), 2.53 (s, 3H), 2.52-2.51 (m, 2H), 1.33 (d, J = 6.5 Hz, 3H) | |
| P53 | HRMS-ESI [M + H]$^+$ calcd for C$_{24}$H$_{21}$Cl$_3$F$_6$N$_2$O$_2$S, 623.034; Found 623.0342 | $^1$H NMR (500 MHz, DMSO-d$_6$) δ 8.74 (d, J = 7.2 Hz, 1H), 8.27 (d, J = 7.5 Hz, 1H), 7.98 (d, J = 1.9 Hz, 1H), 7.92 (s, 2H), 7.89 (d, J = 7.8 Hz, 1H), 7.46 (d, J = 7.9 Hz, 1H), 7.05 (dd, J = 15.7, 9.1 Hz, 1H), 6.86 (d, J = 15.7 Hz, 1H), 5.57 (h, J = 6.8 Hz, 1H), 4.86 (p, J = 9.4 Hz, 1H), 2.65 (t, J = 7.0 Hz, 2H), 2.45-2.31 (m, 2H), 2.06 (s, 3H), 1.32 (d, J = 6.5 Hz, 3H) | IR (thin film) 1662 cm$^{-1}$ |
| P54 | HRMS-ESI [M + H]$^+$ calcd for C$_{23}$H$_{19}$Cl$_3$F$_6$N$_2$O$_2$S; 609.0183; Found, 609.0188 | $^1$H NMR (500 MHz, DMSO-d$_6$) δ 8.81 (d, J = 7.4 Hz, 1H), 8.30 (d, J = 7.6 Hz, 1H), 8.01-7.97 (m, 1H), 7.94-7.87 (m, 3H), 7.47 (d, J = 7.9 Hz, 1H), 7.05 (dd, J = 15.7, 9.1 Hz, 1H), 6.86 (d, J = 15.7 Hz, 1H), 5.59 (h, J = 6.8 Hz, 1H), 4.86 (p, J = 9.4 Hz, 1H), 3.09 (s, 2H), 2.10 (s, 3H), 1.34 (d, J = 6.5 Hz, 3H). | IR (thin film) 1664 cm$^{-1}$ |

TABLE 7

Structure and Preparation Method for FC Series Compounds

| No. | Structure | Prep. according to example: |
|---|---|---|
| FC1 | [Structure: 3,4,5-trichlorophenyl group attached to CH(CF$_3$)-CH=CH-phenyl-C(O)NH-CH(CH$_3$)-NH-C(O)-CH$_2$CH$_2$CF$_3$] | 30 |

TABLE 7-continued

Structure and Preparation Method for FC Series Compounds

| No. | Structure | Prep. according to example: |
|---|---|---|
| FC2 | 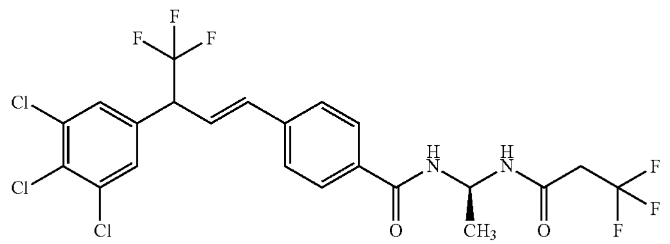 [SMILES: C[C@H](NC(=O)CC(F)(F)F)NC(=O)c1ccc(/C=C/C(c2cc(Cl)c(Cl)c(Cl)c2)C(F)(F)F)cc1] | 30 |

TABLE 8

Analytical Data for Compounds in Table 7

| No. | Mass (m/z) | $^1$H NMR | $^{19}$F NMR/IR |
|---|---|---|---|
| FC1 | HRMS-ESI [M + H]$^+$ calcd for $C_{23}H_{20}Cl_3F_6N_2O_2$; 575.0489; Found, 575.0490 | Rotomers: $^1$H NMR (400 MHz, DMSO-d$_6$) δ 8.63 (d, J = 7.2 Hz, 1H), 8.29 (d, J = 7.1 Hz, 1H), 7.88 (s, 2H), 7.82 (d, J = 8.4 Hz, 2H), 7.63 (d, J = 8.4 Hz, 2H), 6.93-6.88 (m, 1H), 6.77 (d, J = 15.7 Hz, 1H), 5.63 (h, J = 6.7 Hz, 2.47-2.39 (m, 1H), 2.39-2.27 (m, 2H), 1.33 (d, J = 6.5 Hz, 3H). | Rotomers: $^{19}$F NMR (376 MHz, CDCl$_3$) δ −66.76, −68.68 1H), 4.82 (h, J = 9.2 Hz, 1H), |
| FC2 | HRMS-ESI [M + H]$^+$ calcd for $C_{22}H_{18}Cl_3F_6N_2O_2$; 561.0333; Found, 561.0330 | Rotomers: $^1$H NMR (400 MHz, CDCl$_3$) δ 8.51 (d, J = 8.1 Hz, 1H), 8.37 (d, J = 7.9 Hz, 1H), 7.76 (d, J = 8.1 Hz, 2H), 7.37 (d, J = 2.4 Hz, 2H), 7.33-7.28 (m, 2H), 6.64-6.51 (m, 1H), 6.41-6.29 (m, 1H), 6.09 (q, J = 8.3, 7.7 Hz, 1H), 4.17-3.97 (m, 1H), 3.20-3.10 (m, 2H), 1.54 (d, J = 6.5 Hz, 3H) | $^{19}$F NMR (376 MHz, CDCl$_3$) δ −62.90, −65.78, −68.73 |

| % Control (or Mortality) | Rating |
|---|---|
| BAW & CL Rating Table | |
| 50-100 | A |
| More than 0-Less than 50 | B |
| Not Tested | C |
| No activity noticed in this bioassay | D |
| GPA & YFM Rating Table | |
| 80-100 | A |
| More than 0-Less than 80 | B |
| Not Tested | C |
| No activity noticed in this bioassay | D |

TABLE ABC

Assay Results (F)

| | Insect species | | | |
|---|---|---|---|---|
| No. | BAW | CL | GPA | YFM |
| F1 | A | A | C | C |
| F2 | A | A | D | A |
| F3 | A | A | C | A |
| F4 | A | A | C | A |
| F5 | A | A | C | A |
| F6 | A | A | C | A |
| F7 | A | A | C | A |

TABLE ABC-continued

Assay Results (F)

| | Insect species | | | |
|---|---|---|---|---|
| No. | BAW | CL | GPA | YFM |
| F8 | A | A | C | A |
| F9 | A | A | C | A |
| F10 | A | A | C | A |
| F11 | A | A | C | A |
| F12 | A | A | C | A |
| F13 | A | A | C | C |
| F14 | A | A | C | A |
| F15 | A | A | C | A |
| F16 | A | A | C | A |
| F17 | A | A | C | A |
| F18 | A | A | C | A |
| F19 | A | A | C | A |
| F20 | A | A | C | A |
| F21 | A | A | C | B |
| F22 | A | A | C | A |
| F23 | A | A | C | A |

TABLE ABCD

Assay Results (C)

| No. | Insect species | | | |
|---|---|---|---|---|
| | BAW | CL | GPA | YFM |
| C113 | A | A | D | A |
| C115 | A | D | C | C |
| C116 | A | A | C | A |

TABLE ABCDE

Assay Results (P)

| No. | Insect species | | | |
|---|---|---|---|---|
| | BAW | CL | GPA | YFM |
| P1 | A | A | C | C |
| P2 | A | A | C | A |
| P3 | A | A | C | B |
| P4 | A | A | C | A |
| P5 | A | A | C | A |
| P6 | A | A | C | A |
| P7 | A | A | C | A |
| P8 | A | A | C | C |
| P9 | A | A | C | C |
| P10 | A | A | C | A |
| P11 | A | A | C | A |
| P12 | A | A | C | A |
| P13 | A | A | C | A |
| P14 | A | A | C | A |
| P15 | A | A | C | C |
| P16 | A | A | C | C |
| P22 | A | A | C | C |
| P24 | A | A | C | D |
| P25 | A | A | C | C |
| P27 | A | A | C | B |
| P30 | A | A | C | C |
| P33 | A | A | C | A |
| P36 | A | A | D | C |
| P43 | A | A | C | C |
| P47 | A | A | C | C |
| P49 | A | A | B | C |
| P53 | A | A | C | C |
| P54 | A | A | C | C |

Data

Bioassays on BAW and CL were conducted according to the procedures outlined in Example A: Bioassays on Beet Armyworm ("BAW") and Cabbage Looper ("CL") using the following concentrations: 5, 0.5, and 0.05 μg/cm². The results are indicated in Table CD1.

TABLE CD1

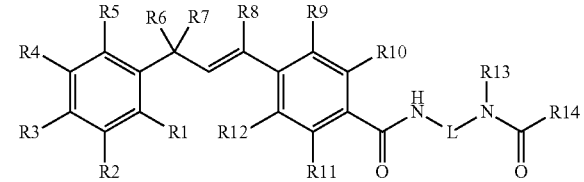

| No. | R10 | R14 | 5 μg/cm² | | 0.5 μg/cm² | | 0.05 μg/cm² | |
|---|---|---|---|---|---|---|---|---|
| | | | BAW | CL | BAW | CL | BAW | CL |
| FC1[†] | H | $CH_2CH_2CF_3$ | 13* | 71 | 0 | 0 | 0 | 0 |
| P25 | $CH_3$ | $CH_2CH_2CF_3$ | 100 | 100 | 100 | 100 | 100 | 100 |
| P27 | Br | $CH_2CH_2CF_3$ | 7 | 100 | 0 | 7 | 0 | 0 |
| F1 | $CF_3$ | $CH_2CH_2CF_3$ | 100 | 100 | 100 | 100 | 100 | 97 |
| FC2 | H | $CH_2CF_3$ | 0 | 0 | 0 | 0 | 0 | 0 |

TABLE CD1-continued

| P22 | $CH_3$ | $CH_2CF_3$ | 100 | 100 | 100 | 100 | 25 | 63 |
| P24 | Br | $CH_2CF_3$ | 87 | 100 | 7 | 19 | 0 | 6 |
| F2 | $CF_3$ | $CH_2CF_3$ | 100 | 100 | 100 | 100 | 100 | 100 |

[†]Compound 30% pure.
*Percent control (or mortality)

We claim:
1. A molecule having the following formula wherein:
(a) R1, R2, R3, R4, and R5, are, each independently, H, F, Cl, Br, I, CN, $(C_1-C_6)$alkyl, $(C_1-C_6)$haloalkyl, $(C_1-C_6)$alkoxy, or $(C_1-C_6)$haloalkoxy;
(b) R6 is $(C_1-C_6)$haloalkyl;
(c) R7 is H;
(d) R8 is H, $(C_1-C_6)$alkyl, or $(C_1-C_6)$haloalkyl;
(e) R9 is H, F, Cl, Br, I, $(C_1-C_6)$alkyl, or $(C_1-C_6)$haloalkyl;
(f) R10 is F, Cl, Br, I, $(C_1-C_6)$alkyl, or $(C_1-C_6)$haloalkyl;
(g) R11 and R12 are, each independently, H, F, Cl, Br, I, $(C_1-C_6)$alkyl, or $(C_1-C_6)$haloalkyl;
(h) L is
(1) a linker that is a bond connecting the two nitrogen atoms, or
(2) a $(C_1-C_6)$alkyl that is optionally substituted with one or more substituents, wherein each substituent is independently selected from F, Cl, Br, I, CN, OH, oxo, $(C_1-C_6)$alkoxy, $S(C_1-C_6)$alkyl, $S(O)(C_1-C_6)$alkyl, $S(O)_2(C_1-C_6)$alkyl, and $N((C_1-C_6)alkyl)_2$ wherein each $(C_1-C_6)$alkyl is independently selected, and wherein each said alkyl or alkoxy has one or more substituents independently selected from H, F, Cl, Br, and I;
(i) R13 is
(1) an H, or
(2) a $(C_1-C_6)$alkyl that is optionally substituted with one or more substituents, wherein each substituent is independently selected from F, Cl, Br, I, CN, OH, oxo, $(C_1-C_6)$alkoxy, $S(C_1-C_6)$alkyl, $S(O)(C_1-C_6)$alkyl, $S(O)_2(C_1-C_6)$alkyl, and $N((C_1-C_6)alkyl)_2$ wherein each $(C_1-C_6)$alkyl is independently selected, and wherein each said alkyl or alkoxy has one or more substituents independently selected from H, F, Cl, Br, and I; and
(j) R14 is independently selected from $(C_1-C_8)$alkyl, $(C_1-C_8)$haloalkyl, $(C_3-C_8)$cycloalkyl, $(C_2-C_8)$alkenyl, or $(C_2-C_8)$alkynyl, wherein each said alkyl, haloalkyl, cycloalkyl, alkenyl, and alkynyl has one or more substituents selected from F, Cl, Br, I, CN, $NO_2$, OH, oxo, $(C_1-C_6)$alkoxy, $S(C_1-C_6)$alkyl, $S(O)(C_1-C_6)$alkyl, $S(O)_2$ $(C_1-C_6)$alkyl, and $N((C_1-C_6)alkyl)_2$ wherein each $(C_1-C_6)$alkyl is independently selected, and wherein each said alkyl or alkoxy has one or more substituents independently selected from H, F, Cl, Br, and I.

2. A molecule according to claim 1 wherein:
(a) R1 is H;
(b) R2 is H, F, Cl, or Br;
(c) R3 is H, F, Cl, or Br;
(d) R4 is H, F, Cl, or Br;
(e) R5 is H;
(f) R6 is $(C_1$-$C_8)$haloalkyl;
(g) R7 is H;
(h) R8 is H;
(i) R9 is H;
(j) R10 is selected from a group consisting of F, Cl, Br, I, $(C_1$-$C_6)$alkyl, and $(C_1$-$C_6)$haloalkyl;
(k) R11 is H;
(l) R12 is H;
(m) L is
  (1) a linker that is bond connecting the two nitrogen atoms, or
  (2) a $(C_1$-$C_6)$alkyl;
(n) R13 is
  (1) an H, or
  (2) a $(C_1$-$C_8)$alkyl;
(o) R14 is independently selected from $(C_1$-$C_8)$alkyl, $(C_1$-$C_8)$haloalkyl, $(C_3$-$C_8)$cycloalkyl, $(C_2$-$C_8)$alkenyl, or $(C_2$-$C_8)$alkynyl, wherein each said alkyl, haloalkyl, cycloalkyl, alkenyl, and alkynyl has one or more substituents selected from F, Cl, Br, I, CN, $NO_2$, OH, oxo, $(C_1$-$C_6)$alkoxy, $S(C_1$-$C_6)$alkyl, $S(O)(C_1$-$C_6)$alkyl, $S(O)_2$ $(C_1$-$C_6)$alkyl, and $N((C_1$-$C_6)$alkyl$)_2$ wherein each $(C_1$-$C_6)$alkyl is independently selected, and wherein each said alkyl or alkoxy has one or more substituents independently selected from H, F, Cl, Br, and I.

3. A molecule according to claim 1 wherein:
(a) R1 is H;
(b) R2 is Cl or Br;
(c) R3 is H, F, Cl, or Br;
(d) R4 is Cl or Br;
(e) R5 is H;
(f) R6 is $(C_1$-$C_8)$haloalkyl;
(g) R7 is H;
(h) R8 is H;
(i) R9 is H;
(j) R10 is Br, $(C_1$-$C_8)$alkyl, $(C_1$-$C_8)$haloalkyl;
(k) R11 is H;
(l) R12 is H;
(m) L is
  (1) a linker that is bond connecting the two nitrogen atoms, or
  (2) a $(C_1$-$C_6)$alkyl;
(n) R13 is
  (1) an H, or
  (2) a $(C_1$-$C_8)$alkyl;
(o) R14 is $(C_1$-$C_8)$alkyl, $(C_1$-$C_8)$haloalkyl, $(C_3$-$C_8)$cycloalkyl, or $(C_2$-$C_8)$alkenyl, wherein each said alkyl or cycloalkyl is substituted with CN, $SCH_3$, $S(O)CH_3$, or $S(O)_2CH_3$.

4. A molecule according to claim 1 wherein said molecule is selected from one of the following molecules

| No. | Structure |
|-----|-----------|

F1
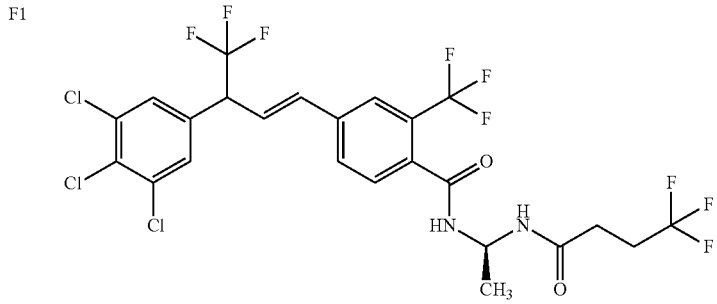

F2
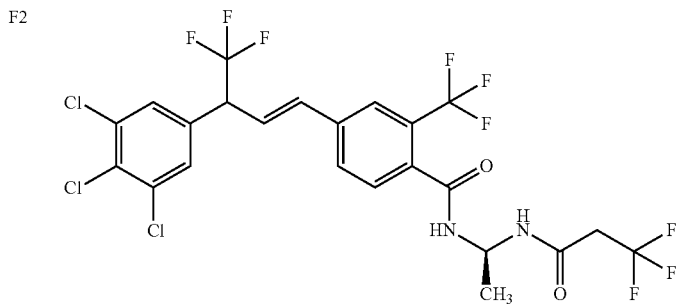

-continued
| No. | Structure |
|---|---|
| F3 | 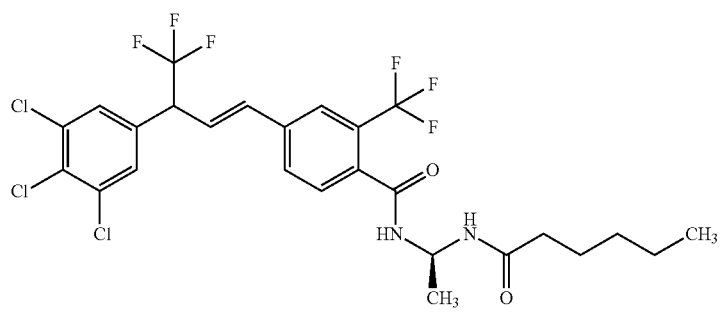 |
| F4 | 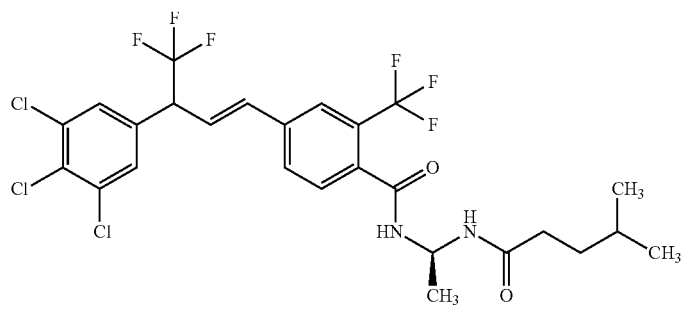 |
| F5 | 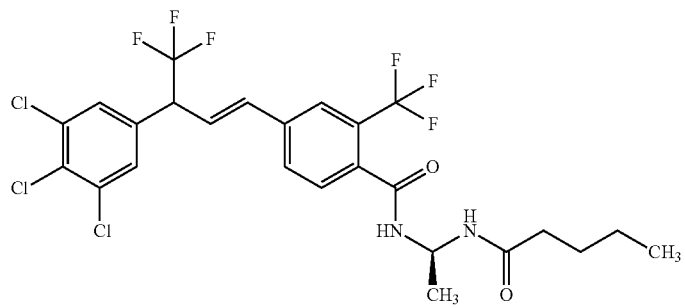 |
| F6 | 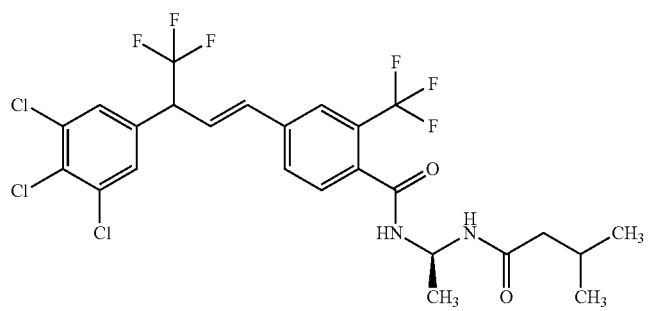 |
| F7 | 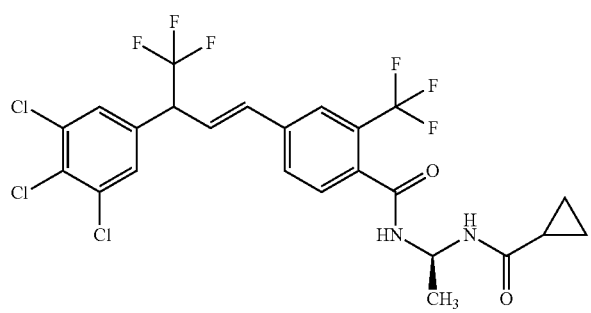 [SMILES: C[C@@H](NC(=O)c1ccc(/C=C/C(c2cc(Cl)c(Cl)c(Cl)c2)C(F)(F)F)cc1C(F)(F)F)NC(=O)C1CC1] |

| No. | Structure |
|---|---|
| F8 | 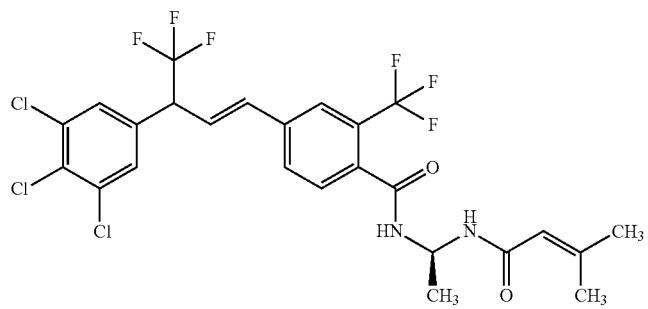 [SMILES: CC(C)=CC(=O)N[C@@H](C)NC(=O)c1ccc(/C=C/C(c2cc(Cl)c(Cl)c(Cl)c2)C(F)(F)F)cc1C(F)(F)F] |
| F9 | 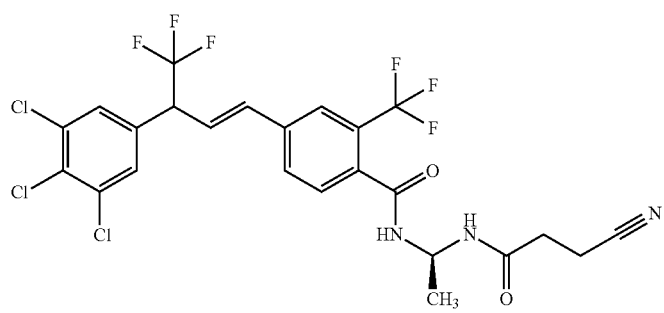 [SMILES: C[C@H](NC(=O)CCC#N)NC(=O)c1ccc(/C=C/C(c2cc(Cl)c(Cl)c(Cl)c2)C(F)(F)F)cc1C(F)(F)F] |
| F10 | 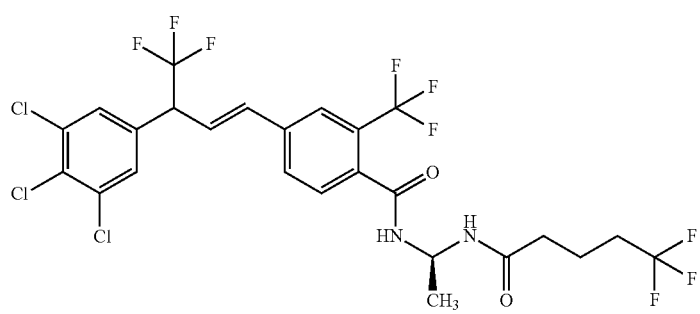 [SMILES: C[C@H](NC(=O)CCCC(F)(F)F)NC(=O)c1ccc(/C=C/C(c2cc(Cl)c(Cl)c(Cl)c2)C(F)(F)F)cc1C(F)(F)F] |
| F11 | 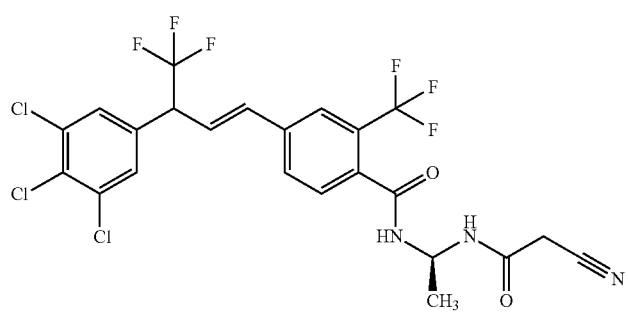 [SMILES: C[C@H](NC(=O)CC#N)NC(=O)c1ccc(/C=C/C(c2cc(Cl)c(Cl)c(Cl)c2)C(F)(F)F)cc1C(F)(F)F] |
| F12 | 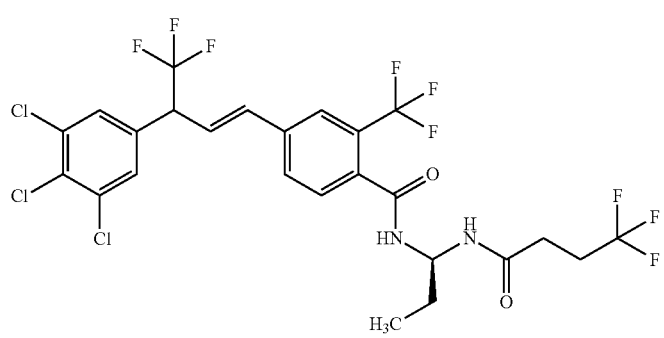 [SMILES: CC[C@H](NC(=O)CCC(F)(F)F)NC(=O)c1ccc(/C=C/C(c2cc(Cl)c(Cl)c(Cl)c2)C(F)(F)F)cc1C(F)(F)F] |

| No. | Structure |
|---|---|
| F13 | 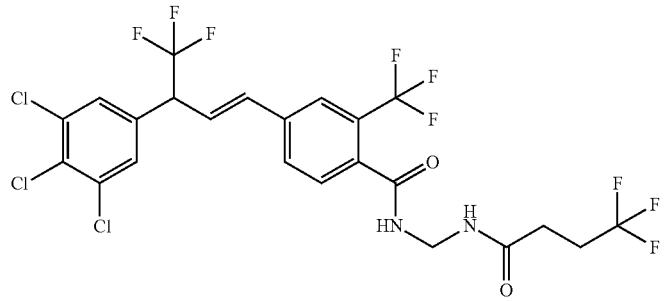 [SMILES: O=C(CCC(F)(F)F)NCNC(=O)c1ccc(/C=C/C(c2cc(Cl)c(Cl)c(Cl)c2)C(F)(F)F)cc1C(F)(F)F] |
| F14 | 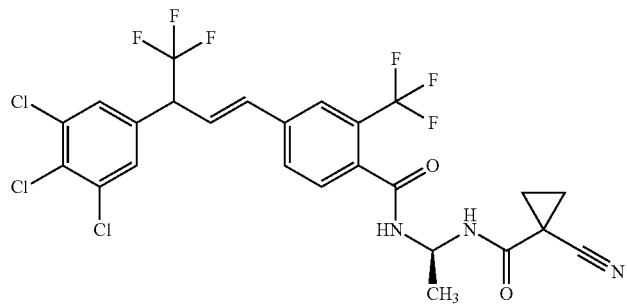 |
| F15 | 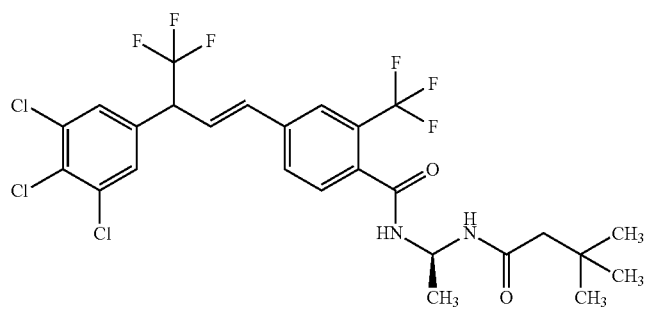 [SMILES: C[C@H](NC(=O)CC(C)(C)C)NC(=O)c1ccc(/C=C/C(c2cc(Cl)c(Cl)c(Cl)c2)C(F)(F)F)cc1C(F)(F)F] |
| F16 | 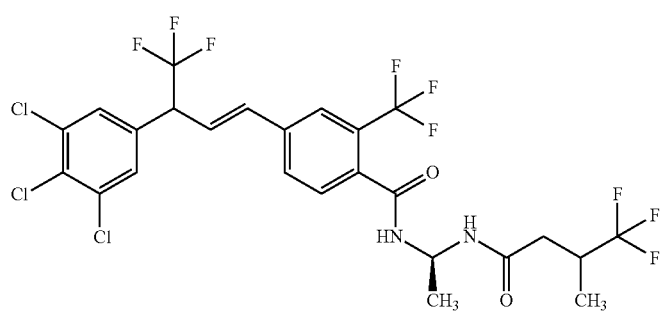 [SMILES: CC(CC(=O)N[C@@H](C)NC(=O)c1ccc(/C=C/C(c2cc(Cl)c(Cl)c(Cl)c2)C(F)(F)F)cc1C(F)(F)F)C(F)(F)F] |
| F17 | 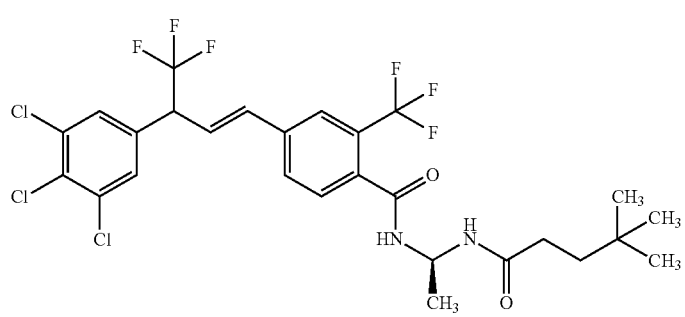 [SMILES: C[C@H](NC(=O)CCC(C)(C)C)NC(=O)c1ccc(/C=C/C(c2cc(Cl)c(Cl)c(Cl)c2)C(F)(F)F)cc1C(F)(F)F] |

-continued
| No. | Structure |
|---|---|
| F18 | 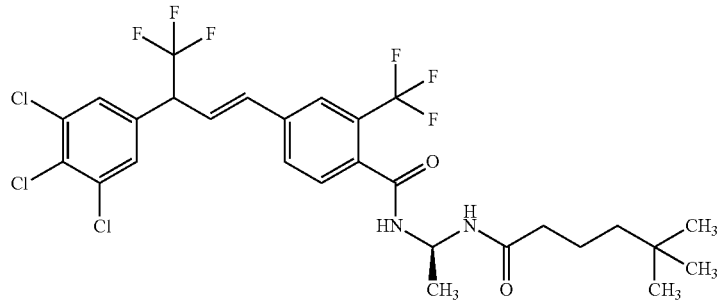 [SMILES: C[C@H](NC(=O)CCCC(C)(C)C)NC(=O)c1ccc(/C=C/C(c2cc(Cl)c(Cl)c(Cl)c2)C(F)(F)F)cc1C(F)(F)F] |
| F19 | 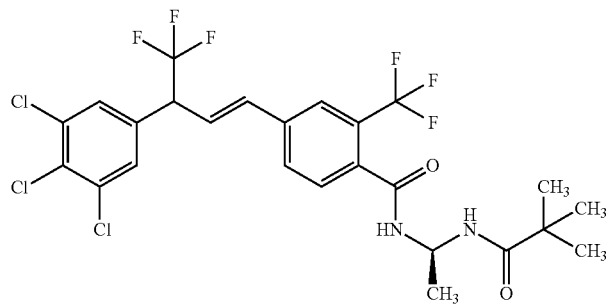 [SMILES: C[C@@H](NC(=O)c1ccc(/C=C/C(c2cc(Cl)c(Cl)c(Cl)c2)C(F)(F)F)cc1C(F)(F)F)NC(=O)C(C)(C)C] |
| F20 | 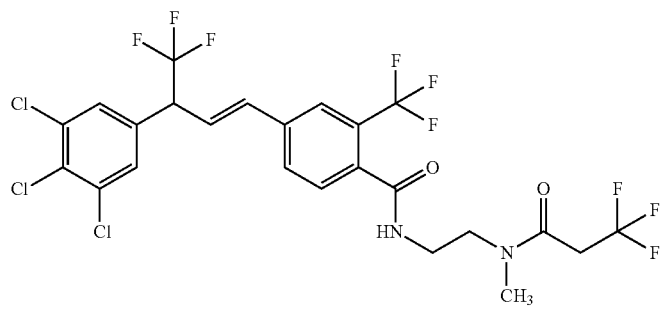 [SMILES: CN(CCNC(=O)c1ccc(/C=C/C(c2cc(Cl)c(Cl)c(Cl)c2)C(F)(F)F)cc1C(F)(F)F)C(=O)CC(F)(F)F] |
| F21 | 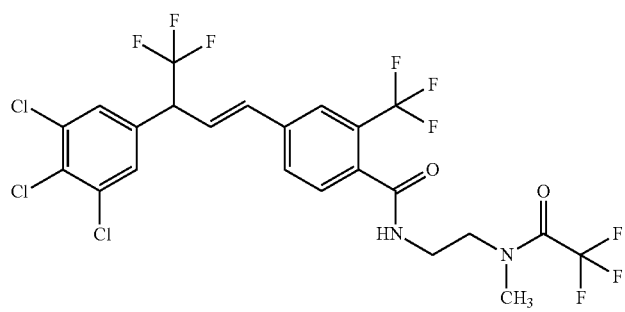 [SMILES: CN(CCNC(=O)c1ccc(/C=C/C(c2cc(Cl)c(Cl)c(Cl)c2)C(F)(F)F)cc1C(F)(F)F)C(=O)C(F)(F)F] |
| F22 | 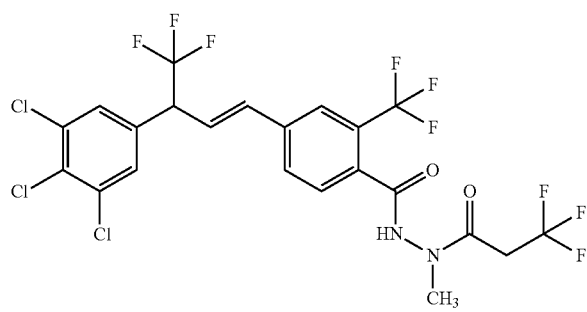 [SMILES: CN(NC(=O)c1ccc(/C=C/C(c2cc(Cl)c(Cl)c(Cl)c2)C(F)(F)F)cc1C(F)(F)F)C(=O)CC(F)(F)F] |

| No. | Structure |
|---|---|
| F23 | 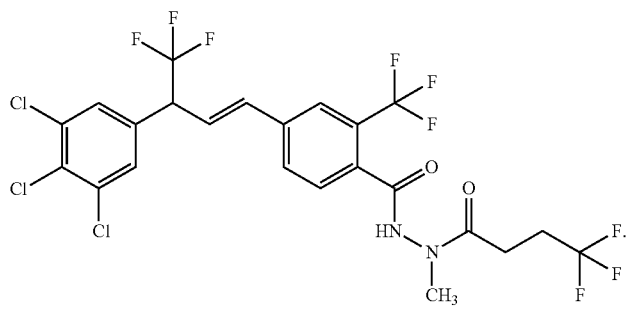 [SMILES: CN(NC(=O)c1ccc(/C=C/C(c2cc(Cl)c(Cl)c(Cl)c2)C(F)(F)F)cc1C(F)(F)F)C(=O)CCC(F)(F)F] |
5. A molecule according to claim 1 wherein said molecule is selected from one of the following molecules
| No. | Structure |
|---|---|
| P1 | 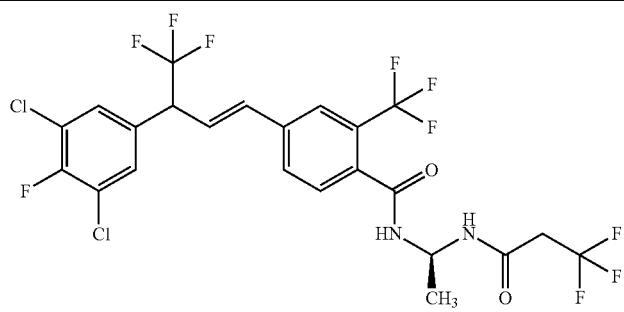 |
| P2 | 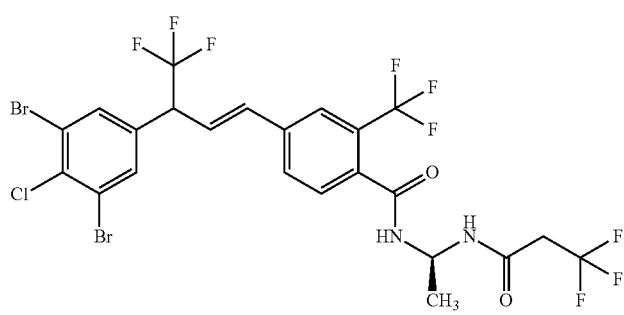 |
| P3 | 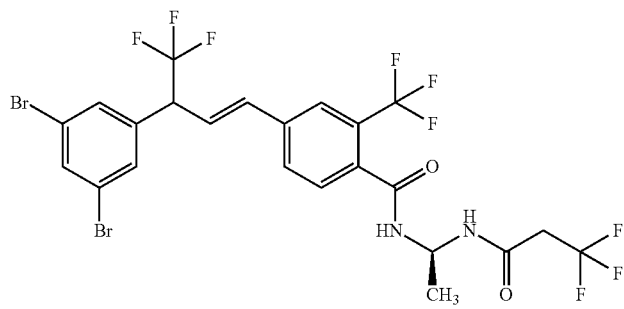 |

| No. | Structure |
|---|---|
| P4 | 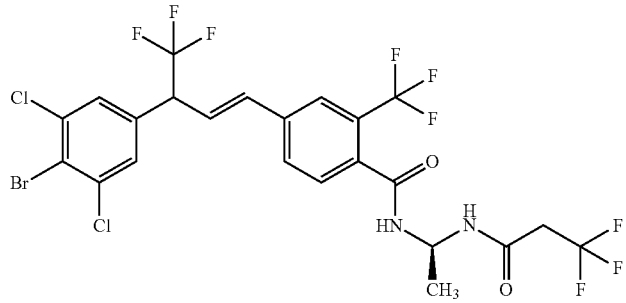 [SMILES: C[C@H](NC(=O)CC(F)(F)F)NC(=O)c1ccc(/C=C/C(c2cc(Cl)c(F)c(Cl)c2)C(F)(F)F)cc1C(F)(F)F] |
| P5 | 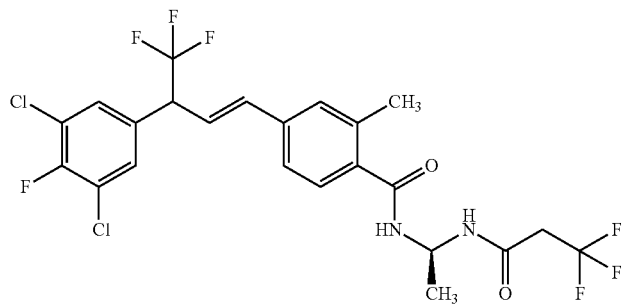 [SMILES: Cc1cc(/C=C/C(c2cc(Cl)c(F)c(Cl)c2)C(F)(F)F)ccc1C(=O)N[C@H](C)NC(=O)CC(F)(F)F] |
| P6 | 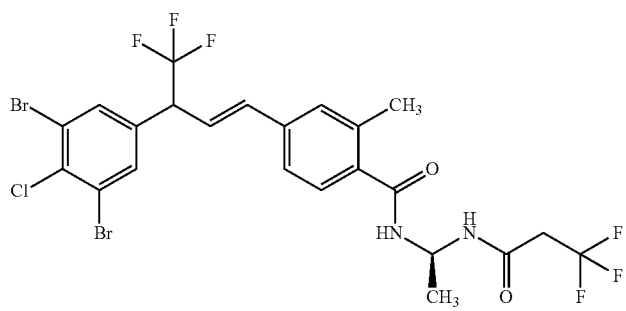 |
| P7 | 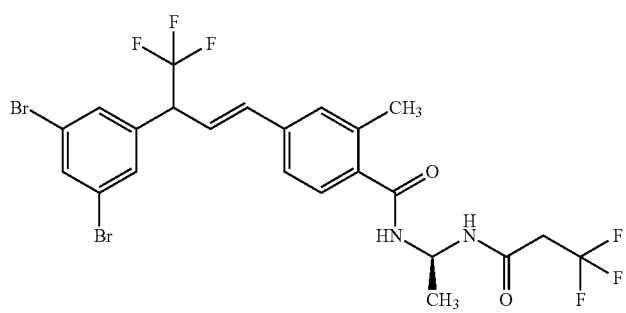 |
| P8 | 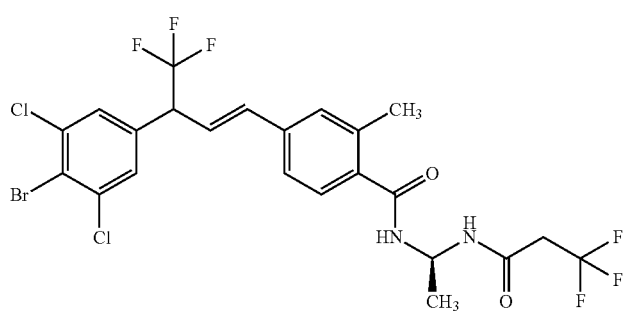 |

-continued
| No. | Structure |
|-----|-----------|
| P9  | 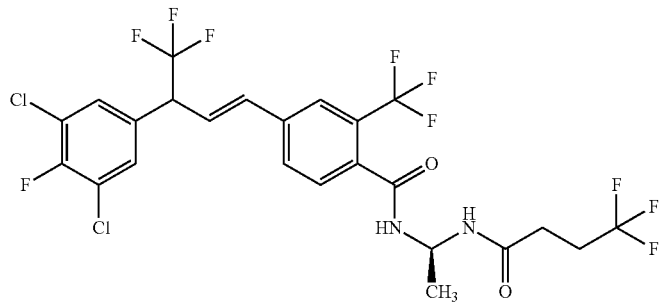 [SMILES: C[C@H](NC(=O)CCC(F)(F)F)NC(=O)c1ccc(/C=C/C(c2cc(Cl)c(F)c(Cl)c2)C(F)(F)F)cc1C(F)(F)F] |
| P10 | 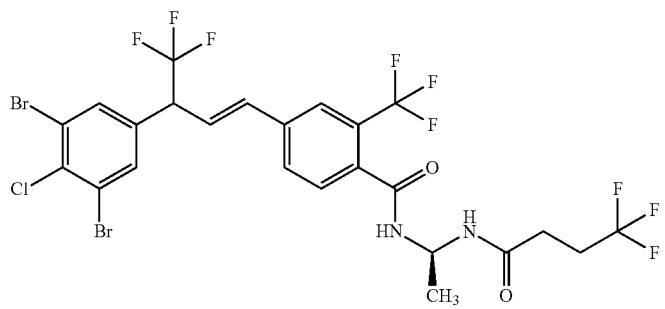 |
| P11 | 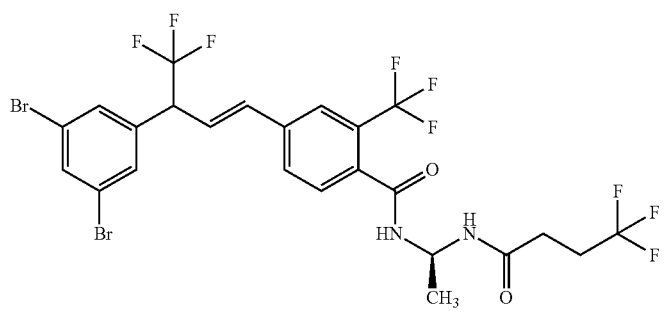 |
| P12 | 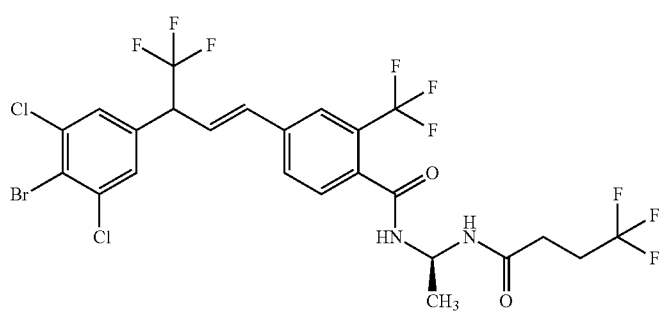 |
| P13 | 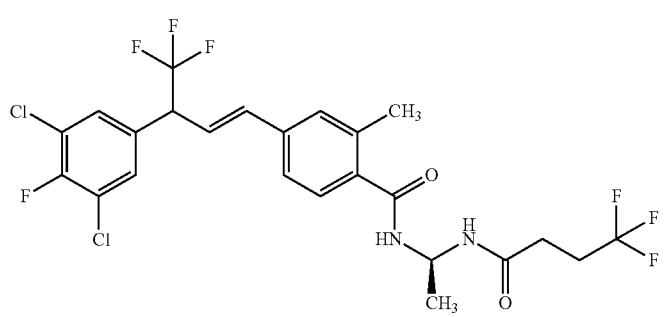 |

| No. | Structure |
|---|---|
| P14 | 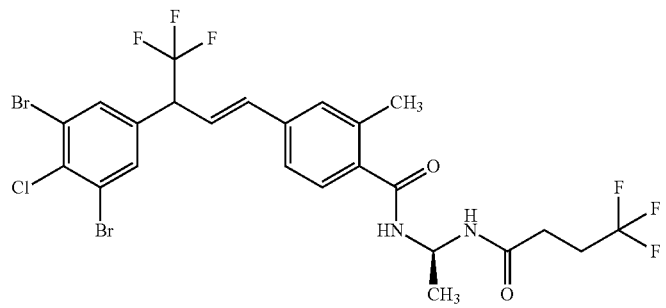 |
| P15 | 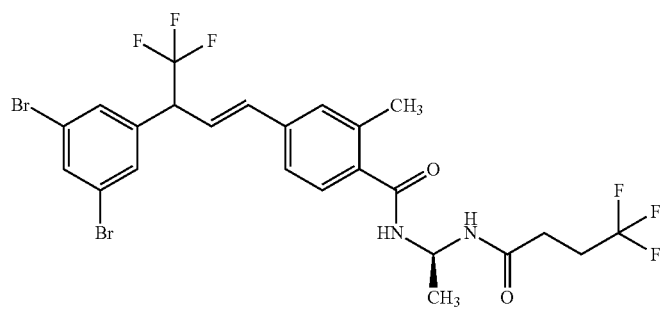 [SMILES: Cc1cc(/C=C/C(c2cc(Br)cc(Br)c2)C(F)(F)F)ccc1C(=O)N[C@H](C)NC(=O)CCC(F)(F)F] |
| P16 | 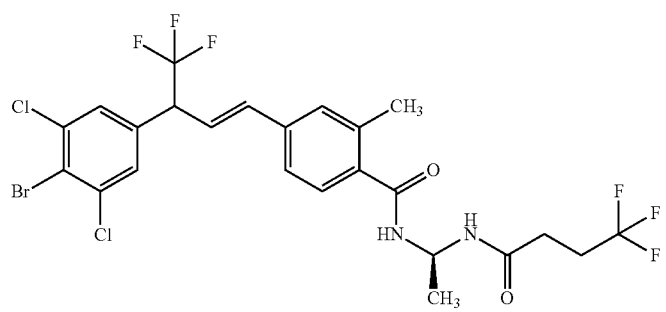 |
| P17 | 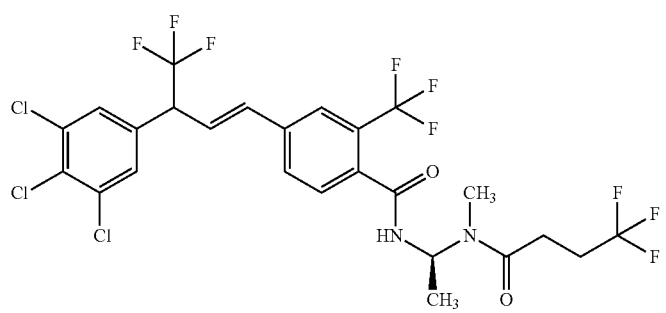 [SMILES: C[C@@H](NC(=O)c1ccc(/C=C/C(c2cc(Cl)c(Cl)c(Cl)c2)C(F)(F)F)cc1C(F)(F)F)N(C)C(=O)CCC(F)(F)F] |
| P18 | 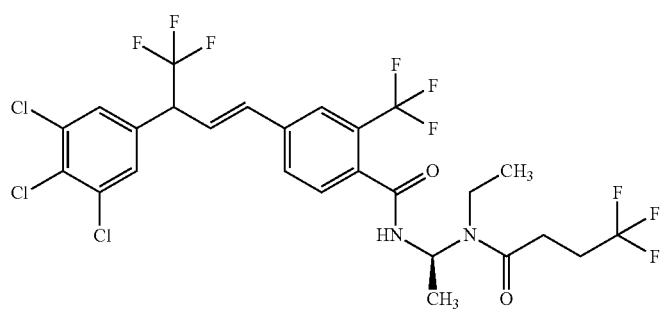 [SMILES: CCN(C(=O)CCC(F)(F)F)[C@@H](C)NC(=O)c1ccc(/C=C/C(c2cc(Cl)c(Cl)c(Cl)c2)C(F)(F)F)cc1C(F)(F)F] |

| No. | Structure |
|---|---|
| P19 | 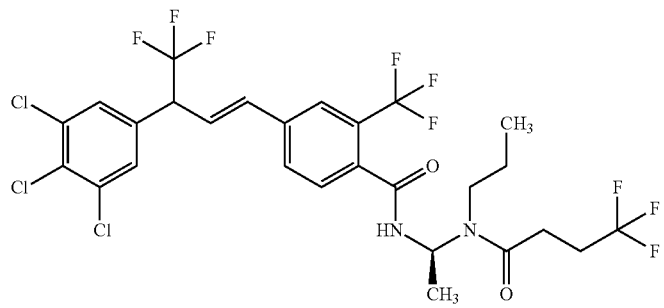 [SMILES: CCCN(C(=O)CCC(F)(F)F)[C@@H](C)NC(=O)c1ccc(/C=C/C(c2cc(Cl)c(Cl)c(Cl)c2)C(F)(F)F)cc1C(F)(F)F] |
| P20 | 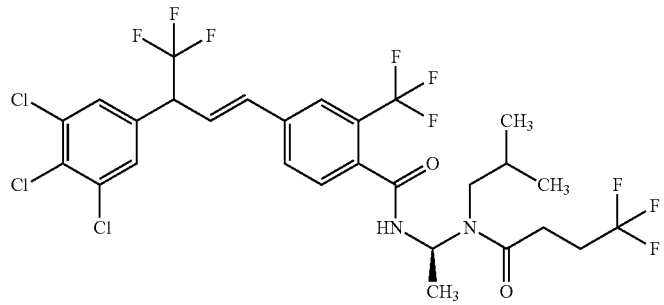 |
| P21 | 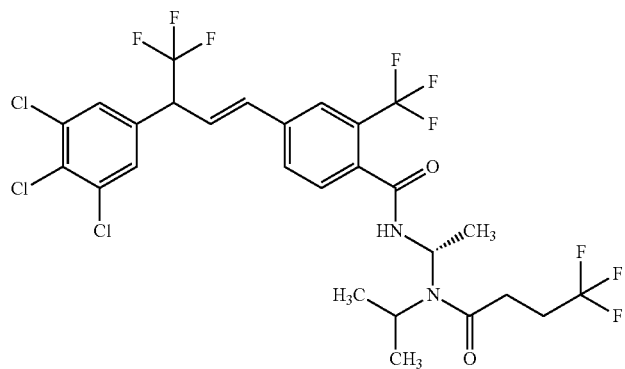 [SMILES: CC(C)N(C(=O)CCC(F)(F)F)[C@@H](C)NC(=O)c1ccc(/C=C/C(c2cc(Cl)c(Cl)c(Cl)c2)C(F)(F)F)cc1C(F)(F)F] |
| P22 | 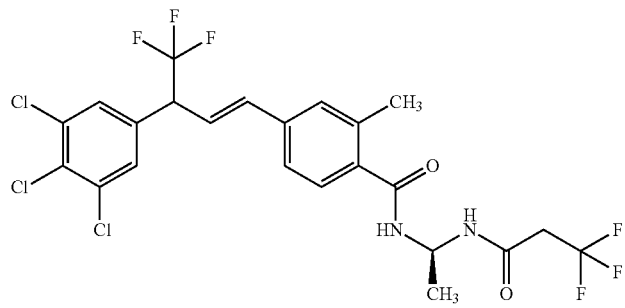 |

-continued
| No. | Structure |
|---|---|
| P23 | 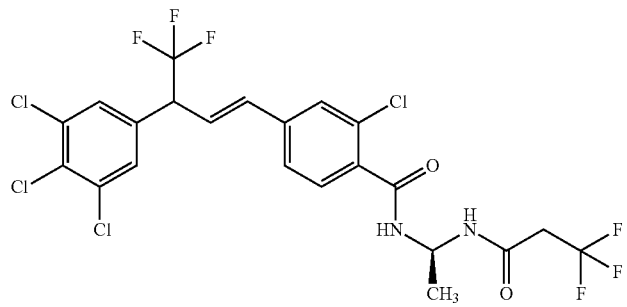 |
| P24 | 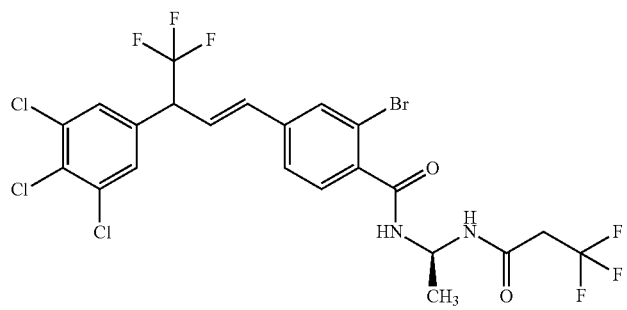 |
| P25 | 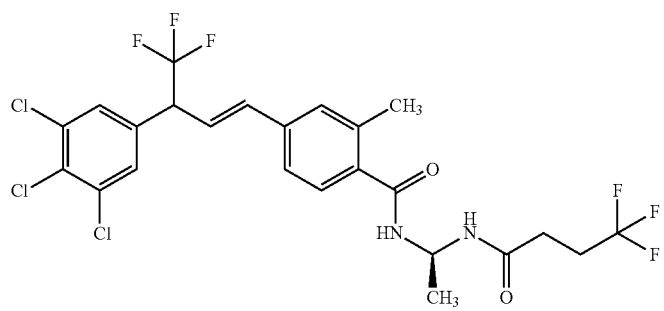 |
| P26 | 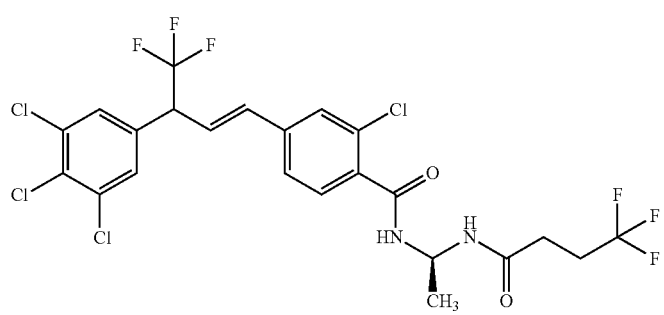 [SMILES: Cc1cc(/C=C/C(c2cc(Cl)c(Cl)c(Cl)c2)C(F)(F)F)ccc1C(=O)N[C@H](C)NC(=O)CCC(F)(F)F] |
| P27 | 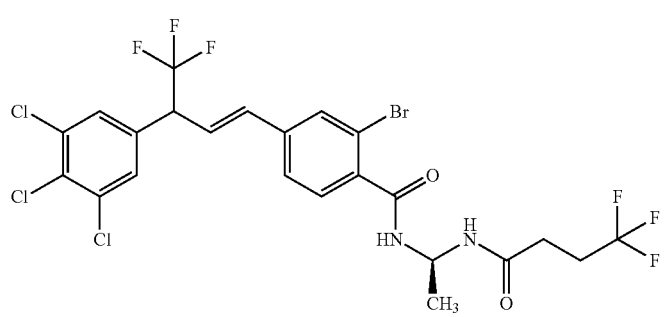 [SMILES: C[C@H](NC(=O)CCC(F)(F)F)NC(=O)c1ccc(/C=C/C(c2cc(Cl)c(Cl)c(Cl)c2)C(F)(F)F)cc1Br] |

| No. | Structure |
|---|---|
| P28 | 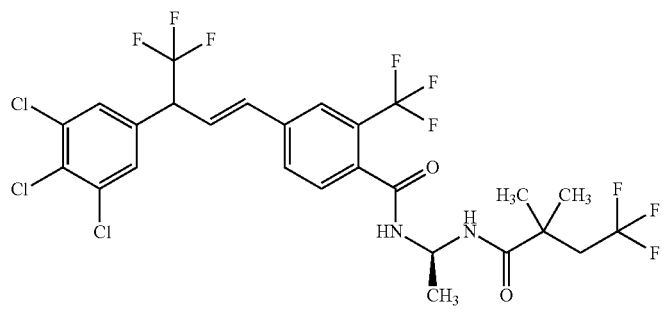 [SMILES: C[C@@H](NC(=O)c1ccc(/C=C/C(c2cc(Cl)c(Cl)c(Cl)c2)C(F)(F)F)cc1C(F)(F)F)NC(=O)C(C)(C)CC(F)(F)F] |
| P29 | 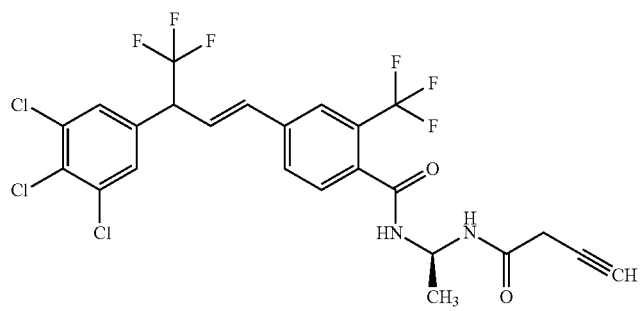 |
| P30 | 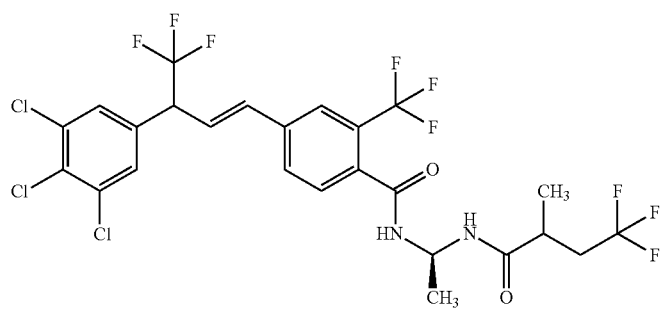 [SMILES: CC(CC(F)(F)F)C(=O)N[C@@H](C)NC(=O)c1ccc(/C=C/C(c2cc(Cl)c(Cl)c(Cl)c2)C(F)(F)F)cc1C(F)(F)F] |
| P31 | 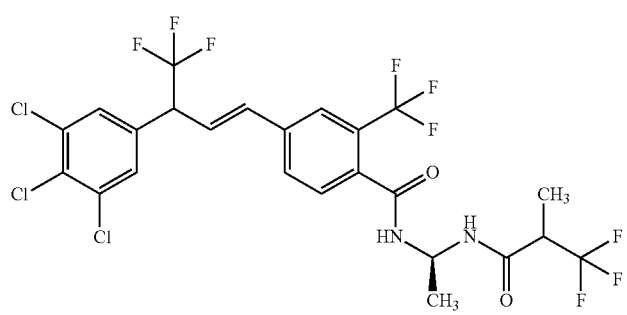 [SMILES: CC(C(=O)N[C@@H](C)NC(=O)c1ccc(/C=C/C(c2cc(Cl)c(Cl)c(Cl)c2)C(F)(F)F)cc1C(F)(F)F)C(F)(F)F] |
| P32 | 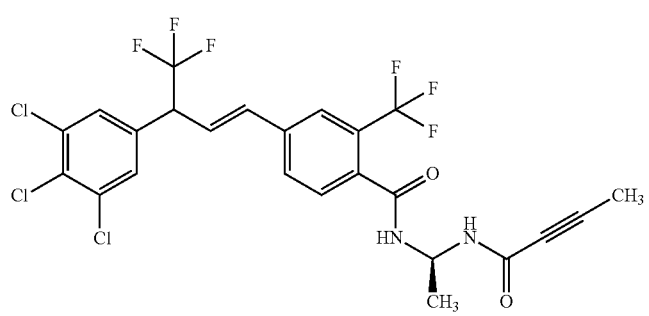 [SMILES: CC#CC(=O)N[C@@H](C)NC(=O)c1ccc(/C=C/C(c2cc(Cl)c(Cl)c(Cl)c2)C(F)(F)F)cc1C(F)(F)F] |

| No. | Structure |
|---|---|
| P33 | 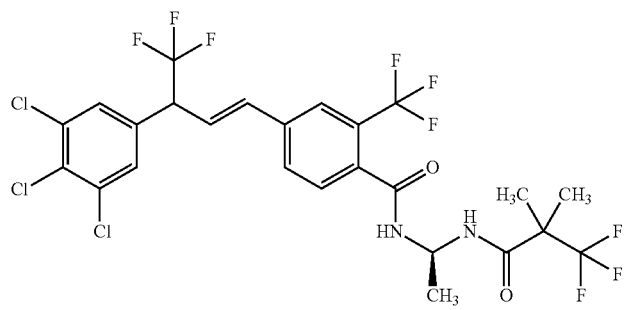 [SMILES: C[C@@H](NC(=O)c1ccc(/C=C/C(c2cc(Cl)c(Cl)c(Cl)c2)C(F)(F)F)cc1C(F)(F)F)NC(=O)C(C)(C)C(F)(F)F] |
| P34 | 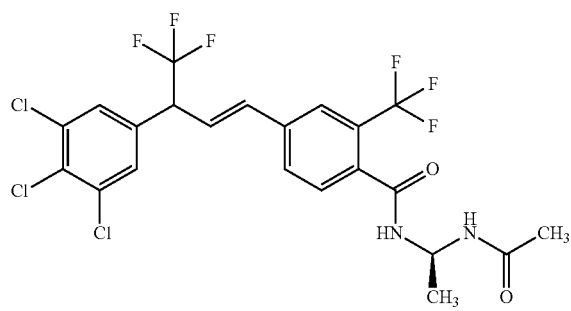 [SMILES: CC(=O)N[C@@H](C)NC(=O)c1ccc(/C=C/C(c2cc(Cl)c(Cl)c(Cl)c2)C(F)(F)F)cc1C(F)(F)F] |
| P35 | 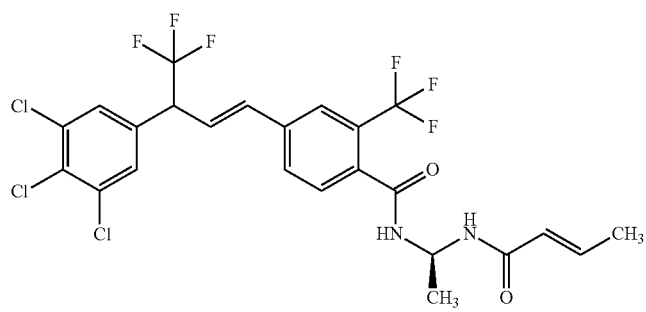 [SMILES: C/C=C/C(=O)N[C@@H](C)NC(=O)c1ccc(/C=C/C(c2cc(Cl)c(Cl)c(Cl)c2)C(F)(F)F)cc1C(F)(F)F] |
| P36 | 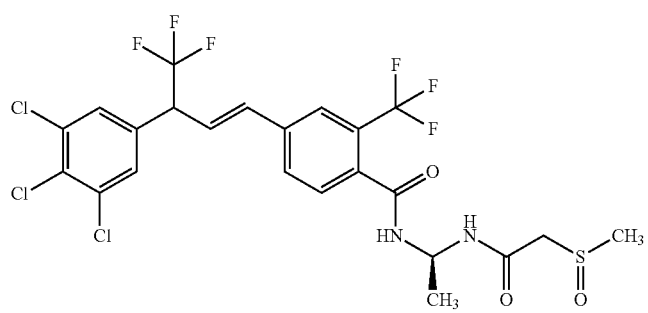 |
| P37 | 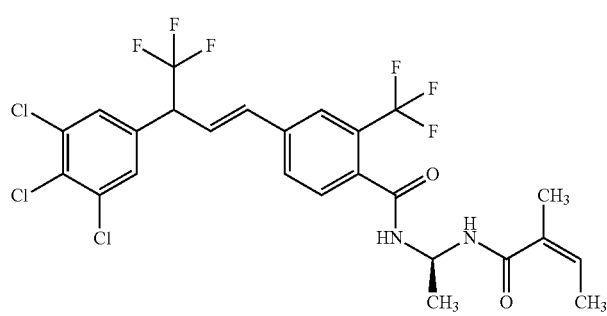 [SMILES: C/C=C(/C)C(=O)N[C@@H](C)NC(=O)c1ccc(/C=C/C(c2cc(Cl)c(Cl)c(Cl)c2)C(F)(F)F)cc1C(F)(F)F] |

| No. | Structure |
|---|---|
| P38 | 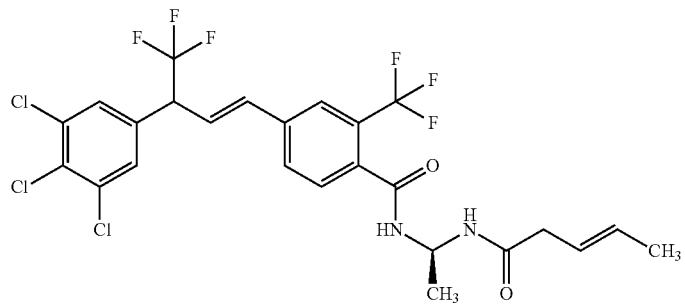 |
| P39 | 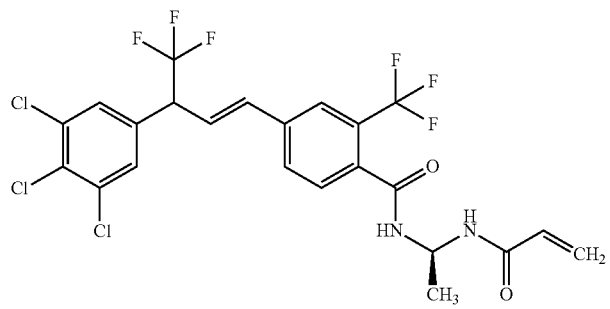 |
| P40 | 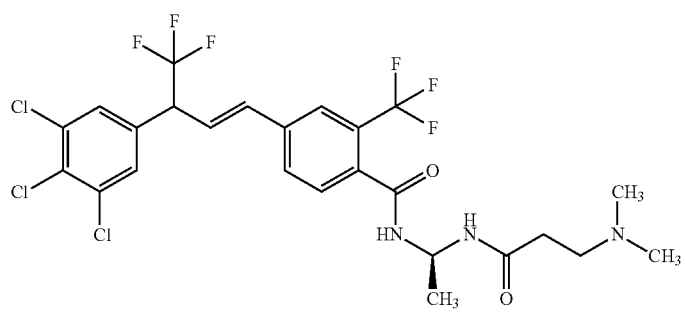 [SMILES: C[C@H](NC(=O)CCN(C)C)NC(=O)c1ccc(/C=C/C(c2cc(Cl)c(Cl)c(Cl)c2)C(F)(F)F)cc1C(F)(F)F] |
| P41 | 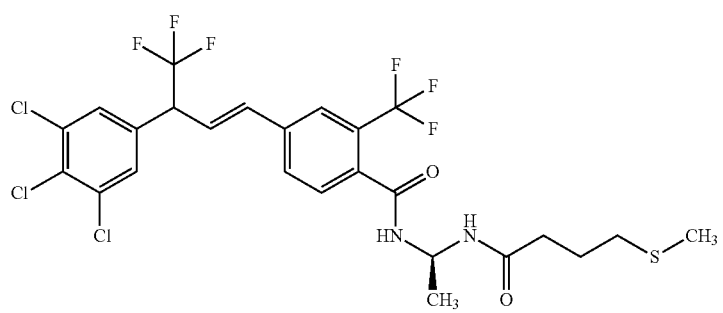 [SMILES: CSCCCC(=O)N[C@@H](C)NC(=O)c1ccc(/C=C/C(c2cc(Cl)c(Cl)c(Cl)c2)C(F)(F)F)cc1C(F)(F)F] |
| P42 | 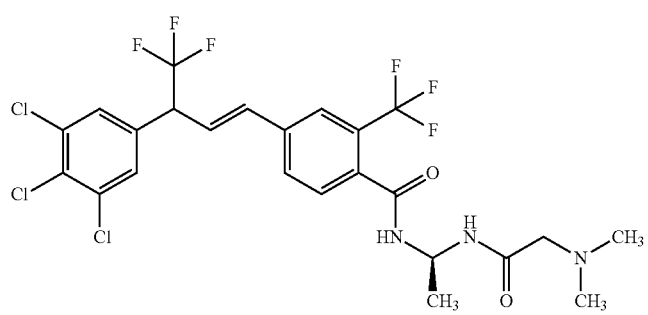 |

-continued

| No. | Structure |
|---|---|
| P43 | 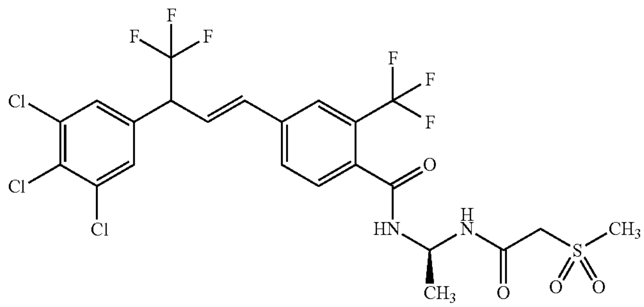 [SMILES: C[C@H](NC(=O)CS(C)(=O)=O)NC(=O)c1ccc(/C=C/C(c2cc(Cl)c(Cl)c(Cl)c2)C(F)(F)F)cc1C(F)(F)F] |
| P44 | 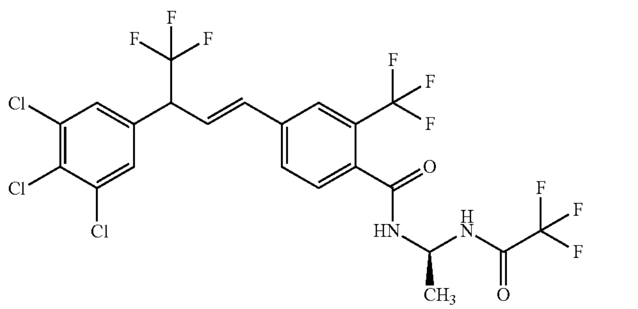 [SMILES: C[C@@H](NC(=O)c1ccc(/C=C/C(c2cc(Cl)c(Cl)c(Cl)c2)C(F)(F)F)cc1C(F)(F)F)NC(=O)C(F)(F)F] |
| P45 | 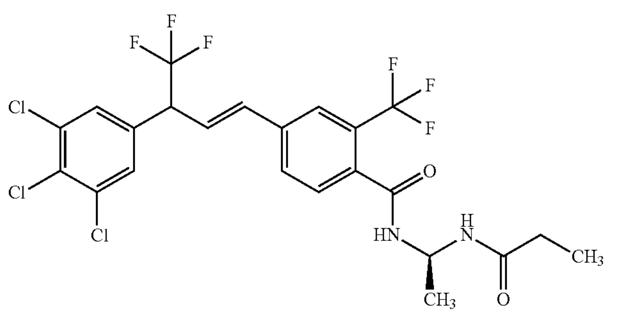 [SMILES: CCC(=O)N[C@@H](C)NC(=O)c1ccc(/C=C/C(c2cc(Cl)c(Cl)c(Cl)c2)C(F)(F)F)cc1C(F)(F)F] |
| P46 | 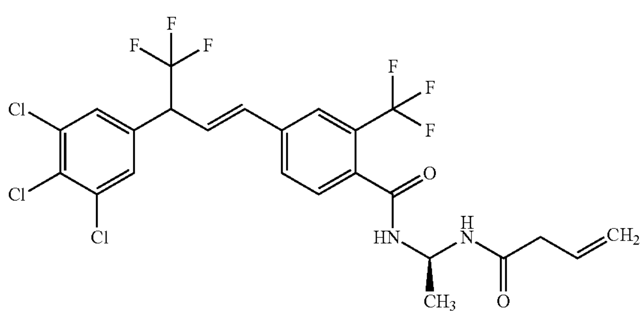 |
| P47 | 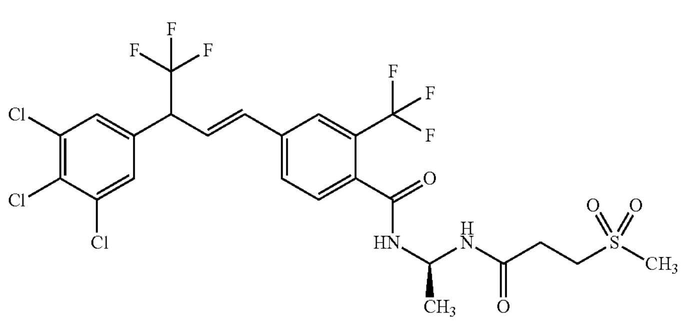 [SMILES: C[C@H](NC(=O)CCS(C)(=O)=O)NC(=O)c1ccc(/C=C/C(c2cc(Cl)c(Cl)c(Cl)c2)C(F)(F)F)cc1C(F)(F)F] |

| No. | Structure |
|---|---|
| P48 | 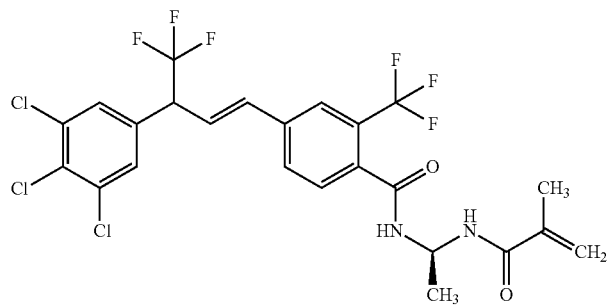 |
| P49 | 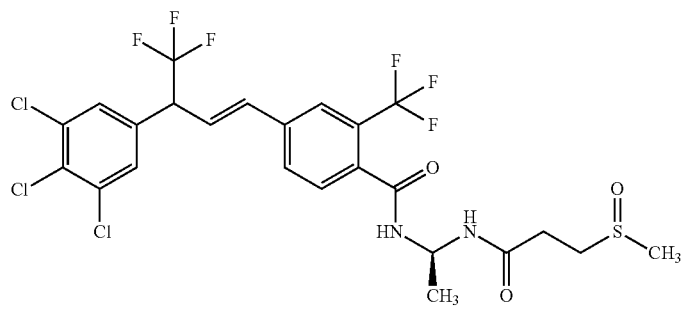 [SMILES: C[C@H](NC(=O)CCS(C)=O)NC(=O)c1ccc(/C=C/C(c2cc(Cl)c(Cl)c(Cl)c2)C(F)(F)F)cc1C(F)(F)F] |
| P50 | 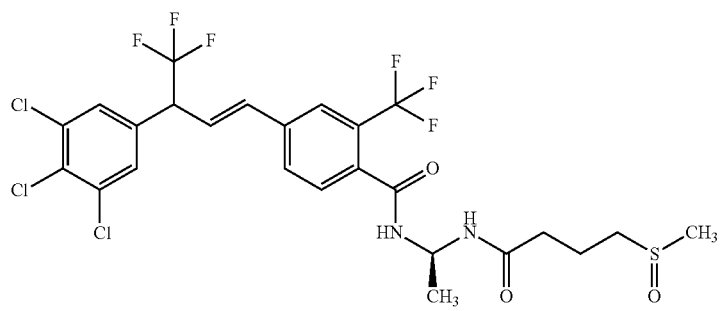 [SMILES: C[C@H](NC(=O)CCCS(C)=O)NC(=O)c1ccc(/C=C/C(c2cc(Cl)c(Cl)c(Cl)c2)C(F)(F)F)cc1C(F)(F)F] |
| P51 | 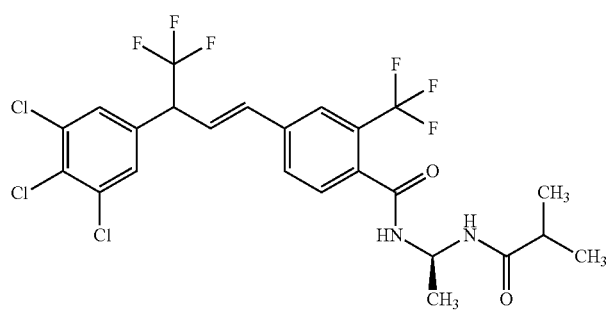 |
| P52 | 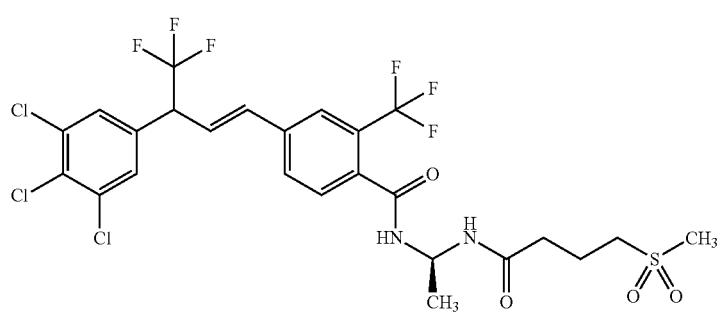 [SMILES: C[C@H](NC(=O)CCCS(C)(=O)=O)NC(=O)c1ccc(/C=C/C(c2cc(Cl)c(Cl)c(Cl)c2)C(F)(F)F)cc1C(F)(F)F] |

| No. | Structure |
|---|---|
| P53 | 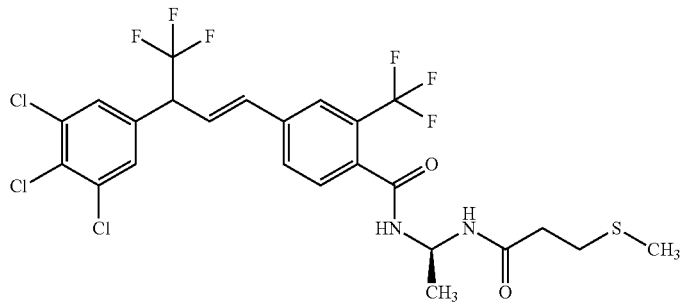 [SMILES: CSCCC(=O)N[C@@H](C)NC(=O)c1ccc(/C=C/C(c2cc(Cl)c(Cl)c(Cl)c2)C(F)(F)F)cc1C(F)(F)F] |
| P54 | 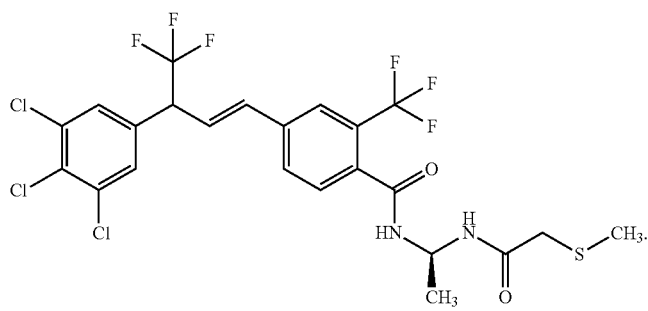 [SMILES: CSCC(=O)N[C@@H](C)NC(=O)c1ccc(/C=C/C(c2cc(Cl)c(Cl)c(Cl)c2)C(F)(F)F)cc1C(F)(F)F] |

6. A molecule according to any one of claims 1, 2, or 3, wherein R14 is $(C_1-C_6)$alkyl or $(C_3-C_6)$cycloalkyl that is substituted with one or more substituents selected from CN, $S(C_1-C_6)$alkyl, $S(O)(C_1-C_6)$alkyl, and $S(O)_2(C_1-C_6)$alkyl.

7. A molecule according to any one of claim 1 or 2 wherein R14 is $CF_3$, $CH_2CF_3$, $CH_2CH_2CF_3$, $CH_2CH_2CH_2CF_3$, $CH_2CH_2CH(CF_3)CH_3$, $CH(CH_3)CH_2CF_3$, $C(CH_3)_2CF_3$, $C(CH_3)_2CH_2CF_3$, $CH_3$, $CH_2CH_3$, $CH_2CH_2CH_3$, $CH_2CH_2CH_2CH_3$, $CH_2CH_2CH_2CH_2CH_3$, $CH(CH_3)_2$, $CH_2CH(CH_3)_2$, $CH_2CH_2CH(CH_3)_2$, $C(CH_3)_3$, $CH_2C(CH_3)_3$, $CH_2CH_2C(CH_3)_3$, $CH_2CH_2CH_2C(CH_3)_3$, cyclopropyl, $CH=CH_2$, $CH=CH(CH_3)$, $CH=C(CH_3)_2$, $CH_2CH=CH_2$, $CH_2CH=CH(CH_3)$, $C(CH_3)=CH_2$, $C(CH_3)=CH(CH_3)$, $C\equiv CH$, $CH_2C\equiv CH$, $CH_2CN$, $CH_2CH_2CN$, $CH_2SCH_3$, $CH_2CH_2SCH_3$, $CH_2S(O)CH_3$, $CH_2CH_2S(O)CH_3$, $CH_2S(O)_2CH_3$, and $CH_2CH_2S(O)_2CH_3$.

8. A pesticidal composition comprising a molecule according to claim 1 and further comprising one or more compounds having a mode of action selected from: acetylcholinesterase (AChE) inhibitors; GABA-gated chloride channel antagonists; sodium channel modulators; nicotinic acetylcholine (nAChR) agonists; nicotinic acetylcholine receptor (nAChR) allosteric activators; chloride channel activators; juvenile hormone mimics; miscellaneous non-specific (multi-site) inhibitors; selective homopteran feeding blockers; mite growth inhibitors; microbial disruptors of insect midgut membranes; inhibitors of chitin biosynthesis, type 0; inhibitors of chitin biosynthesis, type 1; moulting disrupter, dipteran; ecdysone receptor agonists; octopamine receptor agonists; mitochondrial complex III electron transport inhibitors; mitochondrial complex I electron transport inhibitors; voltage-dependent sodium channel blockers; inhibitors of acetyl CoA carboxylase; mitochondrial complex IV electron transport inhibitors; mitochondrial complex II electron transport inhibitors; and ryanodine receptor modulators.

9. A process of controlling a pest comprising applying a pesticidal composition comprising a molecule according to claim 1 to a locus, in a sufficient amount to control said pest.

10. A molecule according to any one of claims 1, 2, or 3, wherein R2, R3, and R4 are Cl.

11. A molecule according to any one of claims 1, 2, or 3, wherein R6 is $CF_3$.

12. A molecule according to any one of claims 1, 2, or 3, wherein R10 is Br, $CH_3$, or $CF_3$.

13. A molecule according to any one of claims 1, 2, or 3, wherein L is —$CH_2$—, —$CH(CH_3)$—, —$CH(CH_2CH_3)$—, or —$CH_2CH_2$—.

14. A molecule according to any one of claims 1, 2, or 3, wherein R13 is H or $CH_3$.

* * * * *